United States Patent
Pietras et al.

(10) Patent No.: US 10,400,006 B2
(45) Date of Patent: Sep. 3, 2019

(54) ESTROGEN RECEPTOR MODULATORS

(71) Applicant: THE REGENTS OF THE UNIVERSITY OF CALIFORNIA, Oakland, CA (US)

(72) Inventors: Richard J. Pietras, Sherman Oaks, CA (US); Michael E. Jung, Los Angeles, CA (US); Diana C. Marquez-Garban, Los Angeles, CA (US); Gang Deng, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/531,245

(22) PCT Filed: Nov. 20, 2015

(86) PCT No.: PCT/US2015/062008
§ 371 (c)(1),
(2) Date: May 26, 2017

(87) PCT Pub. No.: WO2016/085825
PCT Pub. Date: Jun. 2, 2016

(65) Prior Publication Data
US 2018/0086787 A1    Mar. 29, 2018

Related U.S. Application Data

(60) Provisional application No. 62/084,884, filed on Nov. 26, 2014.

(51) Int. Cl.
*C07J 41/00* (2006.01)
*C07J 1/00* (2006.01)
*A61K 31/085* (2006.01)
*C07J 43/00* (2006.01)

(52) U.S. Cl.
CPC ......... *C07J 41/0088* (2013.01); *A61K 31/085* (2013.01); *C07J 1/007* (2013.01); *C07J 41/0072* (2013.01); *C07J 43/003* (2013.01)

(58) Field of Classification Search
CPC ...... C07J 41/0072; C07J 1/007; A61K 31/085
See application file for complete search history.

(56) References Cited

U.S. PATENT DOCUMENTS

| | | |
|---|---|---|
| 3,579,545 A | 5/1971 | Bertin et al. |
| 5,679,788 A | 10/1997 | Nique et al. |
| 2003/0162757 A1 | 8/2003 | Smart et al. |
| 2004/0142915 A1 | 7/2004 | Hochberg |
| 2008/0293683 A1 | 11/2008 | Zhu |

OTHER PUBLICATIONS

Cancer Prevention Overview, http://www.cancer.gov/cancertopics/pdq/prevention/overview/patient, accessed Nov. 14, 2012, p. 1. (Year: 2012).*
Target Cancer Therapies Fact Sheet from NCI, http://www.cancer.gov/about-cancer/treatment/types/targeted-therapies/targeted-therapies-fact-sheet, accessed Dec. 8, 2015, p. 1-6. (Year: 2015).*
Paterni, Estrogen Receptors Alpha (ERa) and Beta (ERb): Subtype-Selective Ligands and Clinical Potential, 2014, Steroids, vol. 0, p. 1-45 (Year: 2014).*
Sareddy, Selective Estrogen Receptor B Agonist LY500307 as a novel therapeutic agent for glioblastoma, Scientific Reports, 2016, vol. 6, p. 1-13 (Year: 2016).*
Hanson, Synthesis and evaluation of 11b-(4-substituted phenyl)estradoil analogs: transition from estrogen receptor agonists to antagonists, 2012, vol. 29, p. 3768-3780. (Year: 2012).*
International Search Report dated Feb. 3, 2016, for PCT Application No. PCT/US2015/062008, filed Nov. 20, 2015, 2 pages.
Written Opinion dated Feb. 3, 2016, for PCT Application No. PCT/US2015/062008, filed Nov. 20, 2015, 3 pages.

* cited by examiner

*Primary Examiner* — Karen Cheng
(74) *Attorney, Agent, or Firm* — Edward D. Grieff; Mintz, Levin, Cohn, Ferris, Glovsky and Popeo, P.C.

(57) ABSTRACT

Described herein, inter alia, are compositions and methods for treating or preventing hyperproliferative disorders, including cancer.

21 Claims, 9 Drawing Sheets

ESTROGEN RECEPTOR MODULATORS

CROSS-REFERENCE TO RELATED APPLICATIONS

This application is a Section 371 National Stage of PCT/US2015/62008 filed Nov. 20, 2015, which claims priority to U.S. Provisional Application No. 62/084,884 filed Nov. 26, 2014, the contents of which are incorporated herein in their entirety and for all purposes.

STATEMENT AS TO RIGHTS TO INVENTIONS MADE UNDER FEDERALLY SPONSORED RESEARCH AND DEVELOPMENT

This invention was made with government support under Grant Number CA143930, awarded by the National Institutes of Health. The government has certain rights in the invention.

BACKGROUND OF THE INVENTION

Breast cancer is the most common malignancy in women in North America. Each year more than 210,000 new cases of breast cancer are diagnosed in the US (1-3). In the clinic, endocrine therapy is an important intervention for cancers that express estrogen receptor (ER), and it has proven to be one of the most effective treatment strategies for breast cancer (3,4). At diagnosis, about 70% of breast cancers contain estrogen receptors and depend on estrogen for growth and progression. Expression of ER in a tumor is predictive of a clinical response to hormonal therapy. Such observations have led to current use of antiestrogens (such as fulvestrant, tamoxifen and its relatives, raloxifene, toremifene, lasofoxifene, etc.) and aromatase inhibitors in treating ER-positive breast cancer (2,3). Tamoxifen and its analogues are among the most highly prescribed drugs for initial estrogen-dependent breast cancer. However, they are not without their drawbacks since they bind to the estrogen receptor in many tissues (bone, uterus, etc.) and can have harmful effects. A substantial proportion of patients presenting with localized disease, and all of the patients with metastatic breast cancer, become resistant to current endocrine therapies (5, 6). Thus, there is an urgent need to develop alternative therapeutics to overcome endocrine resistance and to improve the long-term survival of afflicted patients. Despite remarkable improvements in treatment options, development of endocrine resistance is one reason that breast cancer is the second most frequent cause of cancer death in women (5-7). In most cases, the ER is present in resistant tumors, and in many of these its activity continues to regulate tumor growth.

Classical and nonclassical mechanisms of estrogen action in breast malignancy. Estrogen modulates gene transcription in breast cancers through its receptors using different signaling pathways (2,8) (see FIG. 1). The classical pathway involves direct DNA binding of liganded receptor to estrogen response elements (EREs) in the promoter regions of responsive genes.

The proliferation and survival of breast cancers is closely regulated by growth factor receptors as well as estrogens (E2) and their receptors, estrogen receptor (ER)-α and -β, with ERα generally considered most important in tumor progression (5,6,9). ERα has 6 major functional domains including an N-terminal transactivation domain, an adjacent DNA-binding domain and a C-terminal portion involved in hormone-binding, receptor dimerization and activity of a second transactivation region. In classical models of E2 action, E2 binds ER to promote dimerization and phosphorylation of the receptor. This allows direct binding of the ligand-ER complex with steroid receptor coactivators (CoReg) and E2-responsive elements (ERE) in DNA, leading to changes in gene transcription that regulate growth, differentiation, apoptosis and angiogenesis. In addition, there are alternate pathways of E2 action that involve protein-protein interactions and do not require direct ER binding to DNA. A subset of ER associate with extranuclear sites and interact there with membrane growth factor receptors (EGFR, HER2) and other signaling molecules (components of the ras-MAPK and PI3K/AKT pathways, Shc, src kinases, JAK/STAT, nitric oxide synthase (NOS), G-proteins). Of special note, growth factor and extranuclear estrogen receptors appear to form a structured complex for signal transduction to MAPK and/or PI3K/AKT kinase that interacts, in turn, with nuclear ER and CoReg. Signaling for cell growth involves phosphorylation (P) of nuclear ER and CoReg, and such phosphorylation can occur in ligand-dependent as well as ligand-independent modes. ERE-dependent and alternate transcription sites may be activated. Further, E2 is produced locally in supporting cells by the action of aromatase (ARO), and ARO is regulated by both nulcear and extranuclear ER and growth factor-mediated signaling. In addition, estrogens may regulate tumor-associated angiogenesis by direct interactions with vascular endothelial cells or by indirect stimulation of VEGF secretion from tumors.

However, it is now clear that the ERα can regulate genes that lack a canonical ERE, suggesting additional pathways for estrogen action that may be of paramount importance in modulating tumor progression. Alternate, nonclassical pathways involve indirect modulation of transcription by ER interaction with components of other transcription complexes (AP-1, nuclear factor-kB) or kinase signaling complexes (MAPK, PI3K/AKT kinase) via protein-protein interactions. Emerging data suggest that interactions of ER with growth factor receptor-kinase signaling pathways may play a critical role in promoting estrogen signaling for tumor progression (9). Based on current data in estrogen target cells, nonclassical ER signaling is associated with epithelial proliferation but not other estrogen-responsive events such as fluid accumulation in uterus (8), while classical ER signaling appears more essential for skeletal development, bone health and other differentiated cell functions (10).

ER often continues to play a major role in controlling growth of hormone-resistant cancers. In treatment with aromatase inhibitors (AI's), ER activation by alternate ligands, local E2 production and development of ER hypersensitivity are especially problemsome (2,6). In addition, ligand-independent activation of ER occurs in tumors overexpressing growth factor receptors such as HER2, with growth factor receptors promoting ER phosphorylation even in the absence of estrogen (5,9,11). Such ligand-independent mechanisms likely contribute to resistance to AI's as well as antiestrogens (12,13). These nonclassical events are mediated by ER or adaptor proteins that impact gene expression indirectly by activating growth-promoting kinase cascades to regulate transcription. In breast tumors, significant evidence suggests that regulation of both proliferation and cell death pathways occurs, in part, by the action of nonclassical kinase-mediated pathways (9,11,14-19). Better understanding and targeting of these complex signaling pathways in tumors with endocrine resistance to both antiestrogens and AI's will help in development of individualized and improved treatments in the clinic.

Current antiestrogens are competitive antagonists of estrogen and disrupt ER-induced transcription. However, some antagonists display partial estrogenic activity in a tissue- and gene-dependent manner, hence their description as selective estrogen receptor modulators (SERMs). Tamoxifen, a partial agonist that limits effects of E2 in breast, has been the most widely used hormone therapy for the past 20 years, achieving a 39% reduction in disease recurrence and a 31% reduction in mortality in ER+ early breast cancer (6,20,21). Although effective, tamoxifen has an important drawback—the limited period of activity before resistance develops (7,20). Further, prolonged treatment with tamoxifen is associated with an increased risk for endometrial cancer due to significant agonist activity of the drug in uterus. As long as the ER is present in tumors, growth may still be stimulated by small amounts of estrogens or antiestrogens or by ligand-independent actions. The introduction of AI's for postmenopausal patients, either initially, or sequentially after tamoxifen, may produce better outcomes than the standard treatment of 5 years of tamoxifen (22-24). Nonetheless, in patients with advanced disease, only about ⅓ of HR+ tumors respond to AI's as first-line treatments (6). Further, resistance to AI's also develops due, in part, to E2-independent mechanisms (6,12,13). Consequently, a search has begun to find new antiestrogens that do not display agonist activity or lead to development of resistance. The first prototype drug, fulvestrant (25), is a pure ER antagonist that also exhibits a unique mechanism of action—downregulation of ER due in part to induced hyperubiquitination of ER (26,27). As fulvestrant has no agonistic activity but instead destabilizes ER, the drug elicits marked disruption of ER-mediated growth. However, fulvestrant has a major drawback—very low bioavailability—which is problemsome in the clinic. Although fulvestrant has activity in treating ER+ metastatic breast cancer in postmenopausal women with disease progression after tamoxifen or AI therapy (7,28,29), discovery of new ER antagonists with improved bioavailability and antitumor activity remains an important goal.

ER degradation limits hormone action. Ligand-induced down-regulation of ER is a pivotal step in halting E2 stimulation of growth, and the ubiquitin-proteasome pathway is the major system for selective degradation of such regulatory proteins (30). ERα was among the first of the nuclear receptors identified as substrates for this pathway (31-34). A common feature of proteasome-mediated protein degradation is covalent attachment of ubiquitin to lysine residues of proteins targeted for degradation followed by formation of polyubiquitin chains attached covalently to the protein. Ubiquitinated ERα is recognized and degraded by the multisubunit protease complex, the 26S proteasome (35). ER is degraded in a hormone-dependent manner, with this process contributing to regulation of hormone action; and the proteasome inhibitor, MG132, is well known to promote in vivo accumulation of ER and to block ligand-induced ER degradation (33). As noted above, the proteasome pathway also plays a critical role in interaction of ER with antagonists, such as SERMs and fulvestrant (27,34).

Therefore it would be useful to test new novel ER antagonists to find compounds which inhibit the growth of hyperproliferative cells, including breast cancer. Disclosed herein, inter alia, are solutions to these and other problems in the art.

BRIEF SUMMARY OF THE INVENTION

In an aspect is provided a compound, or a pharmaceutically acceptable salt thereof, having the formula:

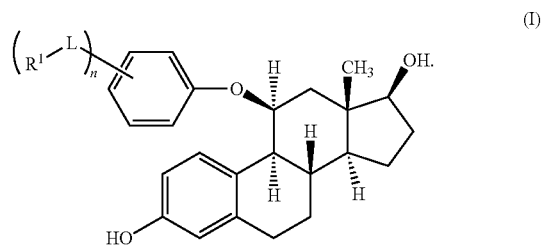

(I)

$R^1$ is independently a hydrogen, halogen, $-NR^2R^3$, $-CX^a_3$, $-CN$, $-SO_2Cl$, $-SO_{n1}R^{10}$, $-SO_{v1}NR^2R^3$, $-NHNR^2R^3$, $-ONR^2R^3$, $-NHC\!\!=\!\!(O)NHNR^2R^3$, $-NHC\!\!=\!\!(O)NR^2R^3$, $-N(O)_{m1}$, $-C(O)R^9$, $-C(O)-OR^9$, $-C(O)NR^2R^3$, $-OR^{10}$, $-NR^2SO_2R^{10}$, $-NR^2C\!\!=\!\!(O)R^9$, $-NR^2C(O)-OR^9$, $-NR^2OR^9$, $-OCX^a_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is independently a hydrogen, halogen, $-CX^b_3$, $-CN$, $-SO_2Cl$, $-SO_{n2}R^{14}$, $-SO_{v2}NR^{11}R^{12}$, $-NHNH_2$, $-ONR^{11}R^{12}$, $-NHC\!\!=\!\!(O)NHNH_2$, $-NHC\!\!=\!\!(O)NR^{11}R^{12}$, $-N(O)_{m2}$, $-NR^{11}R^{12}$, $-C(O)R^{13}$, $-C(O)-OR^{13}$, $-C(O)NR^{11}R^{12}$, $-OR^{14}$, $-NR^{11}SO_2R^{14}$, $-NR^{11}C\!\!=\!\!(O)R^{13}$, $-NR^{11}C(O)-OR^{13}$, $-NR^{11}OR^{13}$, $-OCX^b_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently a hydrogen, halogen, $-CX^c_3$, $-CN$, $-SO_2Cl$, $-SO_{n3}R^{18}$, $-SO_{v3}NR^{15}R^{16}$, $-NHNH_2$, $-ONR^{15}R^{16}$, $-NHC\!\!=\!\!(O)NHNH_2$, $-NHC\!\!=\!\!(O)NR^{15}SR^{16}$, $-N(O)_{m3}$, $-NR^{15}R^{16}$, $-C(O)R^{17}$, $-C(O)-OR^{17}$, $-C(O)NR^{15}R^{16}$, $-OR^{18}$, $-NR^{15}SO_2R^{18}$, $-NR^{15}C\!\!=\!\!(O)R^{17}$, $-NR^{15}C(O)-OR^{17}$, $-NR^{15}OR^7$, $-OCX^c_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ and $R^3$ substituents may optionally be joined to form a substituted or unsubstituted heterocycloalkyl, or substituted or unsubstituted heteroaryl.

L is independently a bond, $-NR^4-$, $-NR^4C(O)-$, $-C(O)NR^4-$, $-O-$, $-S-$, $-C(O)-$, $-S(O)-$, $-S(O)_2-$, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker. $R^4$ is independently a hydrogen, halogen, $-CX^d_3$, $-CN$, $-SO_2Cl$, $-SO_{n4}R^{22}$, $-SO_{v4}NR^{19}R^{20}$, $-NHNH_2$, $-ONR^{19}R^{20}$, $-NHC\!\!=\!\!(O)NHNH_2$, $-NHC\!\!=\!\!(O)NR^{19}R^{20}$, $-N(O)_{m4}$, $-NR^{19}R^{20}$, $-C(O)R^{21}$, $-C(O)-OR^{21}$, $-C(O)NR^{19}R^{20}$, $-OR^{22}$, $-NR^{19}SO_2R^{22}$, $-NR^{19}C\!\!=\!\!(O)R^{21}$, $-NR^{19}C(O)-OR^{21}$, $-NR^{19}OR^{21}$, $-OCX^d_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, —$CX_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCX_3$, —$OCHX_2$, —$CF_3$, —$OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl.

The symbol n is an integer from 0 to 5. The symbols m1, m2, m3, m4, v1, v2, v3, and v4 are independently 1 or 2. The symbols n1, n2, n3, and n4 are independently an integer from 0 to 4. The symbols X, $X^a$, $X^b$, $X^c$ and $X^d$ are independently —Cl, —Br, —I, or —F.

In another aspect is provided a pharmaceutical composition including a pharmaceutically acceptable excipient and a compound, or pharmaceutically acceptable salt thereof, as described herein, including embodiments (e.g. compound of formula I, Ia, Ib, II, IIa, IIb, or any embodiment thereof, or in an example, table, figure, or claim).

In an aspect is provided a method of treating a hyperproliferative disorder in a subject in need thereof, including administering to the subject an effective amount of a compound described herein.

In an aspect is provided a method of inhibiting estrogen receptor activity in a subject in need thereof, including administering to the subject an effective amount of a compound described herein.

In an aspect is provided a method of treating a bone disorder in a subject in need thereof, including administering to the subject an effective amount of a compound described herein.

DETAILED DESCRIPTION OF THE INVENTION

Figure 1:
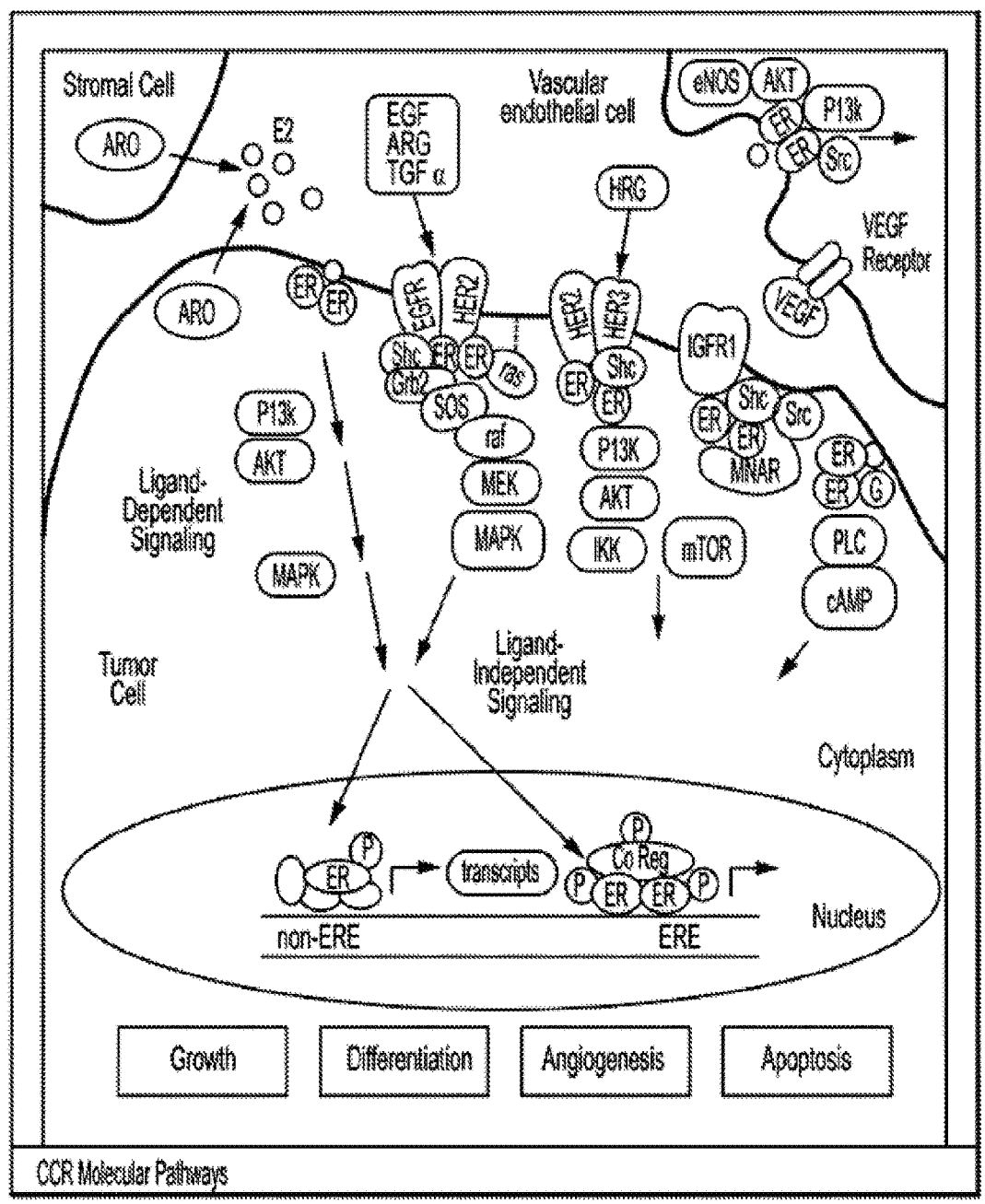
FIG. 1. Interactions of estrogen and growth factor receptor signaling pathways in cancer cells.

A primary goal of this work is to design, synthesize, test and further develop small organic SERMs that elicit ER destabilization/downregulation and inhibit tumor cell growth. This action-suppression of ER protein expression—is critical to stop ligand-dependent and ligand-independent modes of hormone resistance. Described herein are unique, selective ER antagonists that target growth-promoting signaling pathways induced by ER and that exhibit the proper biologic and pharmacologic profile to be ultimately developed as therapeutics for endocrine-sensitive and -resistant cancers in the clinic.

Described herein is the design and synthesis of several novel analogues of estradiol having sterically large and positively charged groups on the β-face of the molecule. These compounds may bind to the ER and cause helix 12 to not fold properly and therefore that would interrupt the transmission of the signal for cancer growth. Biological testing has shown that many of the analogues have excellent growth inhibitory activity, at least as good or better than the commercial drug, Faslodex®. Compounds described herein have great promise as agents against hyperproliferative disorders (e.g., breast cancer).

A. DEFINITIONS

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom (e.g. O, N, P, Si, and S) and wherein the nitrogen and sulfur atoms may optionally be oxidized, and the nitrogen heteroatom may optionally be quaternized. The heteroatom(s) (e.g. O, N, P, S, and Si) may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —C—H=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C=(O)NR"NR"'R"", —CN, —$NO_2$, in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C=(O)NR"NR"'R"", —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R"', and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:
 (A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
 (B) alkyl, heteroalkyl, cycloalkyl, heterocycloalkyl, aryl, heteroaryl, substituted with at least one substituent selected from:
  (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)— OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, heteroaryl, substituted with at least one substituent selected from:
   (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)— OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
   (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject, in a cancer cell, in the extracellular space near a cancer cell).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms.

Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "," denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat diseases associated with estrogen receptor activity. Certain methods described herein may treat diseases associated with estrogen receptor activity (e.g., breast cancer, lung cancer, a gynecological cancer, ovarian cancer, endometrial cancer, or prostate cancer, lymphangioleiomyomatosis (LAM)) by inhibiting estrogen receptor activity. Certain methods described herein may treat diseases associated with estrogen receptor activity by inhibiting ligand binding to estrogen receptor. Certain methods described herein may treat diseases associated with estrogen receptor activity by inducing the degradation of estrogen receptor. Certain methods described herein may treat diseases associated with estrogen receptor activity by inducing a non-active conformation of estrogen receptor. Certain methods described herein may treat diseases associated with hyperproliferation (e.g., of cells). For example, certain methods herein treat cancer. For example certain methods herein treat cancer by decreasing a symptom of cancer. Symptoms of cancer would be known or may be determined by a person of ordinary skill in the art. The term "treating" and conjugations thereof, include prevention of injury, pathology, condition, or disease.

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999);

and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. hyperproliferative disease, cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with estrogen receptor activity may be treated with an agent (e.g. compound as described herein) effective for decreasing the level of estrogen receptor activity.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme.

As defined herein, the term "inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor. In some embodiments inhibition refers to reduction of a disease or symptoms of disease. Thus, inhibition may include, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein.

The term "modulator" refers to a composition that increases or decreases the level of a target molecule or the function of a target molecule. In embodiments, a modulator is an anti-cancer agent. In embodiments, a modulator is an estrogen receptor antagonist. In embodiments, a modulator is a hormone receptor antagonist. In embodiments, a modulator is an estrogen receptor inhibitor. In embodiments, a modulator is an estrogen receptor covalent modifier.

"Anti-cancer agent" or "anti-cancer drug" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent approved by the FDA or similar regulatory agency of a country other than the USA, for treating cancer. Examples of anti-cancer agents include, but are not limited to, anti-androgens (e.g., Casodex, Flutamide, MDV3100, or ARN-509), MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine), anti-metabolites (e.g., 5-azathioprine, leucovorin, capecitabine, fludarabine, gemcitabine, pemetrexed, raltitrexed, folic acid analog (e.g., methotrexate), pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine daclix-imab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, pyrrolo benzodiazepines (e.g. tomaymycin), carboplatin, CC-1065 and CC-1065 analogs including amino-CBIs, nitrogen mustards (such as chlorambucil and melphalan), dolastatin and dolastatin analogs (including auristatins: eg. monomethyl auristatin E), anthracycline antibiotics (such as doxorubicin, daunorubicin, etc.), duocarmycins and duocarmycin analogs, enediynes (such as neocarzinostatin and calicheamicins), leptomycin derivaties, maytansinoids and maytansinoid analogs (e.g. mertansine), methotrexate, mitomycin C, taxoids, vinca alkaloids (such as vinblastine and vincristine), epothilones (e.g. epothilone B), fluvestrant, camptothecin and its clinical analogs topotecan and irinotecan, SERMS (e.g., clomifene, femarelle, ormeloxifene, raloxifene, tamoxifen, toremifene, lasofoxifene, ospemifene), aromatase inhibitors (e.g., anastrozole, letrozole, exemestane, vorozole, formestane, fadrozole, aminoglutethimide, testolactone), or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In some embodiments, the disease is a disease having the symptom of cell hyperproliferation. In some embodiments, the disease is a disease having the symptom of an aberrant level of estrogen receptor activity. In some embodiments, the disease is a cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. In embodiments, the disease is breast cancer. In embodiments, the disease is hormone sensitive breast cancer. In embodiments, the disease is hormone refractory (insensitive) breast cancer. In embodiments, the disease is ER positive breast cancer. In embodiments, the disease is ER negative breast cancer. In embodiments, the disease is breast cancer expressing HER-2.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include cancer of the prostate, thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples may include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. Nucleic acids containing one or more carbocyclic sugars are also included within one definition of nucleic acids.

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

Twenty amino acids are commonly found in proteins. Those amino acids can be grouped into nine classes or groups based on the chemical properties of their side chains. Substitution of one amino acid residue for another within the same class or group is referred to herein as a "conservative" substitution. Conservative amino acid substitutions can frequently be made in a protein without significantly altering the conformation or function of the protein. Substitution of one amino acid residue for another from a different class or group is referred to herein as a "non-conservative" substitution. In contrast, non-conservative amino acid substitutions tend to modify conformation and function of a protein.

Example of Amino Acid Classification
Small/Aliphatic residues: Gly, Ala, Val, Leu, Ile
Cyclic Imino Acid: Pro
Hydroxyl-containing Residues: Ser, Thr
Acidic Residues: Asp, Glu
Amide Residues: Asn, Gln
Basic Residues: Lys, Arg
Imidazole Residue: His
Aromatic Residues: Phe, Tyr, Trp
Sulfur-containing Residues: Met, Cys In some embodiments, the conservative amino acid substitution comprises substituting any of glycine (G), alanine (A), isoleucine (I), valine (V), and leucine (L) for any other of these aliphatic amino acids; serine (S) for threonine (T) and vice versa; aspartic acid (D) for glutamic acid (E) and vice versa; glutamine (Q) for asparagine (N) and vice versa; lysine (K) for arginine (R) and vice versa; phenylalanine (F), tyrosine (Y) and tryptophan (W) for any other of these aromatic amino acids; and methionine (M) for cysteine (C) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Still other changes can be considered "conservative" in particular environments (see, e.g., BIOCHEMISTRY at pp. 13-15, 2nd ed. Lubert Stryer ed. (Stanford University); Henikoff et al., *Proc. Nat'l Acad. Sci. USA* (1992) 89:10915-10919; Lei et al., *J. Biol. Chem.* (1995) 270(20):11882-11886).

"Polypeptide," "peptide," and "protein" are used herein interchangeably and mean any peptide-linked chain of amino acids, regardless of length or post-translational modification. As noted below, the polypeptides described herein can be, e.g., wild-type proteins, biologically-active fragments of the wild-type proteins, or variants of the wild-type proteins or fragments. Variants, in accordance with the disclosure, can contain amino acid substitutions, deletions, or insertions. The substitutions can be conservative or non-conservative.

Following expression, the proteins can be isolated. The term "purified" or "isolated" as applied to any of the proteins described herein refers to a polypeptide that has been separated or purified from components (e.g., proteins or other naturally-occurring biological or organic molecules) which naturally accompany it, e.g., other proteins, lipids, and nucleic acid in a cell expressing the proteins. Typically, a polypeptide is purified when it constitutes at least 60 (e.g., at least 65, 70, 75, 80, 85, 90, 92, 95, 97, or 99) %, by weight, of the total protein in a sample.

An amino acid residue in a protein "corresponds" to a given residue when it occupies the same essential structural position within the protein as the given residue. For example, a selected residue in a selected protein corresponds to Cys784 of human androgen receptor when the selected residue occupies the same essential spatial or other structural relationship as Cys 784 in human androgen receptor. In some embodiments, where a selected protein is aligned for maximum homology with the human androgen receptor protein, the position in the aligned selected protein aligning with Cys784 is said to correspond to Cys784. Instead of a primary sequence alignment, a three dimensional structural alignment can also be used, e.g., where the structure of the selected protein is aligned for maximum correspondence with the human androgen receptor protein and the overall structures compared. In this case, an amino acid that occupies the same essential position as Cys784 in the structural model is said to correspond to the Cys784 residue.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms (e.g. symptoms of cancer or aberrant androgen receptor activity). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer, or with adjunctive agents that may not be effective alone, but may contribute to the efficacy of the active agent.

In embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer such as radiation or surgery.

A "drug-resistant estrogen receptor" is a modified (relative to wildtype) estrogen receptor that is inhibited less effectively by the drug than a wildtype estrogen receptor. A "drug-resistant human estrogen receptor" is a modified (relative to wildtype) human estrogen receptor that is inhibited less effectively by the drug than a wildtype human estrogen receptor.

A "drug-resistant cancer" is a cancer that is inhibited less effectively by the drug than a non-drug resistant cancer. An "antiestrogen-resistant cancer" is a cancer that is inhibited less effectively by the antiestrogen than a non-antiestrogren resistant cancer. An "endocrine therapeutic-resistant cancer" is a cancer that is inhibited less effectively by the endocrine therapeutic than a non-endocrine therapeutic resistant cancer.

The term "antiestrogen" refers to a compound that binds estrogen receptor without one or more of the estrogen receptor activities associated with the binding of estrogen to the estrogen receptor. In embodiments an antiestrogen is a compound that inhibits one or more effects of estrogen (e.g., on ER, on a cell, on a tissue, or on an organism). Examples of an antiestrogen include fluvestrant, clomifene, femarelle, ormeloxifene, raloxifene, tamoxifen, toremifene, lasofoxifene, and ospemifene.

The term "endocrine therapeutic" refers to a compound that is effective for modulating hormone activity in a subject. Use of an endocrine therapeutic in treatment of a subject is "endocrine therapy". Modulation of hormone activity by an endocrine therapeutic may include increasing, decreasing, blocking, removing, or otherwise changing the level of a hormone or the level of activity of a hormone. Examples of endocrine therapeutics include antiestrogens, aromatase inhibitors, SERMs, fluvestrant, clomifene, femarelle, ormeloxifene, raloxifene, tamoxifen, toremifene, lasofoxifene, ospemifene, anastrozole, letrozole, exemestane, vorozole, formestane, fadrozole, aminoglutethimide, and testolactone.

The term "estrogen receptor" or "ER" refers to an established member of the nuclear receptor family of receptors which is a transcription factor activated by binding ligands such as the hormones 17β-estradiol, estriol, estrone, etc. In embodiments, "estrogen receptor" or "ER" refers to a nuclear receptor which is a transcription factor activated by binding ligands such as the hormones 17β-estradiol, estriol, and/or estrone. In embodiments, "estrogen receptor" or "ER" refers to a nuclear receptor which is a transcription factor activated by binding the hormone 17β-estradiol. The term "estrogen receptor" may refer to the nucleotide sequence or protein sequence of human estrogen receptor. The term "estrogen receptor" may refer to the nucleotide sequence or protein sequence of human estrogen receptor 1 (a.k.a. ER-alpha, ERalpha, or ERα) (e.g., Entrez 2099, Uniprot P03372, RefSeq NM_000125, OMIM 133430, NP_000116, NP_000116.2, NM_000125.3, GI:62821794, and/or GI: 170295798). The term "estrogen receptor" may refer to the nucleotide sequence or protein sequence of human estrogen receptor 2 (a.k.a. ER-beta, ERbeta, or ERβ) (e.g., Entrez 2100, Uniprot Q92731, RefSeq NM_001040275, OMIM 601663, and/or GI: 94538324). The term "estrogen receptor" includes both the wild-type form of the nucleotide sequences or proteins as well as any mutants thereof. In some embodiments, "estrogen receptor" is wild-type estrogen receptor. In some embodiments, "estrogen receptor" is one or more mutant forms. The term "estrogen receptor" XYZ refers to a nucleotide sequence or protein of a mutant estrogen receptor wherein the Y numbered amino acid of estrogen receptor that normally has an X amino acid in the wildtype, instead has a Z amino acid in the mutant. In embodiments, an estrogen receptor is the wildtype human estrogen receptor. In embodiments, an estrogen receptor is the wildtype human ERα. In embodiments, an estrogen receptor is the wildtype human ERβ. In embodiments, an estrogen receptor is the wildtype human ERα or ERβ. In embodiments, an estrogen receptor is the wildtype human ERα and ERβ. In embodiments, the estrogen receptor is a mutant estrogen receptor. In embodiments, the mutant estrogen receptor is associated with a disease that is not associated with wildtype estrogen receptor (e.g., drug resistant cancer). In embodiments, the estrogen receptor includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to the sequence above.

B. COMPOUNDS

In an aspect is provided a compound, or a pharmaceutically acceptable salt thereof, having the formula:

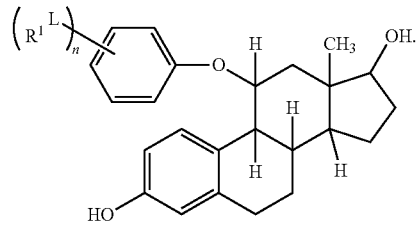

$R^1$ is independently a hydrogen, halogen, —NR²R³, —CX$^a$₃, —CN, —SO₂Cl, —SO$_{n1}$R¹⁰, —SO$_{v1}$NR²R³, —NHNR²R³, —ONR²R³, —NHC═(O)NHNR²R³, —NHC═(O)NR²R³, —N(O)$_{m1}$, —C(O)R⁹, —C(O)—OR⁹, —C(O)NR²R³, —OR¹⁰, —NR²SO₂R¹⁰, —NR²C═(O)R⁹, —NR²C(O)—OR⁹, —NR²OR⁹, —OCX$^a$₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R² is independently a hydrogen, halogen, —CX$^b_3$, —CN, —SO₂Cl, —SO$_{n2}$R¹⁴, —SO$_{v2}$NR″R¹², —NHNH₂, —ONR¹¹R¹², —NHC═(O)NHNH₂, —NHC═(O)NR¹¹R¹², —N(O)$_{m2}$, —NR¹¹R¹², —C(O)R¹³, —C(O)—OR¹³, —C(O)NR¹¹R¹², —OR¹⁴, —NR¹¹SO₂R¹⁴, —NR¹¹C═(O)R¹³, —NR¹¹C(O)—OR¹³, —NR¹¹OR¹³, —OCX$^b_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R³ is independently a hydrogen, halogen, —CX$^c_3$, —CN, —SO₂Cl, —SO$_{n3}$R¹⁸, —SO₃NR¹⁵R¹⁶, —NHNH₂, —ONR¹⁵R¹⁶, —NHC═(O)NHNH₂, —NHC═(O)NR¹⁵R¹⁶, —N(O)$_{m3}$, —NR¹⁵R¹⁶, —C(O)R¹⁷, —C(O)—OR¹⁷, —C(O)NR¹⁵R¹⁶, —OR¹⁸, —NR¹⁵SO₂R¹⁸, —NR¹⁵C═(O)R¹⁷, —NR¹⁵C(O)—OR¹⁷, —NR¹⁵OR¹⁷, —OCX$^c_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R² and R³ substituents may optionally be joined to form a substituted or unsubstituted heterocycloalkyl, or substituted or unsubstituted heteroaryl.

L is independently a bond, —NR⁴—, —NR⁴C(O)—, —C(O)NR⁴—, —O—, —S—, —C(O)—, —S(O)—, —S(O)₂—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker.

R⁴ is independently a hydrogen, halogen, —CX$^d_3$, —CN, —SO₂Cl, —SO$_{n4}$R²², —SO$_{v4}$NR¹⁹R²⁰, —NHNH₂, —ONR¹⁹R²⁰, —NHC═(O)NHNH₂, —NHC═(O)NR¹⁹R²⁰, —N(O)$_{m4}$, —NR¹⁹R²⁰, —C(O)R²¹, —C(O)—OR²¹, —C(O)NR¹⁹R¹², —OR²², —NR¹⁹SO₂R²², —NR¹⁹C═(O)R²¹, —NR¹⁹C(O)—OR²¹, —NR¹⁹OR²¹, —OCX$^d_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R⁹, R¹⁰, R¹¹, R¹², R¹³, R¹⁴, R¹⁵, R¹⁶, R¹⁷, R¹⁸, R¹⁹, R²⁰, R²¹, and R²² are independently hydrogen, halogen, —CX₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC═(O)NHNH₂, —NHC═(O) NH₂, —NHSO₂H, —NHC═(O)H, —NHC(O)—OH, —NHOH, —OCX₃, —OCHX₂, —CF₃, —OCF₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R¹¹ and R¹² substituents bonded to the same nitrogen atom may optionally be joined to form a substituted or unsubstituted heterocycloalkyl or substituted or unsubstituted heteroaryl; R¹⁵ and R¹⁶ substituents bonded to the same nitrogen atom may optionally be joined to form a substituted or unsubstituted heterocycloalkyl or substituted or unsubstituted heteroaryl; R¹⁹ and R²⁰ substituents bonded to the same nitrogen atom may optionally be joined to form a substituted or unsubstituted heterocycloalkyl or substituted or unsubstituted heteroaryl.

The symbol n is an integer from 0 to 5. The symbols m1, m2, m3, m4, v1, v2, v3, and v4 are independently 1 or 2. The symbols n1, n2, n3, and n4 are independently an integer from 0 to 4. The symbols X, X$^a$, X$^b$, X$^c$ and X$^d$ are independently —Cl, —Br, —I, or —F.

In an aspect is provided a compound, or a pharmaceutically acceptable salt thereof, having the formula:

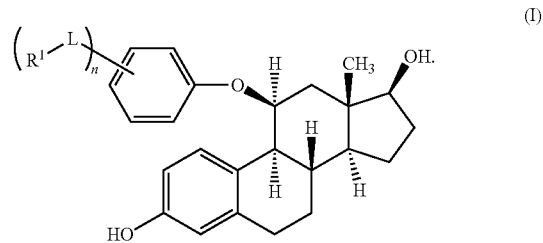

(I)

R¹ is independently a hydrogen, halogen, —NR²R³, —CX$^a_3$, —CN, —SO₂Cl, —SO$_{n1}$R¹⁰, —SO$_{v1}$NR²R³, —NHNR²R³, —ONR²R³, —NHC═(O)NHNR²R³, —NHC═(O)NR²R³, —N(O)$_{m1}$, —C(O)R⁹, —C(O)—OR⁹, —C(O)NR²R³, —OR¹⁰, —NR²SO₂R¹⁰, —NR²C═(O)R⁹, —NR²C(O)—OR⁹, —NR²OR⁹, —OCX$^a_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R² is independently a hydrogen, halogen, —CX$^b_3$, —CN, —SO₂Cl, —SO$_{n2}$R¹⁴, —SO$_{v2}$NR¹¹R¹², —NHNH₂, —ONR¹¹R¹², —NHC═(O)NHNH₂, —NHC═(O)NR¹¹R¹², —N(O)$_{m2}$, —NR¹¹R¹², —C(O)R¹³, —C(O)—OR¹³, —C(O)NR¹¹,R¹², —OR¹⁴, —NR¹¹SO₂R⁴, —NR¹¹C═(O)R¹³, —NR¹¹C(O)—OR¹³, —NR¹¹OR¹³, —OCX$^b_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R³ is independently a hydrogen, halogen, —CX$^c_3$, —CN, —SO₂Cl, —SO$_{n3}$R¹⁸, —SO₃NR¹⁵R¹⁶, —NHNH₂, —ONR¹⁵R¹⁶, —NHC═(O)NHNH₂, —NHC═(O)NR¹⁵R¹⁶, —N(O)$_{m3}$, —NR¹⁵R¹⁶, —C(O)R¹⁷, —C(O)—OR¹⁷, —C(O)NR¹⁵R¹⁶, —OR¹⁸, —NR¹⁵SO₂R¹⁸, —NR¹⁵C═(O)R¹⁷, —NR¹⁵C(O)—OR¹⁷, —NR¹⁵OR¹⁷, —OCX$^c_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R² and R³ substituents may optionally be joined to form a substituted or unsubstituted heterocycloalkyl, or substituted or unsubstituted heteroaryl.

L is independently a bond, —NR⁴—, —NR⁴C(O)—, —C(O)NR⁴—, —O—, —S—, —C(O)—, —S(O)—, —S(O)₂—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker.

R⁴ is independently a hydrogen, halogen, —CX$^d_3$, —CN, —SO₂Cl, —SO$_{n4}$R²², —SO$_{v4}$NR¹⁹R²⁰, —NHNH₂, —ONR¹⁹R²⁰, —NHC═(O)NHNH₂, —NHC═(O)NR¹⁹R²⁰, —N(O)$_{m4}$, —NR¹⁹R²⁰, —C(O)R²¹, —C(O)—OR²¹, —C(O)NR¹⁹R¹², —OR²², —NR¹⁹SO₂R²², —NR¹⁹C═(O)R²¹, —NR¹⁹C(O)—OR²¹, —NR¹⁹OR²¹, —OCX$^d$₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R⁹, R¹⁰, R¹¹, R¹², R¹³, R¹⁴, R¹⁵, R¹⁶, R¹⁷, R¹⁸, R¹⁹, R²⁰, R²¹, and R²² are independently hydrogen, halogen, —CX₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC═(O)NHNH₂, —NHC═(O) NH₂, —NHSO₂H, —NHC═(O)H, —NHC(O)—OH, —NHOH, —OCX₃, —OCHX₂, —CF₃, —OCF₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R¹¹ and R¹² substituents bonded to the same nitrogen atom may optionally be joined to form a substituted or unsubstituted heterocycloalkyl or substituted or unsubstituted heteroaryl; R¹⁵ and R¹⁶ substituents bonded to the same nitrogen atom may optionally be joined to form a substituted or unsubstituted heterocycloalkyl or substituted or unsubstituted heteroaryl; R¹⁹ and R²⁰ substituents bonded to the same nitrogen atom may optionally be joined to form a substituted or unsubstituted heterocycloalkyl or substituted or unsubstituted heteroaryl.

The symbol n is an integer from 0 to 5. The symbols m1, m2, m3, m4, v1, v2, v3, and v4 are independently 1 or 2. The symbols n1, n2, n3, and n4 are independently an integer from 0 to 4. The symbols X, X$^a$, X$^b$, X$^c$ and X$^d$ are independently —Cl, —Br, —I, or —F.

For compounds described herein, the —CH₃ as indicated by an asterisk in the structure below, may be replaced with an unsubstituted C₁-C₁₀ alkyl:

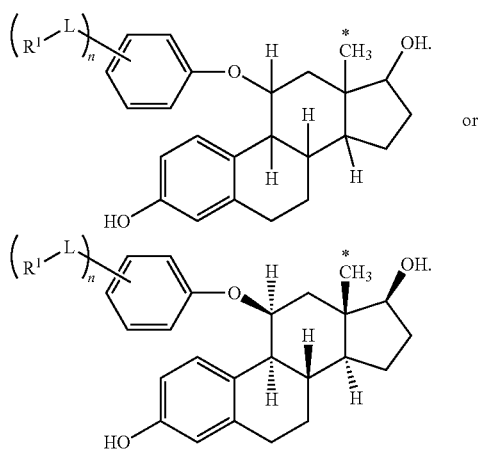

embodiments, the —CH₃ as indicated by the asterisk may be replaced with an unsubstituted C₁-C₅ alkyl.

In embodiments, the compound has the formula:

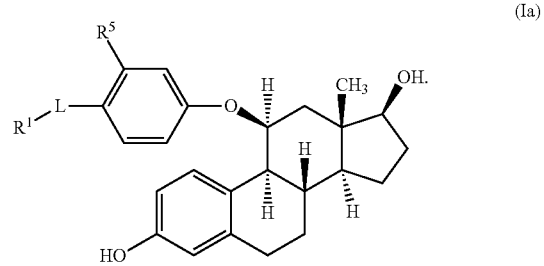

(Ia)

The variables L and R¹ are as described herein.

R⁵ is independently a hydrogen, halogen, —CX$^e$₃, —CN, —SO₂Cl, —SO$_n$₅R²⁶, —SO$_{v5}$NR²³R²⁴, —NHNH₂, —ONR²³R²⁴, —NHC═(O) NHNH₂, —NHC═(O)NR²³R²⁴, —N(O)$_{m5}$, —NR²³R²⁴, —C(O)R²⁵, —C(O)—OR²⁵, —C(O)NR²³R²⁴, —OR²⁶, —NR²³SO₂R²⁶, —NR²³C═(O)R²⁵, —NR²³C(O)—OR²⁵, —NR²³OR²⁵, —OCX$^e$₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R²³, R²⁴, R²⁵, and R²⁶ are independently hydrogen, halogen, —CX₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC═(O)NHNH₂, —NHC═(O) NH₂, —NHSO₂H, —NHC═(O)H, —NHC (O)—OH, —NHOH, —OCX₃, —OCHX₂, —CF₃, —OCF₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R²³ and R²⁴ substituents bonded to the same nitrogen atom may optionally be joined to form a substituted or unsubstituted heterocycloalkyl or substituted or unsubstituted heteroaryl;

The symbols m5 and v5 are independently 1 or 2. The symbol n5 is independently an integer from 0 to 4. The symbol X$^e$ is independently —Cl, —Br, —I, or —F.

In embodiments, the compound has the formula:

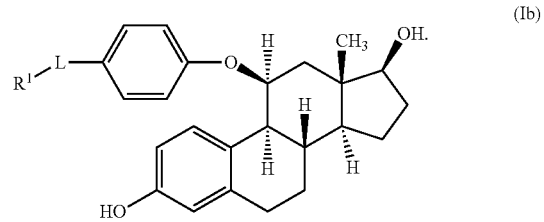

(Ib)

The variables L and R¹ are as described herein.

In embodiments, the compound has the formula:

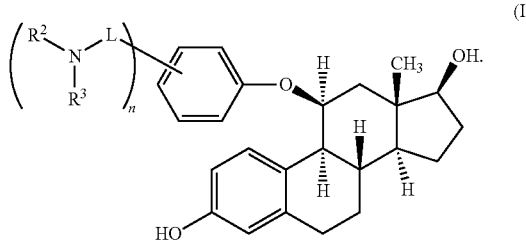

(II)

The variables L, n, $R^2$, and $R^3$ are as described herein.
In embodiments, the compound has the formula:

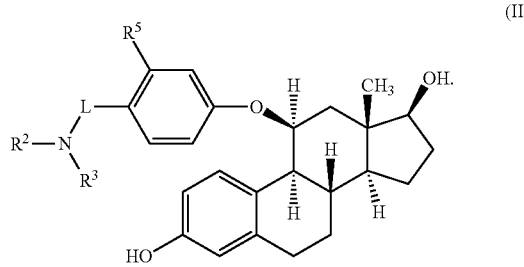

(IIa)

The variables L, $R^2$, $R^3$, and $R^5$ are as described herein.
In embodiments, the compound has the formula:

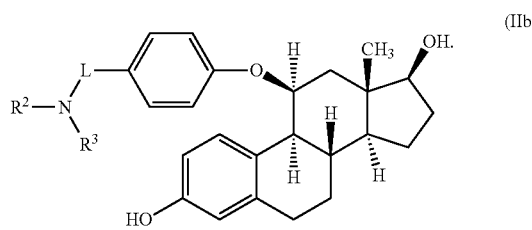

(IIb)

The variables L, $R^2$, and $R^3$ are as described herein.
In embodiments, $R^1$ is independently halogen, $-NR^2R^3$, $-CX^a{}_3$, $-CN$, $-SO_2Cl$, $-SO_{n1}R^{10}$, $-SO_{v1}NR^2R^3$, $-NHNR^2R^3$, $-ONR^2R^3$, $-NHC=(O)NHNR^2R^3$, $-NHC=(O)NR^2R^3$, $-N(O)_{m1}$, $-C(O)R^9$, $-C(O)-OR^9$, $-C(O)NR^2R^3$, $-OR^{10}$, $-NR^2SO_2R^{10}$, $-NR^2C=(O)R^9$, $-NR^2C(O)-OR^9$, $-NR^2OR^9$, $-OCX^a{}_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^1$ is independently hydrogen. In embodiments, $R^1$ is independently $-NR^2R^3$. In embodiments, $R^1$ is independently $-NH_2$. In embodiments, $R^1$ is independently $-CF_3$. In embodiments, $R^1$ is independently $-CCl_3$. In embodiments, $R^1$ is independently $-N(O)_2$. In embodiments, $R^1$ is independently halogen. In embodiments, $R^1$ is independently $-F$. In embodiments, $R^1$ is independently $-Cl$. In embodiments, $R^1$ is independently $-Br$. In embodiments, $R^1$ is independently $-I$. In embodiments, $R^1$ is independently substituted or unsubstituted cycloalkyl, substituted or unsubstituted heterocycloalkyl, substituted or unsubstituted aryl, or substituted or unsubstituted heteroaryl. In embodiments, $R^1$ is independently unsubstituted cycloalkyl, unsubstituted heterocycloalkyl, unsubstituted aryl, or unsubstituted heteroaryl.
In embodiments, $R^1$ is independently substituted or unsubstituted $C_3$-$C_8$ cycloalkyl. In embodiments, $R^1$ is independently unsubstituted $C_3$-$C_8$ cycloalkyl. In embodiments, $R^1$ is independently substituted or unsubstituted $C_3$-$C_7$ cycloalkyl. In embodiments, $R^1$ is independently unsubstituted $C_3$-$C_7$ cycloalkyl. In embodiments, $R^1$ is independently substituted or unsubstituted 3 to 8 membered heterocycloalkyl. In embodiments, $R^1$ is independently unsubstituted 3 to 8 membered heterocycloalkyl. In embodiments, $R^1$ is independently substituted or unsubstituted 3 to 7 membered heterocycloalkyl. In embodiments, $R^1$ is independently unsubstituted 3 to 7 membered heterocycloalkyl. In embodiments, $R^1$ is independently substituted or unsubstituted $C_6$-$C_{12}$ aryl. In embodiments, $R^1$ is independently unsubstituted $C_6$-$C_{12}$ aryl. In embodiments, $R^1$ is independently substituted or unsubstituted $C_6$-$C_{10}$ aryl. In embodiments, $R^1$ is independently unsubstituted $C_6$-$C_{10}$ aryl. In embodiments, $R^1$ is independently substituted or unsubstituted 5 to 10 membered heteroaryl. In embodiments, $R^1$ is independently unsubstituted 5 to 10 membered heteroaryl. In embodiments, $R^1$ is independently substituted or unsubstituted 5 to 9 membered heteroaryl. In embodiments, $R^1$ is independently unsubstituted 5 to 9 membered heteroaryl. In embodiments, $R^1$ is independently piperadine. In embodiments, $R^1$ is independently piperazine. In embodiments, $R^1$ is independently pyridine. In embodiments, $R^1$ is independently pyrazine. In embodiments, $R^1$ is independently dimethylamino. In embodiments, $R^1$ is independently dimethylaminoethyl. In embodiments, $R^1$ is independently dimethylaminopropyl. In embodiments, $R^1$ is independently ethylmorpholinyl. In embodiments, $R^1$ is independently morpholinyl.
In embodiments, $R^2$ is independently halogen, $-CX^b{}_3$, $-CN$, $-SO_2Cl$, $-SO_{n2}R^{14}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$, $-C(O)R^{13}$, $-C(O)-OR^{13}$, $-C(O)NR^{11}R^{12}$, $-OR^{14}$, $-NR^{11}SO_2R^{14}$, $-NR^{11}C=(O)R^{13}$, $-NR^{11}C(O)-OR^{13}$, $-NR^{11}OR^{13}$, $-OCX^b{}_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^2$ is independently hydrogen. In embodiments, $R^2$ is independently halogen. In embodiments, $R^2$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.
In embodiments, $R^2$ is independently substituted or unsubstituted $C_1$-$C_{12}$ alkyl. In embodiments, $R^2$ is independently unsubstituted $C_1$-$C_{12}$ alkyl. In embodiments, $R^2$ is independently substituted or unsubstituted $C_1$-$C_8$ alkyl. In embodiments, $R^2$ is independently unsubstituted $C_1$-$C_8$ alkyl. In embodiments, $R^2$ is independently substituted or unsubstituted $C_1$-$C_4$ alkyl. In embodiments, $R^2$ is independently unsubstituted $C_1$-$C_4$ alkyl. In embodiments, $R^2$ is independently unsubstituted methyl. In embodiments, $R^2$ is independently unsubstituted ethyl. In embodiments, $R^2$ is independently unsubstituted propyl. In embodiments, $R^2$ is independently substituted or unsubstituted 2 to 12 membered heteroalkyl. In embodiments, $R^2$ is independently unsubstituted 2 to 12 membered heteroalkyl. In embodiments, $R^2$ is independently substituted or unsubstituted 2 to 8 membered heteroalkyl. In embodiments, $R^2$ is independently unsubstituted 2 to 8 membered heteroalkyl. In embodiments, $R^2$ is independently substituted or unsubstituted 2 to 4 membered heteroalkyl. In embodiments, $R^2$ is independently unsubstituted 2 to 4 membered heteroalkyl. In embodiments, $R^2$ is independently substituted or unsubstituted alkyl or substituted or unsubstituted heteroalkyl. In embodiments, $R^2$ is independently substituted or unsubstituted $(C_1\text{-}C_{10})$ alkyl or substituted or unsubstituted 2 to 10 membered heteroalkyl.

In embodiments, $R^3$ is independently a halogen, $-CX^c{}_3$, $-CN$, $-SO_2Cl$, $-SO_{n3}R^{18}$, $-SO_{v3}NR^{15}R^{16}$, $-NHNH_2$, $-ONR^{15}R^{16}$, $-NHC=(O)NHNH_2$, $-NHC=(O)NR^{15}R^{16}$, $-N(O)_{m3}$, $-NR^{15}R^{16}$, $-C(O)R^{17}$, $-C(O)-OR^{17}$, $-C(O)NR^{15}R^{16}$, $-OR^{18}$, $-NR^{15}SO_2R^{18}$, $-NR^{15}C=(O)R^{17}$, $-NR^{15}C(O)-OR^{17}$, $-NR^{15}OR^{17}$, $-OCX^c{}_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^3$ is independently hydrogen. In embodiments, $R^3$ is independently halogen. In embodiments, $R^3$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^3$ is independently substituted or unsubstituted $C_1\text{-}C_{12}$ alkyl. In embodiments, $R^3$ is independently unsubstituted $C_1\text{-}C_{12}$ alkyl. In embodiments, $R^3$ is independently substituted or unsubstituted $C_1\text{-}C_8$ alkyl. In embodiments, $R^3$ is independently unsubstituted $C_1\text{-}C_8$ alkyl. In embodiments, $R^3$ is independently substituted or unsubstituted $C_1\text{-}C_4$ alkyl. In embodiments, $R^3$ is independently unsubstituted $C_1\text{-}C_4$ alkyl. In embodiments, $R^3$ is independently unsubstituted methyl. In embodiments, $R^3$ is independently unsubstituted ethyl. In embodiments, $R^3$ is independently unsubstituted propyl. In embodiments, $R^3$ is independently substituted or unsubstituted 2 to 12 membered heteroalkyl. In embodiments, $R^3$ is independently unsubstituted 2 to 12 membered heteroalkyl. In embodiments, $R^3$ is independently substituted or unsubstituted 2 to 8 membered heteroalkyl. In embodiments, $R^3$ is independently unsubstituted 2 to 8 membered heteroalkyl. In embodiments, $R^3$ is independently substituted or unsubstituted 2 to 4 membered heteroalkyl. In embodiments, $R^3$ is independently unsubstituted 2 to 4 membered heteroalkyl. In embodiments, $R^3$ is independently substituted or unsubstituted alkyl or substituted or unsubstituted heteroalkyl. In embodiments, $R^3$ is independently substituted or unsubstituted $(C_1\text{-}C_{10})$ alkyl or substituted or unsubstituted 2 to 10 membered heteroalkyl.

In embodiments, $R^2$ and $R^3$ substituents may optionally be joined to form a substituted or unsubstituted heterocycloalkyl, or substituted or unsubstituted heteroaryl. In embodiments, $R^2$ and $R^3$ substituents are joined to form a substituted or unsubstituted heterocycloalkyl. In embodiments, $R^2$ and $R^3$ substituents are joined to form an unsubstituted heterocycloalkyl. In embodiments, $R^2$ and $R^3$ substituents are joined to form a substituted or unsubstituted 3 to 8 membered heterocycloalkyl. In embodiments, $R^2$ and $R^3$ substituents are joined to form an unsubstituted 3 to 8 membered heterocycloalkyl. In embodiments, $R^2$ and $R^3$ substituents are joined to form a substituted or unsubstituted 3 to 7 membered heterocycloalkyl. In embodiments, $R^2$ and $R^3$ substituents are joined to form an unsubstituted 3 to 7 membered heterocycloalkyl. In embodiments, $R^2$ and $R^3$ substituents are joined to form a substituted or unsubstituted 3 to 6 membered heterocycloalkyl. In embodiments, $R^2$ and $R^3$ substituents are joined to form an unsubstituted 3 to 6 membered heterocycloalkyl.

In embodiments, $R^2$ and $R^3$ substituents are joined to form a substituted or unsubstituted heteroaryl. In embodiments, $R^2$ and $R^3$ substituents are joined to form an unsubstituted heteroaryl. In embodiments, $R^2$ and $R^3$ substituents are joined to form a substituted or unsubstituted 5 to 10 membered heteroaryl. In embodiments, $R^2$ and $R^3$ substituents are joined to form an unsubstituted 5 to 10 membered heteroaryl. In embodiments, $R^2$ and $R^3$ substituents are joined to form a substituted or unsubstituted 5 to 9 membered heteroaryl. In embodiments, $R^2$ and $R^3$ substituents are joined to form an unsubstituted 5 to 9 membered heteroaryl. In embodiments, $R^2$ and $R^3$ substituents are joined to form a substituted or unsubstituted 5 to 6 membered heteroaryl. In embodiments, $R^2$ and $R^3$ substituents are joined to form an unsubstituted 5 to 6 membered heteroaryl. In embodiments, $R^2$ and R substituents are joined to form

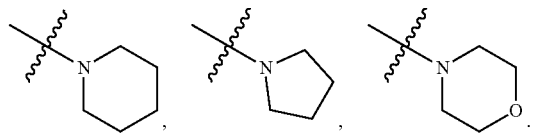 [SMILES: *N1CCCCC1 ; *N1CCCC1 ; *N1CCOCC1]

In embodiments, L is independently a bond, $-NR^4-$, $-NR^4C(O)-$, $-C(O)NR^4-$, $-O-$, $-S-$, $-C(O)-$, $-S(O)-$, $-S(O)_2-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, L is independently a bond. In embodiments, L is independently $-NR^4-$. In embodiments, L is independently $-NR^4C(O)-$. In embodiments, L is independently $-C(O)NR^4-$. In embodiments, L is independently $-O-$. In embodiments, L is independently $-S-$. In embodiments, L is independently $-C(O)-$. In embodiments, L is independently $-S(O)-$. In embodiments, L is independently $-S(O)_2-$. In embodiments, L is independently substituted or unsubstituted alkylene. In embodiments, L is independently unsubstituted alkylene.

In embodiments, L is independently substituted or unsubstituted $C_1\text{-}C_{12}$ alkylene. In embodiments, L is independently unsubstituted $C_1\text{-}C_{12}$ alkylene. In embodiments, L is independently substituted or unsubstituted $C_1\text{-}C_8$ alkylene. In embodiments, L is independently unsubstituted $C_1\text{-}C_8$ alkylene. In embodiments, L is independently substituted or unsubstituted $C_1\text{-}C_6$ alkylene. In embodiments, L is independently unsubstituted $C_1\text{-}C_6$ alkylene. In embodiments, L is independently substituted or unsubstituted $C_1\text{-}C_4$ alkylene. In embodiments, L is independently unsubstituted $C_1\text{-}C_4$ alkylene. In embodiments, L is independently unsubstituted methylene. In embodiments, L is independently unsubstituted ethylene. In embodiments, L is independently unsubstituted propylene. In embodiments, L is independently unsubstituted butylene. In embodiments, L is independently substituted or unsubstituted heteroalkylene. In embodiments, L is independently unsubstituted heteroalkylene. In embodiments, L is independently substituted or unsubstituted 2 to 12 membered heteroalkylene. In embodiments, L is independently unsubstituted 2 to 12 membered heteroalkylene. In embodiments, L is independently substituted or unsubstituted 2 to 8 membered heteroalkylene. In embodiments, L is independently unsubstituted 2 to 8 membered heteroalkylene. In embodiments, L is independently substituted or unsubstituted 2 to 6 membered heteroalkylene. In embodiments, L is independently unsubstituted 2 to 6 membered heteroalkylene. In embodiments, L is independently substituted or unsubstituted 2 to 4 membered heteroalkylene. In embodiments, L is independently unsubstituted 2 to 4 membered heteroalkylene. In embodiments, L is independently substituted or unsubstituted cycloalkylene. In embodiments, L is independently unsubstituted cycloalkylene. In embodiments, L is independently substituted or unsubstituted $C_3$-$C_8$ cycloalkylene. In embodiments, L is independently $C_3$-$C_8$ cycloalkylene. In embodiments, L is independently substituted or unsubstituted heterocycloalkylene. In embodiments, L is independently unsubstituted heterocycloalkylene. In embodiments, L is independently substituted or unsubstituted 3 to 8 membered heterocycloalkylene. In embodiments, L is independently unsubstituted 3 to 8 membered heterocycloalkylene. In embodiments, L is independently substituted or unsubstituted arylene. In embodiments, L is independently unsubstituted arylene. In embodiments, L is independently substituted or unsubstituted $C_6$-$C_{10}$ arylene. In embodiments, L is independently unsubstituted $C_6$-$C_{10}$ arylene. In embodiments, L is independently substituted or unsubstituted heteroarylene. In embodiments, L is independently unsubstituted heteroarylene. In embodiments, L is independently substituted or unsubstituted 5 to 10 membered heteroarylene. In embodiments, L is independently unsubstituted 5 to 10 membered heteroarylene.

In embodiments, L is independently —NH-(substituted or unsubstituted alkylene). In embodiments, L is independently —NH-(unsubstituted alkylene). In embodiments, L is independently —NH-(substituted or unsubstituted ($C_1$-$C_8$) alkylene). In embodiments, L is independently —NH-(unsubstituted ($C_1$-$C_8$) alkylene). In embodiments, L is independently —NH-(substituted or unsubstituted ($C_1$-$C_4$) alkylene). In embodiments, L is independently —NH-(unsubstituted ($C_1$-$C_4$) alkylene). In embodiments, L is independently —NH-(unsubstituted methylene). In embodiments, L is independently —NH-(unsubstituted ethylene). In embodiments, L is independently —NH-(unsubstituted propylene). In embodiments, L is independently —NH-(unsubstituted butylene). In embodiments, L is independently —NH-(unsubstituted n-propylene). In embodiments, L is independently —NH-(unsubstituted n-butylene). In embodiments, L is independently —NHC(O)-(substituted or unsubstituted alkylene). In embodiments, L is independently —NHC(O)-(unsubstituted alkylene). In embodiments, L is independently —NHC(O)-(substituted or unsubstituted ($C_1$-$C_8$) alkylene). In embodiments, L is independently —NHC(O)-(unsubstituted ($C_1$-$C_8$) alkylene). In embodiments, L is independently —NHC(O)-(substituted or unsubstituted ($C_1$-$C_4$) alkylene). In embodiments, L is independently —NHC(O)-(unsubstituted ($C_1$-$C_4$) alkylene). In embodiments, L is independently —NHC(O)-(unsubstituted methylene). In embodiments, L is independently —NHC(O)-(unsubstituted ethylene). In embodiments, L is independently —NHC(O)-(unsubstituted propylene). In embodiments, L is independently —NHC(O)-(unsubstituted butylene). In embodiments, L is independently —NHC(O)-(unsubstituted n-propylene). In embodiments, L is independently —NHC(O)-(unsubstituted n-butylene).

In embodiments, $R^4$ is independently a hydrogen, halogen, —$CX^d_3$, —CN, —$SO_2Cl$, —$SO_{n4}R^{22}$, —$SO_{v4}NR^{19}R^{20}$, —$NHNH_2$, —$ONR^{19}R^{20}$, —NHC=(O) $NHNH_2$, —NHC=(O)$NR^{19}R^{20}$, —$N(O)_{m4}$, —$NR^{19}R^{20}$, —$C(O)R^{21}$, —$C(O)$—$OR^{21}$, —$C(O)NR^{19}R^{12}$, —$OR^{22}$, —$NR^{19}SO_2R^{22}$, —$NR^{19}C$=(O)$R^{21}$, —$NR^9C(O)$—$OR^{21}$, —$NR^{19}OR^{21}$, —$OCX^d_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^4$ is independently hydrogen. In embodiments, $R^4$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^4$ is independently substituted or unsubstituted $C_1$-$C_{12}$ alkyl. In embodiments, $R^4$ is independently unsubstituted $C_1$-$C_{12}$ alkyl. In embodiments, $R^4$ is independently substituted or unsubstituted $C_1$-$C_8$ alkyl. In embodiments, $R^4$ is independently unsubstituted $C_1$-$C_8$ alkyl. In embodiments, $R^4$ is independently substituted or unsubstituted $C_1$-$C_4$ alkyl. In embodiments, $R^4$ is independently unsubstituted $C_1$-$C_4$ alkyl. In embodiments, $R^4$ is independently unsubstituted methyl. In embodiments, $R^4$ is independently unsubstituted ethyl. In embodiments, $R^4$ is independently unsubstituted propyl. In embodiments, $R^4$ is independently substituted or unsubstituted 2 to 12 membered heteroalkyl. In embodiments, $R^4$ is independently unsubstituted 2 to 12 membered heteroalkyl. In embodiments, $R^4$ is independently substituted or unsubstituted 2 to 8 membered heteroalkyl. In embodiments, $R^4$ is independently unsubstituted 2 to 8 membered heteroalkyl. In embodiments, $R^4$ is independently substituted or unsubstituted 2 to 4 membered heteroalkyl. In embodiments, $R^4$ is independently unsubstituted 2 to 4 membered heteroalkyl. In embodiments, $R^4$ is independently substituted or unsubstituted alkyl or substituted or unsubstituted heteroalkyl. In embodiments, $R^4$ is independently substituted or unsubstituted ($C_1$-$C_{10}$) alkyl or substituted or unsubstituted 2 to 10 membered heteroalkyl. In embodiments, $R^4$ is independently unsubstituted methyl. In embodiments, $R^4$ is independently unsubstituted cycloalkyl, unsubstituted heterocycloalkyl, unsubstituted aryl, or unsubstituted heteroaryl. In embodiments, $R^4$ is independently substituted or unsubstituted $C_3$-$C_8$ cycloalkyl. In embodiments, $R^4$ is independently unsubstituted $C_3$-$C_8$ cycloalkyl. In embodiments, $R^4$ is independently substituted or unsubstituted $C_3$-$C_7$ cycloalkyl. In embodiments, $R^4$ is independently unsubstituted $C_3$-$C_7$ cycloalkyl.

In embodiments, $R^4$ is independently substituted or unsubstituted 3 to 8 membered heterocycloalkyl. In embodiments, $R^4$ is independently unsubstituted 3 to 8 membered heterocycloalkyl. In embodiments, $R^4$ is independently substituted or unsubstituted 3 to 7 membered heterocycloalkyl. In embodiments, $R^4$ is independently unsubstituted 3 to 7 membered heterocycloalkyl. In embodiments, $R^4$ is independently substituted or unsubstituted $C_6$-$C_{12}$ aryl. In embodiments, $R^4$ is independently unsubstituted $C_6$-$C_{12}$ aryl. In embodiments, $R^4$ is independently substituted or unsubstituted $C_6$-$C_{10}$ aryl. In embodiments, $R^4$ is independently unsubstituted $C_6$-$C_{10}$ aryl. In embodiments, $R^4$ is independently substituted or unsubstituted 5 to 10 membered heteroaryl. In embodiments, $R^4$ is independently unsubstituted 5 to 10 membered heteroaryl. In embodiments, $R^4$ is independently substituted or unsubstituted 5 to 9 membered heteroaryl. In embodiments, $R^4$ is independently unsubstituted 5 to 9 membered heteroaryl.

In embodiments, $R^5$ is independently a halogen, $-CX^e{}_3$, $-CN$, $-SO_2Cl$, $-SO_{n5}R^{26}$, $-SO_{v5}NR^{23}R^{24}$, $-NHNH_2$, $-ONR^{23}R^{24}$, $-NHC=(O)$ $NHNH_2$, $-NHC=(O)NR^{23}R^{24}$, $-N(O)_{m5}$, $-NR^{23}R^{24}$, $-C(O)R^{25}$, $-C(O)-OR^{25}$, $-C(O)NR^{23}R^{24}$, $-OR^{26}$, $-NR^{23}SO_2R^{26}$, $-NR^{23}C=(O)R^{25}$, $-NR^{23}C(O)-OR^{25}$, $-NR^{23}OR^{25}$, $-OCX^e{}_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^5$ is independently hydrogen. In embodiments, $R^5$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^5$ is independently $-NH_2$. In embodiments, $R^5$ is independently $-CF_3$. In embodiments, $R^5$ is independently $-CCl_3$. In embodiments, $R^5$ is independently $-N(O)_2$. In embodiments, $R^5$ is independently halogen. In embodiments, $R^5$ is independently $-F$. In embodiments, $R^5$ is independently $-Cl$. In embodiments, $R^5$ is independently $-Br$. In embodiments, $R^5$ is independently $-I$. In embodiments, $R^5$ is independently substituted or unsubstituted cycloalkyl, substituted or unsubstituted heterocycloalkyl, substituted or unsubstituted aryl, or substituted or unsubstituted heteroaryl.

In embodiments, $R^5$ is independently substituted or unsubstituted $C_1$-$C_{12}$ alkyl. In embodiments, $R^5$ is independently unsubstituted $C_1$-$C_{12}$ alkyl. In embodiments, $R^5$ is independently substituted or unsubstituted $C_1$-$C_8$ alkyl. In embodiments, $R^5$ is independently unsubstituted $C_1$-$C_8$ alkyl. In embodiments, $R^5$ is independently substituted or unsubstituted $C_1$-$C_4$ alkyl. In embodiments, $R^5$ is independently unsubstituted $C_1$-$C_4$ alkyl. In embodiments, $R^5$ is independently unsubstituted methyl. In embodiments, $R^5$ is independently unsubstituted ethyl. In embodiments, $R^5$ is independently unsubstituted propyl. In embodiments, $R^5$ is independently substituted or unsubstituted 2 to 12 membered heteroalkyl. In embodiments, $R^5$ is independently unsubstituted 2 to 12 membered heteroalkyl. In embodiments, $R^5$ is independently substituted or unsubstituted 2 to 8 membered heteroalkyl. In embodiments, $R^5$ is independently unsubstituted 2 to 8 membered heteroalkyl. In embodiments, $R^5$ is independently substituted or unsubstituted 2 to 4 membered heteroalkyl. In embodiments, $R^5$ is independently unsubstituted 2 to 4 membered heteroalkyl. In embodiments, $R^5$ is independently substituted or unsubstituted alkyl or substituted or unsubstituted heteroalkyl. In embodiments, $R^5$ is independently substituted or unsubstituted ($C_1$-$C_{10}$) alkyl or substituted or unsubstituted 2 to 10 membered heteroalkyl.

In embodiments, $R^5$ is independently unsubstituted cycloalkyl, unsubstituted heterocycloalkyl, unsubstituted aryl, or unsubstituted heteroaryl. In embodiments, $R^5$ is independently substituted or unsubstituted $C_3$-$C_8$ cycloalkyl. In embodiments, $R^5$ is independently unsubstituted $C_3$-$C_8$ cycloalkyl. In embodiments, $R^5$ is independently substituted or unsubstituted $C_3$-$C_7$ cycloalkyl. In embodiments, $R^5$ is independently unsubstituted $C_3$-$C_7$ cycloalkyl. In embodiments, $R^5$ is independently substituted or unsubstituted 3 to 8 membered heterocycloalkyl. In embodiments, $R^5$ is independently unsubstituted 3 to 8 membered heterocycloalkyl. In embodiments, $R^5$ is independently substituted or unsubstituted 3 to 7 membered heterocycloalkyl. In embodiments, $R^5$ is independently unsubstituted 3 to 7 membered heterocycloalkyl.

In embodiments, $R^5$ is independently substituted or unsubstituted $C_6$-$C_{12}$ aryl. In embodiments, $R^5$ is independently unsubstituted $C_6$-$C_{12}$ aryl. In embodiments, $R^5$ is independently substituted or unsubstituted $C_6$-$C_{10}$ aryl. In embodiments, $R^5$ is independently unsubstituted $C_6$-$C_{10}$ aryl. In embodiments, $R^5$ is independently substituted or unsubstituted 5 to 10 membered heteroaryl. In embodiments, $R^5$ is independently unsubstituted 5 to 10 membered heteroaryl. In embodiments, $R^5$ is independently substituted or unsubstituted 5 to 9 membered heteroaryl. In embodiments, $R^5$ is independently unsubstituted 5 to 9 membered heteroaryl.

In embodiments, $R^5$ is independently $-CX^e{}_3$. In embodiments, $R^5$ is independently $-CN$. In embodiments, $R^5$ is independently $-SO_2Cl$. In embodiments, $R^5$ is independently $-SO_{n5}R^{26}$. In embodiments, $R^5$ is independently $-SO_{v5}NR^{23}R^{24}$. In embodiments, $R^5$ is independently $-NHNH_2$. In embodiments, $R^5$ is independently $-ONR^{23}R^{24}$. In embodiments, $R^5$ is independently $-NHC=(O)NHNH_2$. In embodiments, $R^5$ is independently $-NHC=(O)NR^{23}R^{24}$. In embodiments, $R^5$ is independently $-N(O)_{m5}$. In embodiments, $R^5$ is independently $-NR^{23}R^{24}$. In embodiments, $R^5$ is independently $-C(O)R^{25}$. In embodiments, $R^5$ is independently $-C(O)-OR^{25}$. In embodiments, $R^5$ is independently $-C(O)NR^{23}R^{24}$. In embodiments, $R^5$ is independently $-OR^{26}$. In embodiments, $R^5$ is independently $-NR^{23}SO_2R^{26}$. In embodiments, $R^5$ is independently $-NR^{23}C=(O)R^{25}$. In embodiments, $R^5$ is independently $-NR^{23}C(O)-OR^{25}$. In embodiments, $R^5$ is independently $-NR^{23}OR^{25}$. In embodiments, $R^5$ is independently $-OCX^e{}_3$. In embodiments, $R^5$ is independently a hydrogen, halogen, $-CX^e{}_3$, or unsubstituted alkyl. In embodiments, $R^5$ is independently a hydrogen, $-F$, $-CF_3$, or unsubstituted methyl.

In embodiments, each $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, and $R^{26}$ are independently hydrogen, halogen, $-CX_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX_3$, $-OCHX_2$, $-CF_3$, $-OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted $C_1$-$C_{12}$ alkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted $C_1$-$C_{12}$ alkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted $C_1$-$C_8$ alkyl. In embodiments, $R^9$, $R^{10}$, R, $R^2$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted $C_1$-$C_8$ alkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted $C_1$-$C_4$ alkyl. In embodiments, $R^9$, $R_{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted $C_1$-$C_4$ alkyl.

In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted 2 to 12 membered heteroalkyl. In embodiments, $R^9$, R, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted 2 to 12 membered heteroalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted 2 to 8 membered heteroalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted 2 to 8 membered heteroalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted 2 to 4 membered heteroalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted 2 to 4 membered heteroalkyl. In embodiments, $R^9$, $R^{10}$, R, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, r $R^{26}$ is independently substituted or unsubstituted alkyl or substituted or unsubstituted heteroalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted $(C_1$-$C_{10})$ alkyl or substituted or unsubstituted 2 to 10 membered heteroalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted methyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently H.

In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted cycloalkyl, unsubstituted heterocycloalkyl, unsubstituted aryl, or unsubstituted heteroaryl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted $C_3$-$C_8$ cycloalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted $C_3$-$C_8$ cycloalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted $C_3$-$C_7$ cycloalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted $C_3$-$C_7$ cycloalkyl.

In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted 3 to 8 membered heterocycloalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted 3 to 8 membered heterocycloalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted 3 to 7 membered heterocycloalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted 3 to 7 membered heterocycloalkyl.

In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted $C_6$-$C_{12}$ aryl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted $C_6$-$C_{12}$ aryl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted $C_6$-$C_{10}$ aryl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted $C_6$-$C_{10}$ aryl.

In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted 5 to 10 membered heteroaryl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted 5 to 10 membered heteroaryl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted 5 to 9 membered heteroaryl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted 5 to 9 membered heteroaryl.

In embodiments, $R^{11}$ and $R^{12}$ substituents may optionally be joined to form a substituted or unsubstituted heterocycloalkyl, or substituted or unsubstituted heteroaryl. In embodiments, $R^{11}$ and $R^{12}$ substituents are joined to form a substituted or unsubstituted heterocycloalkyl. In embodiments, $R^{11}$ and $R^{12}$ substituents are joined to form an unsubstituted heterocycloalkyl. In embodiments, $R^{11}$ and $R^{12}$ substituents are joined to form a substituted or unsubstituted 3 to 8 membered heterocycloalkyl. In embodiments, $R^{11}$ and $R^{12}$ substituents are joined to form an unsubstituted 3 to 8 membered heterocycloalkyl. In embodiments, $R^{11}$ and $R^{12}$ substituents are joined to form a substituted or unsubstituted 3 to 7 membered heterocycloalkyl. In embodiments, $R^{11}$ and $R^{12}$ substituents are joined to form an unsubstituted 3 to 7 membered heterocycloalkyl. In embodiments, $R^{11}$ and $R^{12}$ substituents are joined to form a substituted or unsubstituted 3 to 6 membered heterocycloalkyl. In embodiments, $R^{11}$ and $R^{12}$ substituents are joined to form an unsubstituted 3 to 6 membered heterocycloalkyl.

In embodiments, $R^{11}$ and $R^{12}$ substituents are joined to form a substituted or unsubstituted heteroaryl. In embodiments, $R^{11}$ and $R^{12}$ substituents are joined to form an unsubstituted heteroaryl. In embodiments, $R^{11}$ and $R^{12}$ substituents are joined to form a substituted or unsubstituted 5 to 10 membered heteroaryl. In embodiments, $R^{11}$ and $R^{12}$ substituents are joined to form an unsubstituted 5 to 10 membered heteroaryl. In embodiments, $R^{11}$ and $R^{12}$ substituents are joined to form a substituted or unsubstituted 5 to 9 membered heteroaryl. In embodiments, $R^{11}$ and $R^{12}$ substituents are joined to form an unsubstituted 5 to 9 membered heteroaryl. In embodiments, $R^{11}$ and $R^{12}$ substituents are joined to form a substituted or unsubstituted 5 to 6 membered heteroaryl.

In embodiments, $R^{15}$ and $R^{16}$ substituents may optionally be joined to form a substituted or unsubstituted heterocycloalkyl, or substituted or unsubstituted heteroaryl. In embodiments, $R^{15}$ and $R^{16}$ substituents are joined to form a substituted or unsubstituted heterocycloalkyl. In embodiments, $R^5$ and $R^{16}$ substituents are joined to form an unsubstituted heterocycloalkyl. In embodiments, $R^{15}$ and $R^{16}$ substituents are joined to form a substituted or unsubstituted 3 to 8 membered heterocycloalkyl. In embodiments, $R^{15}$ and $R^{16}$ substituents are joined to form an unsubstituted 3 to 8 membered heterocycloalkyl. In embodiments, $R^{15}$ and $R^{16}$ substituents are joined to form a substituted or unsubstituted 3 to 7 membered heterocycloalkyl. In embodiments, $R^{15}$ and $R^{16}$ substituents are joined to form an unsubstituted 3 to 7 membered heterocycloalkyl. In embodiments, $R^{15}$ and $R^{16}$ substituents are joined to form a substituted or unsubstituted 3 to 6 membered heterocycloalkyl. In embodiments, $R^{15}$ and $R^{16}$ substituents are joined to form an unsubstituted 3 to 6 membered heterocycloalkyl.

In embodiments, $R^{15}$ and $R^{16}$ substituents are joined to form a substituted or unsubstituted heteroaryl. In embodiments, $R^5$ and $R^{16}$ substituents are joined to form an unsubstituted heteroaryl. In embodiments, $R^{15}$ and $R^{16}$ substituents are joined to form a substituted or unsubstituted 5 to 10 membered heteroaryl. In embodiments, $R^{15}$ and $R^{16}$ substituents are joined to form an unsubstituted 5 to 10 membered heteroaryl. In embodiments, $R^{15}$ and $R^{16}$ substituents are joined to form a substituted or unsubstituted 5 to 9 membered heteroaryl. In embodiments, $R^{15}$ and $R^{16}$ substituents are joined to form an unsubstituted 5 to 9 membered heteroaryl. In embodiments, $R^{15}$ and $R^{16}$ substituents are joined to form a substituted or unsubstituted 5 to 6 membered heteroaryl.

In embodiments, $R^{19}$ and $R^{20}$ substituents may optionally be joined to form a substituted or unsubstituted heterocycloalkyl, or substituted or unsubstituted heteroaryl. In embodiments, $R^{19}$ and $R^{20}$ substituents are joined to form a substituted or unsubstituted heterocycloalkyl. In embodiments, $R^{19}$ and $R^{20}$ substituents are joined to form an unsubstituted heterocycloalkyl. In embodiments, $R^{19}$ and $R^{20}$ substituents are joined to form a substituted or unsubstituted 3 to 8 membered heterocycloalkyl. In embodiments, $R^{19}$ and $R^{20}$ substituents are joined to form an unsubstituted 3 to 8 membered heterocycloalkyl. In embodiments, $R^{19}$ and $R^{20}$ substituents are joined to form a substituted or unsubstituted 3 to 7 membered heterocycloalkyl. In embodiments, $R^{19}$ and $R^{20}$ substituents are joined to form an unsubstituted 3 to 7 membered heterocycloalkyl. In embodiments, $R^{19}$ and $R^{20}$ substituents are joined to form a substituted or unsubstituted 3 to 6 membered heterocycloalkyl. In embodiments, $R^{19}$ and $R^{20}$ substituents are joined to form an unsubstituted 3 to 6 membered heterocycloalkyl.

In embodiments, $R^{19}$ and $R^{20}$ substituents are joined to form a substituted or unsubstituted heteroaryl. In embodiments, $R^{19}$ and $R^{20}$ substituents are joined to form an unsubstituted heteroaryl. In embodiments, $R^{19}$ and $R^{20}$ substituents are joined to form a substituted or unsubstituted 5 to 10 membered heteroaryl. In embodiments, $R^{19}$ and $R^{20}$ substituents are joined to form an unsubstituted 5 to 10 membered heteroaryl. In embodiments, $R^{19}$ and $R^{20}$ substituents are joined to form a substituted or unsubstituted 5 to 9 membered heteroaryl. In embodiments, $R^{19}$ and $R^{20}$ substituents are joined to form an unsubstituted 5 to 9 membered heteroaryl. In embodiments, $R^{19}$ and $R^{20}$ substituents are joined to form a substituted or unsubstituted 5 to 6 membered heteroaryl.

In embodiments, $R^{23}$ and $R^{24}$ substituents may optionally be joined to form a substituted or unsubstituted heterocycloalkyl, or substituted or unsubstituted heteroaryl. In embodiments, $R^{23}$ and $R^{24}$ substituents are joined to form a substituted or unsubstituted heterocycloalkyl. In embodiments, $R^{23}$ and $R^{24}$ substituents are joined to form an unsubstituted heterocycloalkyl. In embodiments, $R^{23}$ and $R^{24}$ substituents are joined to form a substituted or unsubstituted 3 to 8 membered heterocycloalkyl. In embodiments, $R^{23}$ and $R^{24}$ substituents are joined to form an unsubstituted 3 to 8 membered heterocycloalkyl. In embodiments, $R^{23}$ and $R^{24}$ substituents are joined to form a substituted or unsubstituted 3 to 7 membered heterocycloalkyl. In embodiments, $R^{23}$ and $R^{24}$ substituents are joined to form an unsubstituted 3 to 7 membered heterocycloalkyl. In embodiments, $R^{23}$ and $R^{24}$ substituents are joined to form a substituted or unsubstituted 3 to 6 membered heterocycloalkyl. In embodiments, $R^{23}$ and $R^{24}$ substituents are joined to form an unsubstituted 3 to 6 membered heterocycloalkyl.

In embodiments, $R^{23}$ and $R^{24}$ substituents are joined to form a substituted or unsubstituted heteroaryl. In embodiments, $R^{23}$ and $R^{24}$ substituents are joined to form an unsubstituted heteroaryl. In embodiments, $R^{23}$ and $R^{24}$ substituents are joined to form a substituted or unsubstituted 5 to 10 membered heteroaryl. In embodiments, $R^{23}$ and $R^{24}$ substituents are joined to form an unsubstituted 5 to 10 membered heteroaryl. In embodiments, $R^{23}$ and $R^{24}$ substituents are joined to form a substituted or unsubstituted 5 to 9 membered heteroaryl. In embodiments, $R^{23}$ and $R^{24}$ substituents are joined to form an unsubstituted 5 to 9 membered heteroaryl. In embodiments, $R^{23}$ and $R^{24}$ substituents are joined to form a substituted or unsubstituted 5 to 6 membered heteroaryl.

In embodiments, n is 0. In embodiments, n is 1. In embodiments, n is 2. In embodiments, n is 3. In embodiments, n is 4. In embodiments, n is 5. In embodiments, m1 is 1. In embodiments, m1 is 2. In embodiments, m2 is 1. In embodiments, m2 is 2. In embodiments, m3 is 1. In embodiments, m3 is 2. In embodiments, m4 is 1. In embodiments, m4 is 2. In embodiments, m5 is 1. In embodiments, m5 is 2. In embodiments, v1 is 1. In embodiments, v1 is 2. In embodiments, v2 is 1. In embodiments, v2 is 2. In embodiments, v3 is 1. In embodiments, v3 is 2. In embodiments, v4 is 1. In embodiments, v4 is 2. In embodiments, v5 is 1. In embodiments, v5 is 2. In embodiments, n1 is 0. In embodiments, n1 is 1. In embodiments, n1 is 2. In embodiments, n1 is 3. In embodiments, n1 is 4. In embodiments, n2 is 0. In embodiments, n2 is 1. In embodiments, n2 is 2. In embodiments, n2 is 3. In embodiments, n2 is 4. In embodiments, n3 is 0. In embodiments, n3 is 1. In embodiments, n3 is 2. In embodiments, n3 is 3. In embodiments, n3 is 4. In embodiments, n4 is 0. In embodiments, n4 is 1. In embodiments, n4 is 2. In embodiments, n4 is 3. In embodiments, n4 is 4. In embodiments, n5 is 0. In embodiments, n5 is 1. In embodiments, n5 is 2. In embodiments, n5 is 3. In embodiments, n5 is 4.

In embodiments, X is independently —Cl. In embodiments, X is independently —Br. In embodiments, X is independently —I. In embodiments, X is independently —F. In embodiments, $X^a$ is independently —Cl. In embodiments, $X^a$ is independently —Br. In embodiments, $X^a$ is independently —I. In embodiments, $X^a$ is independently —F. In embodiments, $X^b$ is independently —Cl. In embodiments, $X^b$ is independently —Br. In embodiments, $X^b$ is independently —I. In embodiments, $X^b$ is independently —F. In embodiments, $X^c$ is independently —Cl. In embodiments, $X^c$ is independently —Br. In embodiments, $X^c$ is independently —I. In embodiments, $X^c$ is independently —F. In embodiments, $X^d$ is independently —Cl. In embodiments, $X^d$ is independently —Br. In embodiments, $X^d$ is independently —I. In embodiments, $X^d$ is independently —F. In embodiments, $X^e$ is independently —Cl. In embodiments, $X^e$ is independently —Br. In embodiments, $X^e$ is independently —I. In embodiments, $X^e$ is independently —F.

In embodiments, $R^1$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{27}$-substituted or unsubstituted alkyl (e.g. $C_1$-$C_8$ alkyl, $C_1$-$C_6$ alkyl, or $C_1$-$C_4$ alkyl), $R^{27}$-substituted or unsubstituted heteroalkyl (e.g. 2 to 8 membered heteroalkyl, 2 to 6 membered heteroalkyl, or 2 to 4 membered heteroalkyl), $R^{27}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{27}$-substituted or unsubstituted heterocycloalkyl (e.g. 3 to 8 membered heterocycloalkyl, 4 to 8 membered heterocycloalkyl, or 5 to 6 membered heterocycloalkyl), $R^{27}$-substituted or unsubstituted aryl (e.g. $C_6$-$C_{10}$ aryl or $C_6$ aryl), or $R^{27}$-substituted or unsubstituted heteroaryl (e.g. 5 to 10 membered heteroaryl, 5 to 9 membered heteroaryl, or 5 to 6 membered heteroaryl).

$R^{27}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{28}$-substituted or unsubstituted alkyl (e.g. $C_1$-$C_8$ alkyl, $C_1$-$C_6$ alkyl, or $C_1$-$C_4$ alkyl), $R^{28}$-substituted or unsubstituted heteroalkyl (e.g. 2 to 8 membered heteroalkyl, 2 to 6 membered heteroalkyl, or 2 to 4 membered heteroalkyl), $R^{28}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{28}$-substituted or unsubstituted heterocycloalkyl (e.g. 3 to 8 membered heterocycloalkyl, 4 to 8 membered heterocycloalkyl, or 5 to 6 membered heterocycloalkyl), $R^{28}$-substituted or unsubstituted aryl (e.g. $C_6$-$C_{10}$ aryl or $C_6$ aryl), or $R^{28}$-substituted or unsubstituted heteroaryl (e.g. 5 to 10 membered heteroaryl, 5 to 9 membered heteroaryl, or 5 to 6 membered heteroaryl). In embodiments, $R^{27}$ is piperadine. In embodiments, $R^{27}$ is piperazine. In embodiments, $R^{27}$ is pyridine. In embodiments, $R^{27}$ is pyrazine. In embodiments, $R^{27}$ is dimethylamino. In embodiments, $R^{27}$ is dimethylaminoethyl. In embodiments, $R^{27}$ is dimethylaminopropyl. In embodiments, $R^{27}$ is ethylmorpholinyl. In embodiments, $R^{27}$ is morpholinyl.

$R^{28}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{29}$-substituted or unsubstituted alkyl (e.g. $C_1$-$C_8$ alkyl, $C_1$-$C_6$ alkyl, or $C_1$-$C_4$ alkyl), $R^{29}$-substituted or unsubstituted heteroalkyl (e.g. 2 to 8 membered heteroalkyl, 2 to 6 membered heteroalkyl, or 2 to 4 membered heteroalkyl), $R^{29}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{29}$-substituted or unsubstituted heterocycloalkyl (e.g. 3 to 8 membered heterocycloalkyl, 4 to 8 membered heterocycloalkyl, or 5 to 6 membered heterocycloalkyl), $R^{29}$-substituted or unsubstituted aryl (e.g. $C_6$-$C_{10}$ aryl or $C_6$ aryl), or $R^{29}$-substituted or unsubstituted heteroaryl (e.g. 5 to 10 membered heteroaryl, 5 to 9 membered heteroaryl, or 5 to 6 membered heteroaryl). In embodiments, $R^{28}$ is piperadine. In embodiments, $R^{28}$ is piperazine. In embodiments, $R^{28}$ is pyridine. In embodiments, $R^{28}$ is pyrazine. In embodiments, $R^{28}$ is dimethylamino. In embodiments, $R^{28}$ is dimethylaminoethyl. In embodiments, $R^{28}$ is dimethylaminopropyl. In embodiments, $R^{28}$ is ethylmorpholinyl. In embodiments, $R^{28}$ is morpholinyl.

In embodiments, $R^2$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{30}$-substituted or unsubstituted alkyl (e.g. $C_1$-$C_8$ alkyl, $C_1$-$C_6$ alkyl, or $C_1$-$C_4$ alkyl), $R^{30}$-substituted or unsubstituted heteroalkyl (e.g. 2 to 8 membered heteroalkyl, 2 to 6 membered heteroalkyl, or 2 to 4 membered heteroalkyl), $R^{30}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{30}$-substituted or unsubstituted heterocycloalkyl (e.g. 3 to 8 membered heterocycloalkyl, 4 to 8 membered heterocycloalkyl, or 5 to 6 membered heterocycloalkyl), $R^{30}$-substituted or unsubstituted aryl (e.g. $C_6$-$C_{10}$ aryl or $C_6$ aryl), or $R^{30}$-substituted or unsubstituted heteroaryl (e.g. 5 to 10 membered heteroaryl, 5 to 9 membered heteroaryl, or 5 to 6 membered heteroaryl).

$R^{30}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{31}$-substituted or unsubstituted alkyl (e.g. $C_1$-$C_8$ alkyl, $C_1$-$C_6$ alkyl, or $C_1$-$C_4$ alkyl), $R^{31}$-substituted or unsubstituted heteroalkyl (e.g. 2 to 8 membered heteroalkyl, 2 to 6 membered heteroalkyl, or 2 to 4 membered heteroalkyl), $R^{31}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{31}$-substituted or unsubstituted heterocycloalkyl (e.g. 3 to 8 membered heterocycloalkyl, 4 to 8 membered heterocycloalkyl, or 5 to 6 membered heterocycloalkyl), $R^{31}$-substituted or unsubstituted aryl (e.g. $C_6$-$C_{10}$ aryl or $C_6$ aryl), or $R^{31}$-substituted or unsubstituted heteroaryl (e.g. 5 to 10 membered heteroaryl, 5 to 9 membered heteroaryl, or 5 to 6 membered heteroaryl).

$R^{31}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{32}$-substituted or unsubstituted alkyl (e.g. $C_1$-$C_8$ alkyl, $C_1$-$C_6$ alkyl, or $C_1$-$C_4$ alkyl), $R^{32}$-substituted or unsubstituted heteroalkyl (e.g. 2 to 8 membered heteroalkyl, 2 to 6 membered heteroalkyl, or 2 to 4 membered heteroalkyl), $R^{32}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{32}$-substituted or unsubstituted heterocycloalkyl (e.g. 3 to 8 membered heterocycloalkyl, 4 to 8 membered heterocycloalkyl, or 5 to 6 membered heterocycloalkyl), $R^{32}$-substituted or unsubstituted aryl (e.g. $C_6$-$C_{10}$ aryl or $C_6$ aryl), or $R^{32}$-substituted or unsubstituted heteroaryl (e.g. 5 to 10 membered heteroaryl, 5 to 9 membered heteroaryl, or 5 to 6 membered heteroaryl).

In embodiments, $R^3$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{33}$-substituted or unsubstituted alkyl (e.g. $C_1$-$C_8$ alkyl, $C_1$-$C_6$ alkyl, or $C_1$-$C_4$ alkyl), $R^{33}$-substituted or unsubstituted heteroalkyl (e.g. 2 to 8 membered heteroalkyl, 2 to 6 membered heteroalkyl, or 2 to 4 membered heteroalkyl), $R^{33}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{33}$-substituted or unsubstituted heterocycloalkyl (e.g. 3 to 8 membered heterocycloalkyl, 4 to 8 membered heterocycloalkyl, or 5 to 6 membered heterocycloalkyl), $R^{33}$-substituted or unsubstituted aryl (e.g. 6 to 12 membered aryl or 6 membered aryl), or $R^{33}$ substituted or unsubstituted heteroaryl (e.g. 5 to 10 membered heteroaryl, 5 to 9 membered heteroaryl, or 5 to 6 membered heteroaryl).

$R^{33}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{34}$-substituted or unsubstituted alkyl (e.g. $C_1$-$C_8$ alkyl, $C_1$-$C_6$ alkyl, or $C_1$-$C_4$ alkyl), $R^{34}$-substituted or unsubstituted heteroalkyl (e.g. 2 to 8 membered heteroalkyl, 2 to 6 membered heteroalkyl, or 2 to 4 membered heteroalkyl), $R^{34}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{34}$-substituted or unsubstituted heterocycloalkyl (e.g. 3 to 8 membered heterocycloalkyl, 4 to 8 membered heterocycloalkyl, or 5 to 6 membered heterocycloalkyl), $R^{34}$-substituted or unsubstituted aryl (e.g. $C_6$-$C_{10}$ aryl or $C_6$ aryl), or $R^{34}$-substituted or unsubstituted heteroaryl (e.g. 5 to 10 membered heteroaryl, 5 to 9 membered heteroaryl, or 5 to 6 membered heteroaryl).

$R^{34}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{35}$-substituted or unsubstituted alkyl (e.g. $C_1$-$C_8$ alkyl, $C_1$-$C_6$ alkyl, or $C_1$-$C_4$ alkyl), $R^{35}$-substituted or unsubstituted heteroalkyl (e.g. 2 to 8 membered heteroalkyl, 2 to 6 membered heteroalkyl, or 2 to 4 membered heteroalkyl), $R^{35}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{35}$-substituted or unsubstituted heterocycloalkyl (e.g. 3 to 8 membered heterocycloalkyl, 4 to 8 membered heterocycloalkyl, or 5 to 6 membered heterocycloalkyl), $R^{35}$-substituted or unsubstituted aryl (e.g. $C_6$-$C_{10}$ aryl or $C_6$ aryl), or $R^{35}$-substituted or unsubstituted heteroaryl (e.g. 5 to 10 membered heteroaryl, 5 to 9 membered heteroaryl, or 5 to 6 membered heteroaryl).

In embodiments, $R^4$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{36}$-substituted or unsubstituted alkyl (e.g. $C_1$-$C_8$ alkyl, $C_1$-$C_6$ alkyl, or $C_1$-$C_4$ alkyl), $R^{36}$-substituted or unsubstituted heteroalkyl (e.g. 2 to 8 membered heteroalkyl, 2 to 6 membered heteroalkyl, or 2 to 4 membered heteroalkyl), $R^{36}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{36}$-substituted or unsubstituted heterocycloalkyl (e.g. 3 to 8 membered heterocycloalkyl, 4 to 8 membered heterocycloalkyl, or 5 to 6 membered heterocycloalkyl), $R^{36}$-substituted or unsubstituted aryl (e.g. $C_6$-$C_{10}$ aryl or $C_6$ aryl), or $R^{36}$-substituted or unsubstituted heteroaryl (e.g. 5 to 10 membered heteroaryl, 5 to 9 membered heteroaryl, or 5 to 6 membered heteroaryl).

$R^{36}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{37}$-substituted or unsubstituted alkyl (e.g. $C_1$-$C_8$ alkyl, $C_1$-$C_6$ alkyl, or $C_1$-$C_4$ alkyl), $R^{37}$-substituted or unsubstituted heteroalkyl (e.g. 2 to 8 membered heteroalkyl, 2 to 6 membered heteroalkyl, or 2 to 4 membered heteroalkyl), $R^{37}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{37}$-substituted or unsubstituted heterocycloalkyl (e.g. 3 to 8 membered heterocycloalkyl, 4 to 8 membered heterocycloalkyl, or 5 to 6 membered heterocycloalkyl), $R^{37}$-substituted or unsubstituted aryl (e.g. $C_6$-$C_{10}$ aryl or $C_6$ aryl), or $R^{37}$-substituted or unsubstituted heteroaryl (e.g. 5 to 10 membered heteroaryl, 5 to 9 membered heteroaryl, or 5 to 6 membered heteroaryl).

$R^{37}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{38}$-substituted or unsubstituted alkyl (e.g. $C_1$-$C_8$ alkyl, $C_1$-$C_6$ alkyl, or $C_1$-$C_4$ alkyl), $R^{38}$-substituted or unsubstituted heteroalkyl (e.g. 2 to 8 membered heteroalkyl, 2 to 6 membered heteroalkyl, or 2 to 4 membered heteroalkyl), $R^{38}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{38}$-substituted or unsubstituted heterocycloalkyl (e.g. 3 to 8 membered heterocycloalkyl, 4 to 8 membered heterocycloalkyl, or 5 to 6 membered heterocycloalkyl), $R^{38}$-substituted or unsubstituted aryl (e.g. $C_6$-$C_{10}$ aryl or $C_6$ aryl), or $R^{38}$-substituted or unsubstituted heteroaryl (e.g. 5 to 10 membered heteroaryl, 5 to 9 membered heteroaryl, or 5 to 6 membered heteroaryl).

In embodiments, $R^5$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{39}$-substituted or unsubstituted alkyl (e.g. $C_1$-$C_8$ alkyl, $C_1$-$C_6$ alkyl, or $C_1$-$C_4$ alkyl), $R^{39}$-substituted or unsubstituted heteroalkyl (e.g. 2 to 8 membered heteroalkyl, 2 to 6 membered heteroalkyl, or 2 to 4 membered heteroalkyl), $R^{39}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{39}$-substituted or unsubstituted heterocycloalkyl (e.g. 3 to 8 membered heterocycloalkyl, 4 to 8 membered heterocycloalkyl, or 5 to 6 membered heterocycloalkyl), $R^{39}$-substituted or unsubstituted aryl (e.g. $C_6$-$C_{10}$ aryl or $C_6$ aryl), or $R^{39}$-substituted or unsubstituted heteroaryl (e.g. 5 to 10 membered heteroaryl, 5 to 9 membered heteroaryl, or 5 to 6 membered heteroaryl).

$R^{39}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{40}$-substituted or unsubstituted alkyl (e.g. $C_1$-$C_8$ alkyl, $C_1$-$C_6$ alkyl, or $C_1$-$C_4$ alkyl), $R^{40}$-substituted or unsubstituted heteroalkyl (e.g. 2 to 8 membered heteroalkyl, 2 to 6 membered heteroalkyl, or 2 to 4 membered heteroalkyl), $R^{40}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{40}$-substituted or unsubstituted heterocycloalkyl (e.g. 3 to 8 membered heterocycloalkyl, 4 to 8 membered heterocycloalkyl, or 5 to 6 membered heterocycloalkyl), $R^{40}$-substituted or unsubstituted aryl (e.g. $C_6$-$C_{10}$ aryl or $C_6$ aryl), or $R^{40}$-substituted or unsubstituted heteroaryl (e.g. 5 to 10 membered heteroaryl, 5 to 9 membered heteroaryl, or 5 to 6 membered heteroaryl).

$R^{40}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{41}$-substituted or unsubstituted alkyl (e.g. $C_1$-$C_8$ alkyl, $C_1$-$C_6$ alkyl, or $C_1$-$C_4$ alkyl), $R^{41}$-substituted or unsubstituted heteroalkyl (e.g. 2 to 8 membered heteroalkyl, 2 to 6 membered heteroalkyl, or 2 to 4 membered heteroalkyl), $R^{41}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{41}$-substituted or unsubstituted heterocycloalkyl (e.g. 3 to 8 membered heterocycloalkyl, 4 to 8 membered heterocycloalkyl, or 5 to 6 membered heterocycloalkyl), $R^{41}$-substituted or unsubstituted aryl (e.g. $C_6$-$C_{10}$ aryl or $C_6$ aryl), or $R^{41}$-substituted or unsubstituted heteroaryl (e.g. 5 to 10 membered heteroaryl, 5 to 9 membered heteroaryl, or 5 to 6 membered heteroaryl).

In embodiments, $R^9$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{42}$-substituted or unsubstituted alkyl (e.g. $C_1$-$C_8$ alkyl, $C_1$-$C_6$ alkyl, or $C_1$-$C_4$ alkyl), $R^{42}$-substituted or unsubstituted heteroalkyl (e.g. 2 to 8 membered heteroalkyl, 2 to 6 membered heteroalkyl, or 2 to 4 membered heteroalkyl), $R^{42}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{42}$-substituted or unsubstituted heterocycloalkyl (e.g. 3 to 8 membered heterocycloalkyl, 4 to 8 membered heterocycloalkyl, or 5 to 6 membered heterocycloalkyl), $R^{42}$-substituted or unsubstituted aryl (e.g. $C_6$-$C_{10}$ aryl or $C_6$ aryl), or $R^{42}$-substituted or unsubstituted heteroaryl (e.g. 5 to 10 membered heteroaryl, 5 to 9 membered heteroaryl, or 5 to 6 membered heteroaryl).

$R^{42}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{43}$-substituted or unsubstituted alkyl (e.g. $C_1$-$C_8$ alkyl, $C_1$-$C_6$ alkyl, or $C_1$-$C_4$ alkyl), $R^{43}$-substituted or unsubstituted heteroalkyl (e.g. 2 to 8 membered heteroalkyl, 2 to 6 membered heteroalkyl, or 2 to 4 membered heteroalkyl), $R^{43}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{43}$-substituted or unsubstituted heterocycloalkyl (e.g. 3 to 8 membered heterocycloalkyl, 4 to 8 membered heterocycloalkyl, or 5 to 6 membered heterocycloalkyl), $R^{43}$-substituted or unsubstituted aryl (e.g. $C_6$-$C_{10}$ aryl or $C_6$ aryl), or $R^{43}$-substituted or unsubstituted heteroaryl (e.g. 5 to 10 membered heteroaryl, 5 to 9 membered heteroaryl, or 5 to 6 membered heteroaryl).

$R^{43}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{44}$-substituted or unsubstituted alkyl (e.g. $C_1$-$C_8$ alkyl, $C_1$-$C_6$ alkyl, or $C_1$-$C_4$ alkyl), $R^{44}$-substituted or unsubstituted heteroalkyl (e.g. 2 to 8 membered heteroalkyl, 2 to 6 membered heteroalkyl, or 2 to 4 membered heteroalkyl), $R^{44}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{44}$-substituted or unsubstituted heterocycloalkyl (e.g. 3 to 8 membered heterocycloalkyl, 4 to 8 membered heterocycloalkyl, or 5 to 6 membered heterocycloalkyl), $R^{44}$-substituted or unsubstituted aryl (e.g. $C_6$-$C_{10}$ aryl or $C_6$ aryl), or $R^{44}$-substituted or unsubstituted heteroaryl (e.g. 5 to 10 membered heteroaryl, 5 to 9 membered heteroaryl, or 5 to 6 membered heteroaryl).

In embodiments, $R^{10}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{45}$-substituted or unsubstituted alkyl (e.g. $C_1$-$C_8$ alkyl, $C_1$-$C_6$ alkyl, or $C_1$-$C_4$ alkyl), $R^{45}$-substituted or unsubstituted heteroalkyl (e.g. 2 to 8 membered heteroalkyl, 2 to 6 membered heteroalkyl, or 2 to 4 membered heteroalkyl), $R^{45}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{45}$-substituted or unsubstituted heterocycloalkyl (e.g. 3 to 8 membered heterocycloalkyl, 4 to 8 membered heterocycloalkyl, or 5 to 6 membered heterocycloalkyl), $R^{45}$-substituted or unsubstituted aryl (e.g. $C_6$-$C_{10}$ aryl or $C_6$ aryl), or $R^{45}$-substituted or unsubstituted heteroaryl (e.g. 5 to 10 membered heteroaryl, 5 to 9 membered heteroaryl, or 5 to 6 membered heteroaryl).

$R^{45}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{46}$-substituted or unsubstituted alkyl (e.g. $C_1$-$C_8$ alkyl, $C_1$-$C_6$ alkyl, or $C_1$-$C_4$ alkyl), $R^{46}$-substituted or unsubstituted heteroalkyl (e.g. 2 to 8 membered heteroalkyl, 2 to 6 membered heteroalkyl, or 2 to 4 membered heteroalkyl), $R^{46}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{46}$-substituted or unsubstituted heterocycloalkyl (e.g. 3 to 8 membered heterocycloalkyl, 4 to 8 membered heterocycloalkyl, or 5 to 6 membered heterocycloalkyl), $R^{46}$-substituted or unsubstituted aryl (e.g. $C_6$-$C_{10}$ aryl or $C_6$ aryl), or $R^{46}$-substituted or unsubstituted heteroaryl (e.g. 5 to 10 membered heteroaryl, 5 to 9 membered heteroaryl, or 5 to 6 membered heteroaryl).

$R^{46}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{47}$-substituted or unsubstituted alkyl (e.g. $C_1$-$C_8$ alkyl, $C_1$-$C_6$ alkyl, or $C_1$-$C_4$ alkyl), $R^{47}$-substituted or unsubstituted heteroalkyl (e.g. 2 to 8 membered heteroalkyl, 2 to 6 membered heteroalkyl, or 2 to 4 membered heteroalkyl), $R^{47}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{47}$-substituted or unsubstituted heterocycloalkyl (e.g. 3 to 8 membered heterocycloalkyl, 4 to 8 membered heterocycloalkyl, or 5 to 6 membered heterocycloalkyl), $R^{47}$-substituted or unsubstituted aryl (e.g. $C_6$-$C_{10}$ aryl or $C_6$ aryl), or $R^{47}$-substituted or unsubstituted heteroaryl (e.g. 5 to 10 membered heteroaryl, 5 to 9 membered heteroaryl, or 5 to 6 membered heteroaryl).

In embodiments, $R^{11}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{48}$-substituted or unsubstituted alkyl (e.g. $C_1$-$C_8$ alkyl, $C_1$-$C_6$ alkyl, or $C_1$-$C_4$ alkyl), $R^{48}$-substituted or unsubstituted heteroalkyl (e.g. 2 to 8 membered heteroalkyl, 2 to 6 membered heteroalkyl, or 2 to 4 membered heteroalkyl), $R^{48}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{48}$-substituted or unsubstituted heterocycloalkyl (e.g. 3 to 8 membered heterocycloalkyl, 4 to 8 membered heterocycloalkyl, or 5 to 6 membered heterocycloalkyl), $R^{48}$-substituted or unsubstituted aryl (e.g. $C_6$-$C_{10}$ aryl or $C_6$ aryl), or $R^{48}$-substituted or unsubstituted heteroaryl (e.g. 5 to 10 membered heteroaryl, 5 to 9 membered heteroaryl, or 5 to 6 membered heteroaryl).

$R^{48}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{49}$-substituted or unsubstituted alkyl (e.g. $C_1$-$C_8$ alkyl, $C_1$-$C_6$ alkyl, or $C_1$-$C_4$ alkyl), $R^{49}$-substituted or unsubstituted heteroalkyl (e.g. 2 to 8 membered heteroalkyl, 2 to 6 membered heteroalkyl, or 2 to 4 membered heteroalkyl), $R^{49}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{49}$-substituted or unsubstituted heterocycloalkyl (e.g. 3 to 8 membered heterocycloalkyl, 4 to 8 membered heterocycloalkyl, or 5 to 6 membered heterocycloalkyl), $R^{49}$-substituted or unsubstituted aryl (e.g. $C_6$-$C_{10}$ aryl or $C_6$ aryl), or $R^{49}$-substituted or unsubstituted heteroaryl (e.g. 5 to 10 membered heteroaryl, 5 to 9 membered heteroaryl, or 5 to 6 membered heteroaryl).

$R^{49}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{50}$-substituted or unsubstituted alkyl (e.g. $C_1$-$C_8$ alkyl, $C_1$-$C_6$ alkyl, or $C_1$-$C_4$ alkyl), $R^{50}$-substituted or unsubstituted heteroalkyl (e.g. 2 to 8 membered heteroalkyl, 2 to 6 membered heteroalkyl, or 2 to 4 membered heteroalkyl), $R^{50}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{50}$-substituted or unsubstituted heterocycloalkyl (e.g. 3 to 8 membered heterocycloalkyl, 4 to 8 membered heterocycloalkyl, or 5 to 6 membered heterocycloalkyl), $R^{50}$-substituted or unsubstituted aryl (e.g. $C_6$-$C_{10}$ aryl or $C_6$ aryl), or $R^{50}$-substituted or unsubstituted heteroaryl (e.g. 5 to 10 membered heteroaryl, 5 to 9 membered heteroaryl, or 5 to 6 membered heteroaryl).

In embodiments, $R^{12}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{51}$-substituted or unsubstituted alkyl (e.g. $C_1$-$C_8$ alkyl, $C_1$-$C_6$ alkyl, or $C_1$-$C_4$ alkyl), $R^{51}$-substituted or unsubstituted heteroalkyl (e.g. 2 to 8 membered heteroalkyl, 2 to 6 membered heteroalkyl, or 2 to 4 membered heteroalkyl), $R^{51}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{51}$-substituted or unsubstituted heterocycloalkyl (e.g. 3 to 8 membered heterocycloalkyl, 4 to 8 membered heterocycloalkyl, or 5 to 6 membered heterocycloalkyl), $R^{s5}$-substituted or unsubstituted aryl (e.g. $C_6$-$C_{10}$ aryl or $C_6$ aryl), or $R^{s1}$-substituted or unsubstituted heteroaryl (e.g. 5 to 10 membered heteroaryl, 5 to 9 membered heteroaryl, or 5 to 6 membered heteroaryl).

$R^{51}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{52}$-substituted or unsubstituted alkyl (e.g. $C_1$-$C_8$ alkyl, $C_1$-$C_6$ alkyl, or $C_1$-$C_4$ alkyl), $R^{52}$-substituted or unsubstituted heteroalkyl (e.g. 2 to 8 membered heteroalkyl, 2 to 6 membered heteroalkyl, or 2 to 4 membered heteroalkyl), $R^{52}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{52}$-substituted or unsubstituted heterocycloalkyl (e.g. 3 to 8 membered heterocycloalkyl, 4 to 8 membered heterocycloalkyl, or 5 to 6 membered heterocycloalkyl), $R^{52}$-substituted or unsubstituted aryl (e.g. $C_6$-$C_{10}$ aryl or $C_6$ aryl), or $R^{52}$-substituted or unsubstituted heteroaryl (e.g. 5 to 10 membered heteroaryl, 5 to 9 membered heteroaryl, or 5 to 6 membered heteroaryl).

$R^{52}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{53}$-substituted or unsubstituted alkyl (e.g. $C_1$-$C_8$ alkyl, $C_1$-$C_6$ alkyl, or $C_1$-$C_4$ alkyl), $R^{53}$-substituted or unsubstituted heteroalkyl (e.g. 2 to 8 membered heteroalkyl, 2 to 6 membered heteroalkyl, or 2 to 4 membered heteroalkyl), $R^{53}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{53}$-substituted or unsubstituted heterocycloalkyl (e.g. 3 to 8 membered heterocycloalkyl, 4 to 8 membered heterocycloalkyl, or 5 to 6 membered heterocycloalkyl), $R^{53}$-substituted or unsubstituted aryl (e.g. $C_6$-$C_{10}$ aryl or $C_6$ aryl), or $R^{53}$-substituted or unsubstituted heteroaryl (e.g. 5 to 10 membered heteroaryl, 5 to 9 membered heteroaryl, or 5 to 6 membered heteroaryl).

In embodiments, $R^{13}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{54}$-substituted or unsubstituted alkyl (e.g. $C_1$-$C_8$ alkyl, $C_1$-$C_6$ alkyl, or $C_1$-$C_4$ alkyl), $R^{54}$-substituted or unsubstituted heteroalkyl (e.g. 2 to 8 membered heteroalkyl, 2 to 6 membered heteroalkyl, or 2 to 4 membered heteroalkyl), $R^{54}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{54}$-substituted or unsubstituted heterocycloalkyl (e.g. 3 to 8 membered heterocycloalkyl, 4 to 8 membered heterocycloalkyl, or 5 to 6 membered heterocycloalkyl), $R^{54}$-substituted or unsubstituted aryl (e.g. $C_6$-$C_{10}$ aryl or $C_6$ aryl), or $R^{54}$-substituted or unsubstituted heteroaryl (e.g. 5 to 10 membered heteroaryl, 5 to 9 membered heteroaryl, or 5 to 6 membered heteroaryl).

$R^{54}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{55}$-substituted or unsubstituted alkyl (e.g. $C_1$-$C_8$ alkyl, $C_1$-$C_6$ alkyl, or $C_1$-$C_4$ alkyl), $R^{55}$-substituted or unsubstituted heteroalkyl (e.g. 2 to 8 membered heteroalkyl, 2 to 6 membered heteroalkyl, or 2 to 4 membered heteroalkyl), $R^{55}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{55}$-substituted or unsubstituted heterocycloalkyl (e.g. 3 to 8 membered heterocycloalkyl, 4 to 8 membered heterocycloalkyl, or 5 to 6 membered heterocycloalkyl), $R^{55}$-substituted or unsubstituted aryl (e.g. $C_6$-$C_{10}$ aryl or $C_6$ aryl), or $R^{55}$-substituted or unsubstituted heteroaryl (e.g. 5 to 10 membered heteroaryl, 5 to 9 membered heteroaryl, or 5 to 6 membered heteroaryl).

$R^{55}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{56}$-substituted or unsubstituted alkyl (e.g. $C_1$-$C_8$ alkyl, $C_1$-$C_6$ alkyl, or $C_1$-$C_4$ alkyl), $R^{56}$-substituted or unsubstituted heteroalkyl (e.g. 2 to 8 membered heteroalkyl, 2 to 6 membered heteroalkyl, or 2 to 4 membered heteroalkyl), $R^{56}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{56}$-substituted or unsubstituted heterocycloalkyl (e.g. 3 to 8 membered heterocycloalkyl, 4 to 8 membered heterocycloalkyl, or 5 to 6 membered heterocycloalkyl), $R^{56}$-substituted or unsubstituted aryl (e.g. $C_6$-$C_{10}$ aryl or $C_6$ aryl), or $R^{56}$-substituted or unsubstituted heteroaryl (e.g. 5 to 10 membered heteroaryl, 5 to 9 membered heteroaryl, or 5 to 6 membered heteroaryl).

In embodiments, $R^{14}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{57}$-substituted or unsubstituted alkyl (e.g. $C_1$-$C_8$ alkyl, $C_1$-$C_6$ alkyl, or $C_1$-$C_4$ alkyl), $R^{57}$-substituted or unsubstituted heteroalkyl (e.g. 2 to 8 membered heteroalkyl, 2 to 6 membered heteroalkyl, or 2 to 4 membered heteroalkyl), $R^{57}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{57}$-substituted or unsubstituted heterocycloalkyl (e.g. 3 to 8 membered heterocycloalkyl, 4 to 8 membered heterocycloalkyl, or 5 to 6 membered heterocycloalkyl), $R^{57}$-substituted or unsubstituted aryl (e.g. $C_6$-$C_{10}$ aryl or $C_6$ aryl), or $R^{57}$-substituted or unsubstituted heteroaryl (e.g. 5 to 10 membered heteroaryl, 5 to 9 membered heteroaryl, or 5 to 6 membered heteroaryl).

$R^{57}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{58}$-substituted or unsubstituted alkyl (e.g. $C_1$-$C_8$ alkyl, $C_1$-$C_6$ alkyl, or $C_1$-$C_4$ alkyl), $R^{58}$-substituted or unsubstituted heteroalkyl (e.g. 2 to 8 membered heteroalkyl, 2 to 6 membered heteroalkyl, or 2 to 4 membered heteroalkyl), $R^{58}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{58}$-substituted or unsubstituted heterocycloalkyl (e.g. 3 to 8 membered heterocycloalkyl, 4 to 8 membered heterocycloalkyl, or 5 to 6 membered heterocycloalkyl), $R^{58}$-substituted or unsubstituted aryl (e.g. $C_6$-$C_{10}$ aryl or $C_6$ aryl), or $R^{58}$-substituted or unsubstituted heteroaryl (e.g. 5 to 10 membered heteroaryl, 5 to 9 membered heteroaryl, or 5 to 6 membered heteroaryl).

$R^{58}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{59}$-substituted or unsubstituted alkyl (e.g. $C_1$-$C_8$ alkyl, $C_1$-$C_6$ alkyl, or $C_1$-$C_4$ alkyl), $R^{59}$-substituted or unsubstituted heteroalkyl (e.g. 2 to 8 membered heteroalkyl, 2 to 6 membered heteroalkyl, or 2 to 4 membered heteroalkyl), $R^{59}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{59}$-substituted or unsubstituted heterocycloalkyl (e.g. 3 to 8 membered heterocycloalkyl, 4 to 8 membered heterocycloalkyl, or 5 to 6 membered heterocycloalkyl), $R^{59}$-substituted or unsubstituted aryl (e.g. $C_6$-$C_{10}$ aryl or $C_6$ aryl), or $R^{59}$-substituted or unsubstituted heteroaryl (e.g. 5 to 10 membered heteroaryl, 5 to 9 membered heteroaryl, or 5 to 6 membered heteroaryl).

In some embodiments, $R^{15}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{60}$-substituted or unsubstituted alkyl (e.g. $C_1$-$C_8$ alkyl, $C_1$-$C_6$ alkyl, or $C_1$-$C_4$ alkyl), $R^{60}$-substituted or unsubstituted heteroalkyl (e.g. 2 to 8 membered heteroalkyl, 2 to 6 membered heteroalkyl, or 2 to 4 membered heteroalkyl), $R^{60}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{60}$-substituted or unsubstituted heterocycloalkyl (e.g. 3 to 8 membered heterocycloalkyl, 4 to 8 membered heterocycloalkyl, or 5 to 6 membered heterocycloalkyl), $R^{60}$-substituted or unsubstituted aryl (e.g. $C_6$-$C_{10}$ aryl or $C_6$ aryl), or $R^{60}$-substituted or unsubstituted heteroaryl (e.g. 5 to 10 membered heteroaryl, 5 to 9 membered heteroaryl, or 5 to 6 membered heteroaryl).

$R^{60}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{61}$-substituted or unsubstituted alkyl (e.g. $C_1$-$C_8$ alkyl, $C_1$-$C_6$ alkyl, or $C_1$-$C_4$ alkyl), $R^{61}$-substituted or unsubstituted heteroalkyl (e.g. 2 to 8 membered heteroalkyl, 2 to 6 membered heteroalkyl, or 2 to 4 membered heteroalkyl), $R^{61}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{61}$-substituted or unsubstituted heterocycloalkyl (e.g. 3 to 8 membered heterocycloalkyl, 4 to 8 membered heterocycloalkyl, or 5 to 6 membered heterocycloalkyl), $R^{61}$-substituted or unsubstituted aryl (e.g. $C_6$-$C_{10}$ aryl or $C_6$ aryl), or $R^{61}$-substituted or unsubstituted heteroaryl (e.g. 5 to 10 membered heteroaryl, 5 to 9 membered heteroaryl, or 5 to 6 membered heteroaryl).

$R^{61}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{62}$-substituted or unsubstituted alkyl (e.g. $C_1$-$C_8$ alkyl, $C_1$-$C_6$ alkyl, or $C_1$-$C_4$ alkyl), $R^{62}$-substituted or unsubstituted heteroalkyl (e.g. 2 to 8 membered heteroalkyl, 2 to 6 membered heteroalkyl, or 2 to 4 membered heteroalkyl), $R^{62}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{62}$-substituted or unsubstituted heterocycloalkyl (e.g. 3 to 8 membered heterocycloalkyl, 4 to 8 membered heterocycloalkyl, or 5 to 6 membered heterocycloalkyl), $R^{62}$-substituted or unsubstituted aryl (e.g. $C_6$-$C_{10}$ aryl or $C_6$ aryl), or $R^{62}$-substituted or unsubstituted heteroaryl (e.g. 5 to 10 membered heteroaryl, 5 to 9 membered heteroaryl, or 5 to 6 membered heteroaryl).

In embodiments, $R^{16}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{63}$-substituted or unsubstituted alkyl (e.g. $C_1$-$C_8$ alkyl, $C_1$-$C_6$ alkyl, or $C_1$-$C_4$ alkyl), $R^{63}$-substituted or unsubstituted heteroalkyl (e.g. 2 to 8 membered heteroalkyl, 2 to 6 membered heteroalkyl, or 2 to 4 membered heteroalkyl), $R^{63}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{63}$-substituted or unsubstituted heterocycloalkyl (e.g. 3 to 8 membered heterocycloalkyl, 4 to 8 membered heterocycloalkyl, or 5 to 6 membered heterocycloalkyl), $R^{63}$-substituted or unsubstituted aryl (e.g. $C_6$-$C_{10}$ aryl or $C_6$ aryl), or $R^{63}$-substituted or unsubstituted heteroaryl (e.g. 5 to 10 membered heteroaryl, 5 to 9 membered heteroaryl, or 5 to 6 membered heteroaryl).

$R^{63}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC (O)—OH, —NHOH, —OCF$_3$, —OCHF$_2$, R$^{64}$-substituted or unsubstituted alkyl (e.g. C$_1$-C$_8$ alkyl, C$_1$-C$_6$ alkyl, or C$_1$-C$_4$ alkyl), R$^{64}$-substituted or unsubstituted heteroalkyl (e.g. 2 to 8 membered heteroalkyl, 2 to 6 membered heteroalkyl, or 2 to 4 membered heteroalkyl), R$^{64}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{64}$-substituted or unsubstituted heterocycloalkyl (e.g. 3 to 8 membered heterocycloalkyl, 4 to 8 membered heterocycloalkyl, or 5 to 6 membered heterocycloalkyl), R$^{64}$-substituted or unsubstituted aryl (e.g. C$_6$-C$_{10}$ aryl or C$_6$ aryl), or R$^{64}$-substituted or unsubstituted heteroaryl (e.g. 5 to 10 membered heteroaryl, 5 to 9 membered heteroaryl, or 5 to 6 membered heteroaryl).

R$^{64}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{65}$-substituted or unsubstituted alkyl (e.g. C$_1$-C$_8$ alkyl, C$_1$-C$_6$ alkyl, or C$_1$-C$_4$ alkyl), R$^{65}$-substituted or unsubstituted heteroalkyl (e.g. 2 to 8 membered heteroalkyl, 2 to 6 membered heteroalkyl, or 2 to 4 membered heteroalkyl), R$^{65}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{65}$-substituted or unsubstituted heterocycloalkyl (e.g. 3 to 8 membered heterocycloalkyl, 4 to 8 membered heterocycloalkyl, or 5 to 6 membered heterocycloalkyl), R$^{65}$-substituted or unsubstituted aryl (e.g. C$_6$-C$_{10}$ aryl or C$_6$ aryl), or R$^{65}$-substituted or unsubstituted heteroaryl (e.g. 5 to 10 membered heteroaryl, 5 to 9 membered heteroaryl, or 5 to 6 membered heteroaryl).

In embodiments, R$^{17}$ is independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{66}$-substituted or unsubstituted alkyl (e.g. C$_1$-C$_8$ alkyl, C$_1$-C$_6$ alkyl, or C$_1$-C$_4$ alkyl), R$^{66}$-substituted or unsubstituted heteroalkyl (e.g. 2 to 8 membered heteroalkyl, 2 to 6 membered heteroalkyl, or 2 to 4 membered heteroalkyl), R$^{66}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{66}$-substituted or unsubstituted heterocycloalkyl (e.g. 3 to 8 membered heterocycloalkyl, 4 to 8 membered heterocycloalkyl, or 5 to 6 membered heterocycloalkyl), R$^{66}$-substituted or unsubstituted aryl (e.g. C$_6$-C$_{10}$ aryl or C$_6$ aryl), or R$^{66}$-substituted or unsubstituted heteroaryl (e.g. 5 to 10 membered heteroaryl, 5 to 9 membered heteroaryl, or 5 to 6 membered heteroaryl).

R$^{66}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{67}$-substituted or unsubstituted alkyl (e.g. C$_1$-C$_8$ alkyl, C$_1$-C$_6$ alkyl, or C$_1$-C$_4$ alkyl), R$^{67}$-substituted or unsubstituted heteroalkyl (e.g. 2 to 8 membered heteroalkyl, 2 to 6 membered heteroalkyl, or 2 to 4 membered heteroalkyl), R$^{67}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{67}$-substituted or unsubstituted heterocycloalkyl (e.g. 3 to 8 membered heterocycloalkyl, 4 to 8 membered heterocycloalkyl, or 5 to 6 membered heterocycloalkyl), R$^{67}$-substituted or unsubstituted aryl (e.g. C$_6$-C$_{10}$ aryl or C$_6$ aryl), or R$^{67}$-substituted or unsubstituted heteroaryl (e.g. 5 to 10 membered heteroaryl, 5 to 9 membered heteroaryl, or 5 to 6 membered heteroaryl).

R$^{67}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{68}$-substituted or unsubstituted alkyl (e.g. C$_1$-C$_8$ alkyl, C$_1$-C$_6$ alkyl, or C$_1$-C$_4$ alkyl), R$^{68}$-substituted or unsubstituted heteroalkyl (e.g. 2 to 8 membered heteroalkyl, 2 to 6 membered heteroalkyl, or 2 to 4 membered heteroalkyl), R$^{68}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{68}$-substituted or unsubstituted heterocycloalkyl (e.g. 3 to 8 membered heterocycloalkyl, 4 to 8 membered heterocycloalkyl, or 5 to 6 membered heterocycloalkyl), R$^{68}$-substituted or unsubstituted aryl (e.g. C$_6$-C$_{10}$ aryl or C$_6$ aryl), or R$^{68}$-substituted or unsubstituted heteroaryl (e.g. 5 to 10 membered heteroaryl, 5 to 9 membered heteroaryl, or 5 to 6 membered heteroaryl).

In embodiments, R$^{s8}$ is independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{69}$-substituted or unsubstituted alkyl (e.g. C$_1$-C$_8$ alkyl, C$_1$-C$_6$ alkyl, or C$_1$-C$_4$ alkyl), R$^{69}$-substituted or unsubstituted heteroalkyl (e.g. 2 to 8 membered heteroalkyl, 2 to 6 membered heteroalkyl, or 2 to 4 membered heteroalkyl), R$^{69}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{69}$-substituted or unsubstituted heterocycloalkyl (e.g. 3 to 8 membered heterocycloalkyl, 4 to 8 membered heterocycloalkyl, or 5 to 6 membered heterocycloalkyl), R$^{69}$-substituted or unsubstituted aryl (e.g. C$_6$-C$_{10}$ aryl or C$_6$ aryl), or R$^{69}$-substituted or unsubstituted heteroaryl (e.g. 5 to 10 membered heteroaryl, 5 to 9 membered heteroaryl, or 5 to 6 membered heteroaryl).

R$^{69}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{70}$-substituted or unsubstituted alkyl (e.g. C$_1$-C$_8$ alkyl, C$_1$-C$_6$ alkyl, or C$_1$-C$_4$ alkyl), R$^{70}$-substituted or unsubstituted heteroalkyl (e.g. 2 to 8 membered heteroalkyl, 2 to 6 membered heteroalkyl, or 2 to 4 membered heteroalkyl), R$^{70}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{70}$-substituted or unsubstituted heterocycloalkyl (e.g. 3 to 8 membered heterocycloalkyl, 4 to 8 membered heterocycloalkyl, or 5 to 6 membered heterocycloalkyl), R$^{70}$-substituted or unsubstituted aryl (e.g. C$_6$-C$_{10}$ aryl or C$_6$ aryl), or R$^{70}$-substituted or unsubstituted heteroaryl (e.g. 5 to 10 membered heteroaryl, 5 to 9 membered heteroaryl, or 5 to 6 membered heteroaryl).

R$^{70}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{71}$-substituted or unsubstituted alkyl (e.g. C$_1$-C$_8$ alkyl, C$_1$-C$_6$ alkyl, or C$_1$-C$_4$ alkyl), R$^{71}$-substituted or unsubstituted heteroalkyl (e.g. 2 to 8 membered heteroalkyl, 2 to 6 membered heteroalkyl, or 2 to 4 membered heteroalkyl), R$^{71}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{71}$-substituted or unsubstituted heterocycloalkyl (e.g. 3 to 8 membered heterocycloalkyl, 4 to 8 membered heterocycloalkyl, or 5 to 6 membered heterocycloalkyl), $R^{71}$-substituted or unsubstituted aryl (e.g. $C_6$-$C_{10}$ aryl or $C_6$ aryl), or $R^{71}$-substituted or unsubstituted heteroaryl (e.g. 5 to 10 membered heteroaryl, 5 to 9 membered heteroaryl, or 5 to 6 membered heteroaryl).

In embodiments, $R^{19}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{72}$-substituted or unsubstituted alkyl (e.g. $C_1$-$C_8$ alkyl, $C_1$-$C_6$ alkyl, or $C_1$-$C_4$ alkyl), $R^{72}$-substituted or unsubstituted heteroalkyl (e.g. 2 to 8 membered heteroalkyl, 2 to 6 membered heteroalkyl, or 2 to 4 membered heteroalkyl), $R^{72}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{72}$-substituted or unsubstituted heterocycloalkyl (e.g. 3 to 8 membered heterocycloalkyl, 4 to 8 membered heterocycloalkyl, or 5 to 6 membered heterocycloalkyl), $R^{72}$-substituted or unsubstituted aryl (e.g. $C_6$-$C_{10}$ aryl or $C_6$ aryl), or $R^{72}$-substituted or unsubstituted heteroaryl (e.g. 5 to 10 membered heteroaryl, 5 to 9 membered heteroaryl, or 5 to 6 membered heteroaryl).

In embodiments, $R^{20}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{73}$-substituted or unsubstituted alkyl (e.g. $C_1$-$C_8$ alkyl, $C_1$-$C_6$ alkyl, or $C_1$-$C_4$ alkyl), $R^{73}$-substituted or unsubstituted heteroalkyl (e.g. 2 to 8 membered heteroalkyl, 2 to 6 membered heteroalkyl, or 2 to 4 membered heteroalkyl), $R^{73}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{73}$-substituted or unsubstituted heterocycloalkyl (e.g. 3 to 8 membered heterocycloalkyl, 4 to 8 membered heterocycloalkyl, or 5 to 6 membered heterocycloalkyl), $R^{73}$-substituted or unsubstituted aryl (e.g. $C_6$-$C_{10}$ aryl or $C_6$ aryl), or $R^{73}$-substituted or unsubstituted heteroaryl (e.g. 5 to 10 membered heteroaryl, 5 to 9 membered heteroaryl, or 5 to 6 membered heteroaryl).

In embodiments, $R^{21}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{74}$-substituted or unsubstituted alkyl (e.g. $C_1$-$C_8$ alkyl, $C_1$-$C_6$ alkyl, or $C_1$-$C_4$ alkyl), $R^{74}$-substituted or unsubstituted heteroalkyl (e.g. 2 to 8 membered heteroalkyl, 2 to 6 membered heteroalkyl, or 2 to 4 membered heteroalkyl), $R^{74}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{74}$-substituted or unsubstituted heterocycloalkyl (e.g. 3 to 8 membered heterocycloalkyl, 4 to 8 membered heterocycloalkyl, or 5 to 6 membered heterocycloalkyl), $R^{74}$-substituted or unsubstituted aryl (e.g. $C_6$-$C_{10}$ aryl or $C_6$ aryl), or $R^{74}$-substituted or unsubstituted heteroaryl (e.g. 5 to 10 membered heteroaryl, 5 to 9 membered heteroaryl, or 5 to 6 membered heteroaryl).

In embodiments, $R^{22}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{75}$-substituted or unsubstituted alkyl (e.g. $C_1$-$C_8$ alkyl, $C_1$-$C_6$ alkyl, or $C_1$-$C_4$ alkyl), $R^{75}$-substituted or unsubstituted heteroalkyl (e.g. 2 to 8 membered heteroalkyl, 2 to 6 membered heteroalkyl, or 2 to 4 membered heteroalkyl), $R^{75}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{75}$-substituted or unsubstituted heterocycloalkyl (e.g. 3 to 8 membered heterocycloalkyl, 4 to 8 membered heterocycloalkyl, or 5 to 6 membered heterocycloalkyl), $R^{75}$-substituted or unsubstituted aryl (e.g. $C_6$-$C_{10}$ aryl or $C_6$ aryl), or $R^{75}$-substituted or unsubstituted heteroaryl (e.g. 5 to 10 membered heteroaryl, 5 to 9 membered heteroaryl, or 5 to 6 membered heteroaryl).

In embodiments, $R^{23}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{76}$-substituted or unsubstituted alkyl (e.g. $C_1$-$C_8$ alkyl, $C_1$-$C_6$ alkyl, or $C_1$-$C_4$ alkyl), $R^{76}$-substituted or unsubstituted heteroalkyl (e.g. 2 to 8 membered heteroalkyl, 2 to 6 membered heteroalkyl, or 2 to 4 membered heteroalkyl), $R^{76}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{76}$-substituted or unsubstituted heterocycloalkyl (e.g. 3 to 8 membered heterocycloalkyl, 4 to 8 membered heterocycloalkyl, or 5 to 6 membered heterocycloalkyl), $R^{76}$-substituted or unsubstituted aryl (e.g. $C_6$-$C_{10}$ aryl or $C_6$ aryl), or $R^{76}$-substituted or unsubstituted heteroaryl (e.g. 5 to 10 membered heteroaryl, 5 to 9 membered heteroaryl, or 5 to 6 membered heteroaryl).

In embodiments, $R^{24}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{77}$-substituted or unsubstituted alkyl (e.g. $C_1$-$C_8$ alkyl, $C_1$-$C_6$ alkyl, or $C_1$-$C_4$ alkyl), $R^{77}$-substituted or unsubstituted heteroalkyl (e.g. 2 to 8 membered heteroalkyl, 2 to 6 membered heteroalkyl, or 2 to 4 membered heteroalkyl), $R^{77}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{77}$-substituted or unsubstituted heterocycloalkyl (e.g. 3 to 8 membered heterocycloalkyl, 4 to 8 membered heterocycloalkyl, or 5 to 6 membered heterocycloalkyl), $R^{77}$-substituted or unsubstituted aryl (e.g. $C_6$-$C_{10}$ aryl or $C_6$ aryl), or $R^{77}$-substituted or unsubstituted heteroaryl (e.g. 5 to 10 membered heteroaryl, 5 to 9 membered heteroaryl, or 5 to 6 membered heteroaryl).

In embodiments, $R^{25}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{78}$-substituted or unsubstituted alkyl (e.g. $C_1$-$C_8$ alkyl, $C_1$-$C_6$ alkyl, or $C_1$-$C_4$ alkyl), $R^{78}$-substituted or unsubstituted heteroalkyl (e.g. 2 to 8 membered heteroalkyl, 2 to 6 membered heteroalkyl, or 2 to 4 membered heteroalkyl), $R^{78}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{78}$-substituted or unsubstituted heterocycloalkyl (e.g. 3 to 8 membered heterocycloalkyl, 4 to 8 membered heterocycloalkyl, or 5 to 6 membered heterocycloalkyl), $R^{78}$-substituted or unsubstituted aryl (e.g. $C_6$-$C_{10}$ aryl or $C_6$ aryl), or $R^{78}$-substituted or unsubstituted heteroaryl (e.g. 5 to 10 membered heteroaryl, 5 to 9 membered heteroaryl, or 5 to 6 membered heteroaryl).

In embodiments, $R^{26}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC (O)—OH, —NHOH, —OCF$_3$, —OCHF$_2$, R$^{79}$-substituted or unsubstituted alkyl (e.g. C$_1$-C$_8$ alkyl, C$_1$-C$_6$ alkyl, or C$_1$-C$_4$ alkyl), R$^{79}$-substituted or unsubstituted heteroalkyl (e.g. 2 to 8 membered heteroalkyl, 2 to 6 membered heteroalkyl, or 2 to 4 membered heteroalkyl), R$^{79}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{79}$-substituted or unsubstituted heterocycloalkyl (e.g. 3 to 8 membered heterocycloalkyl, 4 to 8 membered heterocycloalkyl, or 5 to 6 membered heterocycloalkyl), R$^{79}$-substituted or unsubstituted aryl (e.g. C$_6$-C$_{10}$ aryl or C$_6$ aryl), or R$^{79}$-substituted or unsubstituted heteroaryl (e.g. 5 to 10 membered heteroaryl, 5 to 9 membered heteroaryl, or 5 to 6 membered heteroaryl).

In embodiments, L is independently a bond, R$^{50}$-substituted or unsubstituted alkylene, R$^{50}$-substituted or unsubstituted heteroalkylene, R$^{50}$-substituted or unsubstituted cycloalkylene, R$^{50}$-substituted or unsubstituted heterocycloalkylene, R$^{50}$-substituted or unsubstituted arylene, or R$^{50}$-substituted or unsubstituted heteroarylene.

R$^{29}$, R$^{32}$, R$^{35}$, R$^{38}$, R$^{41}$, R$^{44}$, R$^{47}$, R$^{50}$, R$^{53}$, R$^{56}$, R$^{59}$, R$^{62}$, R$^{65}$, R$^{68}$, R$^{71}$, R$^{72}$, R$^{73}$, R$^{74}$, R$^{75}$, R$^{76}$, R$^{77}$, R$^{78}$, R$^{79}$, and R$^{80}$ are independently oxo, halogen, —F, —Cl, —Br, —I, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl (e.g. C$_1$-C$_8$ alkyl, C$_1$-C$_6$ alkyl, or C$_1$-C$_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. C$_3$-C$_8$ cycloalkyl, C$_4$-C$_8$ cycloalkyl, or C$_5$-C$_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. C$_6$-C$_{10}$ aryl or C$_6$ aryl), or unsubstituted heteroaryl (e.g. 5 to 10 membered heteroaryl, 5 to 9 membered heteroaryl, or 5 to 6 membered heteroaryl).

In embodiments, the compound is (JD119)

(JD128)

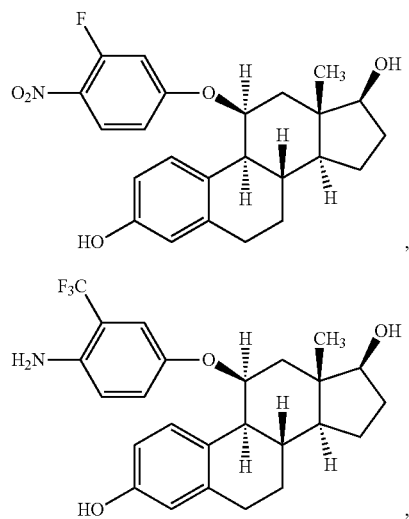

-continued (JD140)

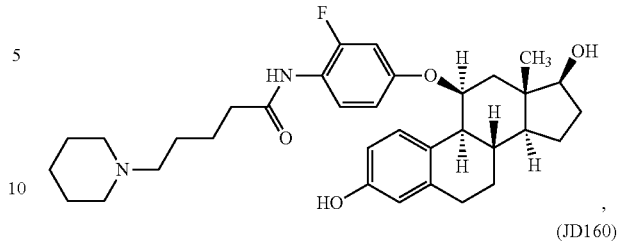

(JD160)

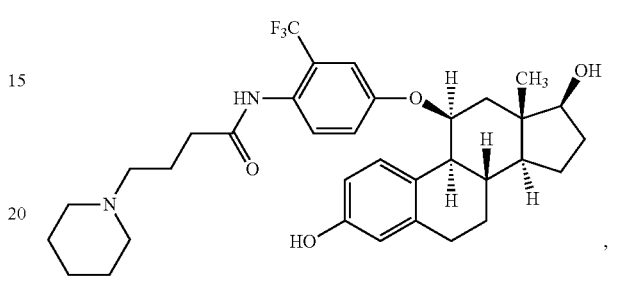

(JD121)

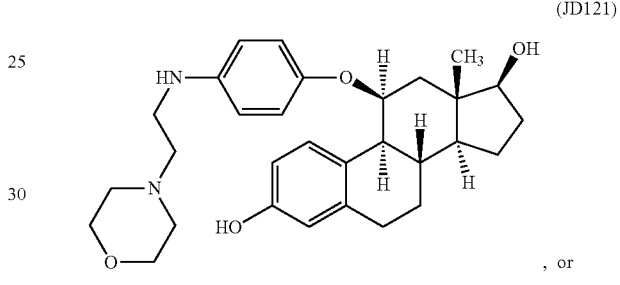

, or (JD109)

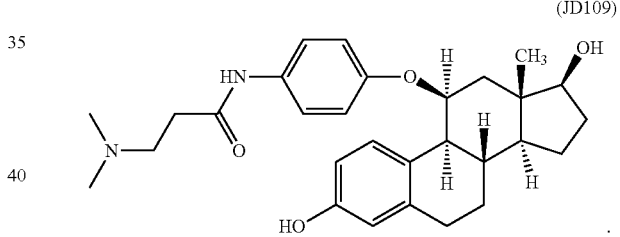

.

In embodiments, the compound is a compound described herein. In some embodiments, the compound is a compound selected from JD101 to JD160 (e.g., JD101, JD102, JD103, JD104, JD105, JD106, JD107, JD108, JD109, JD110, JD111, JD112, JD113, JD114, JD115, JD116, JD117, JD118, JD119, JD120, JD121, JD122, JD123, JD124, JD125, JD126, JD127, JD128, JD129, JD130, JD131, JD132, JD133, JD134, JD135, JD136, JD137, JD138, JD139, JD140, JD141, JD142, JD143, JD144, JD145, JD146, JD147, JD148, JD149, JD150, JD151, JD152, JD153, JD154, JD155, JD156, JD157, JD158, JD159, or JD160). In embodiments, the compound is not a compound selected from JD101 to JD160 (e.g., JD101, JD102, JD103, JD104, JD105, JD106, JD107, JD108, JD109, JD110, JD111, JD112, JD113, JD114, JD115, JD116, JD117, JD118, JD119, JD120, JD121, JD122, JD123, JD124, JD125, JD126, JD127, JD128, JD129, JD130, JD131, JD132, JD133, JD134, JD135, JD136, JD137, JD138, JD139, JD140, JD141, JD142, JD143, JD144, JD145, JD146, JD147, JD148, JD149, JD150, JD151, JD152, JD153, JD154, JD155, JD156, JD157, JD158, JD159, or JD160).

In some embodiments, a compound as described herein may include multiple instances of R$^1$, R$^2$, R$^3$, R$^4$, R$^5$, R$^9$, $R^{10}$, $R^1$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, m1, m2, m3, m4, m5, v1, v2, v3, v4, v5, n1, n2, n3, n4, n5, X, $X^a$, $X^b$, $X^c$, $X^d$ and $X^e$, and/or other variables. In such embodiments, each variable may optional be different and be appropriately labeled to distinguish each group for greater clarity. For example, where each $R^1$, $R^2$, $R^3$, $R^4$, $R^5$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, m1, m2, m3, m4, m5, v1, v2, v3, v4, v5, n1, n2, n3, n4, n5, X, $X^a$, $X^b$, $X^c$, $X^d$ and $X^e$, is different, they may be referred to, for example, as $R^{1.1}$, $R^{1.2}$, $R^{1.3}$, $R^{1.4}$, $R^{1.5}$, $R^{2.1}$, $R^{2.2}$, $R^{2.3}$, $R^{2.4}$, $R^{2.5}$, $R^{3.1}$, $R^{3.2}$, $R^{3.3}$, $R^{3.4}$, $R^{3.5}$, $R^{4.1}$, $R^{4.2}$, $R^{4.3}$, $R^{4.4}$, $R^{4.5}$, $R^{5.1}$, $R^{5.2}$, $R^{5.3}$, $R^{5.4}$, $R^{5.5}$, $R^{9.1}$, $R^{9.2}$, $R^{9.3}$, $R^{9.4}$, $R^{9.5}$, $R^{10.1}$, $R^{10.2}$, $R^{10.3}$, $R^{10.4}$, $R^{10.5}$, $R^{11.1}$, $R^{11.2}$, $R^{11.3}$, $R^{11.4}$, $R^{11.5}$, $R^{12.1}$, $R^{12.2}$, $R^{12.3}$, $R^{12.4}$, $R^{12.5}$, $R^{13.1}$, $R^{13.2}$, $R^{13.3}$, $R^{13.4}$, $R^{13.5}$, $R^{14.1}$, $R^{14.2}$, $R^{14.3}$, $R^{14.4}$, $R^{14.5}$, $R^{15.1}$, $R^{15.2}$, $R^{15.3}$, $R^{15.4}$, $R^{15.5}$, $R^{16.1}$, $R^{16.2}$, $R^{16.3}$, $R^{16.4}$, $R^{16.5}$, $R^{17.1}$, $R^{17.2}$, $R^{17.3}$, $R^{17.4}$, $R^{17.5}$, $R^{18.1}$, $R^{18.2}$, $R^{18.3}$, $R^{18.4}$, $R^{18.5}$, $R^{19.1}$, $R^{19.2}$, $R^{19.3}$, $R^{19.4}$, $R^{19.5}$, $R^{20.1}$, $R^{20.2}$, $R^{20.4}$, $R^{20.5}$, $R^{21.1}$, $R^{21.2}$, $R^{21.3}$, $R^{21.4}$, $R^{21.5}$, $R^{22.1}$, $R^{22.2}$, $R^{22.3}$, $R^{22.4}$, $R^{22.5}$, $R^{23.1}$, $R^{23.2}$, $R^{23.3}$, $R^{23.4}$, $R^{23.5}$, $R^{24.1}$, $R^{24.2}$, $R^{24.3}$, $R^{24.4}$, $R^{24.5}$, $R^{25.1}$, $R^{25.2}$, $R^{25.3}$, $R^{25.4}$, $R^{25.5}$, $R^{26.1}$, $R^{26.2}$, $R^{26.3}$, $R^{26.4}$, $R^{26.5}$, $m1^1$, $m1^2$, $m1^3$, $m1^4$, $m1^5$, $m2^1$, $m2^2$, $m2^3$, $m2^4$, $m2^5$, $m3^1$, $m3^2$, $m3^3$, $m3^4$, $m3^5$, $m4^1$, $m4^2$, $m4^3$, $m4^4$, $m4^5$, $m5^1$, $m5^2$, $m5^3$, $m5^4$, $m5^5$, $m1^1$, $m1^2$, $m1^3$, $m1^4$, $v1^5$, $m2^1$, $v2^2$, $v2^3$, $v2^4$, $v2^5$, $m3^1$, $v3^2$, $v3^3$, $m3^4$, $v3^5$, v4, $m4^2$, $m4^3$, $m4^4$, v4, v5, $m5^2$, $m5^3$, $v5^4$, $v5^5$, n1, $n1^2$, $n1^3$, $n1^4$, $n1^5$, $m2^1$, $m2^2$, $n2^3$, $n2^4$, $m2^5$, $m3^1$, $n3^2$, $n3^3$, $n3^4$, $n3^5$, $n4^1$, $n4^2$, $n4^3$, $n4^4$, $n4^5$, $n5^1$, $n5^2$, $n5^3$, $n5^4$, $n5^5$, $X^1$, $X^2$, $X^3$, $X^5$, $X^{a1}$, $X^aX^2$, $X^{a3}$, $X^{a4}$, $X^{a5}$, $X^{b1}$, $X^{b2}$, $X^{b3}$, $X^{b4}$, $X^{b5}$, $X^{c1}$, $X^{c2}$, $X^{c3}$, $X^{c4}$, $X^{c5}$, $X^{d1}$, $X^{d2}$, $X^{d3}$, $X^{d4}$, $X^{d5}$, $X^{e1}$, $X^{e2}$, $X^{e3}$, $X^{e4}$, and/or $X^{e5}$, respectively, wherein the definition of $R^1$ is assumed by $R^{1.1}$, $R^{1.2}$, $R^{1.3}$, $R^{1.4}$, and/or $R^{1.5}$, wherein the definition of $R^2$ is assumed by $R^{2.1}$, $R^{2.2}$, $R^{2.3}$, $R^{2.4}$, and/or $R^{2.5}$, wherein the definition of $R^3$ is assumed by $R^{3.1}$, $R^{3.2}$, $R^{3.3}$, $R^{3.4}$, and/or $R^{3.5}$, wherein the definition of $R^4$ is assumed by $R^{4.1}$, $R^{4.2}$, $R^{4.3}$, $R^{4.4}$, and/or $R^{4.5}$, wherein the definition of $R^5$ is assumed by $R^{5.1}$, $R^{5.2}$, $R^{5.3}$, $R^{5.4}$, and/or $R^{5.5}$, wherein the definition of $R^9$ is assumed by $R^{9.1}$, $R^{9.2}$, $R^{9.3}$, $R^{9.4}$, and/or $R^{9.5}$, wherein the definition of $R^{10}$ is assumed by $R^{10.1}$, $R^{10.2}$, $R^{10.3}$, $R^{10.4}$, and/or $R^{10.5}$, wherein the definition of $R^{11}$ is assumed by $R^{11.1}$, $R^{11.2}$, $R^{11.3}$, $R^{11.4}$, and/or $R^{11.5}$, wherein the definition of $R^2$ is assumed by $R^{12.1}$, $R^{12.2}$, $R^{12.3}$, $R^{12.4}$, and/or $R^{12.5}$, wherein the definition of $R^{13}$ is assumed by $R^{13.1}$, $R^{13.2}$, $R^{13.3}$, $R^{13.4}$, and/or $R^{13.5}$, wherein the definition of $R^{14}$ is assumed by $R^{14.1}$, $R^{14.2}$, $R^{14.3}$, $R^{14.4}$, and/or $R^{14.5}$, wherein the definition of $R^{15}$ is assumed by $R^{15.1}$, $R^{15.2}$, $R^{15.3}$, $R^{15.4}$, and/or $R^{15.5}$, wherein the definition of $R^{16}$ is assumed by $R^{16.1}$, $R^{16.2}$, $R^{16.3}$, $R^{16.4}$, and/or $R^{16.5}$, wherein the definition of $R^{17}$ is assumed by $R^{17.1}$, $R^{17.2}$, $R^{17.3}$, $R^{17.4}$, and/or $R^{17.5}$, wherein the definition of $R^{18}$ is assumed by $R^{18.1}$, $R^{18.2}$, $R^{18.3}$, $R^{18.4}$, and/or $R^{18.5}$, wherein the definition of $R^{19}$ is assumed by $R^{19.1}$, $R^{19.2}$, $R^{19.3}$, $R^{19.4}$, and/or $R^{19.5}$, wherein the definition of $R^{20}$ is assumed by $R^{20.1}$, $R^{20.2}$, $R^{20.3}$, $R^{20.4}$, and/or $R^{20.5}$, wherein the definition of $R^{21}$ is assumed by $R^{21.1}$, $R^{21.2}$, $R^{21.3}$, $R^{21.4}$, and/or $R^{21.5}$, wherein the definition of $R^{22}$ is assumed by $R^{22.1}$, $R^{22.2}$, $R^{22.3}$, $R^{22.4}$, and/or $R^{22.5}$, wherein the definition of $R^{23}$ is assumed by $R^{23.1}$, $R^{23.2}$, $R^{23.3}$, $R^{23.4}$, and/or $R^{23.5}$, wherein the definition of $R^{24}$ is assumed by $R^{24.1}$, $R^{24.2}$, $R^{24.3}$, $R^{24.4}$, and/or $R^{24.5}$, wherein the definition of $R^{25}$ is assumed by $R^{251}$, $R^{25.2}$, $R^{25.3}$, $R^{25.4}$, and/or $R^{25.5}$, wherein the definition of $R^{26}$ is assumed by $R^{26.1}$, $R^{26.2}$, $R^{26.3}$, $R^{26.4}$, and/or $R^{26.5}$, wherein the definition of m1 is assumed by $m1^1$, $m1^2$, $m1^3$, $m1^4$, and/or $m1^5$, wherein the definition of m2 is assumed by $m2^1$, $m2^2$, $m2^3$, $m2^4$, and/or $m2^5$, wherein the definition of m3 is assumed by $m3^1$, $m3^2$, $m3^3$, $m3^4$, and/or $m3^5$, wherein the definition of m4 is assumed by $m4^1$, $m4^2$, $m4^3$, $m4^4$, and/or $m4^5$, wherein the definition of m5 is assumed by $m5^1$, $m5^2$, $m5^3$, $m5^4$, and/or $m5^5$, wherein the definition of v1 is assumed by $v1^1$, $v1^2$, $V1^3$, $V1^4$, and/or $m1^5$, wherein the definition of v2 is assumed by $v2^1$, $v2^2$, $v2^3$, $v2^4$, and/or $v2^5$, wherein the definition of v3 is assumed by $m3^1$, $m3^2$, $v3^3$, $v3^4$, and/or $v3^5$, wherein the definition of v4 is assumed by $v4^1$, $v4^2$, $v4^3$, $v4^4$, and/or $v4^5$, wherein the definition of v5 is assumed by $v5^1$, $v5^2$, $v5^3$, $v5^4$, and/or $v5^5$, wherein the definition of n1 is assumed by $n1^1$, $n1^2$, $n1^3$, $m1^4$, and/or $n1^5$, wherein the definition of n2 is assumed by $n2^1$, $n2^2$, $n2^3$, $n2^4$, and/or $n2^5$, wherein the definition of n3 is assumed by $n3^1$, $n3^2$, $n3^3$, $n3^4$, and/or $n3^5$, wherein the definition of n4 is assumed by $m4^1$, $m4^2$, $n4^3$, $n4^4$, and/or $n4^5$, wherein the definition of n5 is assumed by $m5^1$, $m5^2$, $n5^3$, $n5^4$, and/or $n5^5$, wherein the definition of X is assumed by $X^1$, $X^2$, $X^3$, $X^4$, and/or $X^5$, wherein the definition of $X^a$ is assumed by $X^{a1}$, $X^aX^2$, $X^{a3}$, $X^{a4}$, and/or $X^{a5}$, wherein the definition of $X^b$ is assumed by $X^{b1}$, $X^{b2}$, $X^{b3}$, $X^{b4}$, and/or $X^{b5}$, wherein the definition of $X^c$ is assumed by $X^{c1}$, $X^{c2}$, $X^{c3}$, $X^{c4}$, and/or $X^{c5}$, wherein the definition of $X^d$ is assumed by $X^{d1}$, $X^{d2}$, $X^{d3}$, $X^{d4}$, and/or $X^{d5}$, wherein the definition of $X^e$ is assumed by $X^{e1}$, $X^{e2}$, $X^{e3}$, $X^{e4}$, and/or $X^{e5}$. The variables used within a definition of $R^1$, $R^2$, $R^3$, $R^4$, $R^5$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, m1, m2, m3, m4, m5, v1, v2, v3, v4, v5, n1, n2, n3, n4, n5, X, $X^a$, $X^b$, $X^c$, $X^d$ and $X^e$, and/or other variables that appear at multiple instances and are different may similarly be appropriately labeled to distinguish each group for greater clarity.

In embodiments, the compound competes with estrogen for binding to estrogen receptor (ER). In embodiments, the compound competes with 4-hydroxy tamoxifen for binding to ER. In embodiments, the compound binds the ligand binding domain of ER. In embodiments, the compound modulates the conformation of helix 12 of ER relative to the conformation of helix 12 when estrogen is bound to ER. In embodiments, the compound modulates (e.g., reduces relative to estrogen bound ER) the binding of ER to estrogen response elements. In embodiments, the compound modulates (e.g., reduces relative to estrogen bound ER) the phosphorylation of ER. In embodiments, the compound modulates (e.g., reduces relative to estrogen bound ER) the activity of a cellular pathway (e.g., ras-MAPK containing pathway, PI3K/AKT containing pathway, She containing pathway, Src kinase containing pathway, JAK/STAT containing pathway, nitric oxide synthase pathway, VEGF secretion pathway). In embodiments, the compound modulates (e.g., reduces relative to estrogen bound ER) DNA synthesis. In embodiments, the compound modulates (e.g., reduces relative to estrogen bound ER) cell growth. In embodiments, the compound modulates (e.g., reduces relative to estrogen bound ER) cell proliferation. In embodiments, the compound modulates (e.g., reduces relative to estrogen bound ER) epithelial cell proliferation. In embodiments, the compound modulates (e.g., increases relative to estrogen bound ER) the degradation of ER. In embodiments, the compound modulates (e.g., increases relative to estrogen bound ER) the ubiquitination of ER. In embodiments, the compound modulates (e.g., increases relative to estrogen bound ER) the degration of ER by the proteasome.

In embodiments, the compounds set forth herein are provided as pharmaceutical compositions including the compound and a pharmaceutically acceptable excipient.

C. PHARMACEUTICAL COMPOSITIONS

In another aspect is provided a pharmaceutical composition including a pharmaceutically acceptable excipient and a compound, or pharmaceutically acceptable salt thereof, as described herein, including embodiments (e.g. compound of formula I, Ia, Ib, II, IIa, IIb, or any embodiment thereof, or in an example, table, figure, or claim). In embodiments, the compound is a compound selected from JD101 to JD160. In embodiments of the pharmaceutical compositions, the compound, or pharmaceutically acceptable salt thereof, as described herein, is included in a therapeutically effective amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating cancer. In embodiments of the pharmaceutical compositions, the second agent is an agent for treating a hyperproliferative disorder. In embodiments, the second agent is an anti-cancer agent. In embodiments, the second agent is a chemotherapeutic. In embodiments, the second agent is an agent for treating breast cancer. In embodiments, the second agent is an agent for treating lung cancer. In embodiments, the second agent is an agent for treating a gynecological cancer. In embodiments, the second agent is an agent for treating ovarian cancer. In embodiments, the second agent is an agent for treating endometrial cancer. In embodiments, the second agent is an agent for treating prostate cancer. In embodiments, the second agent is an agent for treating lymphangioleiomyomatosis. In embodiments, the second agent is an agent for inhibiting estrogen receptor activity. In embodiments, the second agent is an agent for treating a disease associated with estrogen receptor activity. In embodiments, the second agent is an antiestrogen. In embodiments, the second agent is an aromatase inhibitor. In embodiments, the second agent is a HER-2 inhibitor. In embodiments, the second agent is Herceptin. In embodiments, the second agent is fulvestrant, clomifene, femarelle, ormeloxifene, raloxifene, tamoxifen, toremifene, lasofoxifene, ospemifene, anastrozole, letrozole, exemestane, vorozole, formestane, fadrozole, aminoglutethimide, or testolactone. In embodiments, the second agent is tamoxifen. In embodiments, the second agent is an EGFR inhibitor (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, pelitinib/EKB—569, BMS-599626, TAK-285, CUDC-101, OSI-420/desmethyl erlotinib, CP-724714, dacomitinib/PF299804, AG-490, AG-1478, AST-1306, WZ3146, AZD8931,/sapitinib, PD153035, icotinib, ARRY334543/varlitinib, ARRY-380, AEE788, WZ8040, WZ4002, or XL647).

D. METHODS OF TREATMENT

In an aspect is provided a method of treating a hyperproliferative disorder in a subject in need thereof, including administering to the subject an effective amount of a compound described herein.

In an aspect is provided use of a compound as described herein in the manufacture of a medicament for the treatment of a hyperproliferative disorder in a subject in need of such treatment.

In an aspect is provided a compound as described herein for use in the treatment of a hyperproliferative disorder in a subject in need of such treatment. The use includes administering to the subject a compound described herein. The use may include administering to the subject a therapeutically effective amount of a compound described herein.

In embodiments, the hyperproliferative disorder is associated with estrogen receptor activity. In embodiments, the hyperproliferative disorder is lymphangioleiomyomatosis. In embodiments, the hyperproliferative disorder is a cancer. In embodiments, the hyperproliferative disorder is a cancer resistant to an anti-cancer agent (e.g., tamoxifen, an antiestrogen, an aromatase inhibitor). In embodiments, the cancer is breast cancer. In embodiments, the cancer is ER positive breast cancer. In embodiments, the cancer is ER negative breast cancer. In embodiments, the cancer is hormone sensitive breast cancer. In embodiments, the cancer is hormone insensitive breast cancer. In embodiments, the cancer is triple negative breast cancer. In embodiments, the cancer is HER-2 positive breast cancer. In embodiments, the cancer is metastatic breast cancer. In embodiments, the cancer is lung cancer. In embodiments, the cancer is a gynecological cancer. In embodiments, the cancer is ovarian cancer. In embodiments, the cancer is endometrial cancer. In embodiments, the cancer is prostate cancer. In embodiments, the cancer is metastatic cancer. In embodiments, the hyperproliferative disorder (e.g., cancer) is resistant to an antiestrogen. In embodiments, the hyperproliferative disorder (e.g., cancer) is resistant to an endocrine therapy. In embodiments, the hyperproliferative disorder (e.g., cancer) is resistant to an aromatase inhibitor. In embodiments, the hyperproliferative disorder (e.g., cancer) is a cancer of an estrogen target organ or tissue. In embodiments, the cancer is non-small cell lung cancer. In embodiments, the cancer is small cell lung cancer. In embodiments, the lung cancer is adenocarcinoma. In embodiments, the lung cancer is squamous-cell carcinoma. In embodiments, the lung cancer is large-cell carcinoma. In embodiments, the lung cancer is bronchioloalveolar carcinoma. In embodiments, the lung cancer is stage I. In embodiments, the lung cancer is stage II. In embodiments, the lung cancer is stage III. In embodiments, the lung cancer is stage IV.

In embodiments of the method or use, the method or use includes administering a second agent (e.g. therapeutic agent). In embodiments of the method or use, the method or use includes administering a second agent (e.g. therapeutic agent) in a therapeutically effective amount. In embodiments of the method or use, the second agent is an agent for treating cancer. In embodiments of the method or use, the second agent is an agent for treating a hyperproliferative disorder. In embodiments, the second agent is an anti-cancer agent. In embodiments, the second agent is a chemotherapeutic. In embodiments, the second agent is an agent for treating breast cancer. In embodiments, the second agent is an agent for treating lung cancer. In embodiments, the second agent is an agent for treating a gynecological cancer. In embodiments, the second agent is an agent for treating ovarian cancer. In embodiments, the second agent is an agent for treating endometrial cancer. In embodiments, the second agent is an agent for treating prostate cancer. In embodiments, the second agent is an agent for treating lymphangioleiomyomatosis (LAM). In embodiments, the second agent is an agent for inhibiting estrogen receptor activity. In embodiments, the second agent is an agent for treating a disease associated with estrogen receptor activity. In embodiments, the second agent is an antiestrogen. In embodiments, the second agent is an aromatase inhibitor. In embodiments, the second agent is an endocrine therapeutic. In embodiments, the second agent is an anti-cancer agent. In embodiments, the second agent is a chemotherapeutic. In embodiments, the second agent is a HER-2 inhibitor. In embodiments, the second agent is fulvestrant, clomifene, femarelle, ormeloxifene, raloxifene, tamoxifen, toremifene, lasofoxifene, ospemifene, anastrozole, letrozole, exemestane, vorozole, formestane, fadrozole, aminoglutethimide, or testolactone. In embodiments, the second agent is tamoxifen. In embodiments, the method or use does not include an increased risk of endometrial cancer. In embodiments, the method or use does not include an increased risk of a gynecological cancer. In embodiments, the method or use does not include a reduction in bone health.

In an aspect is provided a compound as described herein for use in the treatment of gynecomastia in a subject in need of such treatment. The use includes administering to the subject a compound described herein. The use may include administering to the subject a therapeutically effective amount of a compound described herein.

In embodiments, gynecomastia is associated with estrogen receptor activity. In embodiments, gynecomastia is non-physiologic gynecomastia. In embodiments, gynecomastia is physiologic gynecomastia.

In embodiments, the method or use improves (e.g. increases) bone density relative to the absence of the compound. In embodiments, the method or use improves (e.g. increases) bone mass relative to the absence of the compound. In embodiments, the method or use improves (e.g. increases) bone health relative to the absence of the compound. In embodiments, the method or use is a treatment for osteoporosis, osteogenesis imperfecta, or osteopenia. In embodiments, the method or use is a treatment for osteogenesis imperfecta.

In embodiments, the method or use is used to prevent bone deterioration, prevent bone degradation, prevent bone degeneration, prevent loss of bone mass, prevent loss of bone density, stabilize bone deterioration, stabilize bone degradation, stabilize bone degeneration, stabilize the loss of bone mass, stabilize the loss of bone density, decrease bone deterioration, decrease bone degradation, decrease bone degeneration, decrease loss of bone mass, decrease loss of bone density, increase bone mass, increase bone density, or combinations thereof.

In an aspect is provided a method of treating a bone disorder in a subject in need thereof, including administering to the subject an effective amount of a compound described herein.

In an aspect is provided use of a compound as described herein in the manufacture of a medicament for the treatment of a bone disorder in a subject in need of such treatment.

In an aspect is provided a compound as described herein for use in the treatment of a bone disorder in a subject in need of such treatment. The use includes administering to the subject a compound described herein. The use may include administering to the subject a therapeutically effective amount of a compound described herein.

In embodiments, the bone disorder is osteoporosis, osteogenesis imperfecta, or osteopenia. In embodiments, the bone disorder is osteogenesis imperfecta. In embodiments, the bone disorder is bone deterioration, bone degradation, bone degeneration, loss of bone mass, loss of bone density, or combinations thereof.

In embodiments, the method or use is used to prevent bone deterioration, prevent bone degradation, prevent bone degeneration, prevent loss of bone mass, prevent loss of bone density, stabilize bone deterioration, stabilize bone degradation, stabilize bone degeneration, stabilize the loss of bone mass, stabilize the loss of bone density, decrease bone deterioration, decrease bone degradation, decrease bone degeneration, decrease loss of bone mass, decrease loss of bone density, increase bone mass, increase bone density, or combinations thereof.

In embodiments of the method or use, the method or use includes administering a compound described herein.

E. METHODS OF INHIBITING ESTROGEN RECEPTOR

In an aspect is provided a method of inhibiting estrogen receptor activity in a subject in need thereof, including administering to the subject an effective amount of a compound described herein.

In an aspect is provided use of a compound as described herein in the manufacture of a medicament for inhibiting estrogen receptor activity in a subject in need of such treatment.

In an aspect is provided a compound as described herein for use in inhibiting estrogen receptor activity in a subject in need of such treatment. The use includes administering to the subject a compound described herein. The use may include administering to the subject a therapeutically effective amount of a compound described herein.

In embodiments, the method or use includes modulation (e.g., inhibition or reduction) of the activity of a cellular pathway (e.g., ras-MAPK containing pathway, PI3K/AKT containing pathway, She containing pathway, Src kinase containing pathway, JAK/STAT containing pathway, nitric oxide synthase pathway, VEGF secretion pathway). In embodiments, the method or use includes modulation (e.g., inhibition or reduction) of DNA synthesis. In embodiments, the method or use includes modulation (e.g., inhibition or reduction) of cell growth. In embodiments, the method or use includes modulation (e.g., inhibition or reduction) of cell proliferation. In embodiments, the method or use includes modulation (e.g., inhibition or reduction) of epithelial cell proliferation. In embodiments, the method or use includes modulation (e.g., activation or increasing) of the degradation of ER. In embodiments, the method or use includes modulation (e.g., activation or increasing) of the ubiquitination of ER. In embodiments, the method or use includes modulation (e.g., activation or increasing) of the degration of ER by the proteasome. In embodiments, the method or use includes modulation (e.g., inhibition or reduction) of ER interaction with AP-1, NF-κB, MAPK, PI3K, or AKT kinase. In embodiments, the method or use includes modulation (e.g., inhibition or reduction) of ER phosphorylation. In embodiments, the method or use includes modulation (e.g., activation or increasing) of tumor cell apoptosis. In embodiments, the method or use includes modulation (e.g., activation or increasing) of cancer cell apoptosis. In embodiments, the method or use includes modulation (e.g., activation or increasing) of ER expressing cell apoptosis. In embodiments, the method or use includes modulation (e.g., inhibition or reduction) of ER translocation to the nucleus. In embodiments, the method or use includes modulation (e.g., inhibition or reduction) of ER translocation to the cytosol.

In embodiments of the method or use, the method or use includes administering a compound described herein.

F. EXAMPLES

1. Compound Design and Synthesis

Designed herein are new compounds based on the knowledge of how the ER antagonists, e.g., 4-hydroxy-tamoxifen, OHT, bind to the ER and prevent the downstream message to grow rapidly. The phenolic hydroxyl group of OHT binds to the same part of the ligand binding domain (LBD) as does the phenolic hydroxyl group of E2 but, because of the hindered basic amino group in OHT (not present in E2), the way the protein folds around the bound molecule is altered (helix 12 folds in an unusual way) and the signal for DNA synthesis and cancer growth is inhibited. Therefore compounds were designed which are analogues of estradiol but with an additional large substituent at C11 of the steroid molecule. In particular a series of 11β-aryloxy estradiols, 1, were prepared having a basic amine positioned on the aryl ring. Molecules have been designed to bind in the LDB but not allow helix 12 to fold in an agonist mode but rather in an antagonist mode in a way similar to that of the ER antagonists.

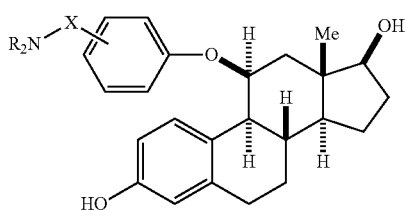

The synthesis of the molecules began from the known ketone 3, itself prepared in four steps from estradiol 2 (Synthesis 1). Reduction of the ketone 3 with sodium borohydride gave the expected 11β-alcohol 4 due to steric hindrance toward attack of hydride from the 3-face. Formation of the anion of 4 with potassium hydride in THF/DMF followed by addition of 4-fluoronitrobenzene afforded the desired nitrophenyl ether 5 via a facile $S_NAr$ reaction. Reduction of the nitro group of 5 with nickel boride gave the aminophenyl ether 6. Removal of the two benzyl ethers from 6 by catalytic hydrogenolysis gave the first analogue, the simple aniline 7, namely 11β-(4-amino-phenyloxy)estradiol. The analogues having a three-atom linker between the aryl ring and the basic amine were all prepared by the same route. Thus the aniline 6 was treated with chloroacetyl chloride in the presence of DMAP to give the intermediate chloromethyl amide which was immediately reacted with any of several secondary amines, e.g., dimethylamine, morpholine, pyrrolidine, and piperidine, to give the amides. Again hydrogenolysis of the benzyl ethers using hydrogen and a palladium catalyst gave the desired analogues, 8a-d (a: $R_2=Me_2$; b: $R_2=(CH_2CH_2)_2O$; c: $R_2=(CH_2)_4$; d: $R_2=(CH_2)_5$). After coupling of 6 with the acid chloride to give the amide, hydride reduction afforded the 2-(dialkylamino) ethyl amines, the benzyl ethers of which were hydrogenolyzed to give another set of analogues 9a-d, namely the N-(2-aminoethyl)anilines. In addition the 4-amino group was completely removed to give the simple 11β-phenyl ether 10.

The availability of this bis(benzyl) aniline 6 allowed for the rapid synthesis of several other analogues (Synthesis 2). Thus reacting 3-chloropropionyl chloride with 6 followed by displacement of the chloride with the secondary amines and subsequent hydrogenolysis afforded the analogues with a 5-atom side chain ending in the basic amine, 11a-d. Likewise using 4-chlorobutanoyl chloride, after displacement of the chloride with the secondary amines and subsequent hydrogenolysis, one obtained the analogues with a 6-atom side chain ending in the basic amine, 12a-d. Finally following the same route starting with 5-chloropentanoyl chloride gave the analogues with a 7-atom side chain, 13a-d. Again after coupling of 6 with the 3-carbon acid chloride to give the amide, hydride reduction afforded the 2-(dialkylamino) ethyl amines, the benzyl ethers of which were hydrogenolyzed to give another set of analogues 14a-d, namely the N-(3-aminopropyl)anilines. By substituting the 4-fluoronitrobenzene unit for other aryl fluorides, one could prepare several other sets of analogues. Thus alkylation of the 11β-alcohol 4 with 2,4-difluoronitrobenzene led to the 3-fluoro-4-nitrophenyl ether (which after hydrogenolysis gave the analogue 15). From that compound were prepared the 16 analogues, 17a-d, 18a-d, 19a-d, and 20a-d and the unsubstituted aniline 16 (Synthesis 3). In a similar manner, using 4-fluoro-3-trifluoro-methylnitrobenzene to alkylate the anion of 4 resulted in the 3-trifluoromethyl-4-nitrophenyl ether (which after hydrogenolysis gave the analogue 21) and thus the 16 additional analogues, 23a-d, 24a-d, 25a-d, and 26a-d and the unsubstituted aniline 22.

Synthesis 1: Preparation of the Novel ER Antagonists 7-10.

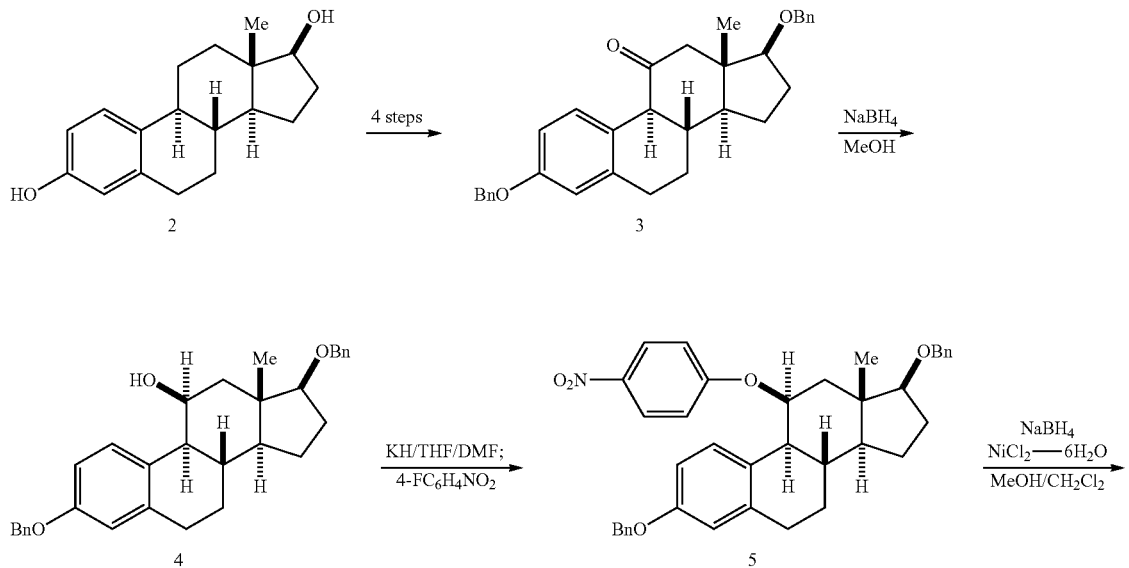

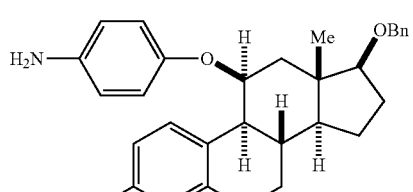
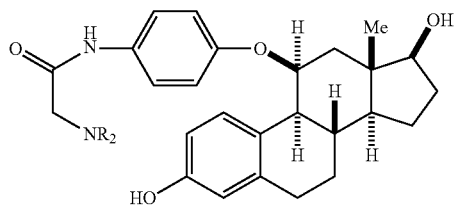
-continued
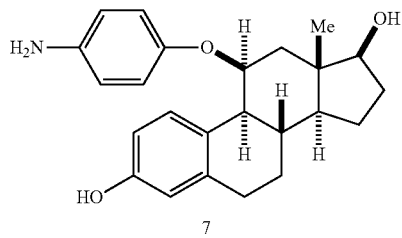
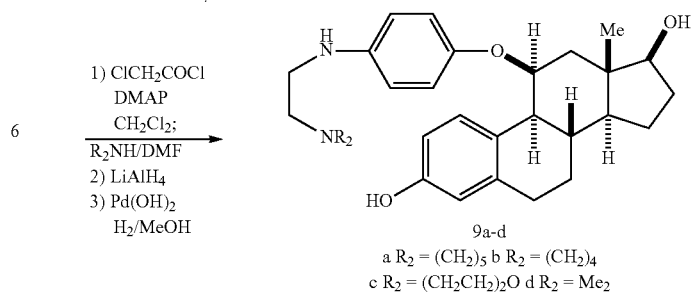
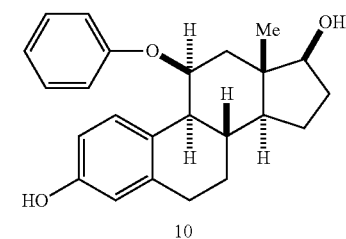
Synthesis 2: Preparation of the Novel ER Antagonists 11-14.
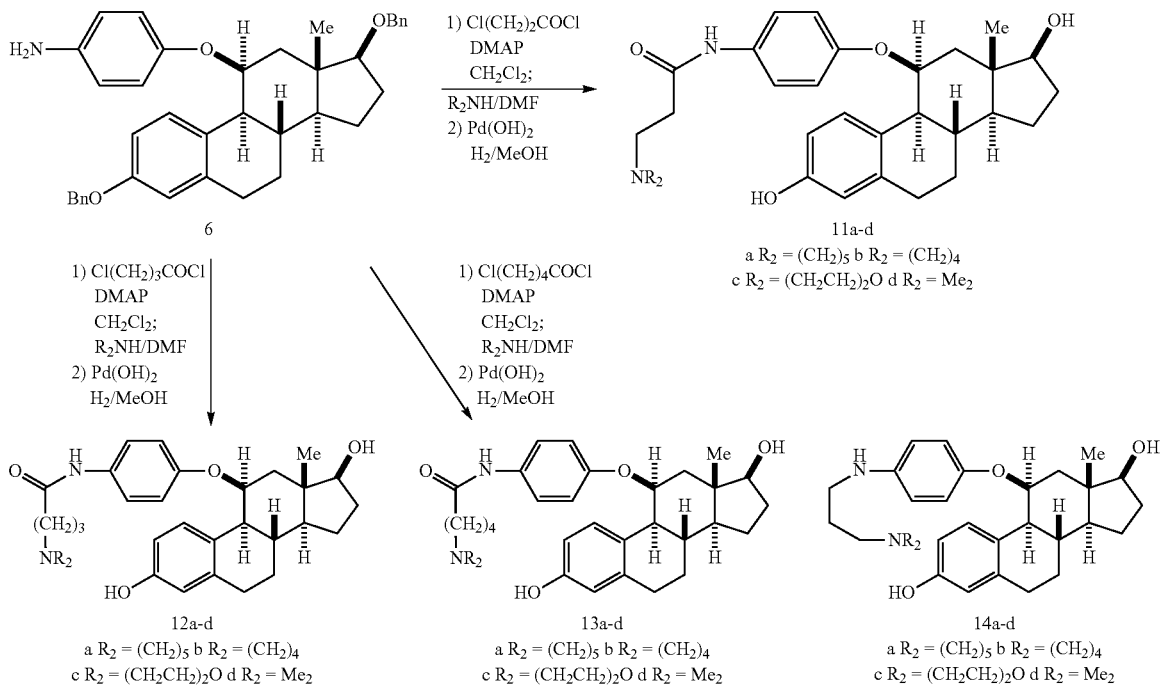

Synthesis 3: Preparation of the Novel ER Antagonists 15-26.

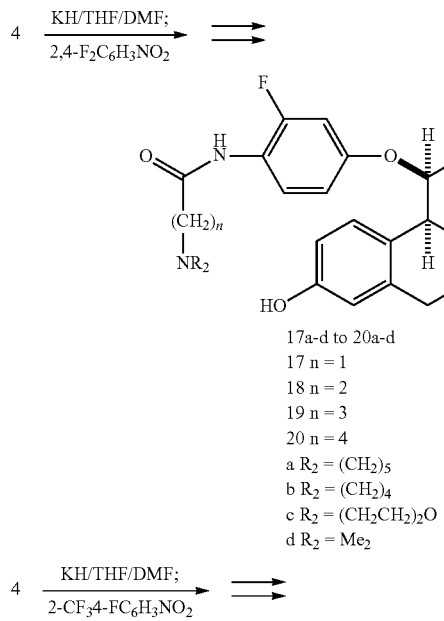

17a-d to 20a-d
17 n = 1
18 n = 2
19 n = 3
20 n = 4
a $R_2$ = $(CH_2)_5$
b $R_2$ = $(CH_2)_4$
c $R_2$ = $(CH_2CH_2)_2O$
d $R_2$ = $Me_2$

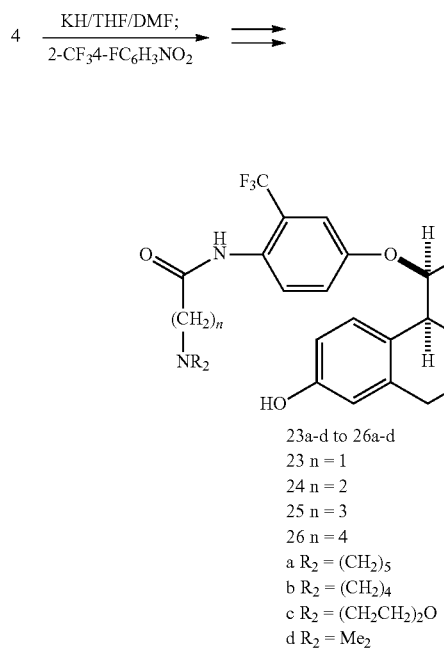

23a-d to 26a-d
23 n = 1
24 n = 2
25 n = 3
26 n = 4
a $R_2$ = $(CH_2)_5$
b $R_2$ = $(CH_2)_4$
c $R_2$ = $(CH_2CH_2)_2O$
d $R_2$ = $Me_2$

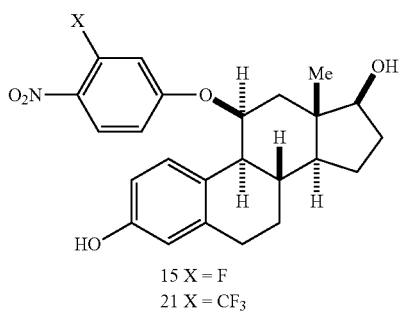

15 X = F
21 X = $CF_3$

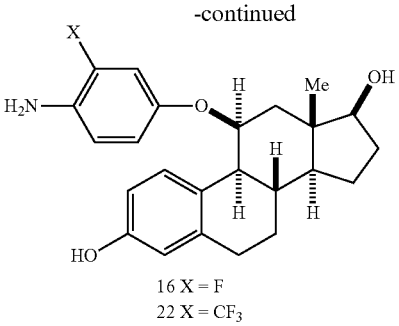

16 X = F
22 X = $CF_3$

General:

Tetrahydrofuran (THF) was distilled from benzoquinone ketyl radical under an argon atmosphere. Dichloromethane, toluene, benzene, and pyridine were distilled from calcium hydride under an argon atmosphere. Anhydrous N,N-dimethylformamide (DMF) was purchased from Sigma-Aldrich. All other solvents or reagents were purified according to literature procedures. (8S,9S,13S,14S,17S)-3,17-bis(Benzyloxy)-13-methyl-6,7,8,9,12,13,14,15,16,17-decahydro-11H-cyclopenta[a]phenanthren-11-one (11-ketone) was prepared using literature procedures.

Instrumentation:

$^1$H NMR, $^{13}$C NMR, and $^{19}$F NMR spectra were obtained at 300 MHz, 400 MHz, or 500 MHz for proton, 75 MHz, 100 MHz, or 125 MHz for carbon, and 282 MHz, or 376 MHz for fluorine are so indicated. The chemical shifts are reported in parts per million (ppm, δ). The coupling constants are reported in Hertz (Hz) and the resonance patterns are reported with notations as the following: br (broad), s (singlet), d (double), t (triplet), q (quartet) and m (multiplet). High-resolution mass spectra were measured on a time-of-flight LC-MS. Thin-layer chromatography (TLC) was carried out using precoated silica gel sheets. Visual detection was performed with ultraviolet light, p-anisaldehyde stain, potassium permanganate stain or iodine. Flash chromatography was performed using silica gel P60 (60 A, 40-63 m) with compressed air.

(8S,9S,11S,13S,14S,17S)-3,17-bis(Benzyloxy)-13-methyl-7,8,9,11,12,13,14,15,16,17-deca-hydro-6H-cyclopenta[a]phenanthren-11-ol A solution of sodium borohydride (12 wt. % in 14 M NaOH, 43.2 µL, 0.188 mmol) was added gradually to a solution of the bis(benzyl-oxy)ketone (0.1459 g, 0.313 mmol) in MeOH (3.0 mL) at 0° C. The mixture was stirred at 22° C. until TLC indicated complete consumption of the starting material. An aqueous saturated $NH_4Cl$ solution was added to quench the reaction. Ethyl acetate (3×40 mL) was added to the mixture. The combined organic phases were washed with water and brine, and dried over anhydrous $MgSO_4$. Flash column chromatography on silica gel eluting with 6/1 hexanes/ethyl acetate gave the target compound, the 11β-alcohol. 1H NMR (400 MHz, $CDCl_3$): δ 7.23-7.50 (m, 10H), 7.21 (d, J=8.5 Hz, 1H), 6.83 (dd, J=8.6, 2.7 Hz, 1H), 6.76 (d, J=2.4 Hz, 1H), 5.04 (s, 2H), 4.71 (m, 1H), 4.61 (d, J=12.1 Hz, 1H), 4.57 (d, J=12.1 Hz, 1H), 3.49 (dd, J=8.6, 7.6 Hz, 1H), 2.75-2.89 (m, 2H), 2.33-2.45 (m, 2H), 1.13 (s, 3H), 0.81-2.10 (m, 10H). $^{13}$C NMR (100 MHz, $CDCl_3$): δ 157.0, 140.1, 139.2, 137.2, 128.6 (2C), 128.3 (2C), 128.2, 127.9, 127.4 (2C), 127.32 (2C), 127.30, 126.1, 115.7, 113.1, 88.8, 71.6, 69.9, 67.7, 50.9, 50.1, 43.9, 43.1, 33.1, 30.0, 27.9, 26.7, 23.0, 14.2.

General Procedure: (8S,9S,11S,13S,14S,17S)-3,17-bis(Benzyloxy)-13-methyl-11-(4-nitro-phenoxy)-7,8,9,11,12,13,14,15,16,17-decahydro-6H-cyclopenta[a]phenanthrene A solution of the 11β-alcohol (0.117 g, 0.25 mmol) in anhydrous THF (2.0 mL) was added gradually to the solution of potassium hydride (25 mg, 0.625 mmol) in DMF (1.0 mL) at 0° C. The mixture was stirred for 10 min at 0° C. The solution of 1-fluoro-4-nitrobenzene (80 μL, 0.75 mmol) in THF (0.5 mL) was added slowly to the reaction system. The reaction was stirred until TLC indicated complete consumption of the starting material. A saturated NH$_4$Cl aqueous solution was added to quench the reaction. Ethyl acetate (3×40 mL) was added to the mixture. The combined organic phases were washed with water and brine, and dried over anhydrous MgSO$_4$. Flash column chromatography on silica gel eluting with 6/1 hexanes/ethyl acetate gave the target compound, the 4-nitrophenyl ether. $^1$H NMR (400 MHz, CDCl$_3$) δ 8.18 (d, J=9.3 Hz, 2H), 8.13 (d, J=9.4 Hz, 1H), 7.10-7.39 (m, 8H), 6.91 (d, J=9.3 Hz, 2H), 6.84 (d, J=8.7 Hz, 1H), 6.73 (d, J=2.6 Hz, 1H), 6.61 (m, 2H), 5.35 (m, 1H), 4.98 (s, 2H), 4.54 (d, J=12.2 Hz, 1H), 4.44 (d, J=12.2 Hz, 1H), 3.50 (dd, J=8.1, 8.1 Hz, 1H), 2.79-2.96 (m, 2H), 2.60 (d, J=10.9 Hz, 1H), 2.51 (dd, J=14.2, 2.4 Hz, 1H), 1.95-2.08 (m, 2H), 0.95 (s, 3H), 0.75-1.8 (m, 7H). $^{13}$C NMR (100 MHz, CDCl$_3$): δ 163.0, 156.8, 141.2, 139.0, 138.6, 137.2, 129.1, 128.5 (2C), 128.3 (2C), 128.0, 127.9, 127.4 (2C), 127.3, 126.3 (2C), 126.0 (2C), 115.2 (2C), 112.6, 110.2, 88.4, 73.1, 71.6, 69.9, 50.6, 48.7, 43.0, 40.3, 39.4, 33.7, 27.6, 27.3, 23.1, 13.8.

General Procedure: (8S,9S,11S,13S,14S,17S)-11l-(4-aminophenoxy)-13-methyl-7,8,9,11,12,13,14,15,16,17-decahydro-6H-cyclopenta[a]phenanthrene-3,17-diol, JD105

Sodium borohydride (30 mg, 0.79 mmol) was added gradually to a solution of NiCl$_2$.6H$_2$O (59 mg, 0.25 mmol) and the 11β-(4-nitrophenyl)ether (0.121 g, 0.205 mmol) in MeOH (1.5 mL) and dichloromethane (3.0 mL) at 0° C. The mixture was stirred at 22° C. until TLC indicated the complete consumption of the starting material. Diethyl ether (15 mL) and citric acid aqueous solution (5%, 10 mL) was added and stirred vigorously to quench the reaction. Diethyl ether (3×40 mL) was added to the mixture. The combined organic phases were washed with water and brine, and dried over anhydrous MgSO$_4$. The mixture was concentrated. The resulting residue was dissolved in MeOH (15 mL) and added with Pd(OH)$_2$ (20 mg). A stream of argon was passed over the mixture and then the argon was replaced with hydrogen and the mixture was stirred vigorously for 1 h. The mixture was filtered through a thick pad of Celite and the organic phase was evaporated. The residue was purified via flash column chromatography on silica gel eluting with 6/1 hexanes/ethyl acetate gave the target compound, the 4-aminophenyl ether diol. $^1$H NMR (500 MHz, CDCl$_3$) δ 6.99 (d, J=8.6 Hz, 1H), 6.76 (d, J=8.4 Hz, 2H), 6.65 (d, J=8.4 Hz, 2H), 6.58 (s, 1H), 6.53 (d, J=7.9 Hz, 1H), 5.16 (m, 1H), 3.74 (m, 1H), 1.00 (s, 3H), 0.69-3.0 (m, 17H). $^{13}$C NMR (125 MHz, CDCl$_3$): δ 153.3, 150.9, 139.4, 138.7, 128.5, 126.8, 116.8 (2C), 116.6 (2C), 115.5, 113.0, 82.4, 72.2, 50.8, 49.0, 43.0, 38.3, 34.0, 30.5, 29.6, 27.4, 23.1, 12.9.

General Procedure: N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-2-(dimethyl-amino)acetamide Sodium borohydride (30 mg, 0.79 mmol) was added gradually to a solution of NiCl$_2$.6H$_2$O (59 mg, 0.25 mmol) and 11β-(4-nitrophenyl)ether (0.121 g, 0.205 mmol) in MeOH (1.5 mL) and dichloromethane (3.0 mL) at 0° C. The mixture was stirred at 22° C. until TLC indicated the complete consumption of the starting material. Diethyl ether (15 mL) and citric acid aqueous solution (5%, 10 mL) was added and stirred vigorously to quench the reaction. Diethyl ether (3×40 mL) was added to the mixture. The combined organic phases were washed with water and brine, dried over anhydrous MgSO$_4$. The mixture was concentrated. The resulting residue was dissolved in dichloromethane (2.0 mL) and DMAP (cat.) and Et$_3$N (0.82 mmol) were added. Chloroacetyl chloride (0.65 mmol) was added gradually to the mixture at 0° C. and the reaction mixture was stirred at 22° C. for 2 h. Ethyl acetate (3×40 mL) was added to the mixture. The combined organic phases were washed with water and brine, and dried over anhydrous MgSO$_4$. The organic phase was concentrated. The resulting residue was dissolved in dimethylformamide (2.0 mL) and dimethylamine (1.0 mmol) was added to the reaction system at 22° C. The reaction was stirred until TLC indicated the complete consumption of the starting material. Ethyl acetate (3×40 mL) was added to the mixture. The combined organic phases were washed with water and brine, dried over anhydrous MgSO$_4$ and the organic phase was evaporated. The residue was purified via flash column chromatography on silica gel eluting with 2/1 hexanes/ethyl acetate gave the targeted compounds. $^1$H NMR (300 MHz, CDCl$_3$): δ 9.00 (s, 1H), 7.12-7.53 (m, 12H), 6.95 (d, J=8.4 Hz, 1H), 6.85 (d, J=8.9 Hz, 2H), 6.68 (d, J=2.6 Hz, 1H), 6.65 (dd, J=8.4, 2.4 Hz, 1H), 5.20 (m, 1H), 4.98 (s, 2H), 4.51 (d, J=12.3 Hz, 1H), 4.47 (d, J=12.3 Hz, 1H), 3.47 (m, 2H), 2.38 (s, 6H), 1.01 (s, 3H), 0.80-3.11 (m, 14H). $^{13}$C NMR (75 MHz, CDCl$_3$): δ 168.4, 156.6, 154.5, 139.1, 138.5, 137.4, 130.5, 128.8, 128.5 (2C), 128.3 (2C), 127.8, 127.5 (2C), 127.4 (2C), 127.35, 126.6, 121.3 (2C), 115.8 (2C), 115.0, 112.6, 88.6, 71.9, 71.6, 69.9, 63.6, 51.0, 48.9, 46.0 (2C), 43.2, 39.4, 33.7, 29.7, 27.8, 27.5, 23.1, 13.7. HR-MS (ESI) calcd for [C$_{42}$H$_{48}$N$_2$O$_4$ H]$^+$ 645.3693, found 645.3707.

General Procedure: N-(4-(((8S,9S,11S,13S,14S,17S)-3,17-Dihydroxy-13-methyl-7,8,9,11,12,13,14,15,16,17-decahydro-6H-cyclopenta[a]phenanthren-11-yl)oxy)phenyl)-2-(dimethyl-amino)acetamide, JD104

To a solution of the dibenzyl amide (0.065 g, 0.1 mmol) in MeOH (5.0 mL) was added Pd(OH)$_2$ (10 mg). Argon was passed over the mixture and then the argon was replaced with hydrogen and the mixture was stirred vigorously for 1 h. The mixture was filtered through a thick pad of Celite and the organic phase was evaporated. The residue was purified via flash column chromatography on silica gel eluting with 15/1 dichloro-methane/MeOH to give the target compound, the amide diol. $^1$H NMR (400 MHz, MeOD): δ 7.41 (d, J=9.7 Hz, 2H), 6.88 (d, J=8.7 Hz, 1H), 6.86 (d, J=9.7 Hz, 2H), 6.48 (d, J=2.7 Hz, 1H), 6.40 (dd, J=8.7, 2.7 Hz, 1H), 5.31 (m, 1H), 3.60-3.69 (m, 1H), 3.33 (s, 2H), 2.40 (br s, 6H), 0.88 (s, 3H), 0.80-3.38 (m, 13H). $^{13}$C NMR (100 MHz, MeOD): δ 169.4, 156.3, 154.8, 138.6, 130.6, 127.7, 126.8, 122.4 (2C), 115.4 (2C), 115.1, 112.9, 81.9, 72.3, 62.8, 50.8, 49.2, 44.8, 43.2 (2C), 38.4, 34.6, 29.8, 29.5, 27.6, 23.0, 12.7. HR-MS (ESI) calcd for $[C_{28}H_{37}N_2O_4 \text{ H}]^+$ 465.2753, found 465.2759.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-2-morpholinoacetamide $^1$H NMR (400 MHz, CDCl$_3$): δ 8.91 (s, 1H), 7.18-7.49 (m, 12H), 6.96 (d, J=8.9 Hz, 1H), 6.86 (d, J=8.9 Hz, 2H), 6.71 (d, J=2.6 Hz, 1H), 6.65 (dd, J=8.6, 2.6 Hz, 1H), 5.22 (m, 1H), 4.98 (s, 2H), 4.51 (d, J=12.0 Hz, 1H), 4.47 (d, J=12.0 Hz, 1H), 4.09 (m, 1H), 3.70-3.82 (m, 2H), 3.40-3.52 (m, 1H), 1.01 (s, 3H), 0.80-3.20 (m, 20H). $^{13}$C NMR (100 MHz, CDCl$_3$): δ 167.6, 156.6, 154.6, 139.1, 138.5, 137.3, 130.2, 128.8, 128.5 (2C), 128.3 (2C), 127.8, 127.5 (2C), 127.4, 127.3 (2C), 126.5, 121.4 (2C), 115.8 (2C), 114.9, 112.6, 88.5, 71.9, 71.5, 69.9, 67.1 (2C), 62.4, 53.8 (2C), 50.9, 48.9, 43.1, 39.3, 33.7, 29.8, 27.7, 23.1, 19.1, 13.7.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-2-morpholinoacetamide, JD103

$^1$H NMR (400 MHz, MeOD): δ 7.41 (d, J=9.0 Hz, 2H), 6.88 (d, J=8.0 Hz, 1H), 6.85 (d, J=9.0 Hz, 2H), 6.48 (d, J=2.3 Hz, 1H), 6.40 (dd, J=8.5, 2.7 Hz, 1H), 5.30 (m, 1H), 3.75 (t, J=4.0 Hz, 4H), 3.13 (s, 2H), 2.57 (t, J=4.0 Hz, 4H), 0.88 (s, 3H), 0.8-3.3 (m, 14H). $^{13}$C NMR (100 MHz, MeOD): δ 169.1, 154.9, 154.4, 138.2, 130.1, 127.3, 126.3, 122.0 (2C), 115.1 (2C), 114.8, 112.5, 81.5, 71.9, 66.4 (2C), 61.8, 53.4 (2C), 50.4, 48.7, 42.8, 38.0, 34.2, 29.4, 29.1, 27.2, 22.6, 12.3. HR-MS (ESI) calcd for $[C_{30}H_{38}N_2O_5 \text{ H}]^+$ 507.2859, found 507.2843.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-2-(pyrrolidin-1-yl)acetamide $^1$H NMR (300 MHz, CDCl$_3$): δ 8.99 (s, 1H), 7.20-7.51 (m, 12H), 6.95 (d, J=8.7 Hz, 1H), 6.84 (d, J=8.7 Hz, 2H), 6.71 (d, J=2.8 Hz, 1H), 6.65 (dd, J=8.9, 3.0 Hz, 1H), 5.20 (m, 1H), 4.98 (s, 2H), 4.51 (d, J=11.7 Hz, 1H), 4.47 (d, J=11.7 Hz, 1H), 3.47 (s, 2H), 2.70 (m, 4H), 1.86 (m, 4H), 1.05 (s, 3H), 0.80-3.56 (m, 14H). $^{13}$C NMR (75 MHz, CDCl$_3$): δ 168.8, 156.6, 154.5, 139.1, 138.5, 137.4, 130.5, 128.8, 128.5 (2C), 128.3 (2C), 127.8, 127.5 (2C), 127.4 (2C), 127.3, 126.6, 121.4 (2C), 115.8 (2C), 115.0, 112.5, 88.5, 71.9, 71.6, 69.9, 59.7, 54.6 (2C), 51.0, 48.9, 43.1, 39.4, 33.7, 29.8, 27.8, 27.5, 24.1 (2C), 23.1, 13.7.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-2-(pyrrolidin-1-yl)acetamide, JD102

$^1$H NMR (400 MHz, MeOD): δ 7.40 (d, J=8.9 Hz, 2H), 6.88 (d, J=8.0 Hz, 1H), 6.85 (d, J=8.9 Hz, 2H), 6.48 (d, J=2.7 Hz, 1H), 6.40 (dd, J=8.0, 2.4 Hz, 1H), 5.32 (m, 1H), 3.65 (m, 1H), 3.40 (s, 2H), 2.78 (m, 4H), 1.88 (m, 4H), 0.88 (s, 3H), 0.80-2.60 (m, 13H). $^{13}$C NMR (100 MHz, MeOD): δ 170.1, 156.3, 155.8, 139.6, 131.6, 128.7, 123.4 (2C), 123.3, 116.5 (2C), 116.2, 113.9, 79.3, 73.3, 55.4 (2C), 51.8, 50.2, 49.5, 44.2, 39.4, 35.6, 30.8, 30.5, 28.6, 24.6 (2C), 24.0, 13.8. MS (ESI) m/z (%) 491 ([M+1]$^+$, 100), 447 (15), 155 (28). HR-MS (ESI) calcd for $[C_{20}H_{22}O_5 \text{ H}]^+$ 491.2910, found 491.2926.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-2-(piperidin-1-yl)acetamide $^1$H NMR (300 MHz, CDCl$_3$): δ 9.05 (s, 1H), 7.10-7.55 (m, 12H), 6.95 (d, J=8.4 Hz, 1H), 6.85 (d, J=9.0 Hz, 2H), 6.71 (d, J=2.4 Hz, 1H), 6.66 (d, J=8.4 Hz, 1H), 5.22 (m, 1H), 4.98 (s, 2H), 4.51 (d, J=12.3 Hz, 1H), 4.47 (d, J=12.3 Hz, 1H), 2.72 (m, 4H), 1.86 (m, 4H), 1.01 (s, 3H), 0.70-3.60 (m, 18H). $^{13}$C NMR (75 MHz, CDCl$_3$): δ 168.5, 156.7, 154.4, 139.0, 138.4, 137.3, 130.5, 128.7, 128.5 (2C), 128.2 (2C), 127.8, 127.4 (2C), 127.3 (2C), 127.27, 126.5, 121.4 (2C), 115.7 (2C), 114.9, 112.5, 88.5, 71.8, 71.5, 69.8, 59.6, 54.5 (2C), 51.0, 48.8, 43.1, 39.3, 38.5, 33.7, 29.7, 29.6, 27.7, 24.0 (2C), 23.0, 14.1.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-2-(piperidin-1-yl)acetamide, JD101

$^1$H NMR (400 MHz, MeOD): δ 7.40 (d, J=8.9 Hz, 2H), 6.88 (d, J=8.4 Hz, 1H), 6.85 (d, J=8.9 Hz, 2H), 6.47 (d, J=2.6 Hz, 1H), 6.39 (dd, J=8.4, 2.6 Hz, 1H), 5.31 (m, 1H), 3.43 (s, 2H), 2.81 (m, 4H), 1.89 (m, 4H), 0.88 (s, 3H), 0.75-3.7 (m, 16H). $^{13}$C NMR (100 MHz, MeOD): δ 169.9, 156.3, 155.8, 139.6, 131.6, 128.7, 127.7, 123.4 (2C), 116.4 (2C), 116.1, 113.9, 82.9, 73.3, 61.5, 59.9, 55.4, 51.8, 50.2, 44.2 (2C), 39.4, 35.6, 30.8, 30.5, 28.6, 24.6 (2C), 24.0, 13.7. HR-MS (ESI) calcd for $[C_{31}H_{40}N_2O_4 \text{ H}]^+$ 491.2910, found 491.2892.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-3-morpholinopropanamide $^1$H NMR (300 MHz, CDCl$_3$): δ 10.5 (s, 1H), 7.20-7.50 (m, 12H), 6.96 (d, J=8.4 Hz, 1H), 6.85 (d, J=8.7 Hz, 2H), 6.71 (d, J=2.4 Hz, 1H), 6.65 (dd, J=7.7, 2.4 Hz, 1H), 5.20 (m, 1H), 4.98 (s, 2H), 4.51 (d, J=12.0 Hz, 1H), 4.47 (d, J=12.0 Hz, 1H), 3.82 (t, J=4.2 Hz, 4H), 2.61 (t, J=4.2 Hz, 4H), 1.01 (s, 3H), 0.72-3.78 (m, 18H). $^{13}$C NMR (75 MHz, CDCl$_3$): δ 169.9, 156.6, 154.1, 139.1, 138.5, 137.3, 131.3, 128.8, 128.5 (2C), 128.2 (2C), 127.8, 127.4 (2C), 127.32, 127.30 (2C), 126.5, 121.2 (2C), 115.8 (2C), 114.9, 112.5, 88.5, 71.9, 71.4, 69.9, 67.0 (2C), 54.3, 52.8 (2C), 50.9, 48.9, 43.1, 39.3, 33.7, 32.1, 29.7, 27.7, 27.4, 23.0, 13.7.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-3-morpholinopropanamide, JD106

$^1$H NMR (300 MHz, MeOD): δ 7.38 (d, J=9.0 Hz, 2H), 6.89 (d, J=8.4 Hz, 1H), 6.85 (d, J=9.0 Hz, 2H), 6.48 (d, J=2.7 Hz, 1H), 6.40 (dd, J=8.4, 2.4 Hz, 1H), 5.32 (m, 1H), 3.71 (t, J=4.5 Hz, 4H), 2.54 (t, J=4.5 Hz, 4H), 0.89 (s, 3H), 0.80-3.69 (m, 18H). $^{13}$C NMR (75 MHz, MeOD): δ 172.5, 156.1, 155.8, 139.6, 132.2, 128.7, 127.7, 123.2 (2C), 116.5 (2C), 116.2, 113.9, 82.9, 73.3, 67.7 (2C), 55.6, 54.4 (2C), 51.8, 50.2, 44.2, 39.4, 35.6, 34.4, 30.8, 30.5, 28.6, 24.0, 13.7. HR-MS (ESI) calcd for [C$_{31}$H$_{40}$N$_2$O$_5$ H]$^+$ 521.3016, found 521.3010.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-3-(piperidin-1-yl)propan-amide $^1$H NMR (300 MHz, CDCl$_3$): δ 10.75 (s, 1H), 7.20-7.55 (m, 12H), 6.96 (d, J=8.4 Hz, 1H), 6.84 (d, J=8.7 Hz, 2H), 6.71 (d, J=2.4 Hz, 1H), 6.66 (dd, J=8.3, 2.4 Hz, 1H), 5.21 (m, 1H), 4.98 (s, 2H), 4.50 (d, J=11.6 Hz, 1H), 4.48 (d, J=11.6 Hz, 1H), 2.60 (m, 4H), 1.72 (m, 4H), 1.01 (s, 3H), 0.70-3.75 (m, 20H). $^{13}$C NMR (75 MHz, CDCl$_3$): δ 169.9, 156.6, 154.0, 139.1, 138.4, 137.3, 131.6, 128.8, 128.5 (2C), 128.2 (2C), 127.8, 127.4 (2C), 127.31 (2C), 127.27, 126.5, 121.1 (2C), 115.8 (2C), 114.9, 112.5, 88.5, 71.8, 71.5, 69.9, 54.3, 53.6 (2C), 51.0, 48.9, 43.1, 39.3, 33.7, 32.4, 29.7, 27.7, 27.5, 25.5 (2C), 23.8, 23.0, 13.7. HR-MS (ESI) calcd for [C$_{46}$H$_{54}$N$_2$O$_4$ H]$^+$ 699.4162, found 699.4180.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-3-(piperidin-1-yl)propanamide, JD107

$^1$H NMR (400 MHz, MeOD): δ 7.41 (d, J=8.8 Hz, 2H), 6.88 (d, J=8.2 Hz, 1H), 6.85 (d, J=8.8 Hz, 2H), 6.48 (d, J=2.6 Hz, 1H), 6.40 (dd, J=8.2, 2.6 Hz, 1H), 5.31 (m, 1H), 2.87 (m, 4H), 1.84 (m, 4H), 0.87 (s, 3H), 0.79-3.75 (m, 20H). $^{13}$C NMR (100 MHz, MeOD): δ 169.7, 156.2, 155.8, 139.6, 132.0, 128.7, 127.8, 123.2 (2C), 116.5 (2C), 116.2, 113.9, 82.8, 73.3, 54.6, 54.3, 51.8, 50.1, 44.2 (2C), 39.4, 35.6, 31.4, 30.9, 30.5, 28.6, 24.4 (2C), 24.0, 22.8, 13.8.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-3-(pyrrolidin-1-yl)propan-amide $^1$H NMR (300 MHz, CDCl$_3$): δ 10.50 (s, 1H), 7.20-7.49 (m, 12H), 6.96 (d, J=8.7 Hz, 1H), 6.84 (d, J=9.0 Hz, 2H), 6.71 (d, J=2.4 Hz, 1H), 6.66 (dd, J=8.6, 2.6 Hz, 1H), 5.20 (m, 1H), 4.98 (s, 2H), 4.50 (d, J=12.6 Hz, 1H), 4.48 (d, J=12.6 Hz, 1H), 2.85 (m, 4H), 1.92 (m, 4H), 1.00 (s, 3H), 0.82-3.55 (m, 18H). $^{13}$C NMR (75 MHz, CDCl$_3$): δ 169.4, 156.5, 154.1, 139.1, 138.4, 137.3, 131.3, 128.8, 128.4 (2C), 128.2 (2C), 127.7, 127.4 (2C), 127.3 (2C), 127.2, 126.5, 121.4 (2C), 115.7 (2C), 112.5, 112.5, 88.5, 71.8, 71.5, 69.8, 53.4 (2C), 51.5, 50.9, 48.8, 43.0, 39.2, 34.1, 33.6, 29.7, 27.7, 27.4, 23.5 (2C), 23.0, 13.6. HR-MS (ESI) calcd for [C$_{45}$H$_{52}$N$_2$O$_4$ H]$^+$ 685.4005, found 685.4021.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-3-(pyrrolidin-1-yl)propanamide, JD108

$^1$H NMR (400 MHz, MeOD): δ 7.40 (d, J=8.7 Hz, 2H), 6.87 (d, J=8.1 Hz, 1H), 6.84 (d, J=8.7 Hz, 2H), 6.50 (d, J=2.6 Hz, 1H), 6.42 (dd, J=8.1, 2.6 Hz, 1H), 5.27 (m, 1H), 2.87 (m, 4H), 1.27 (m, 4H), 0.88 (s, 3H), 0.80-3.74 (m, 18H). $^{13}$C NMR (75 MHz, MeOD): δ 169.0, 155.8, 155.3, 139.4, 131.5, 128.4, 127.4, 122.8 (2C), 116.3 (2C), 116.0, 113.7, 82.5, 73.0, 55.1 (2C), 52.1, 51.5, 43.9, 39.1, 35.2, 32.4, 30.5, 30.4, 30.3, 28.3, 23.8 (2C), 23.7, 13.6. HR-MS (ESI) calcd for [C$_{31}$H$_{40}$N$_2$O$_4$ H]$^+$ 505.3066, found 505.3045.

N-(4-(((8S,9S,11S,13S,14S,17S)-3,17-bis(Benzyloxy)-13-methyl-7,8,9,11,12,13,14,15,16,17-deca-hydro-6H-cyclopenta[a]phenanthren-11-yl)oxy)phenyl)-3-(dimethylamino)propan-amide $^1$H NMR (300 MHz, CDCl$_3$): δ 8.01 (s, 1H), 7.19-7.55 (m, 12H), 6.95 (d, J=8.4 Hz, 1H), 6.84 (d, J=8.9 Hz, 2H), 6.65 (d, J=2.6 Hz, 1H), 6.62 (dd, J=8.4, 2.4 Hz, 1H), 5.18 (m, 1H), 4.98 (s, 2H), 4.51 (d, J=11.3 Hz, 1H), 4.48 (d, J=11.3 Hz, 1H), 2.52 (s, 6H), 1.02 (s, 3H), 0.80-3.80 (m, 18H). $^{13}$C NMR (75 MHz, CDCl$_3$): δ 166.2, 156.5, 154.5, 139.0, 138.4, 137.2, 130.7, 128.7, 128.4 (2C), 128.2 (2C), 127.7, 127.3 (2C), 127.2 (2C), 126.8, 126.4, 121.7 (2C), 115.6 (2C), 114.9, 112.4, 88.4, 72.0, 71.4, 69.7, 50.8, 48.8, 45.8, 43.0 (2C), 39.2, 33.6, 29.7, 29.6, 27.6, 27.3, 23.0, 20.5, 13.6.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-3-(dimethylamino)propanamide, JD109

$^1$H NMR (300 MHz, MeOD): δ 7.38 (d, J=9.0 Hz, 2H), 6.89 (d, J=8.4 Hz, 1H), 6.84 (d, J=9.0 Hz, 2H), 6.48 (d, J=2.7 Hz, 1H), 6.41 (dd, J=8.4, 2.7 Hz, 1H), 5.28 (m, 1H), 2.14 (s, 6H), 0.88 (s, 3H), 0.80-3.70 (m, 18H). $^{13}$C NMR (75 MHz, MeOD): δ 175.1, 156.0, 155.8, 139.5, 132.4, 128.7, 127.7, 123.3 (2C), 116.4 (2C), 116.2, 113.9, 82.9, 73.3, 51.8, 50.1, 44.2 (2C), 39.4, 35.6, 30.8, 30.7, 30.5, 28.6, 24.0, 13.7, 10.4.

N-(4-(((8S,9S,11S,13S,14S,17S)-3,17-bis(Benzyloxy)-13-methyl-7,8,9,11,12,13,14,15,16,17-deca-hydro-6H-cyclopenta[a]phenanthren-11-yl)oxy)phenyl)-4-morpholinobutanamide $^1$H NMR (300 MHz, CDCl$_3$): δ 8.15 (s, 1H), 7.20-7.50 (m, 12H), 6.97 (d, J=8.7 Hz, 1H), 6.85 (d, J=8.7 Hz, 2H), 6.71 (d, J=2.5 Hz, 1H), 6.67 (dd, J=8.4, 2.6 Hz, 1H), 5.19 (m, 1H), 4.99 (s, 2H), 4.52 (d, J=12.9 Hz, 1H), 4.49 (d, J=12.9 Hz, 1H), 3.75 (t, J=4.3 Hz, 4H), 2.53 (t, J=4.3 Hz, 4H), 1.03 (s, 3H), 0.9-3.8 (m, 20H). $^{13}$C NMR (75 MHz, CDCl$_3$): δ 170.8, 156.5, 154.3, 139.0, 138.4, 137.2, 130.8, 128.7, 128.4 (2C), 128.2 (2C), 127.7, 127.3 (2C), 127.26, 127.22 (2C), 126.4, 121.6 (2C), 115.7 (2C), 114.8, 112.4, 88.4, 71.8, 71.4, 69.7, 66.7 (2C), 57.4, 53.3 (2C), 50.8, 48.8, 43.0, 39.2, 35.1, 33.6, 29.7, 27.6, 27.3, 23.0, 21.7, 13.6. HR-MS (ESI) calcd for [C$_{46}$H$_{54}$N$_2$O$_5$ H]$^+$ 715.4111, found 715.4106.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-4-morpholinobutanamide, JD110

$^1$H NMR (300 MHz, MeOD): δ 7.40 (d, J=9.0 Hz, 2H), 6.88 (d, J=8.7 Hz, 1H), 6.85 (d, J=9.0 Hz, 2H), 6.49 (d, J=2.4 Hz, 1H), 6.41 (dd, J=8.1, 2.4 Hz, 1H), 5.28 (m, 1H), 3.82 (m, 4H), 2.49 (m, 4H), 0.88 (s, 3H), 0.80-3.70 (m, 20H). $^{13}$C NMR (75 MHz, MeOD): δ 173.0, 156.1, 155.8, 139.6, 132.1, 128.7, 127.8, 123.4 (2C), 116.5 (2C), 116.2, 113.9, 82.8, 73.3, 66.0 (2C), 58.6, 53.7 (2C), 51.8, 50.0, 44.2, 39.3, 35.6, 34.8, 30.8, 30.5, 28.6, 24.0, 21.6, 13.8.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-4-(pyrrolidin-1-yl)butan-amide $^1$H NMR (300 MHz, MeOD): δ 7.19-7.42 (m, 12H), 6.95 (d, J=8.8 Hz, 1H), 6.82 (d, J=9.0 Hz, 2H), 6.66 (d, J=2.7 Hz, 1H), 6.56 (dd, J=8.7, 2.8 Hz, 1H), 5.26 (m, 1H), 4.93 (s, 2H), 4.46 (d, J=11.4 Hz, 1H), 4.42 (d, J=11.4 Hz, 1H), 2.50 (m, 4H), 2.05 (m, 4H), 0.94 (s, 3H), 0.82-3.60 (m, 20H). $^{13}$C NMR (75 MHz, MeOD): δ 172.4, 157.9, 156.0, 140.4, 139.7, 139.0, 132.2, 130.2, 129.4, 129.3 (2C), 128.7 (2C), 128.6, 128.5 (2C), 128.46 (2C), 127.8, 123.4 (2C), 116.5 (2C), 115.8, 113.6, 90.2, 73.3, 72.8, 70.8, 55.9, 55.1 (2C), 54.8, 51.8, 50.0, 44.3, 40.2, 35.2, 34.2, 30.9, 28.7, 28.5, 24.0 (2C), 23.0, 14.4.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-4-(pyrrolidin-1-yl)butanamide, JD111

$^1$H NMR (300 MHz, MeOD): δ 7.38 (d, J=9.0 Hz, 2H), 6.88 (d, J=8.1 Hz, 1H), 6.85 (d, J=9.0 Hz, 2H), 6.48 (d, J=2.4 Hz, 1H), 6.40 (dd, J=8.7, 2.7 Hz, 1H), 5.33 (m, 1H), 3.00 (m, 4H), 1.95 (m, 4H), 0.89 (s, 3H), 0.79-3.80 (m, 20H). 13C NMR (75 MHz, MeOD): δ 172.7, 156.5, 156.3, 139.4, 132.5, 128.7, 128.0, 123.3 (2C), 116.5 (2C), 116.3, 114.0, 82.9, 73.3, 56.6, 54.9 (2C), 51.6, 50.1, 44.1, 39.3, 35.7, 34.9, 30.8, 30.6, 28.4, 24.3, 24.2 (2C), 24.1, 13.4.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-4-(piperidin-1-yl)butanamide $^1$H NMR (300 MHz, CDCl$_3$): δ 9.52 (s, 1H), 7.56 (d, J=8.7 Hz, 2H), 7.18-7.48 (m, 10H), 6.95 (d, J=8.7 Hz, 1H), 6.81 (d, J=9.0 Hz, 2H), 6.70 (d, J=2.4 Hz, 1H), 6.65 (dd, J=8.4, 2.4 Hz, 1H), 5.18 (m, 1H), 4.97 (s, 2H), 4.49 (d, J=12.3 Hz, 1H), 4.46 (d, J=12.3 Hz, 1H), 2.90 (m, 4H), 1.60 (m, 4H), 0.99 (s, 3H), 0.80-3.78 (m, 22H). $^{13}$C NMR (75 MHz, CDCl$_3$): δ 169.8, 156.5, 154.2, 139.1, 138.4, 137.3, 131.2, 128.8, 128.4 (2C), 128.2 (2C), 127.7, 127.4 (2C), 127.3 (2C), 127.2, 126.5, 121.6 (2C), 115.6 (2C), 114.9, 112.5, 88.4, 71.7, 71.4, 69.8, 60.6, 56.5, 53.5 (2C), 50.9, 48.8, 43.0, 39.2, 33.6, 31.4, 29.6 (2C), 27.7, 27.4, 23.0, 22.7, 20.3, 13.6. HR-MS (ESI) calcd for [C$_{47}$H$_{56}$N$_2$O$_4$ H]$^+$ 713.4318, found 713.4321.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-4-(piperidin-1-yl)butanamide, JD112

$^1$H NMR (300 MHz, MeOD): δ 7.38 (d, J=9.0 Hz, 2H), 6.89 (d, J=9.0 Hz, 1H), 6.84 (d, J=9.0 Hz, 2H), 6.48 (d, J=2.4 Hz, 1H), 6.40 (dd, J=8.4, 2.7 Hz, 1H), 5.29 (m, 1H), 2.50 (m, 4H), 1.65 (m, 4H), 0.88 (s, 3H), 0.80-3.71 (m, 22H). 13C NMR (75 MHz, MeOD): δ 173.5, 156.0, 155.8, 139.5, 132.2, 128.7, 127.7, 123.3 (2C), 116.4 (2C), 116.2, 113.9, 82.8, 73.3, 59.4, 55.2 (2C), 51.8, 50.1, 44.2, 39.3, 35.6, 35.5, 30.8, 30.5, 28.6, 26.1 (2C), 24.8, 24.0, 23.1, 13.7. HR-MS (ESI) calcd for [C$_{33}$H$_{44}$N$_2$O$_4$ H]$^+$ 533.3380, found 533.3358.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-4-(dimethylamino)butan-amide $^1$H NMR (300 MHz, CDCl$_3$): δ 9.50 (s, 1H), 7.15-7.70 (m, 12H), 6.97 (d, J=8.1 Hz, 1H), 6.84 (d, J=8.4 Hz, 2H), 6.71 (d, J=2.6 Hz, 1H), 6.68 (dd, J=8.4, 2.4 Hz, 1H), 5.21 (m, 1H), 4.98 (s, 2H), 4.51 (d, J=11.4 Hz, 1H), 4.49 (d, J=11.4 Hz, 1H), 2.41 (s, 6H), 1.02 (s, 3H), 0.79-3.80 (m, 20H). $^{13}$C NMR (75 MHz, CDCl$_3$): δ 171.1, 156.5, 154.0, 139.0, 138.4, 137.2, 131.5, 128.7, 128.4 (2C), 128.2 (2C), 127.7, 127.4 (2C), 127.3 (2C), 127.2, 126.5, 121.2 (2C), 115.7 (2C), 114.9, 112.4, 88.4, 71.8, 71.4, 69.8, 58.9, 50.8, 48.8, 45.0 (2C), 43.0, 39.2, 36.5, 33.6, 29.7, 27.6, 27.4, 23.0, 22.8, 13.6. HR-MS (ESI) calcd for [C$_{44}$H$_{52}$N$_2$O$_4$ H]$^+$ 673.4005, found 673.4008.

N-(4-(((8S,9S,11S,13S,14S,17S)-3,17-dihydroxy-13-methyl-7,8,9,11,12,13,14,15,16,17-deca-hydro-6H-cyclopenta[a]phenanthren-11-yl)oxy)phenyl)-4-(dimethylamino)butanamide, JD116

$^1$H NMR (300 MHz, MeOD): δ 7.42 (d, J=9.0 Hz, 2H), 6.88 (d, J=8.7 Hz, 1H), 6.84 (d, J=9.0 Hz, 2H), 6.49 (d, J=2.1 Hz, 1H), 6.42 (dd, J=8.6, 2.6 Hz, 1H), 5.29 (m, 1H), 2.90 (s, 6H), 0.87 (s, 3H), 0.80-3.70 (m, 20H). $^{13}$C NMR (75 MHz, MeOD): δ 172.4, 156.0, 155.7, 139.5, 132.0, 128.7, 127.7, 123.4 (2C), 116.4 (2C), 116.2, 113.9, 82.8, 73.3, 58.7, 51.7, 50.0, 44.1, 43.7 (2C), 39.3, 35.5, 34.2 30.8, 30.4, 28.5, 23.9, 21.6, 13.8. HR-MS (ESI) calcd for [C$_{30}$H$_{40}$N$_2$O$_4$ H]$^+$ 493.3066, found 493.3063.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-5-morpholinopentanamide $^1$H NMR (300 MHz, CDCl$_3$): δ 7.50 (s, 1H), 7.20-7.48 (m, 12H), 6.96 (d, J=8.4 Hz, 1H), 6.84 (d, J=9.0 Hz, 2H), 6.71 (d, J=2.4 Hz, 1H), 6.65 (dd, J=8.4, 2.4 Hz, 1H), 5.21 (m, 1H), 4.98 (s, 2H), 4.51 (d, J=12.8 Hz, 1H), 4.48 (d, J=12.8 Hz, 1H), 3.72 (t, J=4.2 Hz, 4H), 2.48 (t J=4.2 Hz, 4H), 1.01 (s, 3H), 0.80-3.70 (m, 22H). $^{13}$C NMR (75 MHz, CDCl$_3$): δ 170.9, 156.5, 154.4, 139.0, 138.4, 137.2, 130.6, 128.7, 128.4 (2C), 128.2 (2C), 127.7, 127.4 (2C), 127.3 (2C), 127.2, 126.4, 121.8 (2C), 115.7 (2C), 114.9, 112.5, 88.4, 71.8, 71.4, 69.8, 66.7 (2C), 58.4, 53.5 (2C), 50.8, 48.8, 43.0, 39.2, 37.1, 33.6, 29.7, 27.6, 27.4, 25.8, 23.4, 23.0, 13.6. HR-MS (ESI) calcd for [C$_{47}$H$_{56}$N$_2$O$_5$ H]$^+$ 729.4268, found 729.4296.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-5-morpholinopentanamide, JD113

$^1$H NMR (300 MHz, MeOD): δ 7.39 (d, J=9.0 Hz, 2H), 6.89 (d, J=8.7 Hz, 1H), 6.84 (d, J=9.0 Hz, 2H), 6.48 (d, J=2.7 Hz, 1H), 6.41 (dd, J=8.4, 2.4 Hz, 1H), 5.29 (m, 1H), 3.76 (d, J=4.2 Hz, 4H), 2.78 (t, J=4.2 Hz, 4H), 0.88 (s, 3H), 0.80-3.70 (m, 22H). $^{13}$C NMR (75 MHz, MeOD): δ 173.7, 156.0, 155.8, 139.6, 132.3, 128.7, 127.8, 123.3 (2C), 116.4 (2C), 116.2, 113.9, 82.8, 73.3, 66.5 (2C), 59.1, 54.1 (2C), 51.8, 50.1, 44.2, 39.3, 37.1, 35.6, 30.8, 30.5, 28.6, 25.7, 24.3, 24.0, 13.8.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-5-(pyrrolidin-1-yl)pentan-amide $^1$H NMR (300 MHz, CDCl$_3$): δ 9.27 (s, 1H), 7.19-7.72 (m, 12H), 6.96 (d, J=8.4 Hz, 1H), 6.81 (m, 2H), 6.69 (d, 1H), 6.64 (d, J=8.4 Hz, 1H), 5.20 (m, 1H), 4.95 (s, 2H), 4.49 (d, J=11.6 Hz, 1H), 4.46 (d, J=11.6 Hz, 1H), 2.80 (m, 4H), 1.78 (m, 4H), 0.99 (s, 3H), 0.80-3.60 (m, 22H). $^{13}$C NMR (75 MHz, CDCl$_3$): δ 171.3, 156.5, 153.9, 139.0, 138.4, 137.2, 131.6, 128.8, 128.4 (2C), 128.2 (2C), 127.7, 127.4 (2C), 127.3 (2C), 127.2, 126.5, 121.7 (2C), 115.5 (2C), 114.8, 112.4, 88.4, 71.6, 71.4, 69.7, 54.8, 53.3 (2C), 50.8, 48.7, 45.5, 43.0, 39.1, 36.5, 33.6, 29.71, 29.68, 27.6, 27.3, 26.0, 23.0 (2C), 13.7.

N-(4-(((8S,9S,11S,13S,14S,17S)-3,17-Dihydroxy-13-methyl-7,8,9,11,12,13,14,15,16,17-decahydro-6H-cyclopenta[a]phenanthren-11-yl)oxy)phenyl)-5-(pyrrolidin-1-yl)pentanamide, JD114

$^1$H NMR (300 MHz, MeOD): δ 7.42 (d, J=8.1 Hz, 2H), 6.90 (m, 1H), 6.89 (d, J=8.1 Hz, 2H), 6.48 (s, 1H), 6.42 (d, J=6.5 Hz, 1H), 5.30 (m, 1H), 2.49 (m, 4H), 1.71 (m, 4H), 0.88 (s, 3H), 0.80-3.70 (m, 22H). $^{13}$C NMR (75 MHz, MeOD): δ 173.5, 156.0, 155.8, 139.6, 132.3, 128.7, 127.7, 123.3 (2C), 116.5 (2C), 116.2, 113.9, 82.8, 73.3, 55.9 (2C), 55.0, 51.8, 50.1, 44.2, 39.4, 36.7, 35.6, 30.8, 30.7, 30.5, 28.6, 26.5, 24.0 (2C), 23.7, 13.8.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-5-(piperidin-1-yl)pentan-amide $^1$H NMR (300 MHz, CDCl$_3$): δ 8.55 (s, 1H), 7.51 (d, J=8.7 Hz, 2H), 7.20-7.46 (m, 10H), 6.96 (d, J=8.4 Hz, 1H), 6.82 (d, J=8.7 Hz, 2H), 6.69 (d, J=2.3 Hz, 1H), 6.65 (dd, J=8.3, 2.5 Hz, 1H), 5.20 (m, 1H), 4.97 (s, 2H), 4.49 (d, J=11.4 Hz, 1H), 4.46 (d, J=11.4 Hz, 1H), 2.58 (m, 4H), 1.71 (m, 4H), 1.00 (s, 3H), 0.80-3.55 (m, 24H). $^{13}$C NMR (75 MHz, CDCl$_3$): δ 171.1, 156.5, 154.2, 139.0, 138.4, 137.2, 131.2, 128.7, 128.4 (2C), 128.2 (2C), 127.7, 127.4 (2C), 127.3 (2C), 127.2, 126.5, 121.8 (2C), 115.6 (2C), 114.8, 112.4, 88.4, 71.8, 71.4, 69.8, 57.6, 53.8 (2C), 50.8, 48.8, 43.0, 39.2, 36.5, 33.6, 29.7, 27.6, 27.3, 24.6, 24.1 (2C), 23.2, 23.1, 23.0, 14.1.

N-(4-(((8S,9S,11S,13S,14S,17S)-3,17-Dihydroxy-13-methyl-7,8,9,11,12,13,14,15,16,17-decahydro-6H-cyclopenta[a]phenanthren-11-yl)oxy)phenyl)-5-(piperidin-1-yl)pentanamide, JD115

$^1$H NMR (300 MHz, MeOD): δ 7.42 (d, J=8.7 Hz, 2H), 6.89 (d, J=8.7 Hz, 1H), 6.85 (d, J=8.7 Hz, 2H), 6.49 (d, J=2.1 Hz, 1H), 6.42 (dd, J=8.4, 2.7 Hz, 1H), 5.30 (m, 1H), 2.42 (m, 4H), 1.75 (m, 4H), 0.88 (s, 3H), 0.80-3.70 (m, 24H). 13C NMR (75 MHz, MeOD): δ 173.4, 156.0, 155.8, 139.6, 132.2, 128.7, 127.8, 123.3 (2C), 116.5 (2C), 116.2, 113.9, 82.8, 73.3, 57.9, 54.3 (2C), 51.8, 50.1, 44.2, 39.2, 36.7, 35.6, 30.8, 30.5, 28.6, 24.5, 24.2 (2C), 24.0, 23.7, 22.7, 13.8.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-5-(dimethylamino)pentan-amide $^1$H NMR (300 MHz, CDCl$_3$): δ 8.04 (s, 1H), 7.18-7.46 (m, 12H), 6.96 (d, J=8.4 Hz, 1H), 6.83 (d, J=8.7 Hz, 2H), 6.70 (d, J=2.3 Hz, 1H), 6.66 (dd, J=8.3, 2.8 Hz, 1H), 5.20 (m, 1H), 4.97 (s, 2H), 4.50 (d, J=11.6 Hz, 1H), 4.47 (d, J=11.6 Hz, 1H), 2.30 (s, 6H), 1.00 (s, 3H), 0.80-3.60 (m, 22H). $^{13}$C NMR (75 MHz, CDCl$_3$): δ 171.1, 156.5, 154.2, 139.0, 138.4, 137.2, 130.9, 128.7, 128.4 (2C), 128.1 (2C), 127.7, 127.3 (2C), 127.2 (2C), 127.15, 126.4, 121.7 (2C), 115.6 (2C), 114.8, 112.4, 88.4, 71.8, 71.4, 69.7, 58.8, 50.8, 48.8, 45.3 (2C), 43.0, 39.2, 36.9, 33.6, 31.8, 29.7, 27.6, 26.5, 23.4, 21.5, 13.8.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-5-(dimethylamino)pentanamide, JD117

$^1$H NMR (300 MHz, MeOD): δ 7.39 (d, J=9.0 Hz, 2H), 6.89 (d, J=8.4 Hz, 1H), 6.85 (d, J=8.7 Hz, 2H), 6.48 (d, J=2.1 Hz, 1H), 6.41 (dd, J=8.3, 2.7 Hz, 1H), 5.29 (m, 1H), 2.50 (s, 6H), 0.88 (s, 3H), 0.80-3.70 (m, 22H). $^{13}$C NMR (75 MHz, MeOD): δ 173.7, 156.0, 155.8, 139.6, 132.3, 128.7, 127.7, 123.3 (2C), 116.4 (2C), 116.2, 113.9, 82.8, 73.3, 59.4, 51.8, 50.1, 44.4 (2C), 44.2, 39.3, 37.1, 35.6 30.8, 30.5, 28.6, 26.5, 24.2, 24.0, 13.8.

(8S,9S,11S,13S,14S,17S)-3,17-bis(Benzyloxy)-1-(3-fluoro-4-nitrophenoxy)-13-methyl-7,8,9,11,12,13,14,15,16,17-decahydro-6H-cyclopenta[a]phenanthrene $^1$H NMR (300 MHz, CDCl$_3$): δ 7.88 (dd, J=9.0, 6.0 Hz, 1H), 7.15-7.5 (m, 10H), 6.87 (dd, J=10.6, 2.4 Hz, 1H), 6.78 (d, J=8.7 Hz, 1H), 6.72 (d, J=2.4 Hz, 1H), 6.66 (tt, J=7.3, 2.3 Hz, 1H), 6.57 (dd, J=8.5, 2.6 Hz, 1H), 5.29 (m, 1H), 4.99 (s, 2H), 4.60 (d, J=12.3 Hz, 1H), 4.50 (d, J=12.3 Hz, 1H), 3.54 (dd, J=8.1, 8.1 Hz, 1H), 1.04 (s, 3H), 0.80-3.12 (m, 13H). $^{13}$C NMR (75 MHz, CDCl$_3$): δ 165.8 (d, J=256.5 Hz), 156.6, 154.2 (d, J=11.8 Hz), 139.0, 138.9, 137.2, 135.9 (d, J=3.5 Hz), 128.5 (d, J=2.4 Hz), 128.4 (2C), 128.2 (2C), 127.7, 127.6, 127.41 (2C), 127.37, 127.31 (2C), 125.4, 115.0, 112.6, 106.7 (d, J=23.9 Hz), 102.0 (d, J=26.8 Hz), 88.5, 76.0, 71.5, 69.8, 50.6, 49.2, 43.0, 39.8, 33.6, 29.8, 27.6, 26.9, 23.0, 13.5. $^{19}$F NMR (282 MHz, CDCl$_3$): δ −100.89.

(8S,9S,11S,13S,14S,17S)-11-(3-Fluoro-4-nitrophenoxy)-13-methyl-7,8,9,11,12,13,14,15,16,17-decahydro-6H-cyclopenta[a]phenanthrene-3,17-diol, JD119

$^1$H NMR (300 MHz, MeOD): δ 7.85 (dd, J=9.0, 6.1 Hz, 1H), 6.86 (dd, J=10.4, 2.4 Hz, 1H), 6.70 (d, J=8.6 Hz, 1H), 6.65 (d, J=1.8 Hz, 1H), 6.53 (d, J=2.1 Hz, 1H), 6.39 (m, 1H), 5.29 (m, 1H), 0.93 (s, 3H), 0.75-3.85 (m, 14H). $^{13}$C NMR (75 MHz, MeOD): δ 165.9 (d, J=256.1 Hz), 154.1 (d, J=11.3 Hz), 153.4, 139.1, 135.9, 128.4 (d, J=11.3 Hz), 127.1, 125.6, 115.8, 112.9, 106.8 (d, J=23.5 Hz), 102.1 (d, J=26.6 Hz), 82.3, 76.0, 50.4, 49.1, 42.9, 38.9, 33.9, 30.6, 29.6, 26.8, 23.0, 12.6. $^{19}$F NMR (282 MHz, CDCl$_3$): δ− 100.74. HR-MS (ESI) calcd for [C$_{24}$H$_{26}$FNO$_5$ H]$^+$ 428.1873, found 428.1879.

(8S,9S,11S,13S,14S,17S)-11-(4-Amino-3-fluorophenoxy)-13-methyl-7,8,9,11,12,13,14,15,16,17-decahydro-6H-cyclopenta[a]phenanthrene-3,17-diol, JD120

$^1$H NMR (300 MHz, CDCl$_3$): δ 7.26 (s, 2H), 6.71 (m, 2H), 6.49 (m, 2H), 6.38 (m, 1H), 5.29 (m, 1H), 0.99 (s, 3H), 0.70-3.80 (m, 18H). $^{13}$C NMR (75 MHz, CDCl$_3$): δ 156.5

(d, J=227.6 Hz), 153.5, 146.6 (d, J=9.7 Hz), 138.6, 132.1, 127.7, 126.4, 115.434 (d, J=9.4 Hz), 115.427, 113.1, 106.2 (d, J=22.2 Hz), 100.2 (d, J=27.1 Hz), 82.2, 74.0, 50.4, 49.1, 42.8, 39.0, 34.4, 30.4, 29.6, 27.1, 23.0, 12.8. $^{19}$F NMR (282 MHz, CDCl$_3$): δ −123.5.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-2-(piperidin-1-yl)acet-amide $^1$H NMR (300 MHz, CDCl$_3$): δ 8.99 (s, 1H), 8.34 (dd, J=8.9, 6.4 Hz, 1H), 7.15-7.50 (m, 10H), 6.68 (m, 5H), 5.28 (m, 1H), 4.94 (s, 2H), 4.50 (d, J=12.3 Hz, 1H), 4.47 (d, J=12.3 Hz, 1H), 2.55 (m, 4H), 1.61 (m, 4H), 1.01 (s, 3H), 0.80-3.60 (m, 18H). $^{13}$C NMR (75 MHz, CDCl$_3$): δ 168.5, 158.9 (d, J=241.2 Hz), 156.7, 147.6 (d, J=9.6 Hz), 138.9, 138.0, 137.1, 128.4 (2C), 128.2 (2C), 127.9, 127.8, 127.5, 127.34 (2C), 127.29 (2C), 126.2, 124.1 (d, J=3.2 Hz), 120.7 (d, J=8.8 Hz), 115.0, 112.2, 106.3 (d, J=22.5 Hz), 99.6 (d, J=26.7 Hz), 88.4, 73.6, 71.6, 69.7, 63.2, 54.7 (2C), 50.5, 48.5, 46.8, 42.7, 40.6, 33.8, 29.1, 27.6, 27.4, 24.6 (2C), 23.7, 13.8. HR-MS (ESI) calcd for [C$_{45}$H$_{51}$FN$_2$O$_4$H]$^+$ 703.3911, found 703.3939.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-2-(piperidin-1-yl)acet-amide, JD122

$^1$H NMR (300 MHz, MeOD): δ 8.10 (dd, J=9.0, 6.3 Hz, 1H), 7.04 (dd, J=10.9, 2.7 Hz, 1H), 6.72 (d, J=8.5 Hz, 1H), 6.63 (dt, J=8.5, 2.6 Hz, 1H), 6.50 (d, J=2.4 Hz, 1H), 6.35 (dd, J=8.6, 2.5 Hz, 1H), 5.37 (m, 1H), 2.45 (m, 4H), 1.48 (m, 4H). 0.89 (s, 3H), 0.80-3.80 (m, 18H). $^{13}$C NMR (75 MHz, MeOD): δ 169.9, 161.2 (d, J=240.8 Hz), 156.1, 150.2 (d, J=10.1 Hz), 139.4, 128.2, 127.6, 124.6, 122.6 (d, J=9.3 Hz), 116.3, 113.9, 107.0 (d, J=21.8 Hz), 101.6 (d, J=27.6 Hz), 82.7, 75.8, 63.2, 55.8 (2C), 51.5, 49.7, 43.9, 40.0, 35.7, 30.4, 30.3, 28.6, 26.5 (2C), 24.5, 24.1, 13.9. $^{19}$F NMR (282 MHz, CDCl$_3$): δ −117.41. HR-MS (ESI) calcd for [C$_{31}$H$_{39}$FN$_2$O$_4$ H]$^+$ 523.2972, found 523.2956.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-2-(pyrrolidin-1-yl)ac-etamide $^1$H NMR (300 MHz, CDCl$_3$): δ 9.00 (s, 1H), 8.37 (dd, J=8.9, 6.4 Hz, 1H), 7.25-7.50 (m, 10H), 6.76 (d, J=2.5 Hz, 1H), 6.72 (d, J=4.2 Hz, 1H), 6.69 (d, J=2.5 Hz, 1H), 6.64 (m, 1H), 6.56 (dd, J=8.6, 2.6 Hz, 1H), 5.19 (m, 1H), 4.97 (s, 2H), 4.56 (d, J=12.3 Hz, 1H), 4.50 (d, J=12.3 Hz, 1H), 2.59 (m, 4H), 1.75 (m, 4H), 0.99 (s, 3H), 0.80-3.60 (m, 16H). $^{13}$C NMR (75 MHz, CDCl$_3$): δ 168.7, 159.0 (d, J=241.0 Hz), 156.6, 147.5 (d, J=9.8 Hz), 138.9, 138.0, 137.1, 128.5 (2C), 128.3 (2C), 127.9, 127.8, 127.41, 127.39 (2C), 127.32 (2C), 126.1, 124.1 (d, J=3.0 Hz), 120.3 (d, J=9.2 Hz), 115.0, 112.3, 106.2 (d, J=22.1 Hz), 99.4 (d, J=26.8 Hz), 88.4, 73.7, 71.6, 69.7, 60.5, 54.6 (2C), 50.5, 48.6, 42.8, 39.7, 33.9, 29.3, 27.6, 27.3, 24.2 (2C), 23.2, 13.7. $^{19}$F NMR (282 MHz, CDCl$_3$): δ −116.81. HR-MS (ESI) calcd for [C$_{44}$H$_{49}$FN$_2$O$_4$ H]$^+$ 689.3755, found 689.3782.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-2-(pyrrolidin-1-yl)acet-amide, JD125

$^1$H NMR (300 MHz, MeOD): δ 8.16 (dd, J=8.9, 6.4 Hz, 1H), 6.99 (dd, J=10.7, 2.4 Hz, 1H), 6.70 (d, J=8.5 Hz, 1H), 6.61 (td, J=8.7, 2.5 Hz, 1H), 6.51 (s, 1H), 6.35 (d, J=8.5 Hz, 1H), 5.32 (m, 1H), 2.55 (m, 4H), 1.79 (m, 4H), 0.86 (s, 3H), 0.80-3.75 (m, 16H). $^{13}$C NMR (75 MHz, MeOD): δ 170.8, 160.9 (d, J=245.4 Hz), 156.1, 149.9 (d, J=10.1 Hz), 139.4, 128.1, 127.5, 124.7 (d, J=3.3 Hz), 121.8 (d, J=9.6 Hz), 116.2, 113.9, 106.8 (d, J=22.0 Hz), 101.2 (d, J=27.4 Hz), 82.7, 75.7, 61.1, 55.6 (2C), 51.4, 49.8, 43.9, 39.9, 35.7, 30.7, 30.5, 28.5, 25.2 (2C), 24.1, 13.9. $^{19}$F NMR (282 MHz, MeOD): δ −117.59.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-2-morpholinoacet-amide $^1$H NMR (300 MHz, CDCl$_3$): δ 8.76 (s, 1H), 8.30 (dd, J=9.1, 6.5 Hz, 1H), 7.20-7.40 (m, 10H), 6.45-6.80 (m, 5H), 5.15 (m, 1H), 4.91 (s, 2H), 4.50 (d, J=12.1 Hz, 1H), 4.43 (d, J=12.1 Hz, 1H), 3.48 (m, 4H), 2.55 (m, 4H), 0.94 (s, 3H), 0.80-3.75 (m, 16H). $^{13}$C NMR (75 MHz, CDCl$_3$): δ 168.7, 159.0 (d, J=242.1 Hz), 156.5, 147.4 (d, J=9.6 Hz), 138.7, 137.7, 136.9, 128.2 (2C), 128.0 (2C), 127.7, 127.6, 127.2, 127.14 (2C), 127.12 (2C), 126.1, 123.7 (d, J=3.3 Hz), 120.4 (d, J=9.6 Hz), 114.6, 112.3, 106.2 (d, J=21.4 Hz), 99.6 (d, J=26.2 Hz), 88.1, 73.7, 71.4, 69.5, 66.4 (2C), 62.7, 53.5 (2C), 50.2, 48.2, 42.5, 33.9, 29.4, 27.4, 27.1, 24.2, 23.0, 13.6. $^{19}$F NMR (282 MHz, CDCl$_3$): δ −116.34. HR-MS (ESI) calcd for [C$_{44}$H$_{49}$FN$_2$O$_5$ H]$^+$ 705.3704, found 705.3690.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-2-morpholinoacetamide, JD126

$^1$H NMR (300 MHz, MeOD): δ 8.17 (dd, J=9.0, 6.3 Hz, 1H), 7.04 (dd, J=10.9, 2.7 Hz, 1H), 6.71 (d, J=8.6 Hz, 1H), 6.63 (dt, J=8.3, 2.7 Hz, 1H), 6.51 (d, J=2.5 Hz, 1H), 6.35 (dd, J=8.5, 2.6 Hz, 1H), 5.37 (m, 1H), 3.30 (m, 4H), 2.39 (m, 4H), 0.89 (s, 3H), 0.80-3.80 (m, 16H). $^{13}$C NMR (75 MHz, MeOD): δ 170.0, 161.2 (d, J=240.6 Hz), 156.2, 149.9 (d, J=9.8 Hz), 139.3, 128.2, 127.6, 124.7 (d, J=3.1 Hz), 122.2 (d, J=9.5 Hz), 116.3, 114.0, 106.9 (d, J=22.2 Hz), 101.5 (d, J=27.7 Hz), 82.7, 75.6, 67.8 (2C), 63.5, 54.8 (2C), 51.5, 49.6, 43.9, 39.9, 35.9, 30.4, 30.3, 28.6, 24.1, 13.9. $^{19}$F NMR (282 MHz, MeOD): δ −117.53. HR-MS (ESI) calcd for [C$_{30}$H$_{37}$FN$_2$O$_5$ H]$^+$ 525.2765, found 525.2782.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-2-(dimethylamino)ac-etamide $^1$H NMR (300 MHz, CDCl$_3$): δ 9.25 (s, 1H), 8.35 (dd, J=8.7, 6.5 Hz, 1H), 7.15-7.55 (m, 10H), 6.50-6.85 (m, 5H), 5.19 (m, 1H), 4.97 (s, 2H), 4.57 (d, J=12.0 Hz, 1H), 4.49 (d, J=12.0 Hz, 1H), 2.11 (s, 6H), 0.97 (s, 3H), 0.80-3.60 (m, 16H). $^{13}$C NMR (75 MHz, CDCl$_3$): δ 168.2, 159.8 (d, J=287.4 Hz), 156.6, 147.3 (d, J=9.6 Hz), 138.9, 138.0, 137.1, 128.4 (2C), 128.2 (2C), 128.0, 127.8, 127.4 (2C), 127.31, 127.3 (2C), 126.1, 124.0 (d, J=2.7 Hz), 119.9 (d, J=9.5 Hz), 115.0, 112.4, 106.1 (d, J=21.6 Hz), 99.1 (d, J=26.8 Hz), 88.4, 73.1, 71.6, 69.7, 63.6, 50.4, 48.7, 45.7 (2C), 42.7, 39.3, 34.1, 29.7, 27.6, 27.4, 23.1, 13.5. $^{19}$F NMR (282 MHz, CDCl$_3$): δ −116.79. HR-MS (ESI) calcd for [C$_{42}$H$_{47}$FN$_2$O$_4$ H]$^+$ 663.3598, found 663.3624.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-2-(dimethylamino)acet-amide, JD129

$^1$H NMR (300 MHz, MeOD): δ 8.14 (dd, J=8.9, 6.3 Hz, 1H), 6.98 (dd, J=10.8, 2.6 Hz, 1H), 6.74 (d, J=8.5 Hz, 1H), 6.61 (dt, J=8.6, 2.7 Hz, 1H), 6.50 (d, J=2.5 Hz, 1H), 6.37 (dd, J=8.5, 2.6 Hz, 1H), 5.33 (m, 1H), 3.70 (dd, J=8.3, 8.3 Hz, 1H), 2.16 (s, 6H), 0.84 (s, 3H), 0.80-3.75 (m, 15H). $^{13}$C NMR (75 MHz, MeOD): δ 170.4, 161.0 (d, J=241.6 Hz), 156.1, 149.6 (d, J=10.2 Hz), 139.4, 128.2, 127.5, 124.7 (d, J=3.1 Hz), 121.4 (d, J=8.7 Hz), 116.3, 114.0, 106.6 (d, J=22.4 Hz), 101.0 (d, J=27.8 Hz), 82.7, 75.1, 64.2, 51.4, 49.9, 46.1 (2C), 43.9, 39.5, 35.9, 30.8, 30.4, 28.6, 24.1, 13.6. $^{19}$F NMR (282 MHz, MeOD): δ −117.74. HR-MS (ESI) calcd for [C$_{28}$H$_{35}$FN$_2$O$_4$ H]$^+$ 483.2659, found 483.2660.

N-(4-(((8S,9S,11S,13S,14S,17S)-3,17-bis(Benzyloxy)-13-methyl-7,8,9,11,12,13,14,15,16,17-deca-hydro-6H-cyclopenta[a]phenanthren-11-yl)oxy)-2-fluorophenyl)-3-(piperidin-1-yl)pro-panamide $^1$H NMR (300 MHz, CDCl$_3$): δ 8.01 (s, 1H), 7.20-7.60 (m, 11H), 6.75 (m, 3H), 6.61 (m, 2H), 5.06 (m, 1H), 4.98 (s, 2H), 4.58 (d, J=12.0 Hz, 1H), 4.50 (d, J=12.0 Hz, 1H), 2.58 (m, 4H), 1.66 (m, 4H), 1.00 (s, 3H), 0.80-3.60 (m, 20H). $^{13}$C NMR (75 MHz, CDCl$_3$): δ 168.4, 159.3 (d, J=243.2 Hz), 156.6, 149.1 (d, J=9.6 Hz), 138.9, 138.7, 137.0, 128.4 (2C), 128.2 (2C), 128.0, 127.8, 127.4, 127.30 (2C), 127.28 (2C), 126.3, 123.8 (d, J=3.2 Hz), 121.7 (d, J=9.0 Hz), 115.5, 112.2, 106.8 (d, J=22.2 Hz), 100.8 (d, J=27.1 Hz), 88.4, 76.9, 71.6, 69.7, 53.5 (2C), 53.3, 50.2, 49.1, 42.9, 40.8, 34.2, 33.0, 29.7, 27.6, 26.9, 24.3 (2C), 23.2, 22.9, 13.7. $^{19}$F NMR (282 MHz, CDCl$_3$): δ −115.87. HR-MS (ESI) calcd for [C$_{46}$H$_{53}$FN$_2$O$_4$ H]$^+$ 717.4067, found 717.4052.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-3-(piperidin-1-yl)propan-amide, JD130

$^1$H NMR (500 MHz, MeOD): δ 7.71 (dd, J=8.8, 6.3 Hz, 1H), 7.02 (dd, J=10.6, 2.4 Hz, 1H), 6.75 (d, J=8.6 Hz, 1H), 6.63 (td, J=8.5, 2.5 Hz, 1H), 6.55 (d, J=2.1 Hz, 1H), 6.38 (dd, J=8.5, 2.3 Hz, 1H), 5.24 (m, 1H), 3.70 (dd, J=8.3, 8.3 Hz, 1H), 2.80 (m, 4H), 1.70 (m, 4H), 0.87 (s, 3H), 0.78-3.40 (m, 19H). $^{13}$C NMR (125 MHz, MeOD): δ 170.6, 161.7 (d, J=242.0 Hz), 156.2, 152.1 (d, J=9.7 Hz), 139.8, 128.3, 127.9, 125.0 (d, J=9.7 Hz), 124.4 (d, J=3.1 Hz), 116.5, 114.3, 107.3 (d, J=22.9 Hz), 102.4 (d, J=26.9 Hz), 82.7, 77.7, 54.73 (2C), 54.65, 51.3, 50.3, 44.1, 40.7, 35.9, 32.6, 30.9, 30.4, 28.3, 25.3 (2C), 24.0, 23.8, 13.7. $^{19}$F NMR (282 MHz, MeOD): δ −116.52. HR-MS (ESI) calcd for [C$_{32}$H$_{41}$FN$_2$O$_4$ H]$^+$ 537.3129, found 537.3132.

N-(4-(((8S,9S,11S,13S,14S,17S)-3,17-bis(Benzyloxy)-13-methyl-7,8,9,11,12,13,14,15,16,17-deca-hydro-6H-cyclopenta[a]phenanthren-11-yl)oxy)-2-fluorophenyl)-3-(pyrrolidin-1-yl)propanamide $^1$H NMR (500 MHz, CDCl$_3$): δ 9.47 (br s, 1H), 7.98 (dd, J=8.9, 6.3 Hz, 1H), 7.20-7.45 (m, 9H), 7.13 (s, 1H), 6.84 (d, J=2.1 Hz, 1H), 6.78 (dd, J=10.1, 2.5 Hz, 1H), 6.72 (d, J=8.7 Hz, 1H), 6.64 (dt, J=8.7, 2.6 Hz, 1H), 6.55 (dd, J=8.6, 2.4 Hz, 1H), 5.03 (m, 1H), 5.01 (d, J=11.7 Hz, 1H), 4.96 (d, J=11.7 Hz, 1H), 4.60 (d, J=12.2 Hz, 1H), 4.50 (d, J=12.2 Hz, 1H), 3.52 (dd, J=8.1, 8.1 Hz, 1H), 2.90 (m, 4H), 1.88 (m, 4H), 1.00 (s, 3H), 0.80-3.20 (m, 17H). $^{13}$C NMR (125 MHz, CDCl$_3$): δ 167.3, 159.3 (d, J=243.2 Hz), 156.5, 149.2 (d, J=9.7 Hz), 139.1, 138.9, 136.9, 128.5 (2C), 128.3 (2C), 128.2, 127.8, 127.4, 127.33 (2C), 127.30 (2C), 126.3, 123.7 (d, J=3.3 Hz), 121.5 (d, J=9.6 Hz), 115.7, 112.1, 107.0 (d, J=21.5 Hz), 101.1 (d, J=26.7 Hz), 88.3, 77.7, 71.6, 69.7, 53.2 (2C), 50.5, 50.1, 49.2, 43.0, 41.1, 34.1, 33.4, 29.7, 27.6, 26.8, 23.2 (2C), 22.9, 13.8. $^{19}$F NMR (282 MHz, CDCl$_3$): δ −115.73. HR-MS (ESI) calcd for [C$_{45}$H$_{51}$FN$_2$O$_4$ H]$^+$ 703.3911, found 703.3906.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-3-(pyrrolidin-1-yl)propan-amide, JD132

$^1$H NMR (500 MHz, MeOD): δ 7.75 (dd, J=8.8, 6.3 Hz, 1H), 7.03 (dd, J=10.6, 2.6 Hz, 1H), 6.75 (d, J=8.6 Hz, 1H), 6.64 (td, J=8.6, 2.6 Hz, 1H), 6.57 (d, J=2.3 Hz, 1H), 6.38 (dd, J=8.5, 2.5 Hz, 1H), 5.23 (m, 1H), 3.71 (dd, J=8.3, 8.3 Hz, 1H), 3.30 (dt, J=3.2, 1.6 Hz, 3H), 3.17 (m, 4H), 2.02 (m, 4H), 0.88 (s, 3H), 0.80-3.10 (m, 13H). $^{13}$C NMR (125 MHz, MeOD): δ 169.8, 161.7 (d, J=243.9 Hz), 156.2, 152.1 (d, J=10.2 Hz), 139.9, 128.4, 127.9, 124.8 (d, J=9.8 Hz), 124.4 (d, J=3.2 Hz), 116.5, 114.3, 107.3 (d, J=22.5 Hz), 102.5 (d, J=26.5 Hz), 82.7, 78.1, 55.2 (2C), 52.1, 51.3, 50.3, 44.1, 40.8, 35.8, 33.2, 30.9, 30.4, 28.3, 24.1 (2C), 24.0, 13.7. $^{19}$F NMR (282 MHz, MeOD): δ −116.52.

N-(4-(((8S,9S,11S,13S,14S,17S)-3,17-bis(Benzyloxy)-13-methyl-7,8,9,11,12,13,14,15,16,17-deca-hydro-6H-cyclopenta[a]phenanthren-11-yl)oxy)-2-fluorophenyl)-3-(dimethylamino)-propanamide $^1$H NMR (500 MHz, CDCl$_3$): δ 8.96 (br s, 1H), 8.01 (dd, J=8.9, 6.3 Hz, 1H), 7.43 (s, 1H), 7.20-7.40 (m, 9H), 6.79 (d, J=2.5 Hz, 1H), 6.77 (dd, J=7.9, 2.6 Hz, 1H), 6.73 (d, J=8.7 Hz, 1H), 6.64 (td, J=8.6, 2.6 Hz, 1H), 6.56 (dd, J=8.6, 2.6 Hz, 1H), 5.06 (m, 1H), 4.98 (d, J=11.5 Hz, 1H), 4.96 (d, J=11.5 Hz, 1H), 4.60 (d, J=12.2 Hz, 1H), 4.50 (d, J=12.2 Hz, 1H), 3.52 (dd, J=8.2, 8.2 Hz, 1H), 2.35 (s, 6H), 1.00 (s, 3H), 0.80-3.00 (m, 17H). $^{13}$C NMR (125 MHz, CDCl$_3$): δ 168.1, 159.3 (d, J=282.8 Hz), 156.6, 149.0 (d, J=9.8 Hz), 138.9, 138.7, 136.9, 128.5 (2C), 128.3 (2C), 128.1, 127.9, 127.4, 127.37 (2C), 127.34 (2C), 126.4, 123.8 (d, J=3.1 Hz), 121.7 (d, J=9.4 Hz), 115.6, 112.2, 106.9 (d, J=21.1 Hz), 100.9 (d, J=27.5 Hz), 88.3, 76.9, 71.6, 69.7, 53.5, 50.2, 49.1, 43.5 (2C), 42.9, 40.8, 34.1, 33.0, 29.6, 27.6, 26.9, 23.0, 13.7. $^{19}$F NMR (282 MHz, CDCl$_3$): δ −115.94. HR-MS (ESI) calcd for [C$_{43}$H$_{49}$FN$_2$O$_4$ H]$^+$ 677.3755, found 677.3738.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-3-(dimethylamino)propan-amide, JD133

$^1$H NMR (500 MHz, MeOD): δ 7.74 (dd, J=8.8, 6.3 Hz, 1H), 6.98 (dd, J=10.7, 2.5 Hz, 1H), 6.73 (d, J=8.6 Hz, 1H), 6.64 (td, J=8.6, 2.5 Hz, 1H), 6.54 (d, J=2.2 Hz, 1H), 6.38 (dd, J=8.5, 2.4 Hz, 1H), 5.20 (m, 1H), 3.56 (dd, J=8.2, 8.2 Hz, 1H), 2.46 (s, 6H), 0.94 (s, 3H), 0.80-3.40 (m, 15H). $^{13}$C NMR (125 MHz, MeOD): δ 169.4, 161.6 (d, J=242.9 Hz), 156.2, 152.0 (d, J=10.4 Hz), 139.9, 128.4, 127.9, 124.9 (d, J=9.7 Hz), 124.3 (d, J=3.3 Hz), 116.5, 114.3, 107.3 (d, J=22.5 Hz), 102.4 (d, J=26.5 Hz), 82.7, 77.8, 55.2, 51.3, 50.3, 44.2 (2C), 44.1, 40.7, 35.8, 32.4, 30.8, 30.4, 28.3, 24.9, 14.3. $^{19}$F NMR (282 MHz, MeOD): δ −116.56.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-3-morpholinopropan-amide $^1$H NMR (500 MHz, CDCl$_3$): δ 9.12 (s, 1H), 8.04 (dd, J=8.8, 6.4 Hz, 1H), 7.20-7.50 (m, 10H), 6.79 (m, 1H), 6.76 (m, 1H), 6.74 (m, 1H), 6.66 (m, 1H), 6.57 (m, 1H), 5.27 (m, 1H), 4.98 (s, 2H), 4.59 (d, J=12.5 Hz, 1H), 4.52 (d, J=12.5 Hz, 1H), 3.65 (t, J=4.1 Hz, 4H), 2.93 (t, J=4.1 Hz, 4H), 0.99 (s, 3H), 0.75-3.40 (m, 18H). $^{13}$C NMR (125 MHz, CDCl$_3$): δ 169.0, 159.2 (d, J=245.3 Hz), 156.7, 148.8 (d, J=9.8 Hz), 138.8, 138.2, 136.8, 128.43 (2C), 128.41, 128.2 (2C), 127.8, 127.4, 127.30 (2C), 127.27 (2C), 126.3, 123.8 (d, J=2.9 Hz), 121.7 (d, J=9.4 Hz), 115.4, 112.3, 106.8 (d, J=21.9 Hz), 100.8 (d, J=12.7 Hz), 88.2, 76.5, 71.6, 69.7, 66.6 (2C), 54.0, 53.1 (2C), 50.0, 49.0, 42.8, 40.6, 34.4, 34.2, 29.8, 27.5, 26.9, 22.9, 13.7. $^{19}$F NMR (282 MHz, CDCl$_3$): δ −116.07. HR-MS (ESI) calcd for [C$_{45}$H$_{51}$FN$_2$O$_5$ H]$^+$ 719.3860, found 719.3887.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-3-morpholinopropan-amide, JD134

$^1$H NMR (500 MHz, MeOD): δ 7.69 (dd, J=8.5, 6.5 Hz, 1H), 7.02 (dd, J=10.7, 2.7 Hz, 1H), 6.76 (d, J=8.6 Hz, 1H), 6.63 (td, J=8.4, 2.1 Hz, 1H), 6.54 (s, 1H), 6.39 (dd, J=8.3, 1.9 Hz, 1H), 5.25 (m, 1H), 3.65 (m, 4H), 2.55 (m, 4H), 0.85 (s, 3H), 0.70-3.80 (m, 18H). $^{13}$C NMR (125 MHz, MeOD): δ 171.8, 161.7 (d, J=242.1 Hz), 156.3, 152.0 (d, J=10.3 Hz), 139.7, 128.2, 127.8, 125.2 (d, J=9.7 Hz), 124.3 (d, J=3.2 Hz), 116.6, 114.3, 107.3 (d, J=22.3 Hz), 102.3 (d, J=27.3 Hz), 82.7, 77.3, 67.4 (2C), 55.2, 54.2 (2C), 51.3, 50.2, 44.0, 40.4, 36.0, 34.1, 30.9, 30.4, 28.3, 24.0, 13.7. $^{19}$F NMR (282 MHz, MeOD): δ −116.52. HR-MS (ESI) calcd for [C$_{45}$H$_{54}$N$_2$O$_4$ H]$^+$ 687.4162, found 687.4188.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-4-morpholinobutan-amide $^1$H NMR (500 MHz, CDCl$_3$): δ 9.89 (s, 1H), 8.12 (dd, J=8.8, 6.4 Hz, 1H), 7.20-7.50 (m, 9H), 6.84 (s, 1H), 6.76 (dd, J=5.9, 2.4 Hz, 1H), 6.74 (m, 2H), 6.64 (td, J=8.6, 2.4 Hz, 1H), 6.57 (dd, J=8.6, 2.4 Hz, 1H), 5.06 (m, 1H), 4.96 (s, 2H), 4.60 (d, J=12.2 Hz, 1H), 4.51 (d, J=12.2 Hz, 1H), 3.65 (t, J=3.2 Hz, 4H), 2.42 (t, J=3.2 Hz, 4H), 0.98 (s, 3H), 0.70-3.70 (m, 20H). $^{13}$C NMR (125 MHz, CDCl$_3$): δ 169.9, 158.9 (d, J=242.4 Hz), 156.8, 148.3 (d, J=9.8 Hz), 138.9, 138.5, 136.8, 128.5 (2C), 128.3 (2C), 127.9, 127.85, 127.5, 127.4 (2C), 127.3 (2C), 126.3, 124.3 (d, J=2.9 Hz), 120.6 (d, J=9.3 Hz), 115.4, 112.4, 107.0 (d, J=21.5 Hz), 100.7 (d, J=26.1 Hz), 88.3, 77.0, 71.7, 69.7, 66.5 (2C), 57.8, 53.2 (2C), 50.1, 49.3, 43.0, 40.9, 34.9, 34.5, 29.9, 27.6, 26.8, 23.0, 21.6, 13.8. $^{19}$F NMR (282 MHz, CDCl$_3$): δ −116.60. HR-MS (ESI) calcd for [C$_{46}$H$_{53}$FN$_2$O$_5$ H]$^+$ 733.4017, found 733.4049.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-4-morpholinobutanamide, JD135

$^1$H NMR (500 MHz, MeOD): δ 7.77 (dd, J=8.9, 6.3 Hz, 1H), 7.01 (dd, J=10.6, 2.6 Hz, 1H), 6.77 (d, J=8.6 Hz, 1H), 6.63 (td, J=8.6, 2.6 Hz, 1H), 6.55 (d, J=2.4 Hz, 1H), 6.39 (dd, J=8.5, 2.5 Hz, 1H), 5.25 (m, 1H), 3.69 (t, J=4.8 Hz, 4H), 2.56 (d, J=4.8 Hz, 4H), 0.86 (s, 3H), 0.75-3.30 (m, 20H). $^{13}$C NMR (125 MHz, MeOD): δ 173.0, 161.4 (d, J=243.5 Hz), 156.3, 151.5 (d, J=10.2 Hz), 139.8, 128.2, 127.8, 124.7 (d, J=3.0 Hz), 124.1 (d, J=9.7 Hz), 116.6, 114.4, 107.3 (d, J=22.6 Hz), 102.3 (d, J=26.7 Hz), 82.7, 77.8, 67.3 (2C), 59.0, 54.4 (2C), 51.2, 50.3, 44.1, 40.6, 36.1, 35.5, 31.0, 30.4, 28.2, 23.9, 22.7, 13.8. $^{19}$F NMR (282 MHz, MeOD): δ −116.93.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-4-(piperidin-1-yl)butanamide $^1$H NMR (300 MHz, CDCl$_3$): δ 9.03 (br. s, 1H), 8.02 (dd, J=8.9, 6.3 Hz, 1H), 7.15-7.40 (m, 10H), 6.78 (d, J=2.5 Hz, 1H), 6.76 (s, 1H), 6.72 (d, J=8.6 Hz, 1H), 6.63 (td, J=8.6, 2.6 Hz, 1H), 6.55 (dd, J=8.5, 2.4 Hz, 1H), 5.03 (m, 1H), 5.00 (d, J=11.8 Hz, 1H), 4.96 (d, J=11.8 Hz, 1H), 4.59 (d, J=12.2 Hz, 1H), 4.50 (d, J=12.2 Hz, 1H), 3.52 (dd, J=8.0, 8.0 Hz, 1H), 2.76 (m, 4H), 1.78 (m, 4H), 0.98 (s, 3H), 0.78-3.00 (m, 21H). $^{13}$C NMR (75 MHz, CDCl$_3$): δ 168.8, 159.1 (d, J=243.1 Hz), 156.7, 148.7 (d, J=9.8 Hz), 138.9, 138.8, 136.8, 128.5 (2C), 128.3 (2C), 128.0, 127.9, 127.5, 127.4 (2C), 127.3 (2C), 126.4, 124.0 (d, J=2.9 Hz), 120.6 (d, J=9.3 Hz), 115.4, 112.6, 107.1 (d, J=21.9 Hz), 101.1 (d, J=26.9 Hz), 88.3, 77.8, 71.6, 69.8, 56.6, 53.0 (2C), 50.1, 49.3, 43.0, 41.2, 34.4, 33.3, 30.0, 27.6, 27.0, 26.7, 23.0 (2C), 22.7, 22.4, 13.9. $^{19}$F NMR (282 MHz, CDCl$_3$): δ −116.13. HR-MS (ESI) calcd for [C$_{47}$H$_{55}$FN$_2$O$_4$ H]$^+$ 731.4224, found 731.4240.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-4-(piperidin-1-yl)butan-amide, JD137

$^1$H NMR (500 MHz, MeOD): δ 7.74 (dd, J=8.9, 6.3 Hz, 1H), 7.03 (dd, J=10.6, 2.6 Hz, 1H), 6.76 (d, J=8.5 Hz, 1H), 6.64 (td, J=8.6, 2.6 Hz, 1H), 6.56 (d, J=2.5 Hz, 1H), 6.38 (dd, J=8.5, 2.6 Hz, 1H), 5.24 (m, 1H), 3.71 (dd, J=8.3, 8.3 Hz, 1H), 2.59 (m, 4H), 1.85 (m, 4H), 0.88 (s, 3H), 0.80-3.40 (m, 21H). $^{13}$C NMR (125 MHz, MeOD): δ 172.1, 161.6 (d, J=242.5 Hz), 156.2, 152.1 (d, J=10.2 Hz), 140.0, 128.34, 127.9, 124.62 (d, J=9.3 Hz), 124.56 (d, J=3.0 Hz), 116.5, 114.3, 107.4 (d, J=22.4 Hz), 102.5 (d, J=27.6 Hz), 82.7, 78.2, 58.0, 54.4 (2C), 51.3, 50.4, 44.2, 40.9, 36.0, 34.1, 31.0, 30.4, 28.3, 24.5 (2C), 24.0, 22.8, 20.6, 13.7. $^{19}$F NMR (376 MHz, MeOD): δ −118.84. HR-MS (ESI) calcd for [C$_{33}$H$_{43}$FN$_2$O$_4$ H]$^+$ 551.3285, found 551.3287.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-4-(pyrrolidin-1-yl)bu-tanamide $^1$H NMR (500 MHz, CDCl$_3$): δ 11.31 (s, 1H), 8.00 (dd, J=8.9, 6.3 Hz, 1H), 7.20-7.45 (m, 10H), 6.78 (d, J=1.8 Hz, 1H), 6.73 (m, 2H), 6.63 (td, J=8.6, 2.5 Hz, 1H), 6.54 (dd, J=8.6, 2.4 Hz, 1H), 5.03 (m, 1H), 4.99 (d, J=11.6 Hz, 1H), 4.95 (d, J=11.7 Hz, 1H), 4.60 (d, J=12.2 Hz, 1H), 4.49 (d, J=12.2 Hz, 1H), 3.52 (dd, J=8.1, 8.1 Hz, 1H), 2.92 (m, 4H), 1.92 (m, 4H), 0.98 (s, 3H), 0.80-3.20 (m, 19H). $^{13}$C NMR (125 MHz, CDCl$_3$): δ 168.6, 159.1 (d, J=243.0 Hz), 156.7, 148.8 (d, J=9.9 Hz), 138.9, 138.8, 136.8, 128.5 (2C), 128.3

(2C), 128.1, 127.9, 127.5, 127.4 (2C), 127.3 (2C), 126.4, 123.9 (d, J=3.1 Hz), 120.5 (d, J=9.4 Hz), 115.4, 112.7, 107.1 (d, J=21.7 Hz), 101.2 (d, J=26.4 Hz), 88.3, 78.0, 71.6, 69.9, 54.5, 53.2 (2C), 50.0, 49.3, 43.0, 41.2, 34.5, 32.8, 30.0, 27.6, 26.7, 23.2 (2C), 22.9, 20.8, 13.9. $^{19}$F NMR (282 MHz, CDCl$_3$): δ −115.96. HR-MS (ESI) calcd for [C$_{46}$H$_{53}$FN$_2$O$_4$ H]$^+$ 717.4067, found 717.4094.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluoro-phenyl)-4-(pyrrolidin-1-yl)butan-amide, JD138

$^1$H NMR (500 MHz, MeOD): δ 7.75 (dd, J=8.9, 6.3 Hz, 1H), 7.03 (dd, J=10.6, 2.5 Hz, 1H), 6.76 (d, J=8.6 Hz, 1H), 6.63 (td, J=8.6, 2.5 Hz, 1H), 6.57 (d, J=2.2 Hz, 1H), 6.38 (dd, J=8.5, 2.4 Hz, 1H), 5.24 (m, 1H), 3.71 (dd, J=8.2, 8.2 Hz, 1H), 2.57 (m, 4H), 1.89 (m, 4H), 0.88 (s, 3H), 0.80-3.40 (m, 19H). $^{13}$C NMR (125 MHz, MeOD): δ 171.8, 161.6 (d, J=242.7 Hz), 156.2, 152.0 (d, J=10.1 Hz), 140.0, 128.3, 127.9, 124.6 (d, J=3.3 Hz), 124.5 (d, J=9.8 Hz), 116.5, 114.3, 107.3 (d, J=22.1 Hz), 102.5 (d, J=27.0 Hz), 82.7, 78.2, 55.8, 55.2 (2C), 51.3, 50.4, 44.2, 40.9, 36.0, 33.8, 31.0, 30.4, 28.3, 24.02 (2C), 23.96, 22.4, 13.7. $^{19}$F NMR (282 MHz, MeOD): δ −116.87. HR-MS (ESI) calcd for [C$_{32}$H$_{41}$FN$_2$O$_4$ H]$^+$ 537.3129, found 537.3135.

N-(4-(((8S,9S,11S,13S,14S,17S)-3,17-bis(Benzyloxy)-13-methyl-7,8,9,11,12,13,14,15,16,17-deca-hydro-6H-cyclopenta[a]phenanthren-11-yl)oxy)-2-fluorophenyl)-4-(dimethylamino)bu-tanamide $^1$H NMR (500 MHz, CDCl$_3$): δ 8.06 (dd, J=8.8, 6.4 Hz, 1H), 7.20-7.50 (m, 10H), 6.82 (s, 1H), 6.77 (m, 2H), 6.73 (d, J=8.8 Hz, 1H), 6.63 (td, J=8.6, 2.4 Hz, 1H), 6.56 (dd, J=8.5, 2.2 Hz, 1H), 5.05 (m, 1H), 4.97 (s, 2H), 4.60 (d, J=12.2 Hz, 1H), 4.50 (d, J=12.2 Hz, 1H), 3.52 (dd, J=8.1, 8.1 Hz, 1H), 2.41 (s, 6H), 0.98 (s, 3H), 0.80-3.00 (m, 19H). $^{13}$C NMR (125 MHz, CDCl$_3$): δ 169.3, 159.1 (d, J=242.8 Hz), 156.8, 148.6 (d, J=9.8 Hz), 138.9, 138.7, 136.9, 128.6 (2C), 128.3 (2C), 128.02, 127.95, 127.5, 127.41 (2C), 127.38 (2C), 126.4, 124.1 (d, J=3.2 Hz), 120.6 (d, J=9.5 Hz), 115.4, 112.6, 107.0 (d, J=21.7 Hz), 100.9 (d, J=27.1 Hz), 88.3, 77.5, 71.7, 69.9, 57.7, 50.1, 49.3, 43.8, 43.0 (2C), 41.1, 34.5, 33.8, 29.9, 27.6, 26.8, 23.0, 21.1, 13.9. $^{19}$F NMR (282 MHz, CDCl$_3$): δ −116.34. HR-MS (ESI) calcd for [C$_{44}$H$_{51}$FN$_2$O$_4$ H]$^+$ 691.3911, found 691.3903.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluoro-phenyl)-4-(dimethylamino)butan-amide, JD139

$^1$H NMR (500 MHz, MeOD): δ 7.77 (dd, J=8.8, 6.3 Hz, 1H), 7.02 (dd, J=10.6, 2.4 Hz, 1H), 6.78 (d, J=8.5 Hz, 1H), 6.63 (td, J=8.7, 2.6 Hz, 1H), 6.54 (d, J=2.0 Hz, 1H), 6.38 (dd, J=8.5, 2.2 Hz, 1H), 5.26 (m, 1H), 3.70 (dd, J=8.3, 8.3 Hz, 1H), 2.30 (s, 6H), 0.87 (s, 3H), 0.80-3.40 (m, 19H). $^{13}$C NMR (125 MHz, MeOD): δ 172.8, 161.4 (d, J=251.5 Hz), 156.4, 151.7 (d, J=10.2 Hz), 139.8, 128.1, 127.8, 124.8 (d, J=3.0 Hz), 124.2 (d, J=9.7 Hz), 116.6, 114.4, 107.3 (d, J=22.3 Hz), 102.3 (d, J=27.0 Hz), 82.7, 77.9, 59.7, 51.3, 50.4, 45.2 (2C), 44.2, 40.8, 36.1, 35.3, 31.0, 30.4, 28.3, 24.0, 23.8, 13.3. $^{19}$F NMR (282 MHz, MeOD): δ −117.24. HR-MS (ESI) calcd for [C$_{30}$H$_{39}$FN$_2$O$_4$ H]$^+$ 511.2972, found 511.2961.

N-(4-(((8S,9S,11S,13S,14S,17S)-3,17-bis(Benzyloxy)-13-methyl-7,8,9,11,12,13,14,15,16,17-deca-hydro-6H-cyclopenta[a]phenanthren-11-yl)oxy)-2-fluorophenyl)-5-(piperidin-1-yl)pen-tanamide $^1$H NMR (500 MHz, CDCl$_3$): δ 8.63 (br s, 1H), 8.06 (dd, J=8.9, 6.3 Hz, 1H), 7.32 (m, 9H), 6.78 (d, J=2.1 Hz, 1H), 6.76 (s, 1H), 6.75 (dd, J=10.4, 2.5 Hz, 1H), 6.71 (d, J=8.7 Hz, 1H), 6.60 (td, J=8.7, 2.4 Hz, 1H), 6.53 (dd, J=8.6, 2.3 Hz, 1H), 5.01 (m, 1H), 4.97 (d, J=11.5 Hz, 1H), 4.94 (d, J=11.5 Hz, 1H), 4.57 (d, J=12.2 Hz, 1H), 4.46 (d, J=12.2 Hz, 1H), 2.69 (m, 4H), 1.72 (m, 4H), 0.96 (s, 3H), 0.80-3.60 (m, 24H). $^{13}$C NMR (125 MHz, CDCl$_3$): δ 169.4, 158.8 (d, J=243.3 Hz), 156.6, 148.1 (d, J=9.8 Hz), 138.78, 138.77, 136.8, 128.4 (2C), 128.2 (2C), 128.0, 127.8, 127.4 (2C), 127.3, 127.2 (2C), 126.2, 124.0 (d, J=3.0 Hz), 120.4 (d, J=9.1 Hz), 115.5, 112.0, 106.8 (d, J=22.5 Hz), 100.7 (d, J=26.6 Hz), 88.2, 77.2, 71.5, 69.7, 56.8, 52.8 (2C), 49.9, 49.1, 42.8, 40.8, 35.9, 34.3, 29.8, 27.4, 26.6, 23.0, 22.8, 22.4 (2C), 22.2, 22.0, 13.8. $^{19}$F NMR (282 MHz, CDCl$_3$): δ −116.30. HR-MS (ESI) calcd for [C$_{48}$H$_{57}$FN$_2$O$_4$ H]$^+$ 745.4380, found 745.4357.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluoro-phenyl)-5-(piperidin-1-yl)pentan-amide, JD140

$^1$H NMR (500 MHz, MeOD): δ 7.81 (dd, J=8.9, 6.3 Hz, 1H), 7.01 (dd, J=10.5, 2.5 Hz, 1H), 6.75 (d, J=8.6 Hz, 1H), 6.63 (td, J=8.6, 2.6 Hz, 1H), 6.59 (d, J=2.3 Hz, 1H), 6.39 (dd, J=8.5, 2.4 Hz, 1H), 5.22 (m, 1H), 3.71 (dd, J=8.3, 8.3 Hz, 1H), 2.57 (m, 4H), 1.86 (m, 4H), 0.86 (s, 3H), 0.80-3.40 (m, 23H). $^{13}$C NMR (125 MHz, MeOD): δ 172.6, 161.3 (d, J=241.8 Hz), 156.3, 151.5 (d, J=10.1 Hz), 139.9, 128.2, 127.8, 124.8 (d, J=3.2 Hz), 123.8 (d, J=10.0 Hz), 116.6, 114.3, 107.3 (d, J=21.8 Hz), 102.3 (d, J=29.8 Hz), 82.6, 78.1, 57.8, 54.2 (2C), 51.2, 50.3, 44.1, 40.8, 36.6, 36.0, 31.0, 30.4, 28.2, 24.5, 24.3 (2C), 23.9, 23.3, 22.7, 13.7. $^{19}$F NMR (376 MHz, MeOD): δ −117.03. HR-MS (ESI) calcd for [C$_{34}$H$_{45}$FN$_2$O$_4$ H]$^+$ 565.3442, found 565.3444.

N-(4-(((8S,9S,11S,13S,14S,17S)-3,17-bis(Benzyloxy)-13-methyl-7,8,9,11,12,13,14,15,16,17-deca-hydro-6H-cyclopenta[a]phenanthren-11-yl)oxy)-2-fluorophenyl)-5-morpholinopentan-amide $^1$H NMR (500 MHz, CDCl$_3$): δ 8.13 (dd, J=8.8, 6.4 Hz, 1H), 7.20-7.40 (m, 10H), 6.81 (s, 1H), 6.76 (m, 3H), 6.64 (td, J=8.7, 2.4 Hz, 1H), 6.57 (dd, J=8.6, 2.4 Hz, 1H), 5.05 (m, 1H), 4.96 (s, 2H), 4.61 (d, J=12.2 Hz, 1H), 4.50 (d, J=12.2 Hz, 1H), 3.71 (t, J=4.4 Hz, 4H), 3.53 (dd, J=8.1, 8.1 Hz, 1H), 2.45 (t, J=4.4 Hz, 4H), 0.98 (s, 3H), 0.80-3.00 (m, 21H). $^{13}$C NMR (125 MHz, CDCl$_3$): δ 170.1, 158.9 (d, J=242.5 Hz), 156.8, 148.3 (d, J=9.7 Hz), 138.9, 138.4, 136.8, 128.5 (2C), 128.3 (2C), 127.87, 127.86, 127.5, 127.4 (2C), 127.3 (2C), 126.3, 124.2 (d, J=3.0 Hz), 120.5 (d, J=9.3 Hz), 115.5, 112.3, 106.9 (d, J=21.6 Hz), 100.6 (d, J=27.4 Hz), 88.3, 76.9, 71.6, 69.7, 66.4 (2C), 58.2, 53.2 (2C), 50.0, 49.2, 42.9, 40.8, 37.1, 34.5, 30.0, 27.6, 26.8, 25.5, 23.1, 23.0, 13.8. $^{19}$F NMR (282 MHz, CDCl$_3$): δ −116.61. HR-MS (ESI) calcd for [C$_{47}$H$_{55}$FN$_2$O$_5$ H]$^+$ 747.4173, found 747.4177.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluoro-phenyl)-5-morpholinopentan-amide, JD141

$^1$H NMR (500 MHz, MeOD): δ 7.81 (dd, J=8.9, 6.3 Hz, 1H), 7.00 (dd, J=10.6, 2.6 Hz, 1H), 6.76 (d, J=8.6 Hz, 1H), 6.62 (td, J=8.6, 2.6 Hz, 1H), 6.56 (d, J=2.4 Hz, 1H), 6.39 (dd, J=8.5, 2.5 Hz, 1H), 5.22 (m, 1H), 3.76 (t, J=4.6 Hz, 4H), 3.70 (dd, J=8.3, 8.3 Hz, 1H), 2.59 (t, J=4.6 Hz, 4H), 0.86 (s, 3H), 0.80-3.35 (m, 21H). $^{13}$C NMR (125 MHz, MeOD): δ 173.0, 161.3 (d, J=242.1 Hz), 156.4, 151.4 (d, J=10.2 Hz), 139.8, 128.1, 127.8, 124.9 (d, J=3.2 Hz), 123.7 (d, J=9.6 Hz), 116.6, 114.4, 107.3 (d, J=21.5 Hz), 102.3 (d, J=26.8 Hz), 82.7, 78.0, 66.7 (2C), 59.1, 54.1 (2C), 51.2, 50.4, 44.1, 40.8, 37.3, 36.1, 31.0, 30.4, 28.3, 25.8, 24.1, 24.0, 13.7. $^{19}$F NMR (282 MHz, MeOD): δ −117.17. HR-MS (ESI) calcd for [$C_{33}H_{43}FN_2O_5$ H]$^+$ 567.3234, found 567.3226.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-5-(dimethylamino)-pentanamide $^1$H NMR (500 MHz, CDCl$_3$): δ 8.08 (dd, J=8.9, 6.3 Hz, 1H), 7.10-7.50 (m, 10H), 6.78 (m, 2H), 6.74 (d, J=9.2 Hz, 2H), 6.63 (td, J=8.6, 2.4 Hz, 1H), 6.57 (dd, J=8.6, 2.3 Hz, 1H), 5.04 (m, 1H), 4.97 (d, J=11.5 Hz, 1H), 4.95 (d, J=11.5 Hz, 1H), 4.60 (d, J=12.2 Hz, 1H), 4.49 (d, J=12.2 Hz, 1H), 3.52 (dd, J=8.1, 8.1 Hz, 1H), 2.52 (s, 6H), 0.98 (s, 3H), 0.80-3.00 (m, 21H). $^{13}$C NMR (125 MHz, CDCl$_3$): δ 169.5, 159.0 (d, J=241.2 Hz), 156.7, 148.5 (d, J=9.9 Hz), 138.91, 138.85, 136.9, 128.6 (2C), 128.3 (2C), 128.1, 128.0, 127.50 (2C), 127.48, 127.4 (2C), 126.4, 124.2 (d, J=3.0 Hz), 120.5 (d, J=9.3 Hz), 115.7, 112.2, 107.0 (d, J=22.0 Hz), 100.9 (d, J=27.1 Hz), 88.3, 77.3, 71.7, 69.8, 57.7, 50.1, 49.2, 43.1 (2C), 43.0, 41.0, 36.1, 34.5, 29.9, 27.6, 26.8, 24.4, 23.0, 22.2, 13.9. $^{19}$F NMR (282 MHz, CDCl$_3$): δ −116.36. HR-MS (ESI) calcd for [$C_{45}H_{53}FN_2O_4$ H]$^+$ 705.4067, found 705.4076.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-5-(dimethylamino)pentan-amide, JD142

$^1$H NMR (500 MHz, MeOD): δ 7.80 (dd, J=8.9, 6.3 Hz, 1H), 7.02 (dd, J=10.6, 2.6 Hz, 1H), 6.77 (d, J=8.6 Hz, 1H), 6.63 (td, J=8.6, 2.6 Hz, 1H), 6.59 (d, J=2.4 Hz, 1H), 6.39 (dd, J=8.5, 2.5 Hz, 1H), 5.25 (m, 1H), 3.71 (dd, J=8.3, 8.3 Hz, 1H), 2.84 (s, 6H), 0.87 (s, 3H), 0.80-3.40 (m, 21H). $^{13}$C NMR (125 MHz, MeOD): δ 172.6, 161.4 (d, J=240.7 Hz), 156.3, 151.5 (d, J=10.1 Hz), 139.9, 128.3, 127.8, 124.8 (d, J=3.1 Hz), 123.9 (d, J=9.8 Hz), 116.6, 114.3, 107.3 (d, J=21.4 Hz), 102.3 (d, J=27.3 Hz), 82.7, 78.1, 58.6, 51.3, 50.4, 44.1, 43.5 (2C), 40.8, 36.6, 36.1, 31.0, 30.4, 28.3, 25.2, 24.0, 23.1, 13.7. $^{19}$F NMR (282 MHz, MeOD): δ −117.17. HR-MS (ESI) calcd for [$C_{31}H_{41}FN_2O_4$H]$^+$ 525.3129, found 525.3121.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-5-(pyrrolidin-1-yl)-pentanamide $^1$H NMR (500 MHz, CDCl$_3$): δ 8.06 (dd, J=9.0, 6.3 Hz, 1H), 7.20-7.45 (m, 10H), 6.78 (d, J=2.5 Hz, 1H), 6.76 (s, 1H), 6.75 (d, J=2.6 Hz, 1H), 6.73 (d, J=8.7 Hz, 1H), 6.61 (td, J=8.6, 2.6 Hz, 1H), 6.55 (dd, J=8.6, 2.6 Hz, 1H), 5.02 (m, 1H), 4.98 (d, J=11.5 Hz, 1H), 4.95 (d, J=11.5 Hz, 1H), 4.58 (d, J=12.2 Hz, 1H), 4.47 (d, J=12.2 Hz, 1H), 3.50 (dd, J=8.1, 8.1 Hz, 1H), 2.81 (m, 4H), 1.76 (m, 4H), 0.97 (s, 3H), 0.80-3.30 (m, 21H). $^{13}$C NMR (125 MHz, CDCl$_3$): δ 169.4, 158.9 (d, J=245.0 Hz), 156.6, 148.4 (d, J=10.1 Hz), 138.83, 138.81, 136.8, 128.4 (2C), 128.2 (2C), 128.1, 127.9, 127.4 (2C), 127.34, 127.27 (2C), 126.3, 124.0 (d, J=3.2 Hz), 120.4 (d, J=9.3 Hz), 115.6, 112.0, 106.8 (d, J=22.1 Hz), 100.8 (d, J=26.9 Hz), 88.2, 77.3, 71.5, 69.7, 54.9, 53.2 (2C), 50.0, 49.2, 42.9, 40.9, 35.9, 34.3, 29.8, 27.5, 26.6, 25.0, 23.1 (2C), 22.8, 22.1, 13.8. $^{19}$F NMR (282 MHz, CDCl$_3$): δ −116.29. HR-MS (ESI) calcd for [$C_{47}H_{55}FN_2O_4$ H]$^+$ 731.4224, found 731.4247.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-5-(pyrrolidin-1-yl)pentan-amide, JD143

$^1$H NMR (500 MHz, MeOD): δ 7.81 (dd, J=8.9, 6.3 Hz, 1H), 7.01 (dd, J=10.6, 2.5 Hz, 1H), 6.75 (d, J=8.6 Hz, 1H), 6.63 (dt, J=8.4, 2.8 Hz, 1H), 6.60 (d, J=2.3 Hz, 1H), 6.40 (dd, J=8.5, 2.4 Hz, 1H), 5.22 (m, 1H), 3.71 (dd, J=8.2, 8.2 Hz, 1H), 2.57 (m, 4H), 1.65 (m, 4H), 0.86 (s, 3H), 0.75-3.50 (m, 21H). $^{13}$C NMR (125 MHz, MeOD): δ 172.6, 161.3 (d, J=242.5 Hz), 156.3, 151.5 (d, J=10.1 Hz), 139.9, 128.2, 127.8, 124.8 (d, J=3.3 Hz), 123.8 (d, J=9.9 Hz), 116.6, 114.3, 107.3 (d, J=22.1 Hz), 102.3 (d, J=27.4 Hz), 82.6, 78.0, 55.7, 55.0 (2C), 51.2, 50.3, 44.1, 40.8, 36.7, 36.0, 31.0, 30.4, 28.2, 26.5, 23.97 (2C), 23.95, 23.3, 13.7. $^{19}$F NMR (282 MHz, MeOD): δ −117.06. HR-MS (ESI) calcd for [$C_{33}H_{43}FN_2O_4$ H]$^+$ 551.3285, found 551.3286.

(8S,9S,11S,13S,14S,17S)-3,17-bis(Benzyloxy)-13-methyl-11-(4-nitro-3-(trifluoromethyl)-phenoxy)-7,8,9,11,12,13,14,15,16,17-decahydro-6H-cyclopenta[a]phenanthrene $^1$H NMR (300 MHz, CDCl$_3$): δ 8.02 (d, J=9.0 Hz, 1H), 7.25-7.50 (m, 11H), 7.22 (d, J=2.4 Hz, 1H), 7.11 (dd, J=9.0, 2.5 Hz, 1H), 6.83 (d, J=8.6 Hz, 1H), 6.76 (d, J=2.2 Hz, 1H), 6.66 (dd, J=8.6, 2.4 Hz, 1H), 5.38 (m, 1H), 5.00 (s, 2H), 4.56 (d, J=12.2 Hz, 1H), 4.47 (d, J=12.2 Hz, 1H), 3.55 (d, J=7.5, 7.5 Hz, 1H), 0.96 (s, 3H), 0.80-3.20 (m, 13H). $^{13}$C NMR (75 MHz, CDCl$_3$): δ 161.1, 156.8, 140.4 (q, J=1.6 Hz), 138.9, 138.6, 137.1, 128.5 (2C), 128.33, 128.25 (2C), 127.8, 127.7, 127.42, 127.37 (2C), 127.3 (2C), 125.7, 124.9 (q, J=182.9 Hz), 120.0 (q, J=5.1 Hz), 116.9, 115.6 (q, J=5.7 Hz), 115.3, 112.6, 88.2, 73.8, 71.6, 69.8, 50.5, 48.6, 43.0, 39.1, 33.7, 29.7, 27.5, 27.2, 23.0, 13.9. $^{19}$F NMR (282 MHz, CDCl$_3$): δ −59.97.

4-(((8S,9S,11S,13S,14S,17S)-3,17-bis(Benzyloxy)-13-methyl-7,8,9,11,12,13,14,15,16,17-deca-hydro-6H-cyclopenta[a]phenanthren-11-yl)oxy)-2-(trifluoromethyl)aniline $^1$H NMR (300 MHz, CDCl$_3$): δ 7.20-7.50 (m, 10H), 7.00 (s, 1H), 6.98 (d, J=3.8 Hz, 1H), 6.89 (dd, J=8.7, 2.7 Hz, 1H), 6.74 (m, 2H), 6.67 (d, J=8.9 Hz, 1H), 5.13 (m, 1H), 5.01 (s, 2H), 4.55 (d, J=12.2 Hz, 1H), 4.50 (d, J=12.2 Hz, 1H), 3.86 (br s, 2H), 3.50 (dd, J=7.9, 7.9 Hz, 1H), 1.05 (s, 3H), 0.90-3.10 (m, 13H). $^{13}$C NMR (75 MHz, CDCl$_3$): δ 156.6, 149.9, 140.4, 139.1, 138.5, 137.9 (q, J=1.8 Hz), 137.3, 128.7, 128.5 (2C), 128.2 (2C), 127.8, 127.4 (2C), 127.3 (2C), 126.5, 122.7 (q, J=195.4 Hz), 121.2, 120.6 (q, J=12.5 Hz), 118.8, 115.0, 113.1 (q, J=5.3 Hz), 112.5, 88.5, 72.8, 71.5, 69.8, 50.9, 48.9, 43.1, 39.2, 33.7, 29.8, 27.7, 27.3, 23.0, 13.8. $^{19}$F NMR (282 MHz, CDCl$_3$): δ −62.57. HR-MS (ESI) calcd for [$C_{39}H_{40}F_3NO_3$ H]$^+$ 628.3038, found 628.3016.

(8S,9S,11S,13S,14S,17S)-11-(4-Amino-3-(trifluoromethyl)phenoxy)-13-methyl-7,8,9,11,12,13,14,15,16,17-decahydro-6H-cyclopenta[a]phenanthrene-3,17-diol, JD128

$^1$H NMR (300 MHz, MeOD): δ 6.90 (m, 3H), 6.79 (m, 1H), 6.49 (m, 2H), 5.17 (m, 1H), 3.64 (dd, J=7.2, 7.2 Hz, 1H), 0.90 (s, 3H), 0.80-3.40 (m, 13H). $^{13}$C NMR (75 MHz, MeOD): δ 155.8, 150.9, 140.3 (q, J=2.0 Hz), 139.6, 128.7, 127.8, 123.1 (q, J=223.5 Hz), 122.5, 120.3, 118.1 (q, J=14.9 Hz), 116.2, 113.9, 113.7 (q, J=5.7 Hz), 82.9, 74.4, 51.8, 50.2, 44.2, 39.3, 35.6, 30.9, 30.5, 28.5, 23.9, 13.8. $^{19}$F NMR (282 MHz, MeOD): δ −64.06. HR-MS (ESI) calcd for $[C_{25}H_{28}F_3NO_3 \text{ H}]^+$ 448.2100, found 448.2087.

(8S,9S,11S,13S,14S,17S)-13-Methyl-11-(4-nitro-3-(trifluoromethyl)phenoxy)-7,8,9,11,12,13,14,15,16,17-decahydro-6H-cyclopenta[a]phenanthrene-3,17-diol, JD146

$^1$H NMR (500 MHz, MeOD): δ 8.05 (d, J=9.0 Hz, 1H), 7.32 (dd, J=9.1, 2.6 Hz, 1H), 7.25 (d, J=2.6 Hz, 1H), 6.84 (d, J=8.5 Hz, 1H), 6.50 (d, J=2.5 Hz, 1H), 6.41 (dd, J=8.5, 2.6 Hz, 1H), 5.54 (m, 1H), 3.68 (dd, J=8.3, 8.3 Hz, 1H), 2.60 (d, J=11.1 Hz, 1H), 2.44 (dd, J=14.5, 2.4 Hz, 1H), 0.84 (s, 3H), 0.80-3.50 (m, 11H). $^{13}$C NMR (125 MHz, MeOD): δ 162.7, 156.0, 141.6, 139.7, 129.5, 127.9, 127.2, 126.7 (q, J=35.4 Hz), 123.4 (q, J=272.8 Hz), 118.8, 116.41, 116.37 (q, J=6.0 Hz), 114.0, 82.6, 75.5, 54.7, 51.4, 44.1, 39.2, 35.5, 30.7, 30.4, 28.3, 23.9, 13.8. $^{19}$F NMR (282 MHz, MeOD): δ −61.45. HR-MS (ESI) calcd for $[C_{25}H_{26}F_3NO_5 \text{ H}]^+$ 478.1841, found 478.1840.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-2-morpho-linoacetamide $^1$H NMR (300 MHz, CDCl$_3$): δ 9.65 (s, 1H), 8.19 (d, J=9.2 Hz, 1H), 7.20-7.41 (m, 11H), 7.07 (s, 1H), 6.89 (d, J=8.7 Hz, 1H), 6.72 (d, J=2.5 Hz, 1H), 6.65 (dd, J=8.6, 2.6 Hz, 1H), 5.24 (m, 1H), 4.98 (s, 2H), 4.52 (d, J=12.3 Hz, 1H), 4.46 (d, J=12.3 Hz, 1H), 3.77 (t, J=4.2 Hz, 4H), 2.62 (t, J=4.2 Hz, 4H), 0.98 (s, 3H), 0.80-3.70 (m, 16H). $^{13}$C NMR (75 MHz, CDCl$_3$): δ 168.4, 156.6, 154.0, 139.0, 138.5, 137.2, 128.4 (2C), 128.3, 128.2 (2C), 127.8, 127.5, 127.4 (2C), 127.31, 127.3 (2C), 126.2, 125.1, 121.3 (q, J=274.6 Hz), 120.7 (q, J=40.7 Hz), 118.5, 115.0, 113.5 (q, J=4.0 Hz), 112.5, 88.3, 72.3, 71.5, 69.8, 66.9 (2C), 62.1, 53.7 (2C), 50.7, 48.7, 43.0, 39.0, 33.7, 29.6, 27.6, 27.3, 23.0, 13.7. $^{19}$F NMR (282 MHz, CDCl$_3$): δ −60.70. HR-MS (ESI) calcd for $[C_{45}H_{49}F_3N_2O_5 \text{ H}]^+$ 755.3672, found 755.3695.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-2-morpholino-acetamide, JD144

$^1$H NMR (300 MHz, MeOD): δ 7.85 (d, J=8.8 Hz, 1H), 7.18 (dd, J=9.0, 2.6 Hz, 1H), 7.13 (d, J=2.7 Hz, 1H), 6.86 (d, J=8.5 Hz, 1H), 6.49 (d, J=2.4 Hz, 1H), 6.40 (dd, J=8.5, 2.5 Hz, 1H), 5.39 (m, 1H), 3.74 (t, J=4.2 Hz, 4H), 3.67 (dd, J=8.3, 8.3 Hz, 1H), 2.61 (m, 4H), 0.87 (s, 3H), 0.80-3.32 (m, 15H). $^{13}$C NMR (75 MHz, MeOD): δ 171.6, 156.8, 156.0, 139.6, 128.9, 128.4, 128.04 (q, J=1.0 Hz), 127.5, 124.6 (q, J=29.9 Hz), 121.9 (q, J=226.6 Hz), 120.1, 116.3, 114.2 (q, J=5.7 Hz), 114.0, 82.8, 74.2, 68.0 (2C), 62.8, 54.8 (2C), 51.7, 50.0, 44.2, 39.2, 35.6, 30.8, 30.5, 28.5, 23.9, 13.8. $^{19}$F NMR (282 MHz, MeOD): δ −62.32. HR-MS (ESI) calcd for $[C_{31}H_{37}F_3N_2O_5 \text{ H}]^+$ 575.2733, found 575.2729.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-2-(piper-idin-1-yl)acetamide $^1$H NMR (300 MHz, CDCl$_3$): δ 9.76 (s, 1H), 8.11 (d, J=8.6 Hz, 1H), 7.64 (dd, J=5.7, 3.3 Hz, 1H), 7.46 (dd, J=5.7, 3.3 Hz, 1H), 7.10-7.40 (m, 9H), 6.99 (s, 1H), 6.83 (d, J=8.6 Hz, 1H), 6.64 (d, J=2.4 Hz, 1H), 6.58 (d, J=8.5 Hz, 1H), 5.18 (m, 1H), 4.91 (s, 2H), 4.45 (d, J=12.2 Hz, 1H), 4.39 (d, J=12.2 Hz, 1H), 2.50 (m, 4H), 1.58 (m, 4H), 0.90 (s, 3H), 0.75-3.50 (m, 18H). $^{13}$C NMR (75 MHz, CDCl$_3$): δ 167.5, 156.4, 153.7, 138.8, 138.3, 137.0, 132.2, 130.7, 128.6, 128.3 (2C), 128.2, 128.0 (2C), 127.6, 127.2 (2C), 127.1 (2C), 126.05, 121.5 (q, J=273.0 Hz), 121.3 (q, J=65.7 Hz), 118.2, 114.8, 112.9 (q, J=61.1 Hz), 112.3, 88.2, 72.1, 71.3, 69.6, 67.9, 54.7 (2C), 48.5, 42.8, 40.5, 38.8, 38.5, 33.5, 29.4, 28.7, 25.8 (2C), 23.5, 22.7, 13.5. $^{19}$F NMR (282 MHz, MeOD): δ −61.14. HR-MS (ESI) calcd for $[C_{46}H_{51}F_3N_2O_4 \text{ H}]^+$ 753.3879, found 753.3917.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-2-(piperidin-1-yl)acetamide, JD145

$^1$H NMR (300 MHz, MeOD): δ 7.83 (d, J=8.7 Hz, 1H), 7.18 (d, J=9.0 Hz, 1H), 7.13 (d, J=3.1 Hz, 1H), 6.87 (d, J=8.5 Hz, 1H), 6.49 (d, J=2.4 Hz, 1H), 6.42 (d, J=8.2 Hz, 1H), 5.40 (m, 1H), 3.67 (dd, J=7.2, 7.2 Hz, 1H), 2.67 (m, 4H), 1.69 (m, 4H), 0.87 (s, 3H), 0.75-3.40 (m, 17H). $^{13}$C NMR (75 MHz, MeOD): δ 171.3, 156.8, 156.0, 139.6, 129.0, 128.4, 127.9 127.5, 125.1 (q, J=272.4 Hz), 124.8 (q, J=29.9 Hz), 120.1, 116.3, 114.1 (q, J=5.5 Hz), 114.0, 82.8, 74.2, 62.6, 55.8 (2C), 51.7, 50.0, 44.2, 39.2, 35.6, 30.8, 30.5, 28.5, 26.7 (2C), 24.4, 24.0, 13.8. $^{19}$F NMR (282 MHz, MeOD): δ −62.47. HR-MS (ESI) calcd for $[C_{32}H_{39}F_3N_2O_4 \text{ H}]^+$ 573.2940, found 573.2942.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-2-(pyrro-lidin-1-yl)acetamide $^1$H NMR (300 MHz, CDCl$_3$): δ 9.76 (s, 1H), 8.22 (t, J=10.3 Hz, 1H), 7.71 (m, 1H), 7.53 (m, 1H), 7.10-7.40 (m, 8H), 7.06 (s, 1H), 6.91 (d, J=8.8 Hz, 1H), 6.72 (m, 2H), 6.66 (d, J=8.7 Hz, 1H), 5.24 (m, 1H), 4.99 (s, 2H), 4.52 (d, J=12.1 Hz, 1H), 4.47 (d, J=12.1 Hz, 1H), 2.72 (m, 4H), 1.60 (m, 4H), 0.98 (s, 3H), 0.80-4.30 (m, 16H). $^{13}$C NMR (75 MHz, CDCl$_3$): δ 167.7, 156.7, 153.9, 139.0, 138.5, 137.2, 132.4, 130.8, 128.8, 128.5 (2C), 128.2 (2C), 127.8, 127.4 (2C), 127.3 (2C), 126.2, 125.1, 124.6 (q, J=274.9 Hz), 118.4, 117.9 (q, J=7.9 Hz), 115.1, 113.6 (q, J=4.3 Hz), 112.5, 88.4, 72.3, 71.5, 69.8, 68.1, 54.3 (2C), 50.7, 48.7, 43.0, 39.1, 38.7, 30.3, 29.7, 28.9, 24.0 (2C), 22.9, 14.0. $^{19}$F NMR (282 MHz, CDCl$_3$): δ −61.20. HR-MS (ESI) calcd for $[C_{45}H_{49}F_3N_2O_4 \text{ H}]^+$ 739.3723, found 739.3746.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-2-(pyrrolidin-1-yl)acetamide, JD147

$^1$H NMR (500 MHz, MeOD): δ 7.70 (d, J=8.9 Hz, 1H), 7.19 (dd, J=8.9, 2.7 Hz, 1H), 7.14 (d, J=2.7 Hz, 1H), 6.87 (d, J=8.6 Hz, 1H), 6.49 (d, J=2.4 Hz, 1H), 6.41 (dd, J=8.5, 2.6 Hz, 1H), 5.42 (m, 1H), 3.67 (dd, J=8.3, 8.3 Hz, 1H), 2.89 (m, 4H), 1.92 (m, 4H), 0.86 (s, 3H), 0.80-3.60 (m, 15H). $^{13}$C NMR (125 MHz, MeOD): δ 171.1, 157.2, 155.9, 139.6, 130.1, 128.4, 127.7, 127.5, 126.0 (q, J=30.3 Hz), 125.0 (q, J=272.3 Hz), 120.1, 116.3, 114.2 (q, J=5.4 Hz), 114.0, 82.8, 74.1, 59.1, 55.4 (2C), 51.6, 50.0, 44.2, 39.2, 35.6, 30.8, 30.4, 28.5, 24.7 (2C), 23.9, 13.8. $^{19}$F NMR (282 MHz, MeOD): δ −62.61. HR-MS (ESI) calcd for [C$_{31}$H$_{37}$F$_3$N$_2$O$_4$ H]$^+$ 559.2784, found 559.2797.

N-(4-(((8S,9S,11S,13S,14S,17S)-3,17-bis(Benzyloxy)-13-methyl-7,8,9,11,12,13,14,15,16,17-deca-hydro-6H-cyclopenta[a]phenanthren-11-yl)oxy)-2-(trifluoromethyl)phenyl)-2-(dimeth-ylamino)acetamide $^1$H NMR (300 MHz, CDCl$_3$): δ 9.62 (s, 1H), 8.14 (d, J=9.6 Hz, 1H), 7.10-7.50 (m, 9H), 7.07 (s, 1H), 6.90 (d, J=8.5 Hz, 1H), 6.72 (m, 2H), 6.67 (d, J=8.5 Hz, 2H), 5.24 (m, 1H), 4.99 (s, 2H), 4.53 (d, J=12.2 Hz, 1H), 4.48 (d, J=12.2 Hz, 1H), 3.48 (dd, J=8.3, 8.3 Hz, 1H), 2.40 (s, 6H), 0.99 (s, 3H), 0.75-3.40 (m, 15H). $^{13}$C NMR (75 MHz, CDCl$_3$): δ 169.3, 156.7, 154.1, 139.0, 138.5, 137.2, 128.5 (2C), 128.4, 128.2 (2C), 128.1, 127.8, 127.7, 127.4 (2C), 127.3 (2C), 126.2, 125.5, 123.1 (q, J=250.0 Hz), 121.6 (q, J=28.3 Hz), 118.4, 115.1, 113.6 (q, J=5.6 Hz), 112.5, 88.4, 72.3, 71.5, 69.8, 63.3, 50.8, 48.7, 45.8 (2C), 43.0, 39.1, 33.7, 29.7, 27.6, 27.3, 23.0, 13.7. $^{19}$F NMR (282 MHz, CDCl$_3$): δ −61.15. HR-MS (ESI) calcd for [C$_{43}$H$_{47}$F$_3$N$_2$O$_4$ H]$^+$ 713.3566, found 713.3575.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-2-(dimethylam-ino)acetamide, JD148

$^1$H NMR (500 MHz, MeOD): δ 7.67 (d, J=8.9 Hz, 1H), 7.19 (dd, J=8.9, 2.7 Hz, 1H), 7.14 (d, J=2.8 Hz, 1H), 6.87 (d, J=8.5 Hz, 1H), 6.49 (d, J=2.4 Hz, 1H), 6.41 (dd, J=8.5, 2.5 Hz, 1H), 5.41 (m, 1H), 3.67 (dd, J=8.2, 8.2 Hz, 1H), 2.48 (s, 6H), 0.86 (s, 3H), 0.78-3.50 (m, 15H). $^{13}$C NMR (125 MHz, MeOD): δ 171.3, 157.3, 155.9, 139.6, 130.4, 128.4, 127.7, 127.5, 126.2 (q, J=30.4 Hz), 124.9 (q, J=271.4 Hz), 120.0, 116.3, 114.2 (q, J=5.5 Hz), 114.0, 82.8, 74.1, 63.1, 51.6, 50.0, 45.8 (2C), 44.2, 39.1, 35.6, 30.8, 30.4, 28.5, 23.9, 13.8. $^{19}$F NMR (282 MHz, MeOD): δ −62.60. HR-MS (ESI) calcd for [C$_{29}$H$_{35}$F$_3$N$_2$O$_4$ H]$^+$ 533.2627, found 533.2650.

N-(4-(((8S,9S,11S,13S,14S,17S)-3,17-bis(Benzyloxy)-13-methyl-7,8,9,11,12,13,14,15,16,17-deca-hydro-6H-cyclopenta[a]phenanthren-11-yl)oxy)-2-(trifluoromethyl)phenyl)-3-(piper-idin-1-yl)propanamide $^1$H NMR (500 MHz, CDCl$_3$): δ 10.60 (s, 1H), 7.71 (d, J=9.7 Hz, 1H), 7.10-7.48 (m, 10H), 7.06 (s, 1H), 7.05 (dd, J=6.9, 3.1 Hz, 1H), 6.90 (d, J=8.6 Hz, 1H), 6.71 (d, J=2.5 Hz, 1H), 6.67 (dd, J=8.6, 2.6 Hz, 1H), 5.24 (m, 1H), 4.98 (s, 2H), 4.53 (d, J=12.3 Hz, 1H), 4.46 (d, J=12.3 Hz, 1H), 3.47 (d, J=6.5, 6.5 Hz, 1H), 2.48 (m, 4H), 1.60 (m, 4H), 0.97 (s, 3H), 0.80-3.30 (m, 19H). $^{13}$C NMR (125 MHz, CDCl$_3$): δ 171.7, 156.5, 154.5, 138.9, 138.4, 137.1, 129.0, 128.4 (2C), 128.3, 128.2 (2C), 127.7, 127.4 (2C), 127.28 (2C), 127.27, 126.2, 124.1 (q, J=29.6 Hz), 123.4 (q, J=273.6 Hz), 119.2 (q, J=20.8 Hz), 117.9, 115.0, 113.2 (q, J=5.4 Hz), 112.5, 88.2, 71.9, 71.4, 69.7, 54.3, 53.8 (2C), 50.6, 48.6, 46.7, 42.9, 40.5, 38.9, 33.6, 32.1, 29.6, 26.5, 25.1 (2C), 24.6, 13.6. $^{19}$F NMR (282 MHz, CDCl$_3$): δ −60.92. HR-MS (ESI) calcd for [C$_{47}$H$_{53}$F$_3$N$_2$O$_4$ H]$^+$ 767.4036, found 767.4003.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-3-(piperidin-1-yl)propanamide, JD149

$^1$H NMR (500 MHz, MeOD): δ 7.53 (d, J=8.8 Hz, 1H), 7.33 (d, J=8.9 Hz, 1H), 7.28 (d, J=2.1 Hz, 1H), 7.02 (d, J=8.6 Hz, 1H), 6.65 (d, J=1.7 Hz, 1H), 6.57 (dd, J=8.4, 2.0 Hz, 1H), 5.56 (m, 1H), 3.83 (dd, J=8.2, 8.2 Hz, 1H), 2.98 (m, 4H), 1.92 (m, 4H), 1.01 (s, 3H), 0.90-3.60 (m, 19H). 13C NMR (125 MHz, MeOD): δ 172.8, 157.9, 155.9, 139.6, 133.0, 128.4, 128.5 (q, J=30.0 Hz), 127.5, 127.4, 124.8 (q, J=272.7 Hz), 119.9, 116.3, 114.1 (q, J=4.6 Hz), 114.0, 82.7, 74.0, 54.6 (2C), 54.5, 51.6, 49.9, 44.2, 39.1, 35.6, 31.8, 30.8, 30.4, 28.5, 25.1 (2C), 23.9, 23.6, 13.8. $^{19}$F NMR (282 MHz, MeOD): δ −62.44. HR-MS (ESI) calcd for [C$_{33}$H$_{41}$F$_3$N$_2$O$_4$ H]$^+$ 587.3097, found 587.3116.

N-(4-(((8S,9S,11S,13S,14S,17S)-3,17-bis(Benzyloxy)-13-methyl-7,8,9,11,12,13,14,15,16,17-deca-hydro-6H-cyclopenta[a]phenanthren-11-yl)oxy)-2-(trifluoromethyl)phenyl)-3-morpho-linopropanamide $^1$H NMR (500 MHz, CDCl$_3$): δ 10.27 (s, 1H), 7.80 (d, J=9.7 Hz, 1H), 7.20-7.49 (m, 10H), 7.08 (m, 2H), 6.91 (d, J=8.7 Hz, 1H), 6.73 (d, J=2.6 Hz, 1H), 6.67 (dd, J=8.6, 2.6 Hz, 1H), 5.26 (m, 1H), 4.99 (s, 2H), 4.54 (d, J=12.3 Hz, 1H), 4.46 (d, J=12.2 Hz, 1H), 3.76 (m, 4H), 3.58 (dd, J=5.5, 5.5 Hz, 1H), 2.60 (m, 4H), 0.98 (s, 3H), 0.80-3.90 (m, 17H). $^{13}$C NMR (125 MHz, CDCl$_3$): δ 171.1, 156.6, 154.4, 138.9, 138.4, 137.1, 128.5, 128.4 (2C), 128.3, 128.2 (2C), 128.1, 127.7, 127.4 (2C), 127.3 (2C), 126.2, 123.6 (q, J=273.9 Hz), 123.5 (q, J=29.8 Hz), 119.3 (q, J=22.2 Hz), 118.0, 115.0, 113.2 (q, J=4.8 Hz), 112.5, 88.2, 72.0, 71.4, 69.7, 66.2 (2C), 54.3, 53.0 (2C), 50.6, 48.6, 42.9, 38.9, 33.6, 31.8, 29.6, 27.5, 27.3, 23.0, 13.7. $^{19}$F NMR (282 MHz, CDCl$_3$): δ −60.71. HR-MS (ESI) calcd for [C$_{46}$H$_{51}$F$_3$N$_2$O$_5$ H]$^+$ 769.3828, found 769.3804.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-3-morpholino-propanamide, JD152

$^1$H NMR (500 MHz, MeOD): δ 7.44 (d, J=8.8 Hz, 1H), 7.19 (dd, J=8.5, 2.1 Hz, 1H), 7.14 (d, J=2.4 Hz, 1H), 6.88 (d, J=8.6 Hz, 1H), 6.50 (d, J=1.9 Hz, 1H), 6.42 (dd, J=8.5, 2.2 Hz, 1H), 5.41 (m, 1H), 3.72 (t, J=4.2 Hz, 4H), 3.68 (dd, J=8.4, 8.4 Hz, 1H), 2.62 (m, 4H), 0.87 (s, 3H), 0.80-3.50 (m, 17H). $^{13}$C NMR (125 MHz, MeOD): δ 174.4, 157.6, 155.9, 139.6, 132.5, 128.4, 127.8 (q, J=29.5 Hz), 127.7, 127.5, 124.9 (q, J=272.6 Hz), 119.9, 116.3, 114.04 (q, J=2.5 Hz), 114.0, 82.7, 74.0, 67.5 (2C), 55.3, 54.2 (2C), 51.6, 49.9, 44.2, 39.1, 35.6, 33.2, 30.8, 30.4, 28.5, 23.9, 13.8. $^{19}$F NMR (282 MHz, MeOD): δ −62.30. HR-MS (ESI) calcd for $[C_{32}H_{39}F_3N_2O_5 H]^+$ 589.2889, found 589.2883.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-3-(pyrro-lidin-1-yl)propanamide $^1$H NMR (500 MHz, CDCl$_3$): δ 10.96 (s, 1H), 7.90 (d, J=8.6 Hz, 1H), 7.20-7.45 (m, 10H), 7.08 (d, J=2.7 Hz, 1H), 7.06 (s, 1H), 6.91 (d, J=8.7 Hz, 1H), 6.72 (d, J=2.4 Hz, 1H), 6.67 (dd, J=8.6, 2.5 Hz, 1H), 5.25 (m, 1H), 4.99 (s, 2H), 4.54 (d, J=12.3 Hz, 1H), 4.47 (d, J=12.3 Hz, 1H), 3.48 (dd, J=6.0, 6.0 Hz, 1H), 2.66 (m, 4H), 1.84 (m, 4H), 0.98 (s, 3H), 0.80-3.50 (m, 17H). $^{13}$C NMR (125 MHz, CDCl$_3$): δ 171.4, 156.6, 154.1, 139.0, 138.4, 137.2, 128.4 (2C), 128.3, 128.2 (2C), 127.8, 127.7, 127.4 (2C), 127.28 (2C), 127.27, 126.2, 123.5 (q, J=273.7 Hz), 123.1 (q, J=29.9 Hz), 119.2 (q, J=21.6 Hz), 118.0, 115.0, 113.2 (q, J=5.4 Hz), 112.5, 88.3, 72.0, 71.4, 69.7, 53.2 (2C), 51.4, 50.7, 48.6, 42.9, 38.9, 34.3, 33.6, 29.7, 27.6, 27.3, 23.2 (2C), 23.0, 13.6. $^{19}$F NMR (282 MHz, CDCl$_3$): δ −61.58. HR-MS (ESI) calcd for $[C_{46}H_{51}F_3N_2O_4 H]^+$ 753.3879, found 753.3881.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-3-(pyrrolidin-1-yl)propanamide, JD150

$^1$H NMR (500 MHz, MeOD): δ 7.43 (d, J=8.8 Hz, 1H), 7.18 (dd, J=8.8, 2.1 Hz, 1H), 7.13 (d, J=2.4 Hz, 1H), 6.87 (d, J=8.6 Hz, 1H), 6.50 (d, J=1.9 Hz, 1H), 6.42 (dd, J=8.4, 2.2 Hz, 1H), 5.40 (m, 1H), 3.67 (dd, J=8.2, 8.2 Hz, 1H), 2.82 (t, J=6.7 Hz, 4H), 1.98 (m, 4H), 0.85 (s, 3H), 0.80-3.40 (m, 17H). $^{13}$C NMR (125 MHz, MeOD): δ 172.6, 157.8, 155.9, 139.6, 132.7, 128.4, 127.5, 128.12, 128.10 (q, J=15.8 Hz), 124.7 (q, J=276.1 Hz), 119.9, 116.3, 114.1 (q, J=5.3 Hz), 114.0, 82.7, 74.0, 55.0 (2C), 52.1, 51.5, 49.8, 44.1, 39.1, 35.6, 33.5, 30.8, 30.4, 28.5, 24.1 (2C), 23.9, 13.8. $^{19}$F NMR (282 MHz, MeOD): δ −62.51. HR-MS (ESI) calcd for $[C_{32}H_{39}F_3N_2O_4 H]^+$ 573.2940, found 573.2943.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-3-(dimeth-ylamino)propanamide $^1$H NMR (500 MHz, CDCl$_3$): δ 11.22 (s, 1H), 7.97 (d, J=9.7 Hz, 1H), 7.20-7.45 (m, 10H), 7.06 (m, 2H), 6.91 (d, J=8.7 Hz, 1H), 6.72 (d, J=2.6 Hz, 1H), 6.67 (dd, J=8.6, 2.7 Hz, 1H), 5.24 (m, 1H), 4.99 (s, 2H), 4.54 (d, J=12.3 Hz, 1H), 4.47 (d, J=12.3 Hz, 1H), 3.48 (dd, J=8.1, 8.1 Hz, 1H), 2.32 (s, 6H), 0.98 (s, 3H), 0.80-3.00 (m, 17H). $^{13}$C NMR (125 MHz, CDCl$_3$): δ 171.2, 156.6, 153.9, 139.0, 138.4, 137.2, 128.5 (2C), 128.4, 128.2 (2C), 127.8, 127.4 (2C), 127.3 (2C), 127.28, 127.26, 126.2, 123.7 (q, J=230.8 Hz), 122.5 (q, J=12.0 Hz), 119.2 (q, J=22.1 Hz), 118.0, 115.0, 113.4 (q, J=5.1 Hz), 112.5, 88.3, 72.0, 71.5, 69.8, 54.5, 50.7, 48.6, 44.1 (2C), 43.0, 39.0, 33.6, 33.0, 29.7, 27.6, 27.3, 23.0, 13.7. $^{19}$F NMR (282 MHz, CDCl$_3$): δ −61.80. HR-MS (ESI) calcd for $[C_{44}H_{49}F_3N_2O_4 H]^+$ 727.3723, found 727.3730.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-3-(dimethylam-ino)propanamide, JD151

$^1$H NMR (500 MHz, MeOD): δ 7.47 (d, J=8.8 Hz, 1H), 7.19 (dd, J=8.8, 2.5 Hz, 1H), 7.14 (d, J=2.6 Hz, 1H), 6.88 (d, J=8.6 Hz, 1H), 6.51 (d, J=2.3 Hz, 1H), 6.42 (dd, J=8.5, 2.4 Hz, 1H), 5.42 (m, 1H), 3.68 (dd, J=8.2, 8.2 Hz, 1H), 2.57 (s, 6H), 0.87 (s, 3H), 0.80-3.50 (m, 17H). $^{13}$C NMR (125 MHz, MeOD): δ 173.2, 157.7, 155.9, 139.6, 132.4, 128.4, 128.1 (q, J=29.7 Hz), 127.7, 127.5, 124.8 (q, J=273.4 Hz), 120.2, 116.3, 114.1 (q, J=5.2 Hz), 114.0, 82.7, 74.0, 55.4, 51.6, 49.9, 44.4 (2C), 44.2, 39.1, 35.6, 32.7, 30.8, 30.4, 28.5, 23.9, 13.8. $^{19}$F NMR (282 MHz, MeOD): δ −62.65. HR-MS (ESI) calcd for $[C_{30}H_{37}F_3N_2O_4 H]^+$ 547.2784, found 547.2759.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-4-(piperi-din-1-yl)butanamide $^1$H NMR (500 MHz, CDCl$_3$): δ 8.44 (s, 1H), 7.52 (d, J=8.7 Hz, 1H), 7.20-7.40 (m, 10H), 7.05 (s, 1H), 7.02 (d, J=9.1 Hz, 1H), 6.85 (d, J=8.6 Hz, 1H), 6.69 (s, 1H), 6.64 (d, J=8.6 Hz, 1H), 5.22 (m, 1H), 4.96 (s, 2H), 4.50 (d, J=12.2 Hz, 1H), 4.43 (d, J=12.3 Hz, 1H), 3.45 (dd, J=6.8, 6.8 Hz, 1H), 2.65 (m, 4H), 1.58 (m, 4H), 0.94 (s, 3H), 0.80-3.30 (m, 21H). $^{13}$C NMR (125 MHz, CDCl$_3$): δ 171.1, 156.5, 155.5, 138.9, 138.4, 137.1, 129.9, 128.39 (2C), 128.2 (2C), 127.7, 127.35 (2C), 127.26 (2C), 127.23, 126.6, 126.1, 125.6 (q, J=29.0 Hz), 123.3 (q, J=272.5 Hz), 118.1, 115.0, 113.4 (q, J=5.4 Hz), 112.4, 88.2, 72.1, 71.4, 69.7, 56.4, 53.3 (2C), 50.6, 48.5, 42.9, 38.9, 33.6, 33.1, 32.3, 29.6, 27.5, 22.9, 22.7 (2C), 22.2, 19.8, 13.6. $^{19}$F NMR (282 MHz, CDCl$_3$): δ −60.65. HR-MS (ESI) calcd for $[C_{48}H_{55}F_3N_2O_4 H]^+$ 781.4192, found 781.4221.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-4-(piperidin-1-yl)butanamide, JD160

$^1$H NMR (500 MHz, MeOD): δ 7.31 (d, J=8.8 Hz, 1H), 7.18 (dd, J=8.8, 2.7 Hz, 1H), 7.14 (d, J=2.7 Hz, 1H), 6.87 (d, J=8.5 Hz, 1H), 6.49 (d, J=2.5 Hz, 1H), 6.41 (dd, J=8.5, 2.6 Hz, 1H), 5.42 (m, 1H), 3.67 (dd, J=8.3, 8.3 Hz, 1H), 2.40 (m, 4H), 1.48 (m, 4H), 0.86 (s, 3H), 0.80-3.50 (m, 21H). $^{13}$C NMR (125 MHz, MeOD): δ 175.6, 158.1, 155.9, 139.6, 133.3, 129.1 (q, J=31.4 Hz), 128.4, 127.8, 127.5, 124.8 (q, J=270.6 Hz), 119.9, 116.3, 114.2 (q, J=5.5 Hz), 114.0, 82.7, 74.1, 59.3, 55.3 (2C), 51.6, 50.0, 44.2, 43.7, 39.1, 35.6, 34.8, 30.8, 28.5, 26.1 (2C), 24.8, 23.9, 23.0, 13.8. $^{19}$F NMR (282 MHz, MeOD): δ −62.51. HR-MS (ESI) calcd for $[C_{34}H_{43}F_3N_2O_4 H]^+$ 601.3253, found 601.3267.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-4-morpho-linobutanamide $^1$H NMR (500 MHz, CDCl$_3$): δ 7.84 (d, J=9.6 Hz, 1H), 7.70 (s, 1H), 7.20-7.50 (m, 10H), 7.06 (m, 2H), 6.89 (d, J=8.7 Hz, 1H), 6.72 (d, J=2.5 Hz, 1H), 6.67 (dd, J=8.6, 2.7

Hz, 1H), 5.25 (m, 1H), 4.99 (s, 2H), 4.54 (d, J=12.3 Hz, 1H), 4.46 (d, J=12.3 Hz, 1H), 3.70 (m, 4H), 3.48 (dd, J=8.2, 8.2 Hz, 1H), 2.45 (m, 4H), 0.97 (s, 3H), 0.80-3.80 (m, 19H). $^{13}$C NMR (125 MHz, CDCl$_3$): δ 171.5, 156.6, 154.7, 138.9, 138.5, 137.1, 128.5 (2C), 128.2 (2C), 128.1, 127.8, 127.5, 127.4 (2C), 127.34, 127.32 (2C), 127.1, 126.2, 123.6 (q, J=273.7 Hz), 123.3 (q, J=30.8 Hz), 118.3, 115.0, 113.5 (q, J=5.5 Hz), 112.5, 88.2, 72.2, 71.5, 69.8, 66.8 (2C), 57.5, 53.5 (2C), 50.7, 48.7, 43.0, 38.9, 35.0, 33.6, 29.7, 27.6, 27.3, 23.0, 21.9, 13.7. $^{19}$F NMR (282 MHz, CDCl$_3$): δ −60.74. HR-MS (ESI) calcd for [C$_{47}$H$_{53}$F$_3$N$_2$O$_5$ H]$^+$ 783.3985, found 783.3984.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-4-morpholino-butanamide, JD153

$^1$H NMR (500 MHz, MeOD): δ 7.32 (d, J=8.7 Hz, 1H), 7.18 (dd, J=8.7, 1.7 Hz, 1H), 7.14 (s, 1H), 6.87 (d, J=8.6 Hz, 1H), 6.49 (d, J=1.7 Hz, 1H), 6.41 (dd, J=8.5, 2.1 Hz, 1H), 5.42 (m, 1H), 3.73 (t, J=4.3 Hz, 4H), 3.67 (dd, J=8.2, 8.2 Hz, 1H), 2.64 (m, 4H), 0.86 (s, 3H), 0.80-3.40 (m, 19H). $^{13}$C NMR (125 MHz, MeOD): δ 175.5, 158.0, 155.9, 139.6, 133.2, 129.0 (q, J=30.8 Hz), 128.4, 127.8, 127.5, 124.8 (q, J=273.1 Hz), 119.9, 116.3, 114.2 (q, J=5.3 Hz), 114.0, 82.7, 74.1, 67.2 (2C), 59.0, 54.5 (2C), 51.6, 49.9, 44.2, 39.1, 35.6, 34.5, 30.8, 30.4, 28.5, 23.9, 22.7, 13.8. $^{19}$F NMR (282 MHz, MeOD): δ −62.47. HR-MS (ESI) calcd for [C$_{33}$H$_{41}$F$_3$N$_2$O$_5$ H]$^+$ 603.3046, found 603.3047.

N-(4-(((8S,9S,11S,13S,14S,17S)-3,17-bis(Benzyloxy)-13-methyl-7,8,9,11,12,13,14,15,16,17-deca-hydro-6H-cyclopenta[a]phenanthren-11-yl)oxy)-2-(trifluoromethyl)phenyl)-4-(pyrroli-din-1-yl)butanamide $^1$H NMR (500 MHz, CDCl$_3$): δ 8.35 (s, 1H), 7.53 (d, J=8.7 Hz, 1H), 7.20-7.40 (m, 10H), 7.06 (s, 1H), 7.04 (d, J=9.0 Hz, 1H), 6.85 (d, J=8.6 Hz, 1H), 6.70 (s, 1H), 6.65 (d, J=8.6 Hz, 1H), 5.23 (m, 1H), 4.97 (s, 2H), 4.52 (d, J=12.2 Hz, 1H), 4.44 (d, J=12.2 Hz, 1H), 0.95 (s, 3H), 0.80-3.50 (m, 28H). $^{13}$C NMR (125 MHz, CDCl$_3$): δ 171.0, 156.6, 155.6, 138.9, 138.4, 137.1, 130.0, 128.5, 128.4 (2C), 128.2 (2C), 127.8, 127.4 (2C), 127.31 (2C), 127.29, 126.5, 126.1, 125.6 (q, J=27.6 Hz), 123.4 (q, J=274.1 Hz), 118.2, 115.0, 113.5 (q, J=5.3 Hz), 112.5, 88.2, 72.2, 71.5, 69.8, 54.4, 53.7 (2C), 50.6, 48.6, 42.9, 38.9, 33.6, 32.8, 29.6, 27.6, 27.3, 23.3 (2C), 23.0, 21.8, 13.7. $^{19}$F NMR (282 MHz, CDCl$_3$): δ −60.61. HR-MS (ESI) calcd for [C$_{47}$H$_{53}$F$_3$N$_2$O$_4$ H]$^+$ 767.4036, found 767.4067.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-4-(pyrrolidin-1-yl)butanamide, JD154

$^1$H NMR (500 MHz, MeOD): δ 7.31 (d, J=8.7 Hz, 1H), 7.18 (dd, J=8.8, 2.3 Hz, 1H), 7.14 (d, J=2.5 Hz, 1H), 6.86 (d, J=8.6 Hz, 1H), 6.48 (d, J=2.0 Hz, 1H), 6.40 (dd, J=8.5, 2.2 Hz, 1H), 5.42 (m, 1H), 3.67 (dd, J=8.2, 8.2 Hz, 1H), 2.57 (m, 4H), 1.81 (m, 4H), 0.86 (s, 3H), 0.80-3.50 (m, 19H). $^{13}$C NMR (125 MHz, MeOD): δ 175.7, 158.0, 156.4, 139.6, 133.2, 129.0 (q, J=29.3 Hz), 128.1, 127.9, 127.5, 124.8 (q, J=272.2 Hz), 119.9, 116.4, 114.2 (q, J=5.0 Hz), 114.16, 82.8, 74.1, 56.8, 55.0 (2C), 51.7, 50.0, 44.2, 39.2, 35.7, 35.0, 30.8, 30.5, 28.6, 25.7, 24.2 (2C), 24.0, 13.8. $^{19}$F NMR (282 MHz, MeOD): δ −62.53. HR-MS (ESI) calcd for [C$_{33}$H$_{41}$F$_3$N$_2$O$_4$ H]$^+$ 587.3097, found 587.3122.

N-(4-(((8S,9S,11S,13S,14S,17S)-3,17-bis(Benzyloxy)-13-methyl-7,8,9,11,12,13,14,15,16,17-deca-hydro-6H-cyclopenta[a]phenanthren-11-yl)oxy)-2-(trifluoromethyl)phenyl)-4-(dimeth-ylamino)butanamide $^1$H NMR (500 MHz, CDCl$_3$): δ 8.36 (s, 1H), 7.61 (d, J=8.7 Hz, 1H), 7.20-7.40 (m, 10H), 7.07 (s, 1H), 7.05 (d, J=12.3 Hz, 1H), 6.87 (d, J=8.7 Hz, 1H), 6.71 (s, 1H), 6.67 (dd, J=8.6, 2.2 Hz, 1H), 5.24 (m, 1H), 4.98 (s, 2H), 4.53 (d, J=12.3 Hz, 1H), 4.45 (d, J=12.3 Hz, 1H), 3.47 (dd, J=7.7, 7.7 Hz, 1H), 2.61 (s, 6H), 0.96 (s, 3H), 0.80-3.00 (m, 19H). $^{13}$C NMR (125 MHz, CDCl$_3$): δ 171.1, 156.6, 155.3, 138.9, 138.4, 137.1, 129.4, 128.5, 128.4 (2C), 128.2 (2C), 127.8, 127.4 (2C), 127.34, 127.3 (2C), 126.7, 126.1, 125.0 (q, J=32.4 Hz), 123.4 (q, J=275.1 Hz), 118.2, 115.0, 113.4 (q, J=5.0 Hz), 112.5, 88.2, 72.2, 71.4, 69.8, 57.4, 50.6, 48.6, 43.5 (2C), 42.9, 38.9, 33.6, 33.5, 29.6, 27.5, 27.3, 23.0, 21.1, 13.7. $^{19}$F NMR (282 MHz, CDCl$_3$): δ −60.68. HR-MS (ESI) calcd for [C$_{45}$H$_{51}$F$_3$N$_2$O$_4$H]$^+$ 741.3879, found 741.3911.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-4-(dimethylam-ino)butanamide, JD155

$^1$H NMR (500 MHz, MeOD): δ 7.31 (d, J=8.7 Hz, 1H), 7.17 (dd, J=8.8, 2.6 Hz, 1H), 7.14 (d, J=2.7 Hz, 1H), 6.86 (d, J=8.5 Hz, 1H), 6.48 (d, J=2.4 Hz, 1H), 6.40 (dd, J=8.5, 2.6 Hz, 1H), 5.41 (m, 1H), 3.67 (dd, J=8.3, 8.3 Hz, 1H), 2.25 (s, 6H), 0.86 (s, 3H), 0.80-3.40 (m, 19H). $^{13}$C NMR (125 MHz, MeOD): δ 175.6, 158.0, 156.4, 139.6, 133.2, 129.0 (q, J=29.9 Hz), 128.1, 127.9, 127.5, 124.8 (q, J=273.0 Hz), 119.9, 116.5, 114.2 (q, J=5.2 Hz), 114.17, 82.8, 74.1, 59.9, 51.7, 50.0, 45.4 (2C), 44.2, 39.1, 35.7, 34.8, 30.8, 30.5, 28.6, 24.3, 24.0, 13.8. $^{19}$F NMR (282 MHz, MeOD): δ −62.52. HR-MS (ESI) calcd for [C$_{31}$H$_{39}$F$_3$N$_2$O$_4$ H]$^+$ 561.2940, found 561.2912.

N-(4-(((8S,9S,11S,13S,14S,17S)-3,17-bis(Benzyloxy)-13-methyl-7,8,9,11,12,13,14,15,16,17-deca-hydro-6H-cyclopenta[a]phenanthren-11-yl)oxy)-2-(trifluoromethyl)phenyl)-5-(piperid-in-1-yl)pentanamide $^1$H NMR (500 MHz, CDCl$_3$): δ 7.75 (d, J=9.5 Hz, 1H), 7.62 (s, 1H), 7.20-7.40 (m, 10H), 7.05 (s, 1H), 7.04 (dd, J=7.4, 2.9 Hz, 1H), 6.87 (d, J=8.7 Hz, 1H), 6.70 (d, J=2.1 Hz, 1H), 6.65 (dd, J=8.6, 2.3 Hz, 1H), 5.85 (br.s, 1H), 5.23 (m, 1H), 4.97 (s, 2H), 4.52 (d, J=12.3 Hz, 1H), 4.44 (d, J=12.2 Hz, 1H), 3.47 (dd, J=8.1, 8.1 Hz, 1H), 2.61 (m, 4H), 1.48 (m, 4H), 0.96 (s, 3H), 0.80-3.00 (m, 23H). $^{13}$C NMR (125 MHz, CDCl$_3$): δ 171.5, 156.6, 154.8, 138.9, 138.4, 137.1, 128.43, 128.39 (2C), 128.2, 128.15 (2C), 127.7, 127.34 (2C), 127.29, 127.26 (2C), 127.0, 126.1, 123.8 (q, J=29.3 Hz), 123.5 (q, J=273.3 Hz), 118.2, 115.0, 113.4 (q, J=5.1 Hz), 112.4, 88.2, 72.2, 71.4, 69.7, 57.9, 53.9 (2C), 50.6, 48.6, 42.9, 38.9, 36.5, 33.8, 33.6, 29.6, 27.5, 27.2, 24.8, 24.4 (2C), 23.4, 23.1, 13.6. $^{19}$F NMR (282 MHz, CDCl$_3$): δ −60.75. HR-MS (ESI) calcd for [C$_{49}$H$_{57}$F$_3$N$_2$O$_4$ H]$^+$ 795.4349, found 795.4334.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-5-(piperidin-1-yl)pentanamide, JD156

$^1$H NMR (500 MHz, MeOD): δ 7.33 (d, J=8.7 Hz, 1H), 7.18 (d, J=8.8 Hz, 1H), 7.13 (d, J=1.9 Hz, 1H), 6.87 (d, J=8.6 Hz, 1H), 6.50 (s, 1H), 6.42 (dd, J=8.4, 2.0 Hz, 1H), 5.40 (m, 1H), 3.67 (dd, J=8.2, 8.2 Hz, 1H), 2.48 (t, J=7.6 Hz, 4H), 1.74 (t, J=7.6 Hz, 4H), 0.85 (s, 3H), 0.80-3.40 (m, 23H). $^{13}$C NMR (125 MHz, MeOD): δ 175.3, 158.0, 155.9, 139.6, 133.4, 129.0 (q, J=30.7 Hz), 128.4, 127.8, 127.5, 124.8 (q, J=271.6 Hz), 119.9, 116.3, 114.2 (q, J=5.4 Hz), 114.0, 82.7, 74.0, 57.8, 54.2 (2C), 51.6, 49.9, 44.2, 39.1, 35.9, 35.6, 30.8, 30.4, 28.5, 24.5, 24.2 (2C), 23.9, 23.7, 22.8, 13.8. $^{19}$F NMR (376 MHz, MeOD): δ −62.96. HR-MS (ESI) calcd for [$C_{35}H_{45}F_3N_2O_4$ H]$^+$ 615.3409, found 615.3400.

N-(4-(((8S,9S,11S,13S,14S,17S)-3,17-bis(Benzyloxy)-13-methyl-7,8,9,11,12,13,14,15,16,17-deca-hydro-6H-cyclopenta[a]phenanthren-11-yl)oxy)-2-(trifluoromethyl)phenyl)-5-morpho-linopentanamide $^1$H NMR (500 MHz, CDCl$_3$): δ 7.87 (d, J=9.6 Hz, 1H), 7.35 (m, 11H), 7.07 (d, J=2.7 Hz, 2H), 6.90 (d, J=8.7 Hz, 1H), 6.73 (d, J=2.4 Hz, 1H), 6.67 (dd, J=8.6, 2.6 Hz, 1H), 5.25 (m, 1H), 4.99 (s, 2H), 4.55 (d, J=12.3 Hz, 1H), 4.46 (d, J=12.3 Hz, 1H), 3.73 (t, J=4.4 Hz, 4H), 3.49 (dd, J=8.1, 8.1 Hz, 1H), 2.45 (m, 4H), 0.99 (s, 3H), 0.80-3.80 (m, 21H). $^{13}$C NMR (125 MHz, CDCl$_3$): δ 171.3, 156.6, 154.6, 138.9, 138.4, 137.1, 128.5, 128.4 (2C), 128.21, 128.17 (2C), 127.7, 127.6, 127.35 (2C), 127.27 (2C), 127.1, 126.1, 123.6 (q, J=273.4 Hz), 123.0 (q, J=29.7 Hz), 118.2, 115.0, 113.4 (q, J=5.2 Hz), 112.5, 88.2, 72.2, 71.4, 69.7, 66.8 (2C), 58.4, 53.6 (2C), 50.6, 48.6, 42.9, 38.9, 37.1, 33.6, 29.7, 27.5, 27.3, 25.8, 23.3, 22.9, 13.7. $^{19}$F NMR (282 MHz, CDCl$_3$): δ −60.73. HR-MS (ESI) calcd for [$C_{48}H_{55}F_3N_2O_5$ H]$^+$ 797.4141, found 797.4163.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-5-morpholino-pentanamide, JD157

$^1$H NMR (500 MHz, MeOD): δ 7.31 (d, J=8.7 Hz, 1H), 7.17 (dd, J=8.8, 2.6 Hz, 1H), 7.13 (d, J=2.7 Hz, 1H), 6.86 (d, J=8.6 Hz, 1H), 6.49 (d, J=2.4 Hz, 1H), 6.41 (dd, J=8.5, 2.6 Hz, 1H), 5.40 (m, 1H), 3.72 (t, J=4.6 Hz, 4H), 3.67 (dd, J=8.3, 8.3 Hz, 1H), 2.59 (m, 4H), 0.86 (s, 3H), 0.80-3.50 (m, 21H). $^{13}$C NMR (125 MHz, MeOD): δ 175.9, 158.0, 155.9, 139.6, 133.3, 129.0 (q, J=29.7 Hz), 128.4, 127.9, 127.5, 124.8 (q, J=272.4 Hz), 119.9, 116.3, 114.2 (q, J=6.7 Hz), 114.0, 82.7, 74.0, 67.2 (2C), 59.4, 54.5 (2C), 51.6, 49.9, 44.2, 39.1, 36.6, 35.6, 30.8, 30.4, 28.5, 26.2, 24.5, 23.9, 13.8. $^{19}$F NMR (376 MHz, MeOD): δ −63.01. HR-MS (ESI) calcd for [$C_{34}H_{43}F_3N_2O_5$ H]$^+$ 617.3203, found 617.3230.

N-(4-(((8S,9S,11S,13S,14S,17S)-3,17-bis(Benzyloxy)-13-methyl-7,8,9,11,12,13,14,15,16,17-deca-hydro-6H-cyclopenta[a]phenanthren-11-yl)oxy)-2-(trifluoromethyl)phenyl)-5-(pyrro-lidin-1-yl)pentanamide $^1$H NMR (500 MHz, CDCl$_3$): δ 7.74 (s, 1H), 7.65 (d, J=8.6 Hz, 1H), 7.20-7.40 (m, 10H), 7.05 (s, 1H), 7.043 (d, J=9.2 Hz, 1H), 6.87 (d, J=8.7 Hz, 1H), 6.71 (d, J=2.2 Hz, 1H), 6.65 (dd, J=8.6, 2.3 Hz, 1H), 5.23 (m, 1H), 4.97 (s, 2H), 4.52 (d, J=12.3 Hz, 1H), 4.44 (d, J=12.2 Hz, 1H), 3.47 (dd, J=8.4, 8.4 Hz, 1H), 2.48 (m, 4H), 1.25 (m, 4H), 0.95 (s, 3H), 0.80-3.40 (m, 21H). $^{13}$C NMR (125 MHz, CDCl$_3$): δ 171.3, 156.6, 155.2, 138.9, 138.4, 137.2, 129.1, 128.49, 128.45 (2C), 128.23, 128.21 (2C), 127.8, 127.41 (2C), 127.36, 127.32 (2C), 126.7, 126.2, 123.5 (q, J=274.5 Hz), 118.2, 115.0, 113.4 (q, J=5.5 Hz), 112.5, 88.3, 72.2, 71.5, 69.8, 54.7, 53.4 (2C), 50.6, 48.6, 43.0, 38.9, 35.7, 33.6, 29.7, 27.6, 27.3, 25.0, 23.2 (2C), 23.0, 22.3, 13.7. $^{19}$F NMR (282 MHz, CDCl$_3$): δ −60.75. HR-MS (ESI) calcd for [$C_{48}H_{55}F_3N_2O_4$ H]$^+$ 781.4192, found 781.4170.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-5-(pyrrolidin-1-yl)pentanamide, JD158

$^1$H NMR (500 MHz, MeOD): δ 7.33 (d, J=8.8 Hz, 1H), 7.19 (dd, J=8.8, 2.7 Hz, 1H), 7.14 (d, J=2.7 Hz, 1H), 6.87 (d, J=8.6 Hz, 1H), 6.50 (d, J=2.4 Hz, 1H), 6.41 (dd, J=8.5, 2.6 Hz, 1H), 5.41 (m, 1H), 3.67 (dd, J=8.1, 8.1 Hz, 1H), 2.48 (t, J=6.9 Hz, 4H), 2.07 (m, 4H), 0.86 (s, 3H), 0.80-3.50 (m, 21H). $^{13}$C NMR (125 MHz, MeOD): δ 175.4, 158.1, 155.9, 139.6, 133.4, 129.1 (q, J=30.3 Hz), 128.4, 127.8, 127.5, 124.8 (q, J=272.5 Hz), 119.9, 116.3, 114.2 (q, J=5.1 Hz), 114.0, 82.7, 74.1, 55.8, 55.0 (2C), 51.6, 49.9, 44.2, 39.1, 35.9, 35.6, 30.8, 30.4, 28.5, 26.4, 24.0 (2C), 23.9, 23.5, 13.8. $^{19}$F NMR (376 MHz, MeOD): δ −63.01. HR-MS (ESI) calcd for [$C_{34}H_{43}F_3N_2O_4$ H]$^+$ 601.3253, found 601.3257.

N-(4-(((8S,9S,11S,13S,14S,17S)-3,17-bis(Benzyloxy)-13-methyl-7,8,9,11,12,13,14,15,16,17-deca-hydro-6H-cyclopenta[a]phenanthren-11-yl)oxy)-2-(trifluoromethyl)phenyl)-5-(dimeth-ylamino)pentanamide $^1$H NMR (500 MHz, CDCl$_3$): δ 7.74 (d, J=9.6 Hz, 1H), 7.57 (s, 1H), 7.20-7.40 (m, 10H), 7.06 (s, 1H), 7.05 (dd, J=6.6, 3.1 Hz, 1H), 6.87 (d, J=8.7 Hz, 1H), 6.71 (d, J=2.3 Hz, 1H), 6.66 (dd, J=8.6, 2.5 Hz, 1H), 5.24 (m, 1H), 4.98 (s, 2H), 4.53 (d, J=12.3 Hz, 1H), 4.45 (d, J=12.3 Hz, 1H), 3.47 (dd, J=8.1, 8.1 Hz, 1H), 2.55 (s, 6H), 0.96 (s, 3H), 0.80-3.00 (m, 21H). $^{13}$C NMR (125 MHz, CDCl$_3$): δ 171.3, 156.6, 155.0, 139.0, 138.5, 137.2, 128.52, 128.48 (2C), 128.3, 128.2 (2C), 128.1, 127.8, 127.4 (2C), 127.35 (2C), 126.9, 126.2, 124.0 (q, J=30.4 Hz), 123.6 (q, J=273.4 Hz), 118.3, 115.0, 113.5 (q, J=5.3 Hz), 112.5, 88.3, 72.3, 71.5, 69.8, 57.9, 50.7, 48.7, 43.7 (2C), 43.0, 39.0, 36.2, 33.7, 29.7, 27.6, 27.3, 24.8, 23.0, 22.6, 13.7. $^{19}$F NMR (376 MHz, CDCl$_3$): δ −61.39. HR-MS (ESI) calcd for [$C_{46}H_{53}F_3N_2O_4$ H]$^+$ 755.4036, found 755.4004.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-5-(dimethylam-ino)pentanamide, JD159

$^1$H NMR (500 MHz, MeOD): δ 7.31 (d, J=8.7 Hz, 1H), 7.17 (dd, J=8.8, 2.6 Hz, 1H), 7.14 (d, J=2.7 Hz, 1H), 6.87 (d, J=8.6 Hz, 1H), 6.49 (d, J=2.3 Hz, 1H), 6.41 (dd, J=8.5, 2.5 Hz, 1H), 5.41 (m, 1H), 3.67 (dd, J=8.3, 8.3 Hz, 1H), 2.35 (s, 6H), 0.86 (s, 3H), 0.80-3.50 (m, 21H). $^{13}$C NMR (125 MHz, MeOD): δ 175.8, 158.0, 156.0, 139.6, 133.3, 129.0 (q,

J=30.2 Hz), 128.3, 127.9, 127.5, 124.8 (q, J=274.7 Hz), 119.9, 116.3, 114.2 (q, J=5.2 Hz), 114.0, 82.7, 74.1, 60.0, 51.6, 49.9, 45.0 (2C), 44.2, 39.1, 36.6, 35.6, 30.8, 30.4, 28.5, 27.2, 24.4, 23.9, 13.8. $^{19}$F NMR (376 MHz, MeOD): δ −63.08. HR-MS (ESI) calcd for $[C_{32}H_{41}F_3N_2O_4 \ H]^+$ 575.3097, found 575.3123.

2. Compound Functional Characterization

For the biological testing alternative code names for the compounds were used, namely JD101-JD160. The correspondence of the compound numbers in the design and synthesis and the code names for functional characterization are given in Table 1.

TABLE 1

Correspondence of the Novel ER Antagonists Chemical names and their alternative Code Names for Functional Characterization.

| Cmpd | Code |
| --- | --- |
| 8a | JD101 |
| 8b | JD102 |
| 8c | JD103 |
| 8d | JD104 |
| 7 | JD105 |
| 11c | JD106 |
| 11a | JD107 |
| 11b | JD108 |
| 11d | JD109 |
| 12c | JD110 |
| 12b | JD111 |
| 12a | JD112 |
| 13c | JD113 |
| 13b | JD114 |
| 13a | JD115 |
| 12d | JD116 |
| 13d | JD117 |
| 10 | JD118 |
| 15 | JD119 |
| 20, 16 | JD120 |
| 9c | JD121 |
| 17a | JD122 |
| 9b | JD123 |
| 9a | JD124 |
| 17b | JD125 |
| 17c | JD126 |
| 9d | JD127 |
| 22 | JD128 |
| 17d | JD129 |
| 18a | JD130 |
| 14c | JD131 |
| 18b | JD132 |
| 18d | JD133 |
| 18c | JD134 |
| 19c | JD135 |
| 14a | JD136 |
| 19a | JD137 |
| 19b | JD138 |
| 19d | JD139 |
| 20a | JD140 |
| 20c | JD141 |
| 20d | JD142 |
| 20b | JD143 |
| 23c | JD144 |
| 23a | JD145 |
| 21 | JD146 |
| 23b | JD147 |
| 23d | JD148 |
| 24a | JD149 |
| 24b | JD150 |
| 24d | JD151 |
| 24c | JD152 |
| 25c | JD153 |
| 25b | JD154 |
| 25d | JD155 |
| 26a | JD156 |
| 26c | JD157 |
| 26b | JD158 |

TABLE 1-continued

Correspondence of the Novel ER Antagonists Chemical names and their alternative Code Names for Functional Characterization.

| Cmpd | Code |
| --- | --- |
| 26d | JD159 |
| 25a | JD160 |

Assays for Cell Proliferation.

In experiments to assess potential proliferative effects of novel estrogen receptor ligands, human breast cancer cells were grown in phenol red-free, estrogen-free media with 1% dextran-coated charcoal-treated (DCC)-fetal bovine serum (FBS) for 48 hrs (15,44), then treated with either 1 μM or 50 μM doses of estrogen receptor antagonists in the presence of 1 nM estradiol-17β. Cell counts and viability tests (Trypan blue) were done every 24 hr for 3 days. After 72 hr, proliferation was assessed using the BrdU Cell proliferation ELISA (Roche). Cell numbers were also assessed initially by cell counts to confirm ELISA data. Each antiestrogen was tested at least in three different experiments.

Gel Electrophoresis and Immunoblotting.

MCF-7 breast cancer cells were maintained in estrogen-free conditions 48 h before experiments as described above. Cells were then incubated with vehicle control or either 1 μM or 10 μM antiestrogens in the presence of 1 nM estradiol-17β for 48 hrs. After lysis, total cell proteins were resolved by 4-15% SDS-PAGE, transferred to polyvinylidene difluoride membranes and probed with mouse monoclonal antibody directed against estrogen receptor-alpha (Assay Designs, #SRA1010). Membranes were stripped and re-probed with Ribosomal Protein L13A (Santa Cruz Biotechnology, C11) as a loading control (45).

Figure 2:
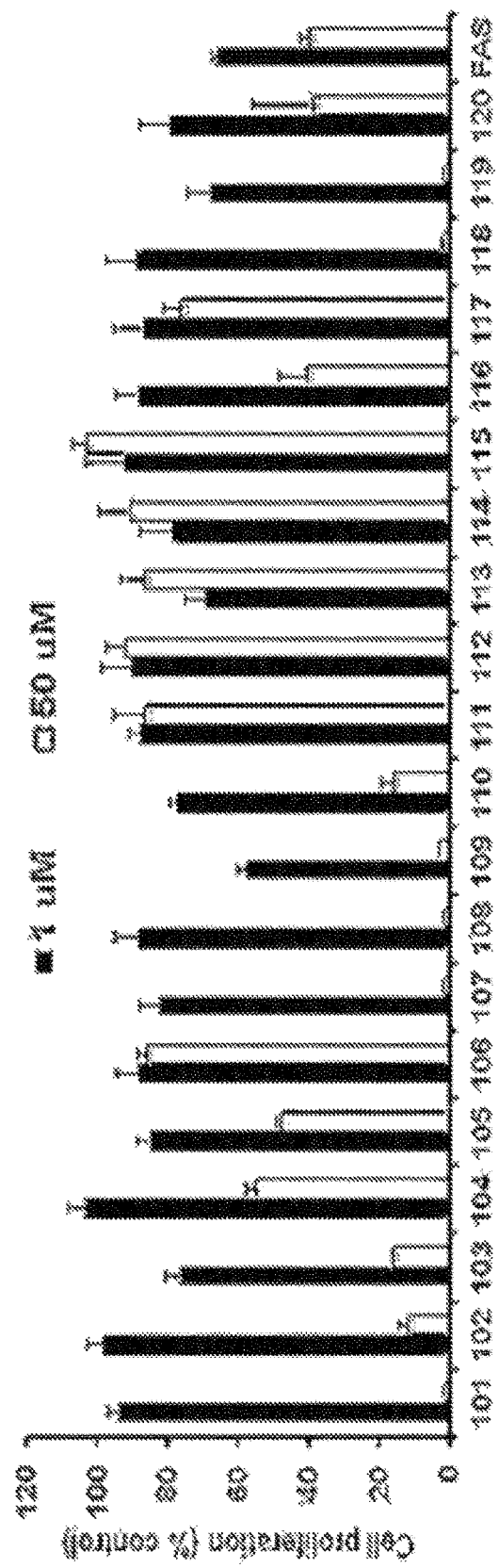
FIG. 2. Inhibition of estrogen receptor-positive human breast cancer cell proliferation by novel antiestrogens.
Figure 2:
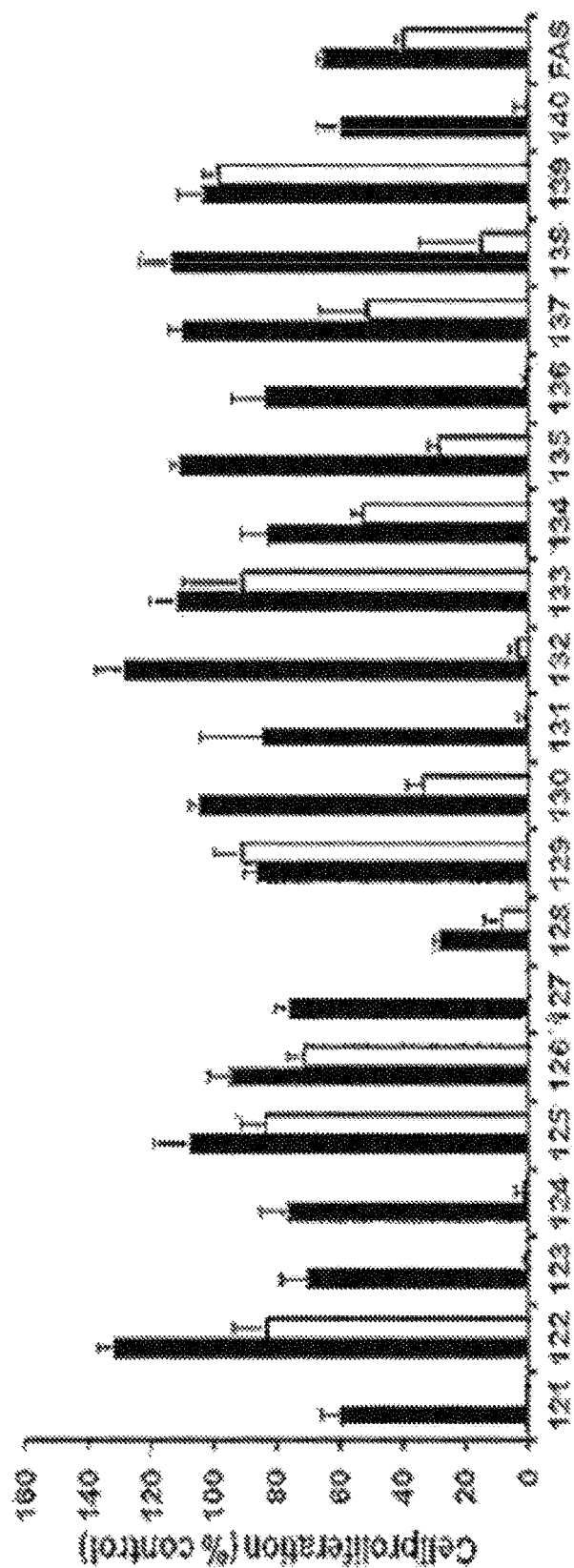
Figure 2:
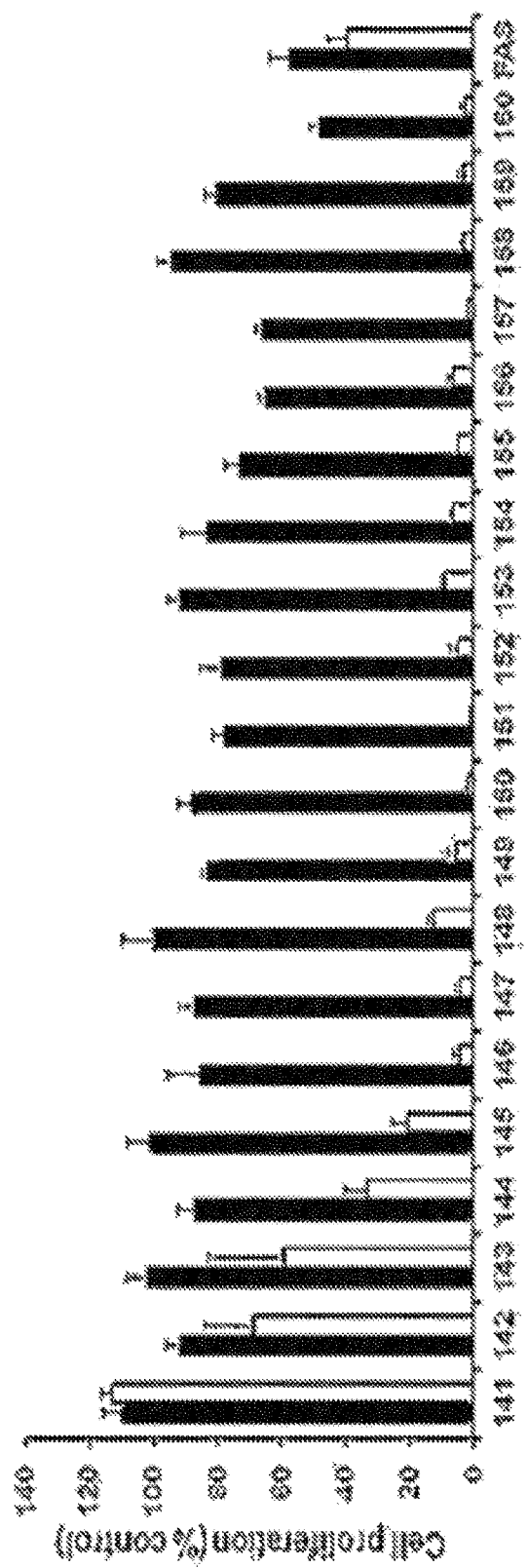

In order to assess the antitumor action of novel estrogen receptor antagonists, we cultured human MCF-7 breast cancer cells with known expression of ERα. Cells were grown in 1% DCC-FBS for 48 hr and then treated with vehicle control or either 1 μM or 50 μM concentrations of antiestrogens JD 101-160 or the pure antiestrogen fulvestrant (FAS), all in the presence of 1 nM estradiol-17β. The results indicate that several novel antiestrogens exert significant inhibition of MCF-7 cell proliferation/survival, particularly JD128 and JD140. Moreover, these compounds appear to be more effective than the ER-downregulator fulvestrant when administered at the same doses in vitro. Shown in FIG. 2 are results from MCF-7 cells grown in 1% DCC-FBS for 48 hr and then treated with vehicle control, 1 nM estradiol-17β and either 1 μM or 50 μM concentrations of antiestrogens JD 101-160 or the known pure antiestrogen fulvestrant (FAS) in the presence of 1 nM estradiol-17β. Cell proliferation is expressed as percentage of that determined in the 1 nM estradiol-17β-treated control group. The graph shows the percentage of surviving cells relative to estradiol-treated controls, defined as 100% survival (data represents at least 3 independent experiments).

Novel Antiestrogen Compounds can Act as ERα Downregulators.

Figure 3:
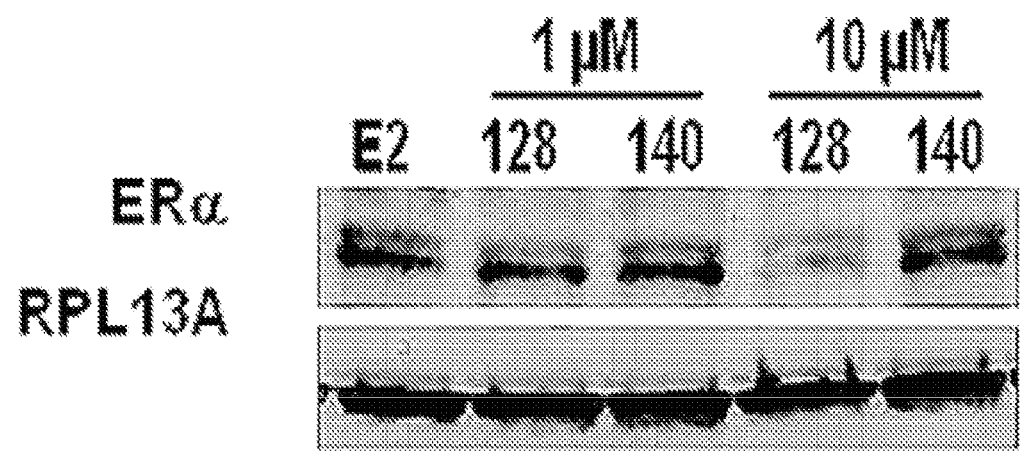
FIG. 3. Estrogen receptor-alpha is down-regulated by antiestrogens.

Fulvestrant (Faslodex®) has been characterized as a selective ERα downregulator and a pure anti-estrogen. Fulvestrant inhibits the transcriptional response to estrogen stimulation and induces the degradation of estrogen receptor proteins (46,47). This drug has been demonstrated to be clinically effective in treating metastatic breast cancer and represents an important option to extend the window of endocrine interventions before cytotoxic chemotherapy becomes the only other systemic treatment available for patients. One problem with fulvestrant is that the drug requires intramuscular injection and may not achieve optimal antitumor effects due to the limited doses that can be administered by this drug delivery method. Hence, we assessed some of our new antiestrogen analogues to find if they, as fulvestrant, affect expression of ERα protein levels in breast cancer cells. MCF-7 breast cancer cells with high expression of ERα protein were treated with estradiol-17β and either 1 μM or 10 μM concentrations of JD128 and JD140 for 48 hours. FIG. 3 shows results of Western immunoblots of ERα protein levels after treatments. Compound JD128 showed the greatest effect at suppressing estrogen receptor-alpha expression in MCF-7 breast cancer cells. As shown in FIG. 3, estrogen receptor-alpha is down-regulated by antiestrogens. MCF-7 breast cancer cells were estrogen-deprived for 48 hrs, then treated with 1 nM estradiol-17β (E2) or antiestrogens JD128 (128) or JD140 (140) at 1 μM or 10 μM concentrations in the presence of 1 nM estradiol-17β. After 48 hrs, PAGE and immunoblotting was performed with antibody directed to anti-ERα (SRA1010) and anti-RPL13A for a loading control. Given that recent FES-PET studies show significant residual ER availability in tumors during fulvestrant therapy in 38% of patients which was related to early cancer progression (48), novel antiestrogens described herein may prove more effective than fulvestrant in suppressing ERα.

3. ER Pathway Interactions and Drug Resistance

Breast tumors with ER and HER2 overexpression are an unresolved clinical problem and a major cause of endocrine-treatment failure and mortality. Early resistance to hormonal therapy, especially in HER-2-overexpressing tumors, is a significant issue in the clinic. Several studies indicate that ER+/HER-2+ cancer is less responsive to tamoxifen and estrogen-deprivation therapies with AI's than tumors negative for ER and HER-2 expression, indicating that HER-2 overexpression elicits a dominant phenotype. Overexpression or activation of HER-2 or related HER family receptors occurs in two-thirds of breast tumors, while HER-2 overexpression occurs in about 25% of breast cancers (2,21). Blockade of HER-2 with trastuzumab (Herceptin), a humanized monoclonal antibody targeted to HER-2, has provided an important clinical tool to manage patients with tumors bearing HER-2 overexpression or amplification (45,46).

Growth factors (EGF, heregulin) and estrogens are known mitogens for breast cancer, and activation of ER by growth factors in the absence of estrogen is a phenomenon that may be critical in cancer (14,47-49). ER signaling may mediate gene transcription by integrating signals from growth factor-activated pathways as well as from E2 binding (33,50). There is increasing evidence that endocrine resistance is a consequence of such bidirectional crosstalk between ER and EGFR/HER family signaling networks (6,9). ER is a phosphoprotein, with ER phosphorylation occurring early in it's activation by ligand (14,28, 29,51,52). Several studies show that phosphorylation at serine and tyrosine residues contribute to ER activation and, possibly, DNA binding (14,28, 52). Conversion of estrogen-sensitive to -resistant tumors after starting antiestrogen therapy (47) may be due, in part, to enhanced growth factor signaling, a cell response to antiestrogen treatment that eventually results in increased phosphorylation of ER and/or coactivators, such as AIB1 (28,33). Since these two receptors systems (ER and HER) have the capacity to activate each other, it has been suggested that a rational treatment strategy would be the combined targeting of both receptors by use of antihormone therapy with anti-HER-2 agents, such as trastuzumab (Herceptin).

Panels of human ER-positive breast tumor cells with endocrine sensitivity and resistance. For this work, a panel of MCF-7 human breast cancer cells (ATCC) with different properties was used. This panel includes cell lines reported previously and include: a) MCF-7/CON:MCF-7 parent breast tumor cells with ER expression; b) TAM-R: MCF-7 cells with acquired tamoxifen-resistance, c) MCF-7/ER−: MCF-7 cells with no ER expression; no E2-induced activation of MAPK or cell growth; and d) ER-positive T47D and ZR75 breast cancer cells.

Figure 4A:
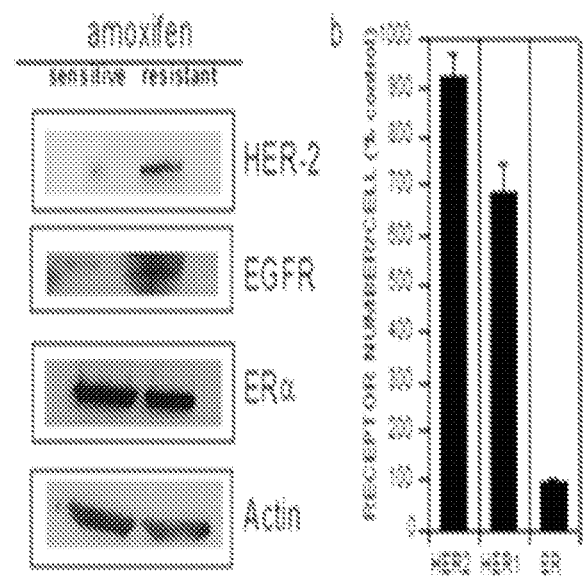
FIGS. 4A-4B. MCF-7 cells with acquired tamoxifen resistance show increased expression of HER-1/EGFR and HER-2 receptors.
Figure 4B:
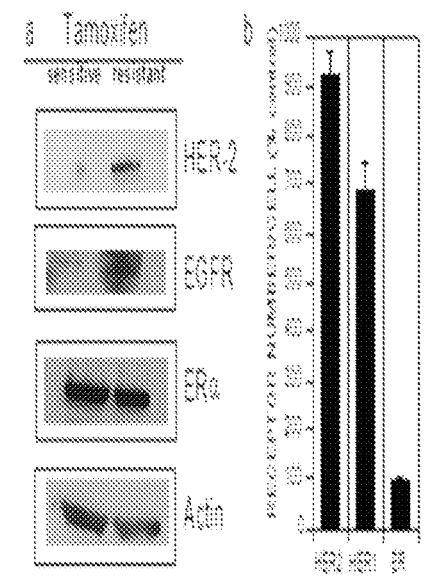

Properties of TAM-R cells: To develop TAM-R cells, MCF-7 breast cells were cultivated in vitro in the presence of tamoxifen as reported before (72). In brief, MCF-7 cell monolayers were cultivated in phenol-red-free RPMI medium containing 5% charcoal-stripped steroid-depleted (DCC)-fetal calf serum, antibiotics, glutamine (200 mM), and 4-hydroxytamoxifen (1×10-7 M 4-OH-TAM). Cells were continuously exposed to this treatment for 12 months, during which time medium was replaced every 4 days, and cell cultures were passaged by trypsinization after 70% confluency was reached. Initially, MCF-7 cell growth rates were reduced but, after 4 months' exposure to the medium, cell growth gradually increased, indicating development of a cell line resistant to the growth-inhibitory properties of 4-OH-TAM. This cell line, termed TAM-resistant, was cultured for a further 8 months in medium containing 4-OH-TAM before characterization studies. These cells were evaluated for expression of EGFR, HER-2 and ERα (FIG. 2). The results show that TAM-resistant cells have higher levels of HER-2 and EGFR as compared with tamoxifen-sensitive progenitor MCF-7 cells, while expression levels of ER remain essentially unchanged. This finding may have important implications for the design of future therapeutic interventions. FIG. 4a-b. shows MCF-7 cells with acquired tamoxifen resistance show increased expression of HER-1/EGFR and HER-2 receptors. FIG. 4a shows a Western blot showing protein expression level of HER2, EGFR, ERα and actin loading control in MCF-7 cells that were tamoxifen-sensitive (left) versus those that were tamoxifen-resistant (right). ERβ3 was also assessed and was low to absent in both sensitive and resistant cells. FIG. 4b shows levels of HER-2, HER-1/EGFR and ERα receptors in MCF-7/TAM-R cells that were quantitated using established ELISA methods (73), with results based on 3 determinations. The average number of receptors/tamoxifen-resistant cell was calculated and expressed relative to that of tamoxifen-sensitive MCF-7 cells.

Properties of MCF-7/TAM-R, MCF-7/ER− and parental cells: MCF-7/CON (parental) cells are tamoxifen-sensitive, while MCF-7/TAM-R and MCF-7/ER− cells are known to be tamoxifen-resistant (11,14-16). Except for TAM-R (72) and MCF-7/ER− (16), cells are routinely cultured in RPMI 1640 media with 10% heat-inactivated FBS. For E2-free conditions, medium is changed 48 h before studies to phenol-red free RPMI 1640 with 1% dextran-coated, charcoal-treated (DCC) FBS. Levels of ERα and HER2 were assessed by immunofluorescence microscopy in MCF-7/CON and other cells. MCF-7/CON cells express ERα but few HER2 receptors, while MCF-7/TAM-R cells express both ER and HER2. ER and HER2 were detected by established immunofluorescence microscopy methods with labeled antibodies to ERα and HER2 (14-16). TAM-R cells also show increased expression of HER2 by immunofluorescence (72). In contrast, expression of ERα appears to be relatively stable among the several cell lines, with only modestly less intensity of immunofluorescence in TAM-R cells as compared to their paired controls.

In previous studies to evaluate the role of activated HER-2 in antiestrogen resistance, estrogen-responsive, MCF-7 parental cells and paired MCF-7 cells with HER2-overexpression cells were grown as xenografts in nude mice (14). Parent tumors were suppressed by tamoxifen and by fulvestrant, while MCF-7/HER-2 cells were insensitive to tamoxifen but were partially sensitive to fulvestrant (14,74, 75). This finding correlates well with data from the clinic suggesting tamoxifen resistance in breast tumors with high levels of HER2 expression (42). In the clinic, HER2 overexpression also associates with low ER levels (76) and a PR-negative phenotype (43) in breast tumors. Similarly, in the laboratory, overexpression of HER2 in breast cells elicits a modest reduction in ER transcripts and in estrogen binding capacity with no change in steroid binding affinity, as assessed by specific binding of [$^3$H]-estradiol in cells with and without HER2 overexpression (14,36,74). This modest downregulation of ER may account, in part, for reduced endocrine sensitivity of HER2-expressing tumors, but other mechanisms are clearly operative (9,11,14,76).

Figure 5:
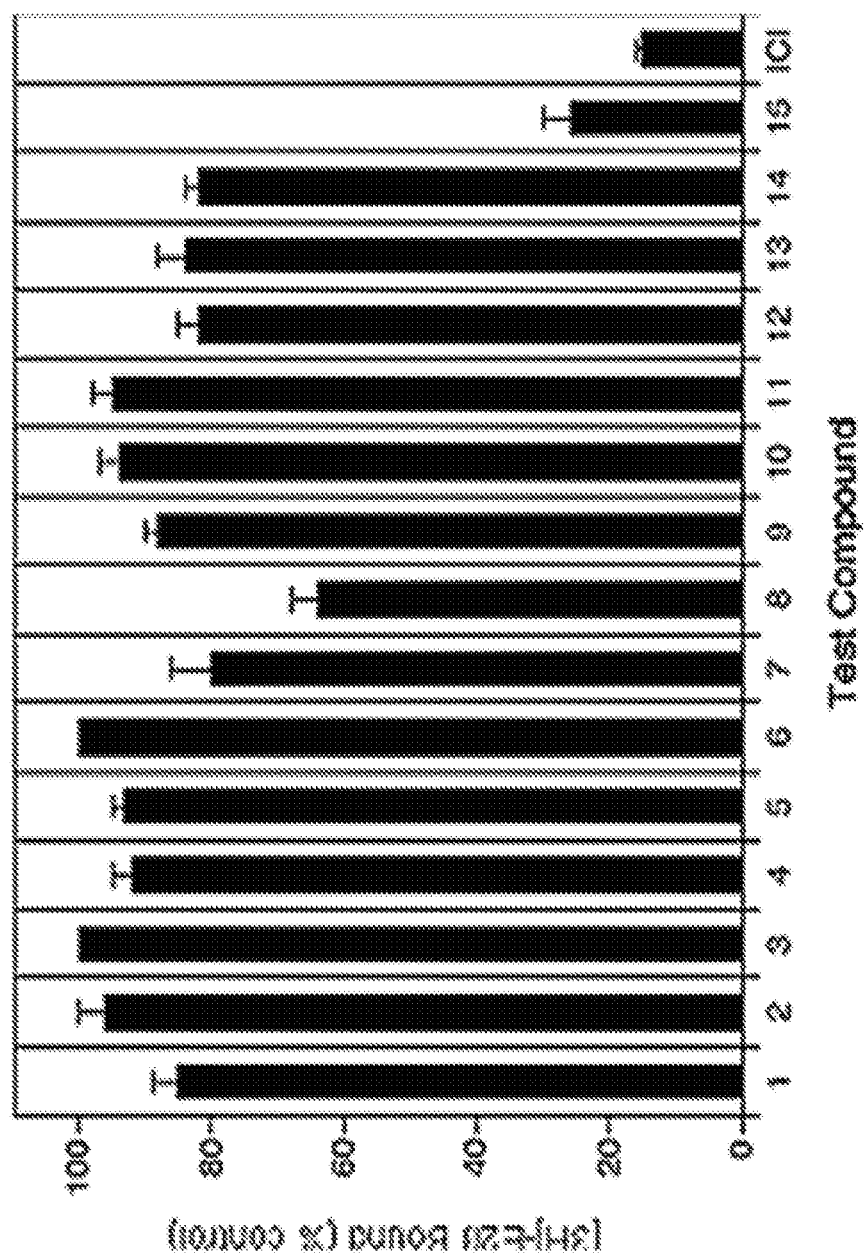
FIG. 5. Specific binding of [3H]estradiol-17β by MCF-7 parental breast cancer cells is suppressed by ERD compound 15 (JD105). Compounds S1-S14 in the present figure are comparative test compounds (different from individual compounds described herein) showing less inhibition than compound S15 in the present assay.

Specific estradiol binding: Specific estradiol-17β (E2) binding was assessed in MCF-7 parental breast cancer cells as before (14-16). Briefly, cells were incubated with 2 nM [$^3$H]estradiol-17β and varying concentrations (1 nM-10 μM) of new estrogen receptor downregulator (ERD) analogues. The efficiency of the binding of compounds was measured by the loss of radioactivity of the [$^3$H]estradiol-17β. A 100-fold molar excess of unlabeled E2 was present with [3H]estradiol-17β in paired samples for determination of displaceable binding. ICI 182,780 (fulvestrant, 1 nM-10 μM) was used as a control. As shown in FIG. 5, the ligand binding specificity of labeled estradiol-17β was suppressed effectively by 10 μM of ERD compound S15 (JD105) compared to select test compounds. FIG. 5 shows specific binding of [$^3$H]estradiol-17β by MCF-7 parental breast cancer cells is suppressed by our ERD compound S15 in this series of analogues (15). MCF-7 cells were incubated with 2 nM [$^3$H]estradiol-17β and antiestrogens (all at 10 μM concentration; numbers S1 to S15), with ICI 182,780 (ICI; fulvestrant) used as a control (n=3). Compounds S1-S14 show less activity in the assay above than compound S15 (JD105) as shown in FIG. 5. Compounds S1-S14 are test compounds different from the exemplified compounds described herein.

Figure 6:
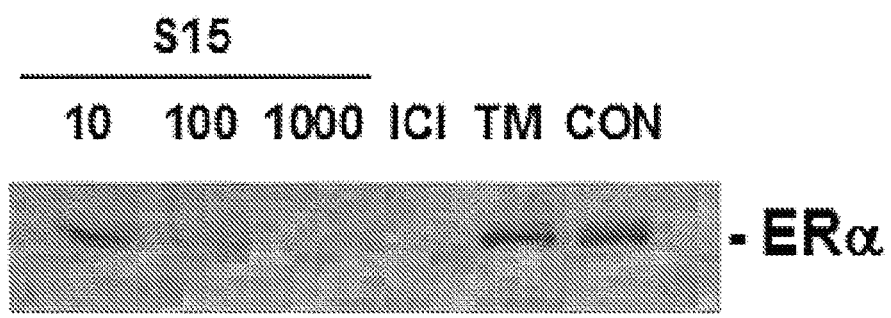
FIG. 6. ERD S15 reduces ER protein levels in MCF-7 breast tumor cells.

ER down-regulation: To determine if selected compounds can down-regulate ER protein, we treated cells for 24-48 hrs in vitro with candidate compounds at varying doses. Then, cells were disrupted and prepared for PAGE and Western immunoblots using anti-ERα antibodies (see FIG. 6). A representative experiment shows that a selected ERD at doses of >100 nM elicits reduced ER levels. Those ERDs with optimal activity in down-regulating ER were investigated further in the chemistry laboratory to further refine and develop such agents. Downregulation of ER could prove to be an important drug property to overcome endocrine resistance due to ligand-independent ER signaling (47, 71). FIG. 6 shows ERD S15 reduces ER protein levels in MCF-7 breast tumor cells. Western immunoblot analysis of ER (66 kD) after treatment of MCF-7 cells for 24 hours with SERM S15 at various concentrations (10, 100 and 1000 nM), ICI 182,780 (ICI; fulvestrant; 100 nM), tamoxifen (TM; 100 nM) or control vehicle (CON).

Figure 7:
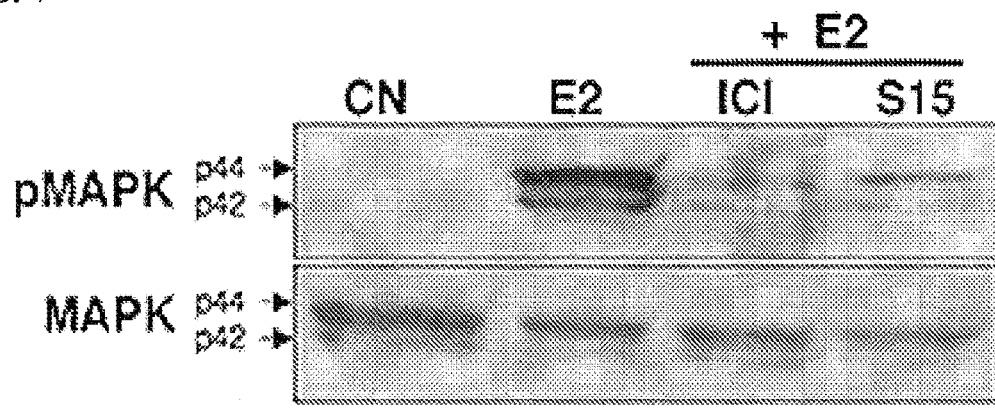
FIG. 7. Treatment of MCF-7 parent cells with 1 nM estradiol 17β (E2) induces rapid phosphorylation of MAPK (pMAPK).
Figure 8:
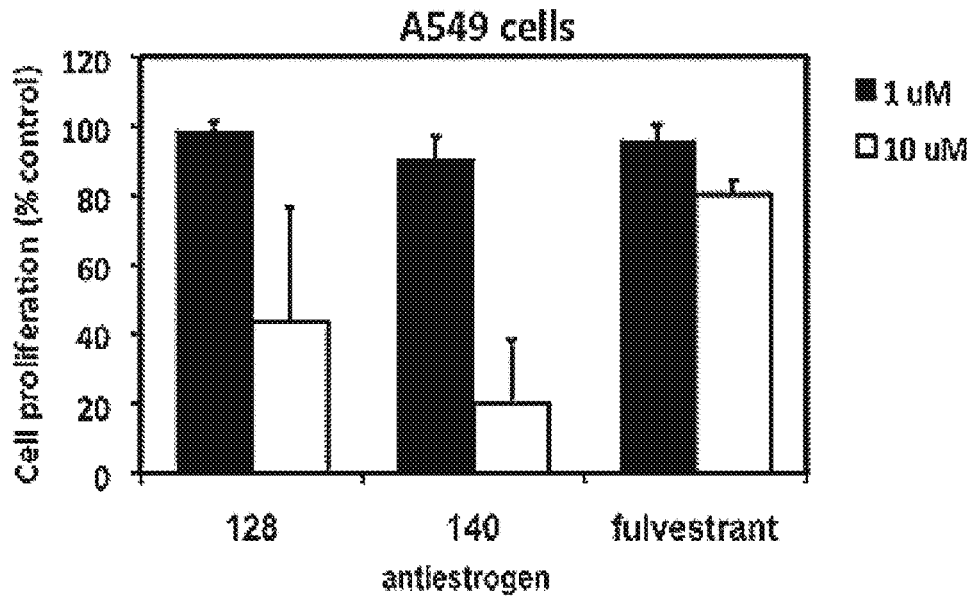
FIG. 8. Novel antiestrogen JD140 elicits significant antiproliferative effects in human non-small cell lung cancer cells A549 as compared with the activity of fulvestrant.
Figure 9:
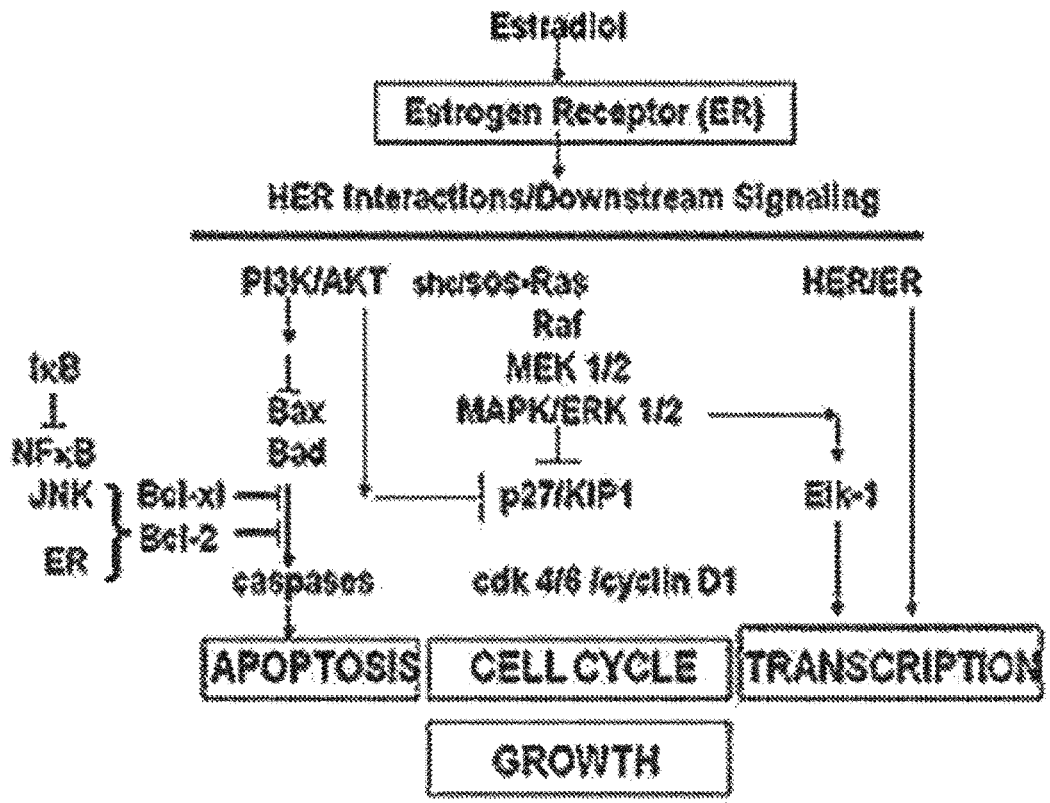
FIG. 9. Activation of estrogen receptor (ER) by estradiol-17β or by growth factor receptor signaling promotes gene transcription for tumor cell proliferation and inhibition of apoptosis. Disruption by selective estrogen receptor downregulators of critical steps in these pathways includes downstream actions such as modulation of cyclin D expression in the control of the cell cycle and proliferation and regulation of apoptosis.

ERD inhibition of phosphorylation of MAPK, at both extracellular signal-regulated kinases ERK-1 (p44) and ERK-2 (p42) and downstream effects. As illustrated in FIG. 1, signal transduction induced by estrogen contributes to breast tumor proliferation, a late event that correlates with early activation of MAPK by estradiol in breast tumor cells (9,15,16). Thus, we measured estrogen-induced phosphorylation of MAPK by established methods (9,15,16). Briefly, MCF-7 parental cells were estrogen deprived for 48 hrs, then treated with 1 nM estradiol-17β in the presence of new compounds (10 nM-10 μM) to be tested for antagonist activity. After treatments, cell lysates were separated by SDS-PAGE followed by Western blot using a polyclonal antibody directed to phospho-p44/p42 MAP kinase (Thr202/Tyr204) (Cell Signaling). Immunodetection with antibody against total p44/p42 (Cell Signaling) was done as a control for gel loading. As shown in FIG. 7, ERD S15 inhibits phosphorylation of MAPK, at both extracellular signal-regulated kinases ERK-1 (p44) and ERK-2 (p42). ERD S15 was as effective as fulvestrant in inhibiting the rapid estrogen-induced MAPK phosphorylation in breast tumor cells in vitro. FIG. 7 shows treatment of MCF-7 parent cells with 1 nM estradiol 17β (E2) induces rapid phosphorylation of MAPK (pMAPK). E2 but not vehicle (CN) induced rapid phosphorylation of ERK-1 (p44) and ERK-2 (p42). This activation was prevented when cells were pre-incubated with 1000 nM ICI 182,780 (ICI; Faslodex) or 1000 nM compound S15 in the presence of estradiol (E2).

4. Assays for Antiestrogen Effects on Non-Small Cell Lung Cancer Cell Proliferation.

To assess potential antiproliferative effects of novel antiestrogens such as compounds JD128 and JD140 in non-small cell lung cancer, human non-small cell lung cancer cells A549 were grown in RPMI 1640 medium with 10% fetal bovine serum (FBS), then treated with either 1 μM or 10 μM doses of estrogen receptor antagonists JD128, JD140 or fulvestrant. Cell counts and viability tests (Trypan blue) were done every 24 hours for 3 days. After 72 hours, proliferation was assessed using the CellTiter 96™ AQ$_{ueous}$ One Solution Cell Proliferation Assay (MTS) from Promega. Cell numbers were also assessed initially by cell counts to confirm ELISA data. Each antiestrogen was tested in at least in three independent experiments.

ER has a major role in controlling breast cancer growth. Antiestrogen tamoxifen has been the most widely used hormone therapy, achieving a 39% reduction in breast cancer recurrence and 31% reduction in mortality in ER-positive early breast cancer. Tamoxifen has important drawbacks: a limited period of activity before resistance develops; and undesirable side-effects in normal tissues such as uterus due to the activity as a partial agonist. As long as ER is present, growth may be stimulated by estrogen, partial agonists or estrogen-independent action. Introduction of aromatase inhibitors for postmenopausal patients, either initially or after tamoxifen, has yielded better outcomes than tamoxifen. However, in patients with advanced breast cancer, only about one third of ER-positive breast cancers respond to aromatase inhibitors, and resistance can evolve due to ER activation by ER hypersensitivity or ligand-independent ER activation that occurs in breast cancers with activated growth factor receptors such as HER2. Such data offered a rationale to target both ER and HER2 in ER-positive/HER2-positive breast cancers to overcome endocrine resistance.

A prototype drug in this class, fulvestrant is a pure ER antagonist with no major agonist activity and with a unique mechanism of action, i.e. downregulation of ER, due in part to induced destabilization and hyper-ubiquitination of ER leading to growth inhibition. But, fulvestrant suffers from low bioavailability which presents a problem in the clinic. In about 14% of metastatic ER-positive breast cancers from patients with multiple prior endocrine therapies, there is emerging evidence for the acquisition of functionally-aberrant ESR1 with point mutations. Although such mutated ESR1 variants continue to respond to ER antagonists such as fulvestrant, elevated doses appear to be required to achieve wild-type levels of inhibition. However, the poor bioavailability of fulvestrant (which may require multiple intramuscular injections of significant volumes of drug) appears to limit optimal drug levels in vivo. Such data underscores the need to search for more potent selective estrogen receptor downregulators.

1. Ma C, et al. (2009). Oncology 23: 133-142. 2. Hurvitz S, Pietras R (2008). Cancer 113:2385-97. 3. Early Breast Cancer Trialists' Collaborative Group (1998). Lancet 351: 1451-67. 4. McGuire W L, Clark G (1992). N. Engl. J. Med., 326: 1756-1762. 5. Ali S, Coombes R (2002). Nature Rev Cancer 21: 101-113. 6. Prat A, Baselga J (2008). Nat Clin Pract Oncol 5: 531-542. 7. Hoffmann J, et al. (2004). J Natl Cancer Inst 96: 210-218. 8. O'Brien J, et al. (2006). J Biol Chem 281: 26683-92. 9. Pietras R J, et al. (2007). Clin Cancer Res 13: 4672-4676. 10. Syed F, et al. (2007). Endocrinology 148:1902-10. 11. Massarweh S, et al. (2008). Cancer Res 68:826-33. 12. Lipton A et al. (2003) J Clin Oncol 21: 1967-1972. 13. Ellis M J et al. (2006) J Clin Oncol 24: 3019-3025. 14. Pietras, R, J et al. (1995). Oncogene 10: 2435-2446. 15. Marquez D C, Pietras R J (2001). Oncogene 20:5420-30. 16. Marquez D C, et al. (2006). Mol Cell Endocrinol. 246:91-100. 17. Mintz P, et al. (2008). Cancer 113: 1489-1495. 18. Madak-Erdogan Z, Kieser K, Kim S et al. (2008). Mol Endocrinol 22: 2116-2127. 19. Hammes S, Levin E (2007). Endocr Rev 28: 726-41. 20. Beug H. and T. Graf (1989). Eur. J. Clin. Invest., 19: 491-501. 21. Slamon D. J., et al. (1987). Science, 235: 177-181. 22. Adnane J, et al. (1989). Oncogene, 4: 1389-1395. 23. Zeillinger R, et al. (1989). Oncogene, 4: 109-113. 24. Read L., D. et al. (1990). Cancer Res., 50: 3947-3955. 25. Nicholson S., et al. (1990). J. Steroid Biochem., 37: 811-818. 26. Reddy, K., et al. (1992). Cancer Res., 52: 3636-3644 27. Benz C., et al. (1993). Breast Cancer Res. Treatment, 24: 85-92. 28. Kato, S., et al. (1995). Science, 270: 1491-1494. 29. Pietras R J et al. (2005). Steroids 70: 372-381. 30. Liu Y, et al. (1995). Breast Cancer Res Trtmt 34: 97-117. 31. Witters I, et al. (1997). Breast Cancer Res. Trtmt 42: 1-5. 32. Bouras T, et al. (2001). Cancer Res 61: 903-907. 33. Font de Mora J, Brown M (2000). Mol Cell Biol 20: 5041-7. 34. Dowsett M, et al. (2001). Cancer Res 61: 8452-8458. 35. Kurokawa H, et al. (2000). Cancer Res 60: 5887-5894. 36. Marquez, D, Pietras, R J (2001). Oncogene, 20: 5420-5430. 37. Simoncini T, et al. (2000). Nature 407: 538-41. 38. Oh A, et al. (2001). Mol Endocrinol 15: 1344-1359. 39. Marquez, D, et al. (2001). Endocrine 16: 73-81. 40. Chung Y L, et al. (2002). Int. J. Cancer 97: 306-312. 41. Osborne C K, et al. (2003). J Natl Cancer Inst. 95:353-361. 42. De Laurentis M et al, 2005. Clin Cancer Res 11:4741-48. 43. Arpino G, et al. (2005). J Natl Cancer Inst 97: 1254-1239. 44. Yarden Y, Sliwkowski M X (2001). Nat Rev Mol Cell Biol 2: 127-137. 45. Carter P, et al. (1992). Proc Natl Acad Sci USA 89: 4285-4289. 46. Slamon D J, et al. (2001) N Engl J Med 344: 783-792. 47. Weinberg O, et al. (2005). Drug Resistance Updates (in press). 48. Bange J, et al. (2001). Nat Med 7:548-52. 49. Knowlden J, et al. (2003). Endocrinology 144:1032-44. 50. Ciana P, et al. (2003). Nature Med. 9: 82-86. 51. Migliaccio A, et al. (1986). EMBO J. 5: 2867-2872. 52. Weigel N (1996). Biochem J 319: 657-667. 53. Dowsett M (2001). Endocrine-Related Cancer 8: 191-195. 54. Early Breast Cancer Trialists' Collaborative Group (2005). Lancet 365: 1687-1717. 55. Coombes R C et al. (2004) N Engl J Med 350: 1081-1092. 56. The Breast International Group 1-98 Collaborative Group (2005) N Engl J Med 353: 2747-2757. 57. ATAC Trialists' Group (2005). Lancet 365: 60-62. 58. Wakeling A E, et al. (1991). Cancer Res 51:3867-73. 59. Wakeling A, et al. (2001). Clin. Cancer Res. 7: 4350s-4355s. 60. Wijayaratne, A. L. and McDonnell, D. P. (2001) J. Biol. Chem. 276, 35684-356892 61. Robertson J, et al. (2009). J Clin Oncol August 24. 62. Osborne C K, et al. (2002) J Clin Oncol 20: 3386-3395. 63. Haas A, Siepmann T (1997). FASEB J. 11, 1257-1268. 64. Lange, C. A., et al. (2000). Proc. Natl Acad. Sci. 97, 1032-1037. 65. Alarid, E. T., et al. (1999). Mol. Endocrinol. 13, 1522-1534. 66. Nawaz, Z., et al. (1999) Proc. Natl Acad. Sci. USA 96: 1858-1862. 67. Wang Y, et al. (2009). J. Biochem. 145: 331-343. 68. Kim T K, Maniatis T (1996). Science 273, 1717-1719. 69. Ring A, Dowsett M (2004) Endocr Relat Cancer 11: 643-658. 70. Pike A C, et al. 2001 Structure (Camb) 9:145-153. 71. Dauvois S, et al. (1992). Proc. Natl. Acad. Sci. U.S.A. 89: 4037-4041. 72. Knowlden J, et al. (2003). Endocrinology 144:1032-44. 73. Aguilar Z, et al. (1999). Oncogene 18:6050-62. 74. Pietras, R J, et al. (2003). Breast Cancer Res Trtmt 82, Suppl 1:12-13. 75. Pietras R J (2003). Breast Journal 9:361-373. 76. Konecny G, et al. (2003). J Natl Cancer Inst. 95:142-153. 77. Song R X, et al. (2002). Mol Endocrinol 16: 116-127. 78. Hennessy B, et al. (2005). Mol Cellular Endocrinol 229: 39-47. 79. Ernst M, et al. (1991). Mol Endocrinol 5:1597-606. 80. Lenferink A, et al. (2001). Cancer Res 61: 6583-6591. 81. Thiantanawat A, et al. (2003). Cancer Res 63:8037-50. 82. Teixeira C, et al. (1995). Cancer Res 55:3902-7. 83. Razandi M, et al. (2000). Mol Endocrinol 14:1434-47. 84. Kunisue H, et al. (2000). Brit. J. Cancer 82: 46-51. 85. Wang C-X, et al. (2005). Breast Cancer Res Treatment 92: 251-263. 86. Tran C, et al. (2009). Science 324: 787-790. 87. Stephan E, et al. (1995). Steroids 60, 809-11. 88. Liang C, et al. (1976). Tetrahedron 32, 2067-9. 89. Labaree D, et al. (2003). J Med Chem 46: 1886-1904. 90. Tedesco R, et al. (1995). J Org Chem 60: 5316-18. 91. Hanson J, et al. (1985). J Chem Res (S): 46-7. 92. Murdoch F, et al. (1990). Biochemistry 29: 8377-8385. 93. Pietras R, Szego C (1980). Biochem J 191: 743-760. [PMCID: PMC1162274] 94. Jones S, et al. (2003). Methods in Enzymology 364: 53-71. 95. Laios I, et al. (2005). J Steroid Biochem Molecular Biol 94: 347-359. 96. Mollerup S, et al. (2002). Lung Cancer 37: 153-159. 97. Brunner N, et al. (1993). Eur. J. Cancer 29A: 562-569. 98. Wu X, J et al. (2009). Cancer Res 69:1722-7. 99. Dubik D, et al. (1987). Cancer Res. 47, 6517-6521. 100. Navarro F, et al. (2003). Fertility Sterility 79: 1409-1415. 101. Greb R, O. et al. (1997). Hum Reprod 12: 1280-1292. 102. Wu W, et al. (2007). Mol Cancer Therap 6: 471-483. 103. Li D, et al. (2002). Oncogene. 21:2805-14. 104. Pegram M, et al. (2004). J Natl Cancer Inst 96:739-49. 105. Pietras R J, Szego C M (1977). Nature 265: 69-72. 106. Pietras R, et al. (1998). Oncogene 17:2235-49. 107. Chou T, Talalay P (1984). Adv Enzyme Regul. 22: 27-55. 108. Pegram, M., et al. (1999). Oncogene, 18: 2241-2251. 109. Verrier F, et al. (2001). J Virol 75: 9177-9186. 110. Chou T C (2002). J Virol 76: 10577; author reply: 10578. 111. Geyer C E, et al. (2006) N Engl J Med 355: 2733-2743. 112. Osborne C, et al. (1995). J Natl Cancer Inst 87: 746-60. 113. Mah V, et al. (2007). Cancer Res 67: 10484-90. 114. Kobayashi N, et al. (2008). Cancer Res 68:3066-73. 115. Reckamp K, et al. (2008). J Thorac Oncol 3:117-24. 116. Detre S, et al. (2003). Cancer Res 63: 6516-22. 1. Ma C, et al. (2009). Oncology 23: 133-142. 2. Hurvitz S, Pietras R (2008). Cancer 113:2385-97. 3. Early Breast Cancer Trialists' Collaborative Group (1998). Lancet 351:1451-67. 4. McGuire W L, Clark G (1992). N. Engl. J. Med., 326: 1756-1762. 5. Ali S, Coombes R (2002). Nature Rev Cancer 21: 101-113. 6. Prat A, Baselga J (2008). Nat Clin Pract Oncol 5: 531-542. 7. Hoffmann J, et al. (2004). J Natl Cancer Inst 96: 210-218. 8. O'Brien J, et al. (2006). J Biol Chem 281: 26683-92. 9. Pietras R J, et al. (2007). Clin Cancer Res 13: 4672-4676. 10. Syed F, et al. (2007). Endocrinology 148:1902-10. 11. Massarweh S, et al. (2008). Cancer Res 68:826-33. 12. Lipton A et al. (2003) J Clin Oncol 21: 1967-1972. 13. Ellis M J et al. (2006) J Clin Oncol 24: 3019-3025. 14. Pietras, R, et al. (1995). Oncogene 10: 2435-2446. 15. Marquez D C, Pietras R J (2001). Oncogene 20:5420-30. 16. Marquez D C, et al. (2006). Mol Cell Endocrinol. 246:91-100. 17. Mintz P, et al. (2008). Cancer 113: 1489-1495. 18. Madak-Erdogan Z, et al. (2008). Mol Endocrinol 22: 2116-2127. 19. Hammes S, Levin E (2007). Endocr Rev 28: 726-41. 20. Weinberg O, et al. (2005). Drug Resistance Updates 8:219-233. 21. Early Breast Cancer Trialists' Collaborative Group (2005). Lancet 365: 1687-1717. 22. Dowsett M, et al. (2005). Breast Cancer Res Treat. 93 Suppl 1: S11-18. 23. The Breast International Group 1-98 Collaborative Group (2005). N Engl J Med 353: 2747-2757. 24. ATAC Trialists' Group (2005). Lancet 365: 60-62. 25. Wakeling A E, et al. (1991). Cancer Res 51:3867-73. 26. Wakeling A, et al. (2001). Clin. Cancer Res. 7: 4350s-4355s. 27. Wijayaratne, A. L. and McDonnell, D. P. (2001) J. Biol. Chem. 276, 35684-356892 28. Robertson J, et al. (2009). J Clin Oncol 27:4530-5. 29. Osborne C K, et al. (2002) J Clin Oncol 20: 3386-3395. 30. Haas A, Siepmann T (1997). FASEB J. 11, 1257-1268. 31. Lange, C. A., et al. (2000). Proc. Natl Acad. Sci. 97, 1032-1037. 32. Alarid, E. T., et al. (1999). Mol. Endocrinol. 13, 1522-1534. 33. Nawaz, Z., et al. (1999) Proc. Natl Acad. Sci. USA 96: 1858-1862. 34. Wang Y, et al. (2009). J. Biochem. 145: 331-343. 35. Kim T K, Maniatis T (1996). Science 273, 1717-1719. 36. Ring A, Dowsett M (2004) Endocr Relat Cancer 11: 643-658. 37. Pike A C, et al. 2001 Structure (Camb) 9:145-153. 38. Dauvois S, et al. (1992). Proc. Natl. Acad. Sci. U.S.A. 89: 4037-4041. 39. Clemons M J, et al. (2014). Breast Cancer Res Treat. 146:153-62. 40. Di Leo A, et al. (2014). J Natl Cancer Inst. 106 337-44. 41. Robertson J F, et al. (2012). Breast Cancer Res Treat. 136:503-11. 42. Estévez L, et al. (2013). Cancer Treat Rev. 39:136-41. 43. Di Leo A, et al. (2010). J Clin Oncol 28:4594-600. 44. Pietras R J, et al. (2005). Steroids, 70:372-81. 45. Shah K N, Faridi, J S (2011). J Steroid Biochem Mol Biol 125:219-225. 46. Robertson J F R G E, et al. (2004). Breast Cancer Res Treat 88:S236-S7. 47. Wakeling A E, et al. (1991). Cancer Res 51:3867-73. 48. Michel van Kruchten, et al. (2014). Proc American Assoc Clin Oncol Annual Meeting: 588. 1) Laszlo Kurti, et al. Org. Lett., 2008, 10, 5247-5250. 2) Chongsoo Lim, et al. Tetrahedron Lett., 2006, 47, 6417-6420. 3) David C. Labaree, et al. J. Med. Chem. 2003, 46, 1886-1904. 1. http://www.cancer.org/research/cancerfactsstatistics/cancer-factsfigures2014/index (estimate of the American Cancer Society for 2014). 2. D. J. Kojetin, et al. Endocrine-Related Cancer 2008, 15, 851-870. A. K. Shiau, et al. Cell, 1998, 95, 927-937. 3. D. C. Labaree, et al. Med. Chem. 2003, 46, 1886-1904. R. Tedesco, et al. J. Org. Chem. 1995, 60, 5316-5318. 4. Nose, A.; Kudo, T. Chem. Pharm. Bull. 1988, 36, 1529-1533. Osby, J. O.; Ganem, B. Tetrahedron Lett. 1985, 26, 6413-6416.

Additional references 1. Hurvitz S, Pietras R (2008). Rational management of endocrine resistance in breast cancer: a compre-hensive review of estrogen receptor biology, treatment options and future direction. Cancer 113:2385-97. 2. Early Breast Cancer Trialists' Collaborative Group (1998). Tamoxifen for early breast cancer: an overview of the randomised trials. Lancet 351:1451-67. 3. Ali S, Coombes R (2002). Endocrine-responsive breast cancer and strategies for combating resistance. Nature Rev Cancer 21: 101-113. 4. Prat A, Baselga J (2008). The role of hormonal therapy in the management of hormonal receptor-positive breast cancer with co-expression of HER2. Nat Clin Pract Oncol 5: 531-542. 5. Robertson J F, Lindemann J, Garnett S, Anderson E, Nicholson R I, Kuter I, Gee J M (2014). A Good Drug Made Better: The Fulvestrant Dose-Response Story. Clin Breast Cancer. 14:381-3 89. 6. van Kruchten M, de Vries E, Glaudemans A et al. Measuring residual estrogen receptor availability during fulvestrant therapy in patients with metastatic breast cancer. Cancer Discov 2014: ii: CD-14-0697. 7. O'Brien J, Peterson T, Tong M et al. (2006). Estrogen-induced proliferation of uterine epithelial cells is independent of ERα binding to classical estrogen response elements. J Biol Chem 281: 26683-92. 8. Pietras R J, Marquez-Garban D C (2007). Membrane-associated estrogen receptor signaling pathways in human cancers. Clin Cancer Res 13: 4672-4676. 9. Syed F, Fraser D, Spelsberg T, Rosen C, Krust A, Chambon P, Jameson J, Khosla S (2007). Effects of loss of classical estrogen response element signaling on bone in male mice. Endocrinology 148:1902-10. 10. Early Breast Cancer Trialists' Collaborative Group (2005). Effects of chemotherapy and hormonal therapy for early breast cancer on recurrence and 15-year survival: an overview of the randomised trials. Lancet 365: 1687-1717. 11. Weinberg O, Marquez D and Pietras R (2005). New approaches to reverse resistance to hormonal therapy in human breast cancer. Drug Resistance Updates 8:219-33. 12. The Breast International Group 1-98 Collaborative Group (2005) A comparison of letrozole and tamoxifen in postmenopausal women with early breast cancer. N Engl J Med 353: 2747-2757. 13. ATAC Trialists' Group (2005). Results of the ATAC (Arimidex, Tamoxifen, Alone or in Combination) trial after completion of 5 years' adjuvant treatment for breast cancer. Lancet 365: 60-62. 14. Massarweh S, Osborne C K, Creighton C et al. (2008). Tamoxifen resistance in breast tumors is driven by growth factor receptor signaling with repression of classic E R genomic function. Cancer Res 68:826-33. 15. Ellis M J et al. (2006) Estrogen-independent proliferation is present in estrogen-receptor HER2-positive primary breast cancer after neoadjuvant letrozole. J Clin Oncol 24: 3019-3025. 16. Johnston S, Pippen J Jr, Pivot X et al. (2009). Lapatinib combined with letrozole versus letrozole and placebo as first-line therapy for postmenopausal hormone receptor-positive metastatic breast cancer. J Clin Oncol. 27:5538-46. 17. Kieser K J, Kim D W, Carlson K E, Katzenellenbogen B S, Katzenellenbogen J A (2010). Characterization of the pharmacophore properties of novel selective estrogen receptor downregulators (SERDs). J Med Chem. 53:3320-9. PMCID: PMC2916745. 18. Fan M, Rickert E, Chen L, Aftab S, Nephew K, Weatherman R V (2007). Characterization of molecular and structural determinants of selective E R downregulators. Breast Cancer Res Treat 103:37-44. 19. Wakeling A E, Dukes M, Bowler J (1991). A potent specific pure antiestrogen with clinical potential. Cancer Res 51:3867-73. 20. Wijayaratne, A. L. and McDonnell, D. P. (2001) the human estrogen receptor-alpha is an ubiquitinated protein whose stability is affected differentially by agonists, antagonists, and selective estrogen receptor modulators. J. Biol. Chem. 276, 35684-356892. 21. Robinson D R, Wu Y M, Vats P et al. (2013). Activating ESR1 mutations in hormone-resistant metastatic breast cancer. Nat Genet 2013, 45:1446-1451.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

G. EMBODIMENTS

Embodiment 1

A compound having the formula

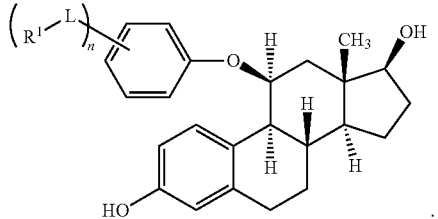

(I)

$R^1$ is independently a hydrogen, halogen, —$NR^2R^3$, —$CX^a_3$, —CN, —$SO_2Cl$, —$SO_{n1}R^{10}$, —$SO_{v1}NR^2R^3$, —$NHNR^2R^3$, —$ONR^2R^3$, —NHC=(O)NHNR^2R^3$, NHC=(O)$NR^2R^3$, —$N(O)_{m1}$, —$C(O)R^9$, —C(O)—$OR^9$, —C(O)$NR^2R^3$, —$OR^{10}$, —$NR^2SO_2R^{10}$, —$NR^2C$=(O)$R^9$, —$NR^2C(O)$—$OR^9$, —$NR^2OR^9$, —$OCX^a_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. L is independently a bond, —$NR^4$—, —$NR^4C(O)$—, —C(O)$NR^4$—, —O—, —S—, —C(O)—, —S(O)—, —$S(O)_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker. $R^2$ is independently a hydrogen, halogen, —$CX^b_3$, —CN, —$SO_2Cl$, —$SO_{n2}R^{14}$, —$SO_{v2}NR^{11}R^{12}$, —$NHNH_2$, —$ONR^{11}R^{12}$, —NHC=(O)NHNH_2$, —NHC=(O)$NR^{11}R^{12}$, —$N(O)_{m2}$, —$NR^{11}R^{12}$, —$C(O)R^{13}$, —C(O)—$OR^{13}$, —C(O)$NR^{11}R^{12}$, —$OR^{14}$, —$NR^{11}SO_2R^{14}$, —$NR^{11}C$=(O)$R^{13}$, —$NR^{11}C(O)$—$OR^{13}$, —$NR^{11}OR^{13}$, —$OCX^b_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently a hydrogen, halogen, —$CX^c_3$, —CN, —$SO_2Cl$, —$SO_3R^1$, —$SO_{v3}NR^{15}R^{16}$, —$NHNH_2$, —$ONR^{15}R^{16}$, —NHC=(O)NHNH_2$, —NHC=(O)$NR^{15}R^{16}$, —$N(O)_{m3}$, —$NR^{15}R^{16}$, —$C(O)R^{17}$, —C(O)—$OR^{17}$, —C(O)$NR^{15}R^{16}$, —$OR^{18}$, —$NR^{15}SO_2R^{18}$, —$NR^{15}C$=(O)$R^{17}$, —$NR^{15}C(O)$—$OR^{17}$, —$NR^{15}OR^{17}$, —$OCX^c_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ and $R^3$ substituents may optionally be joined to form a substituted or unsubstituted heterocycloalkyl, or substituted or unsubstituted heteroaryl. $R^4$ is independently a hydrogen, halogen, —$CX^d_3$, —CN, —$SO_2Cl$, —$SO_{n4}R^{22}$, —$SO_{v4}NR^{19}R^{20}$, —$NHNH_2$, —$ONR^{19}R^{20}$, —NHC=(O)NHNH_2$, —NHC=(O)$NR^{19}R^{20}$, —$N(O)_{m4}$, —$NR^{19}R^{20}$, —$C(O)R^{21}$, —C(O)—$OR^{21}$, —C(O)$NR^{19}R^{20}$, —$OR^{22}$, —$NR^{19}SO_2R^{22}$, —$NR^{19}C$=(O)$R^{21}$, —$NR^{19}C(O)$—$OR^{21}$, —$NR^{19}OR^{21}$, —$OCX^d_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, —$CX_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCX_3$, —$OCHX_2$, —$CF_3$, —$OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl. The symbol n is an integer from 0 to 5. The symbols m1, m2, m3, m4, v1, v2, v3, and v4 are independently 1 or 2. The symbols n1, n2, n3, and n4 are independently an integer from 0 to 4. The symbols X, $X^a$, $X^b$, $X^c$ and $X^d$ are independently —Cl, —Br, —I, or —F.

Embodiment 2

The compound of Embodiment 1, having the formula:

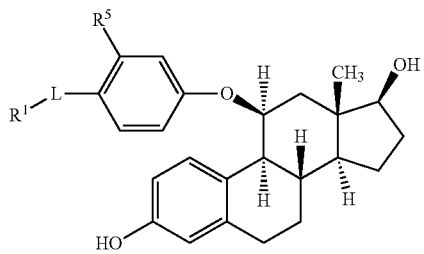

(Ia)

$R^5$ is independently a hydrogen, halogen, —$CX^e_3$, —CN, —$SO_2Cl$, —$SO_{n5}R^{26}$, —$SO_{v5}NR^{23}R^{24}$, —$NHNH_2$, —$ONR^{23}R^{24}$, —NHC=(O)NHNH_2$, —NHC=(O)$NR^{23}R^{24}$, —$N(O)_{m5}$, —$NR^{23}R^{24}$, —$C(O)R^{25}$, —C(O)—$OR^{25}$, —C(O)$NR^{23}R^{24}$, —$OR^{26}$, —$NR^{23}SO_2R^{26}$, —$NR^{23}C$=(O)$R^{25}$, —$NR^{23}C(O)$—$OR^{25}$, —$NR^{23}OR^{25}$, —$OCX^e_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{23}$, $R^{24}$, $R^{25}$, and $R^{26}$ are independently hydrogen, halogen, —CX₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC=(O)NHNH₂, —NHC=(O) NH₂, —NHSO₂H, —NHC=(O)H, —NHC(O)—OH, —NHOH, —OCX₃, —OCHX₂, —CF₃, —OCF₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R²³ and R²⁴ substituents bonded to the same nitrogen atom may optionally be joined to form a substituted or unsubstituted heterocycloalkyl or substituted or unsubstituted heteroaryl. The symbols m5 and v5 are independently 1 or 2. The symbol n5 is independently an integer from 0 to 4. The symbol $X^e$ is independently —Cl, —Br, —I, or —F.

Embodiment 3

The compound of Embodiment 2, wherein $R^5$ is independently a hydrogen, halogen, $—CX^e_3$, or unsubstituted alkyl.

Embodiment 4

The compound of Embodiment 2, wherein $R^5$ is independently a hydrogen, —F, —CF₃, or unsubstituted methyl.

Embodiment 5

The compound of Embodiment 1, having the formula:

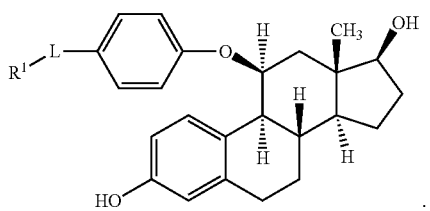

(Ib)

Embodiment 6

The compound of Embodiment 1, having the formula:

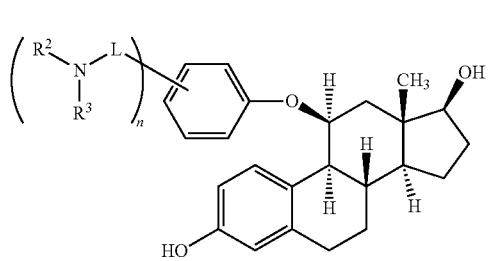

(II)

Embodiment 7

The compound of Embodiment 1, having the formula:

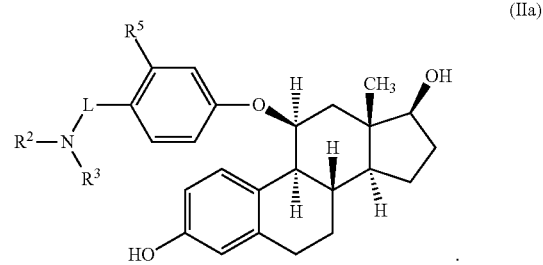

(IIa)

$R^5$ is independently a hydrogen, halogen, $—CX^e_3$, —CN, —SO₂Cl, $—SO_{n5}R^{26}$, $—SO_{v5}NR^{23}R^{24}$, —NHNH₂, $—ONR^{23}R^{24}$, —NHC=(O)NHNH₂, $—NHC=(O)NR^{23}R^{24}$, $—N(O)_{m5}$, $—NR^{23}R^{24}$, $—C(O)R^{25}$, $—C(O)—OR^{25}$, $—C(O)NR^{23}R^{24}$, $—OR^{26}$, $—NR^{23}SO_2R^{26}$, $—NR^{23}C=(O)R^{25}$, $—NR^{23}C(O)—OR^{25}$, $—NR^{23}OR^{25}$, $—OCX^e_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{23}$, $R^{24}$, $R^{25}$, and $R^{26}$ are independently hydrogen, halogen, —CX₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC=(O)NHNH₂, —NHC=(O) NH₂, —NHSO₂H, —NHC=(O)H, —NHC(O)—OH, —NHOH, —OCX₃, —OCHX₂, —CF₃, —OCF₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R²³ and R²⁴ substituents bonded to the same nitrogen atom may optionally be joined to form a substituted or unsubstituted heterocycloalkyl or substituted or unsubstituted heteroaryl. The symbols m5 and v5 are independently 1 or 2. The symbol n5 is independently an integer from 0 to 4, and the symbol $X^e$ is independently —Cl, —Br, —I, or —F.

Embodiment 8

The compound of Embodiment 7, wherein $R^5$ is independently a hydrogen, halogen, $—CX^e_3$, or unsubstituted alkyl.

Embodiment 9

The compound of Embodiment 7, wherein $R^5$ is independently a hydrogen, —F, —CF₃, or unsubstituted methyl.

Embodiment 10

The compound of Embodiment 1, having the formula:

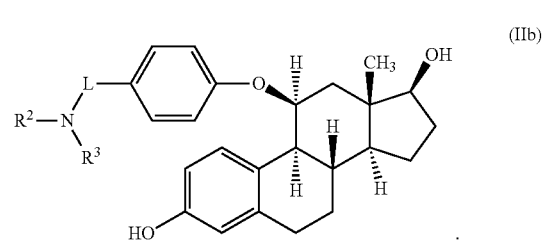

(IIb)

Embodiment 11

The compound of one of Embodiments 1 to 10, wherein L is a bond.

Embodiment 12

The compound of one of Embodiments 1 to 10, wherein L is a heteroalkylene.

Embodiment 13

The compound of one of Embodiments 1 to 10, wherein L is independently a 2 to 8 membered heteroalkylene.

Embodiment 14

The compound of one of Embodiments 1 to 10, wherein L is independently a 3 to 6 membered heteroalkylene.

Embodiment 15

The compound of one of Embodiments 1 to 10, wherein L is independently —NH-(substituted or unsubstituted ($C_1$-$C_4$) alkylene).

Embodiment 16

The compound of one of Embodiments 1 to 10, wherein L is independently —NH-(unsubstituted ($C_1$-$C_4$) alkylene).

Embodiment 17

The compound of one of Embodiments 1 to 10, wherein L is independently —NHC(O)-(substituted or unsubstituted ($C_1$-$C_4$) alkylene).

Embodiment 18

The compound of one of Embodiments 1 to 10, wherein L is independently —NHC(O)-(unsubstituted ($C_1$-$C_4$) alkylene).

Embodiment 19

The compound of one of Embodiments 1 to 18, wherein $R^2$ is independently substituted or unsubstituted alkyl or substituted or unsubstituted heteroalkyl.

Embodiment 20

The compound of one of Embodiments 1 to 18, wherein $R^2$ is independently substituted or unsubstituted ($C_1$-$C_{10}$) alkyl or substituted or unsubstituted 2 to 10 membered heteroalkyl.

Embodiment 21

The compound of one of Embodiments 1 to 18, wherein $R^2$ is unsubstituted methyl.

Embodiment 22

The compound of one of Embodiments 1 to 18, wherein $R^2$ is H.

Embodiment 23

The compound of one of Embodiments 1 to 22, wherein $R^3$ is independently substituted or unsubstituted alkyl or substituted or unsubstituted heteroalkyl.

Embodiment 24

The compound of one of Embodiments 1 to 22, wherein $R^3$ is independently substituted or unsubstituted ($C_1$-$C_{10}$) alkyl or substituted or unsubstituted 2 to 10 membered heteroalkyl.

Embodiment 25

The compound of one of Embodiments 1 to 22, wherein $R^3$ is unsubstituted methyl.

Embodiment 26

The compound of one of Embodiments 1 to 22, wherein $R^3$ is H.

Embodiment 27

The compound of one of Embodiments 1 to 26, wherein $R^2$ and $R^3$ are joined to form a substituted or unsubstituted heterocycloalkyl.

Embodiment 28

The compound of one of Embodiments 1 to 26, wherein $R^2$ and $R^3$ are joined to form a substituted or unsubstituted 3 to 8 membered heterocycloalkyl.

Embodiment 29

The compound of one of Embodiments 1 to 26, wherein $R^2$ and $R^3$ are joined to form a substituted or unsubstituted 3 to 6 membered heterocycloalkyl.

Embodiment 30

The compound of one of Embodiments 1 to 26, wherein $R^2$ and $R^3$ are joined to form an unsubstituted 3 to 6 membered heterocycloalkyl.

Embodiment 31

The compound of one of Embodiments 1 to 26, wherein $R^2$ and $R^3$ and the nitrogen to which they are bonded form

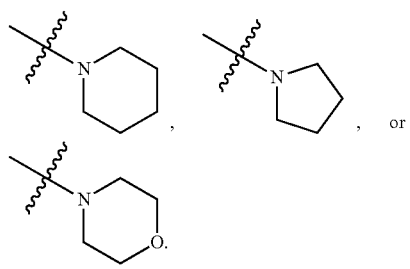

Embodiment 32

The compound of one of Embodiments 1 to 31, wherein n is 2.

Embodiment 33

The compound of one of Embodiments 1 to 31, wherein n is 1.

Embodiment 34

The compound of one of Embodiments 1 to 5, wherein $R^1$ is —$NO_2$ or —$NH_2$.

Embodiment 35

The compound of Embodiment 34, wherein L is a bond.

Embodiment 36

The compound of Embodiment 1, having the formula:

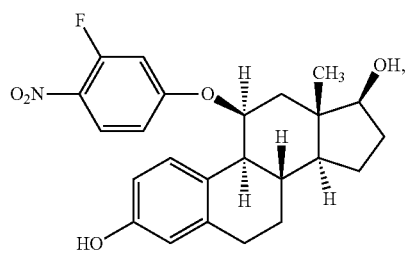
(JD119)

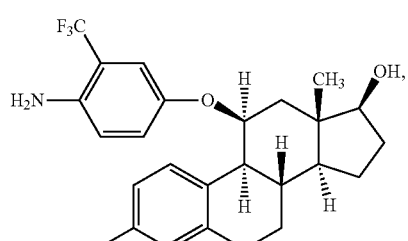
(JD128)

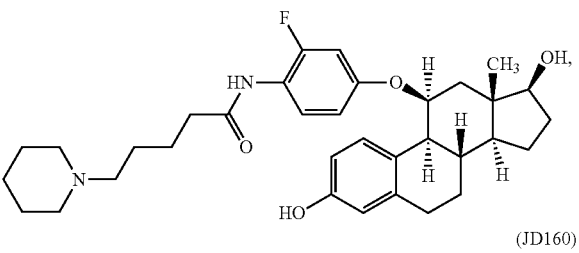
(JD140)

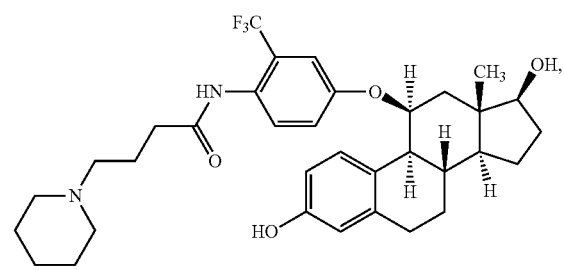
(JD160)

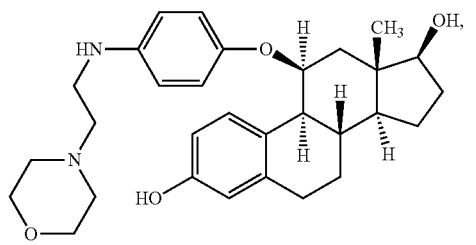
(JD121)

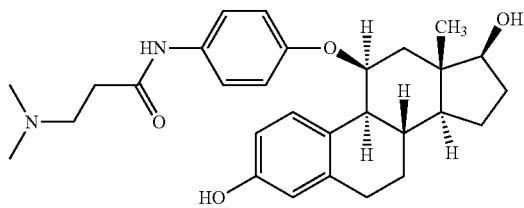
(JD109)

Embodiment 37

A pharmaceutical composition comprising a compound of one of Embodiments 1 to 36 or a pharmaceutically acceptable salt thereof, and a pharmaceutically acceptable excipient.

Embodiment 38

A method of treating a hyperproliferative disorder in a subject in need thereof, comprising administering to the subject an effective amount of a compound of one of Embodiments 1 to 36, or a pharmaceutically acceptable salt thereof.

Embodiment 39

The method of Embodiment 39, wherein the hyperproliferative disorder is associated with estrogen receptor activity.

Embodiment 40

The method of one of Embodiments 38 to 39, wherein the hyperproliferative disorder is lymphangioleiomyomatosis.

Embodiment 41

The method of one of Embodiments 38 to 39, wherein the hyperproliferative disorder is a cancer.

Embodiment 42

The method of Embodiment 41, wherein the cancer is resistant to an anti-cancer agent.

Embodiment 43

The method of one of Embodiments 41 to 42, wherein the cancer is breast cancer, lung cancer (e.g., non-small cell lung cancer), a gynecological cancer, ovarian cancer, endometrial cancer, or prostate cancer.

Embodiment 44

The method of one of Embodiments 41 to 42, wherein the cancer is a cancer of an estrogen target organ or tissue.

Embodiment 45

A method of inhibiting estrogen receptor activity in a subject in need thereof, comprising administering to the subject an effective amount of a compound of one of Embodiments 1 to 36, or a pharmaceutically acceptable salt thereof.

Embodiment 46

A method of treating gynecomastia in a subject in need thereof, comprising administering to the subject an effective amount of a compound of one of Embodiments 1 to 36, or a pharmaceutically acceptable salt thereof.

Embodiment 47

A method of treating a bone disorder in a subject in need thereof, comprising administering to the subject an effective amount of a compound of one of Embodiments 1 to 36, or a pharmaceutically acceptable salt thereof.

What is claimed is:
1. A compound having the formula:

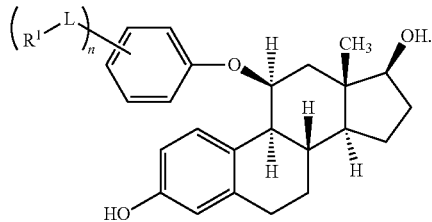

(I)

wherein
$R^1$ is independently a hydrogen, halogen, —$NR^2R^3$, —$CX^a_3$, —CN, —$SO_2Cl$, —$SO_{n1}R^{10}$, —$SO_{v1}NR^2R^3$, —$NHNR^2R^3$, —$ONR^2R^3$, —$NHC$=(O)$NHNR^2R^3$, —$NHC$=(O)$NR^2R^3$, —$N(O)_{m1}$, —$C(O)R^9$, —$C(O)$—$OR^9$, —$C(O)NR^2R^3$, —$OR^{10}$, —$NR^2SO_2R^{10}$, —$NR^2C$=(O)$R^9$, —$NR^2C(O)$—$OR^9$, —$NR^2OR^9$, —$OCX^a_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L is independently a bond, —$NR^4$—, —$NR^4C(O)$—, —$C(O)NR^4$—, —O—, —S—, —C(O)—, —S(O)—, —$S(O)_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker;

$R^2$ is independently a hydrogen, halogen, —$CX^b_3$, —CN, —$SO_2Cl$, —$SO_{n2}R^{14}$, —$SO_{v2}NR^{11}R^{12}$, —$NHNH_2$, —$ONR^{11}R^{12}$, —$NHC$=(O)$NHNH_2$, —$NHC$=(O)$NR^{11}R^{12}$, —$N(O)_{m2}$, —$NR^{11}R^{12}$, —$C(O)R^{13}$, —$C(O)$—$OR^{13}$, —$C(O)NR^{11}R^{12}$, —$OR^{14}$, —$NR^{11}SO_2R^{14}$, —$NR^{11}C$=(O)$R^{13}$, —$NR^{11}C(O)$—$OR^{13}$, —$NR^{11}OR^{13}$, —$OCX^b_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently a hydrogen, halogen, —$CX^c_3$, —CN, —$SO_2Cl$, —$SO_{n3}R^{18}$, —$SO_{v3}NR^{15}R^{16}$, —$NHNH_2$, —$ONR^{15}R^{16}$, —$NHC$=(O)$NHNH_2$, —$NHC$=(O)$NR^{15}R^{16}$, —$N(O)_{m3}$, —$NR^{15}R^{16}$, —$C(O)R^{17}$, —$C(O)$—$OR^{17}$, —$C(O)NR^{15}R^{16}$, $R^{18}$, —$NR^{15}SO_2R^{18}$, —$NR^{15}C$=(O)$R^{17}$, —$NR^{15}C(O)$—$OR^{17}$, —$NR^{15}OR^{17}$, —$OCX^c_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ and $R^3$ substituents may optionally be joined to form a substituted or unsubstituted heterocycloalkyl, or substituted or unsubstituted heteroaryl;

$R^4$ is independently a hydrogen, halogen, —$CX^d_3$, —CN, —$SO_2Cl$, —$SO_{n4}R^{22}$, —$SO_{v4}NR^{19}R^{20}$, —$NHNH_2$, —$ONR^{19}R^{20}$, —$NHC$=(O)$NHNH_2$, —$NHC$=(O)$NR^{19}R^{20}$, —$N(O)_{m4}$, —$NR^{19}R^{20}$, —$C(O)R^{21}$, —$C(O)$—$OR^{21}$, —$C(O)NR^{19}R^{20}$, —$OR^{22}$, —$NR^{19}SO_2R^{22}$, —$NR^{19}C$=(O)$R^{21}$, —$NR^{19}C(O)$—$OR^{21}$, —$NR^{19}OR^{21}$, —$OCX^d_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, —$CX_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC$=(O) $NHNH_2$, —$NHC$=(O) $NH_2$, —$NHSO_2H$, —$NHC$=(O)H, —$NHC(O)$—OH, —NHOH, —$OCX_3$, —$OCHX_2$, —$CF_3$, —$OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{11}$ and $R^{12}$ substituents bonded to the same nitrogen atom may optionally be joined to form a substituted or unsubstituted heterocycloalkyl or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl;

n is an integer from 0 to 5;

m1, m2, m3, m4, v1, v2, v3, and v4 are independently 1 or 2;

n1, n2, n3, and n4 are independently an integer from 0 to 4;

X, $X^a$, $X^b$, $X^c$ and $X^d$ are independently —Cl, —Br, —I, or –F.

2. The compound of claim 1, having the formula:

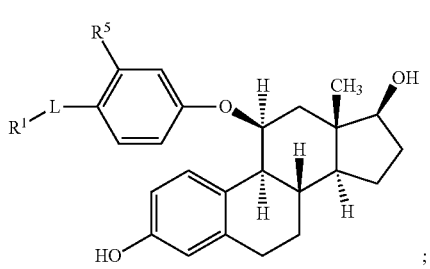
(Ia)

wherein $R^5$ is independently a hydrogen, halogen, —$CX^e_3$, —CN, —$SO_2Cl$, —$SO_{n5}R^{26}$, —$SO_{v5}NR^{23}R^{24}$, —$NHNH_2$, —$ONR^{23}R^{24}$, —NHC=(O)$NHNH_2$, —NHC=(O)$NR^{23}R^{24}$, —N(O)$_{m5}$, —$NR^{23}R^{24}$, —C(O)$R^{25}$, —C(O)—$OR^{25}$, —C(O)$NR^{23}R^{24}$, —$OR^{26}$, —$NR^{23}SO_2R^{26}$, —$NR^{23}C$=(O)$R^{25}$, —$NR^{23}C(O)$—$OR^{25}$, —$NR^{23}OR^{25}$, —$OCX^e_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{23}$, $R^{24}$, $R^{25}$, and $R^{26}$ are independently hydrogen, halogen, —$CX_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCX_3$, —$OCHX_2$, —$CF_3$, —$OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{23}$ and $R^{24}$ substituents bonded to the same nitrogen atom may optionally be joined to form a substituted or unsubstituted heterocycloalkyl or substituted or unsubstituted heteroaryl;

m5 and v5 are independently 1 or 2;

n5 is independently an integer from 0 to 4;

$X^e$ is independently —Cl, —Br, —I, or –F.

3. The compound of claim 1, having the formula:

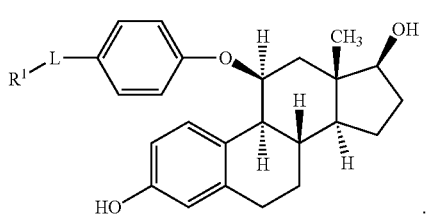
(Ib)

4. The compound of claim 1, having the formula:

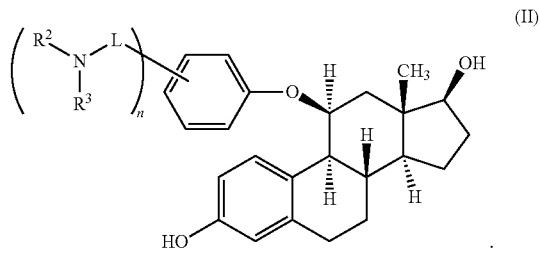
(II)

5. The compound of claim 1, having the formula:

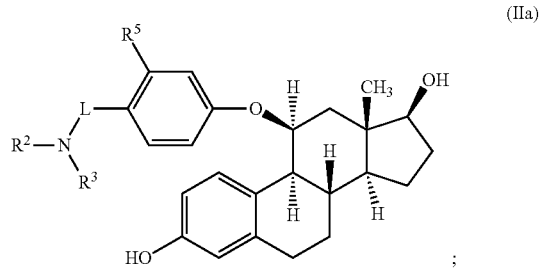
(IIa)

wherein $R^5$ is independently a hydrogen, halogen, —$CX^e_3$, —CN, —$SO_2Cl$, —$SO_{n5}R^{26}$, —$SO_{v5}NR^{23}R^{24}$, —$NHNH_2$, —$ONR^{23}R^{24}$, —NHC=(O)$NHNH_2$, —NHC=(O) $NR^{23}R^{24}$, —N(O)$_{m5}$, —$NR^{23}R^{24}$, —C(O)$R^{25}$, —C(O)—$OR^{25}$, —C(O)$NR^{23}R^{24}$, —$OR^{26}$, —$NR^{23}SO_2R^{26}$, —$NR^{23}C$=(O)$R^{25}$, —$NR^{23}C(O)$ $OR^{25}$, —$NR^{23}OR^{25}$, —$OCX^e_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{23}$, $R^{24}$, $R^{25}$, and $R^{26}$ are independently hydrogen, halogen, —$CX_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCX_3$, —$OCHX_2$, —$CF_3$, —$OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{23}$ and $R^{24}$ substituents bonded to the same nitrogen atom may optionally be joined to form a substituted or unsubstituted heterocycloalkyl or substituted or unsubstituted heteroaryl;

m5 and v5 are independently 1 or 2;

n5 is independently an integer from 0 to 4;

$X^e$ is independently —Cl, —Br, —I, or —F.

6. The compound of claim 1, having the formula:

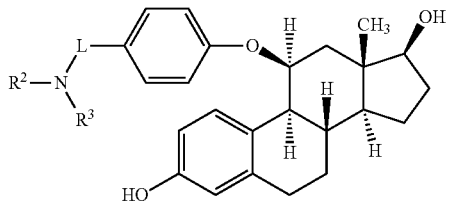
(IIb)

7. The compound of claim 1, wherein L is —NH-(unsubstituted ($C_1$-$C_4$) alkylene).

8. The compound of claim 1, wherein L is —NHC(O)-(unsubstituted ($C_1$-$C_4$) alkylene).

9. The compound of claim 1, wherein $R^2$ is hydrogen, substituted or unsubstituted ($C_1$-$C_{10}$) alkyl, or substituted or unsubstituted 2 to 10 membered heteroalkyl; or $R^2$ and $R^3$ are joined to form a substituted or unsubstituted 3 to 6 membered heterocycloalkyl.

10. The compound of claim 1, wherein $R^3$ is hydrogen, substituted or unsubstituted ($C_1$-$C_{10}$) alkyl or substituted, or unsubstituted 2 to 10 membered heteroalkyl; or $R^2$ and $R^3$ are joined to form a substituted or unsubstituted 3 to 6 membered heterocycloalkyl.

11. The compound of claim 1, wherein $R^2$ and $R^3$ and the nitrogen to which they are bonded form

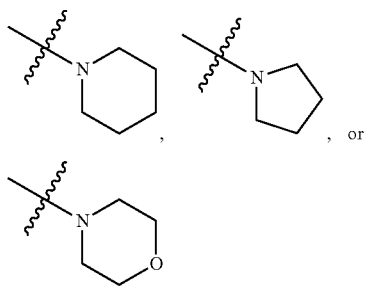

12. The compound of claim 1, wherein n is 2.

13. The compound of claim 1, wherein n is 1.

14. The compound of claim 1, wherein $R^1$ is —$NO_2$ or —$NH_2$.

15. The compound of claim 14, wherein L is a bond.

16. The compound of claim 1, having the formula:

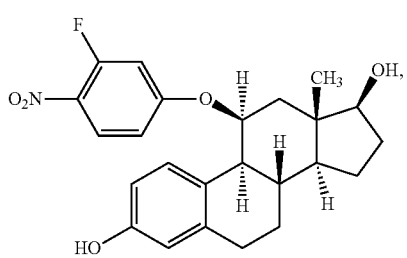
(JD119)

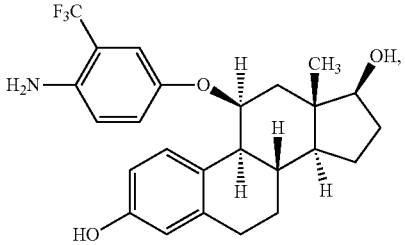
(JD128)

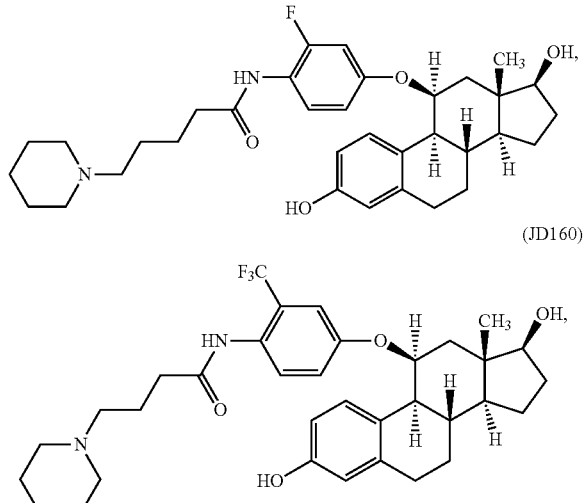
(JD140)

(JD160)

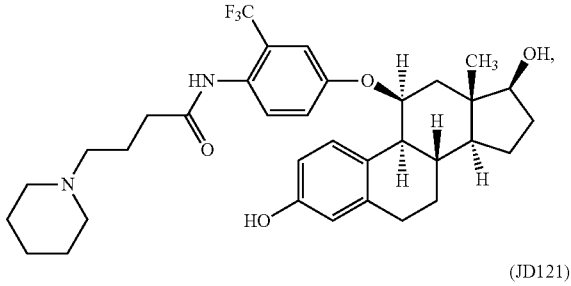
(JD121)

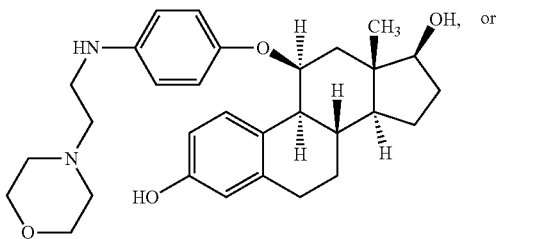
(JD109)

17. A pharmaceutical composition comprising the compound of claim 1 or a pharmaceutically acceptable salt thereof, and a pharmaceutically acceptable excipient.

18. A method of treating a hyperproliferative disorder in a subject in need thereof, comprising administering to the subject an effective amount of the compound of claim 1, or a pharmaceutically acceptable salt thereof, wherein the hyperproliferative disorder is sensitive to inhibition of estrogen receptor activity.

19. The method of claim 18, wherein the hyperproliferative disorder is lymphangioleiomyomatosis or cancer.

20. A method of inhibiting estrogen receptor activity in a subject in need thereof, comprising administering to the subject an effective amount of the compound of claim 1, or a pharmaceutically acceptable salt thereof.

21. The method of claim 19, wherein the cancer is breast cancer, non-small cell lung cancer, ovarian cancer, endometrial cancer, or prostate cancer.

\* \* \* \* \*